United States Patent
Thompson

(10) Patent No.: US 9,730,912 B2
(45) Date of Patent: *Aug. 15, 2017

(54) PHARMACEUTICAL COMPOUNDS

(75) Inventor: Neil Thomas Thompson, Cambridge (GB)

(73) Assignee: ASTEX THERAPEUTICS LIMITED, Cambridge (GB)

( * ) Notice: Subject to any disclaimer, the term of this patent is extended or adjusted under 35 U.S.C. 154(b) by 1123 days.

This patent is subject to a terminal disclaimer.

(21) Appl. No.: 12/445,163

(22) PCT Filed: Oct. 12, 2007

(86) PCT No.: PCT/GB2007/003915
§ 371 (c)(1),
(2), (4) Date: Aug. 14, 2009

(87) PCT Pub. No.: WO2008/044054
PCT Pub. Date: Apr. 17, 2008

(65) Prior Publication Data
US 2009/0298818 A1 Dec. 3, 2009

Related U.S. Application Data

(60) Provisional application No. 60/829,251, filed on Oct. 12, 2006, provisional application No. 60/829,208, filed on Oct. 12, 2006.

(51) Int. Cl.
*A61K 31/4035* (2006.01)
*A61K 31/437* (2006.01)
(Continued)

(52) U.S. Cl.
CPC ........ *A61K 31/4035* (2013.01); *A61K 31/437* (2013.01); *A61K 31/454* (2013.01);
(Continued)

(58) Field of Classification Search
None
See application file for complete search history.

(56) References Cited

U.S. PATENT DOCUMENTS

| | | |
|---|---|---|
| 4,582,909 A | 4/1986 | Butler et al. |
| 4,760,064 A | 7/1988 | Tominaga et al. |

(Continued)

FOREIGN PATENT DOCUMENTS

| | | |
|---|---|---|
| DE | 19955283 | 5/2001 |
| DE | 10 2004 049 078 | 4/2006 |

(Continued)

OTHER PUBLICATIONS

Connor et al. "Antiviral Activity and RNA Polymerase Degradation Following HSP90 Inhibition in a Range of Negative Strand Viruses". Virology; 362, 2007:109-119.*

(Continued)

*Primary Examiner* — Leslie A. Royds Draper
(74) *Attorney, Agent, or Firm* — Vedder Price P.C.; Thomas J. Kowalski; Deborah L. Lu

(57) ABSTRACT

The invention provides the use of a compound for the manufacture of a medicament for the treatment of pain, wherein the compound is a compound of the formula (VI):

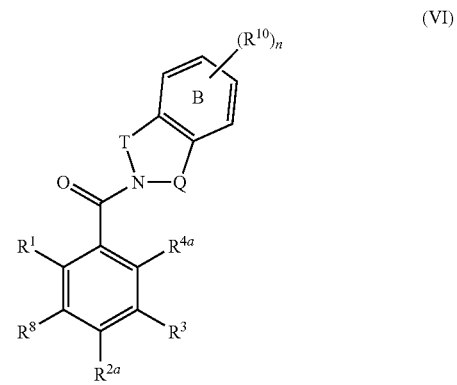

(VI)

Figure 1:
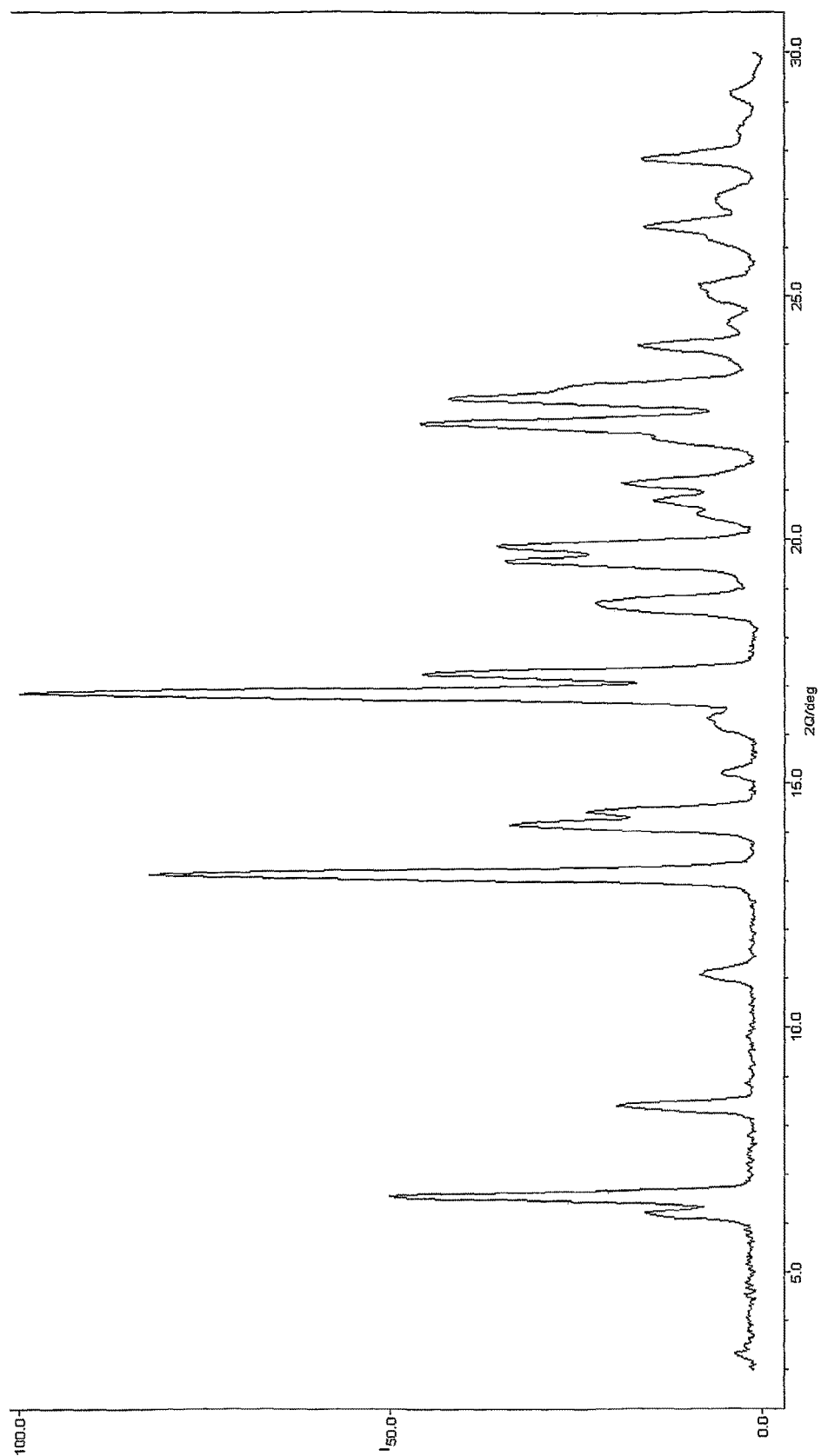

or a salt, solvate, tautomer or N-oxide thereof;

wherein the bicyclic group:

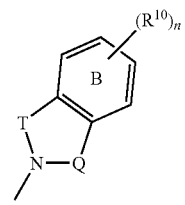

is selected from the structures C1, C5 and C6:

C1

C5

(Continued)

-continued

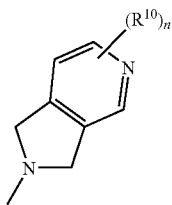

C6 wherein n, $R^1$, $R^{2a}$, $R^3$, $R^{4a}$, $R^8$ and $R^{10}$ are as defined in the claims.

The invention also provides the use of a compound of the formula (VI) for the manufacture of a medicament for the prophylaxis or treatment of a fungal, protozoal, viral or parasitic disease state or condition (other than a disease state or condition due to *Plasmodium falciparum*) or for use in the prophylaxis or treatment of Ewing's sarcoma, atherosclerosis or lupus erythematosus.

2 Claims, 4 Drawing Sheets

(51) Int. Cl.
| | | |
|---|---|---|
| A61K 31/454 | (2006.01) | |
| A61K 31/496 | (2006.01) | |
| A61K 31/5377 | (2006.01) | |
| A61K 45/06 | (2006.01) | |

(52) U.S. Cl.
CPC ........ *A61K 31/496* (2013.01); *A61K 31/5377* (2013.01); *A61K 45/06* (2013.01)

(56) References Cited

U.S. PATENT DOCUMENTS

| | | | |
|---|---|---|---|
| 5,310,951 | A | 5/1994 | Djuric et al. |
| 5,332,735 | A | 7/1994 | Rault et al. |
| 6,469,024 | B2 | 10/2002 | Li et al. |
| 6,649,606 | B1 | 11/2003 | Hermsmeier et al. |
| 7,208,630 | B2 | 4/2007 | Blagg et al. |
| 7,229,986 | B2 | 6/2007 | Ishihara et al. |
| 7,385,059 | B2 | 6/2008 | Berdini et al. |
| 7,425,633 | B2 | 9/2008 | Jiaang |
| 7,538,224 | B2 | 5/2009 | Nara et al. |
| 7,577,114 | B2 | 8/2009 | Hsieh et al. |
| 7,700,625 | B2 | 4/2010 | Chessari et al. |
| 7,754,725 | B2 | 7/2010 | Chessari et al. |
| 8,101,648 | B2 | 1/2012 | Chessari et al. |
| 8,106,057 | B2 | 1/2012 | Chessari et al. |
| 8,110,573 | B2 | 2/2012 | Berdini et al. |
| 8,277,807 | B2 | 10/2012 | Gallagher et al. |
| 8,277,857 | B2 | 10/2012 | Shimizu et al. |
| 8,383,619 | B2 | 2/2013 | Williams et al. |
| 8,530,469 | B2 | 9/2013 | Chessari et al. |
| 8,653,084 | B2 | 2/2014 | Frederickson et al. |
| 8,664,218 | B2 | 3/2014 | Williams et al. |
| 8,779,132 | B2 | 7/2014 | Congreve et al. |
| 8,816,087 | B2 | 8/2014 | Chessari et al. |
| 8,883,790 | B2 | 11/2014 | Gallagher et al. |
| 8,916,552 | B2 | 12/2014 | Gallagher et al. |
| 9,428,439 | B2 | 8/2016 | Frederickson et al. |
| 2003/0158177 | A1 | 8/2003 | Ishihara et al. |
| 2003/0203898 | A1 | 10/2003 | Haning et al. |
| 2004/0039038 | A1 | 2/2004 | Bernardon et al. |
| 2004/0253228 | A1 | 12/2004 | Srivastava et al. |
| 2004/0259877 | A1 | 12/2004 | Muto et al. |
| 2005/0037922 | A1 | 2/2005 | Bickers et al. |
| 2006/0019958 | A1 | 1/2006 | Muto et al. |
| 2006/0019961 | A1 | 1/2006 | Mahaney et al. |
| 2006/0084647 | A1 | 4/2006 | Wang et al. |
| 2006/0089495 | A1 | 4/2006 | Blagg et al. |
| 2006/0100257 | A1 | 5/2006 | Muto et al. |
| 2006/0111409 | A1 | 5/2006 | Muto et al. |
| 2006/0122243 | A1 | 6/2006 | Muto et al. |
| 2006/0173188 | A1 | 8/2006 | Seki et al. |
| 2006/0178381 | A1 | 8/2006 | Jolidon et al. |
| 2006/0183902 | A1 | 8/2006 | Baxter et al. |
| 2007/0042997 | A1 | 2/2007 | Ital et al. |
| 2007/0184516 | A1 | 8/2007 | Marahiel et al. |
| 2007/0185059 | A1 | 8/2007 | Muto et al. |
| 2007/0259871 | A1 | 11/2007 | Chessari et al. |
| 2007/0259886 | A1 | 11/2007 | Chessari et al. |
| 2007/0265268 | A1 | 11/2007 | Kitamura et al. |
| 2007/0276026 | A1 | 11/2007 | Chessari et al. |
| 2008/0090880 | A1 | 4/2008 | Eggenweiler et al. |
| 2008/0132495 | A1 | 6/2008 | Berdini et al. |
| 2008/0306054 | A1 | 12/2008 | Chessari et al. |
| 2009/0215742 | A1 | 8/2009 | Funk et al. |
| 2009/0215771 | A1 | 8/2009 | Graczyk et al. |
| 2009/0215772 | A1 | 8/2009 | Chessari et al. |
| 2010/0092474 | A1 | 4/2010 | Gallagher et al. |
| 2010/0152184 | A1 | 6/2010 | Congreve et al. |
| 2010/0179145 | A1 | 7/2010 | Gallagher et al. |
| 2010/0286167 | A1 | 11/2010 | Chessari et al. |
| 2011/0046155 | A1 | 2/2011 | Frederickson et al. |
| 2011/0098290 | A1 | 4/2011 | Williams et al. |
| 2011/0105501 | A1 | 5/2011 | Gallagher et al. |
| 2012/0251545 | A1 | 10/2012 | Chessari et al. |
| 2013/0210820 | A1 | 8/2013 | Williams et al. |
| 2014/0221394 | A1 | 8/2014 | Frederickson et al. |
| 2015/0045362 | A1 | 2/2015 | Chessari et al. |

FOREIGN PATENT DOCUMENTS

| | | |
|---|---|---|
| EP | 347168 | 12/1989 |
| EP | 353753 | 2/1990 |
| EP | 0474403 | 3/1992 |
| EP | 0486386 | 5/1992 |
| EP | 0500336 | 8/1992 |
| EP | 0722723 | 7/1996 |
| EP | 1283199 | 2/2003 |
| EP | 1352650 | 10/2003 |
| EP | 1510207 | 3/2005 |
| EP | 1510210 | 3/2005 |
| EP | 1512396 | 3/2005 |
| EP | 1514544 | 3/2005 |
| EP | 1642880 | 4/2006 |
| EP | 1704856 | 9/2006 |
| EP | 1852112 | 11/2007 |
| JP | 49010506 | 1/1974 |
| JP | 09194450 | 7/1997 |
| WO | WO 91/08205 | 6/1991 |
| WO | WO 92/17467 | 10/1992 |
| WO | WO 97/26884 | 7/1997 |
| WO | WO 97/35999 | 10/1997 |
| WO | WO 97/36876 | 10/1997 |
| WO | WO 97/39750 | 10/1997 |
| WO | WO 97/47270 | 12/1997 |
| WO | WO 98/40385 | 9/1998 |
| WO | WO 98/45255 | 10/1998 |
| WO | WO 98/47885 | 10/1998 |
| WO | WO 98/50036 | 11/1998 |
| WO | WO 99/21422 | 5/1999 |
| WO | WO 99/29705 | 6/1999 |
| WO | WO 00/59867 | 10/2000 |
| WO | WO 01/36351 | 5/2001 |
| WO | WO 01/60369 | 8/2001 |
| WO | WO 01/87834 | 11/2001 |
| WO | WO 01/87887 | 11/2001 |
| WO | WO 01/90053 | 11/2001 |
| WO | WO 02/12210 | 2/2002 |
| WO | WO 02/18319 | 3/2002 |
| WO | WO 03/051877 | 6/2003 |
| WO | WO 03/053366 | 7/2003 |
| WO | WO 03/055860 | 7/2003 |
| WO | WO 03/086282 | 10/2003 |
| WO | WO 03/103665 | 12/2003 |
| WO | WO 2004/005295 | 1/2004 |

(56) References Cited

FOREIGN PATENT DOCUMENTS

| | | |
|---|---|---|
| WO | WO 2004/007501 | 1/2004 |
| WO | WO 2004/035571 | 4/2004 |
| WO | WO 2004/072051 | 8/2004 |
| WO | WO 2004/074283 | 9/2004 |
| WO | WO 2004/096757 | 11/2004 |
| WO | WO 2005/000300 | 1/2005 |
| WO | WO 2005/000839 | 1/2005 |
| WO | WO 2005/007151 | 1/2005 |
| WO | WO 2005/009940 | 2/2005 |
| WO | WO 2005/012256 | 2/2005 |
| WO | WO 2005/012297 | 2/2005 |
| WO | WO 2005/012541 | 2/2005 |
| WO | WO 2005/016889 | 2/2005 |
| WO | WO 2005/023818 | 3/2005 |
| WO | WO 2005/037214 | 4/2005 |
| WO | WO 2005/047249 | 5/2005 |
| WO | WO 2005/000778 | 6/2005 |
| WO | WO 2005/063222 | 7/2005 |
| WO | WO 2006/015123 | 2/2006 |
| WO | WO 2006/023778 | 3/2006 |
| WO | WO 2006/047740 | 5/2006 |
| WO | WO 2006/051808 | 5/2006 |
| WO | WO 2006/055760 | 5/2006 |
| WO | WO 2006/070195 | 7/2006 |
| WO | WO 2006/077426 | 7/2006 |
| WO | WO 2006/082001 | 8/2006 |
| WO | WO 2006/088193 | 8/2006 |
| WO | WO 2006/109085 | 10/2006 |
| WO | WO 2006/117669 | 11/2006 |
| WO | WO 2006/125119 | 11/2006 |
| WO | WO 2007/050124 | 5/2007 |
| WO | WO 2008/044027 | 4/2008 |
| WO | WO 2008/044029 | 4/2008 |
| WO | WO 2008/044034 | 4/2008 |
| WO | WO 2008/044041 | 4/2008 |
| WO | WO 2008/044045 | 4/2008 |
| WO | WO 2008/044054 | 4/2008 |
| WO | WO 2008/053319 | 5/2008 |

OTHER PUBLICATIONS

Waxman et al. "Host Cell Factor Requirement for Hepatitis C Virus Enzyme Maturation". PNAS. 2001; 98(24):13931-13935.*
Nakagawa et al. "HSP90 Inhibitors Suppress HCV Replication in Replicon Cells and Humanized Liver Mice". Biochemical and Biophysical Research Communications. 2007; 353:882-888.*
Mutschler et al. Drug Action: Basic Principles and Therapeutic Aspects. CRC Press. 1995. pp. 515-580.*
Dymock et al. "Inhibitors of HSP90 and Other Chaperones for the Treatment of Cancer". Expert Opin. Ther. Patents. 2004; 14(6):837-847.*
Goetz et al. "The HSP90 Chaperone Complex as a Novel Target for Cancer Therapy". Annals of Oncology. 2003; 14:1169-1176.*
Bagatell et al. "Altered HSP90 Function in Cancer: A Unique Therapeutic Opportunity". Mol Cancer Ther. 2004; 3:1021-1030.*
Calderwood et al. (eds.) Chapter 13 ("Targeting HSP90 Function to Treat Cancer: Much More to be Learned"). Heat Shock Proteins in Cancer. 2007:253-274.*
Trepel et al. "Targeting the Dynamic HSP90 Complex in Cancer". Nat. Rev. Cancer. 2010; 10(8):537-549.*
Ozben T. "Mechanisms and Strategies to Overcome Multiple Drug Resistance in Cancer". FEBS Letters. 2006; 580:2903-2909.*
Krishna et al. "Multidrug Resistance (MDR) in Cancer: Mechanisms, Reversal Using Modulators of MDR and the Role of MDR Modulators in Influencing the Pharmacokinetics of Anticancer Drugs". European Journal of Pharmaceutical Sciences. 2000; 11:265-283.*
Cole BE. "Pain Management: Classifying, Understanding, and Treating Pain". Hospital Physician, Jun. 2002, p. 23-30.*
Joshi et al. "Animal Models of Pain for Drug Discovery". Expert Opin. Drug Discov, Sep. 2006; 1(4):341-352.*
Janicki et al. "Animal Models for Pain Research". Current Pain and Headache Reports, 1997; 1:271-277.*
Veneroni et al. "Anti-Allodynic Effect of NW-1029, a Novel Na+ Channel Blocker, In Experimental Animal Models of Inflammatory and Neuropathic Pain". Pain, 2003; 102:17-25.*
Blackburn-Munro et al. "The Anticonvulsant Retigabine Attenuates Nociceptive Behaviours in Rat Models of Persistent and Neuropathic Pain". European Journal of Pharmacology. 2003; 46:109-116.*
Bomholt et al. "Antinociceptive Effects of the Antidepressants Amitriptyline, Duloxetine, Mirtazapine and Citalopram in Animal Models of Acute, Persistent and Neuropathic Pain". Neuropharmacology. 2005; 48:252-263.*
Hutchinson et al. "Evidence for a Role of Heat Shock Protein-90 (HSP90) in Toll Like Receptor 4 Mediated Pain Enhancement in Rats". Neuroscience, 2009; 164(4):1821-1832.*
Jhaveri et al. "Advances in the Clinical Development of Heat Shock Protein 90 (HSP90) Inhibitors in Cancers". Biochimica et Biophysica Acta, 2012; 1823:742-755.*
Portenoy RK. "Chronic Nociceptive Pain Syndromes: Cancer Pain". Neurosurgical Management of Pain. Springer-Verlag. 1997. pp. 62-74.*
Hunter, et al., Cdc37: A Protein Kinase Chaperone? Trends In Cell Biology, vol. 7, 157-161.
UK Patent Office Search Report for GB 0604111.5.
International Search Report for PCT/GB2006/001382.
Brown, Michael E. "Chapter 5: Thermoptometry", *Introduction to Thermal Analysis: Techniques and Applications*, Second Edition, Netherlands, 2001.
UK Patent Office Search Report for GB 0507474.5.
Bryn et al., Solid State Chemistry of Drugs, 2nd edition, 1999, pp. 233-247.
Chemical Abstracts, Accession No. 81:120448 (Abstract of JP 49010506, Mar. 11, 1994).
Y. Otani et al., "An Evaluation Of Amide Group Planarity In 7-azabicyclo[2.2.1]Heptane Amids. Low Amide Bond Barrier In Solution." *J. Amer. Chem. Soc.*, 125(49), 15191-15199, 1983.
Golub et al., Molecular Classification Of Cancer: Class Discovery And Class Prediction By Gene Expression Monitoring. Science. Oct. 15, 1999;286(5439):531-7.
Lala et al., Role Of Nitric Oxide In Tumor Progression: Lessons From Experimental Tumors. Cancer Metastasis Rev. Mar. 1998:17 (1):91-106.
Mahaney et al., Synthesis And Activity Of A New Class Of Pathway-Selective Estrogen Receptor Ligands: Hydroxybenzoyl-3,4-dihydroquinoxalin-2(1H)-ones. Bioorg Med Chem. May 15, 2006;14(10):3455-66.
Madsen et al., Glucose-6-Phosphatase Catalytic Enzyme Inhibitors: Synthesis And In Vitro Evaluation Of Novel 4,5,6,7-tetrahydrothieno[3,2-c]-and -[2,3c]pyridines. Bioorg Med Chem. Sep. 2000;8(9):2277-89.
Vippagunta et al., Adv. Drug Delivery Reviews (2001) vol. 48, p. 3-26.
Dymock, et al., Expert Opin. Ther. Patents (2004) vol. 14, p. 837-847.
Kubinyi et al., 3D QSAR in Drug Design: Ligand-Protein Interactions and Molecular Similarity, Springer (988)vol. 2-3, 800 pages, TOC and pp. 243-244 provided.
Bohonowych et al., Journal of Oncology, vol. 2010, pp. 1-17 (2010). Stephen Neidle Ed,. Cancer Drug Design and Discovery, Elsevier/Academic Press, 2008, pp. 427-431.
Gura, Science, Nov. 7, 1997, vol. 278, No. 5340, pp. 1041-1042.
Roberts et al, JAMA, 292(17): 2130-2140 (2004).
Ju huai-qiang et al: "Synthesis and in vitro anti-HSV-1 activity of a novel Hsp90 inhibitor BJ-B11.", Bioorganic & Medicinal Chemistry Letters Mar. 15, 2011, vol. 21, No. 6, p. 1675-1677.
Galam, et al. Bioog. Med. Chem. (2007) vol. 15, p. 1939-1946.
Wermuth, The Practice of Medicinal Chemistry, 2d ed. (2003) 768 pages, Chapters 9-10 provided.
U.S. Appl. No. 13/271,678, filed Oct. 12, 2011, and, Preliminary Amendment therefor.

(56) References Cited

OTHER PUBLICATIONS

Abstract: JP 9-221476: Hidenori, et al, Preparation And Formulation of Benzazepine Denvatives And analogs As Pharmaceuticals With Affinity For Vasopressin Receptors, STN Database Accession No. 127:248027.
Berge, et al., Pharmaceutical Salts, Pharmaceutical Sciences (1977) vol. 66, No. 1, p. 1-19.
Bundgaard Chapter 5 in "A Textbook of Drug Design and Development," (1991), Harwood Academic Publishers, 643 pages.
Grant & Hackh's Chemical Dictionary (5th ed.) 1987, p. 542.
Huff, "HIV Protease: A Novel Chemotherapeutic Target for Aids", Journal of Medicinal Chemistry, 1991, 34(8):305-2314.
Maloney et al. "HSP90 as a new therapeutic target for cancer therapy: the story unfolds" Expert Opinion on Biological Therapy, 2:1, 3-24 (2002).

\* cited by examiner

PHARMACEUTICAL COMPOUNDS

This application is a National Stage filing under 35 U.S.C. §371 of PCT Application No. PCT/GB2007/003915, filed Oct. 12, 2007, and published as WO 2008/044054 on Apr. 17, 2008, which claims priority to provisional application U.S. Ser. No. 60/829,208, filed Oct. 12, 2006, and U.S. Ser. No. 60/829,251, filed Oct. 12, 2006.

This invention relates to hydroxy-substituted benzoic acid amide compounds for use in the prophylaxis or treatment of neuropathic conditions and diseases and pain and methods for the prophylaxis or treatment of neuropathic conditions and diseases and pain. The invention also provides compounds for the treatment of stroke and for use as neuroprotective agents as well as methods of treating stroke and methods of neuroprotection following stroke. The invention further relates to compounds for use in the prophylaxis or treatment of fungal, protozoal, viral or parasitic diseases and conditions.

BACKGROUND OF THE INVENTION

In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major inducible form Hsp90α and minor constitutively expressed form Hsp90β and two other closely related chaperones which are restricted in their intracellular location (Endoplasmic reticulum GP96/GRP94; mitochondrial TRAP1). The term HSP90 as used here includes all these analogues unless stated. Hsp90 binds proteins at a late stage of folding and is distinguished from other Hsps in that most of its protein substrates are involved in signal transduction. Hsp90 has a distinct ATP binding site, including a Bergerat fold characteristic of bacterial gyrase, topoisomerases and histidine kinases. It has been shown that ATP bound at the N-terminal pocket of Hsp90 is hydrolysed. This ATPase activity results in a conformational change in Hsp90 that is required to enable conformational changes in the client protein.

A dimerization domain and a second ATP binding site, which may regulate ATPase activity, is found near the c-terminus of Hsp90. Dimerization of HSP90 appears critical for chaperone function. Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind HSP90. A simplified model has emerged in which ATP binding to the amino terminal pocket alters Hsp90 conformation to allow association with a multichaperone complex. First the client protein is bound to an Hsp70/Hsp40 complex. This complex then associates with Hsp90 via Hop. When ADP is replaced by ATP, the conformation of Hsp90 is altered, Hop and Hsp70 are released and a different set of co-chaperones is recruited including p50cdc37 and p23. ATP hydrolysis results in the release of these co-chaperones and the client protein from the mature complex. The requirement for different co-chaperones can vary depending on the particular client protein associated with the complex. Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et al., 1997. J Biol Chem., 272: 23834-23850).

Despite Hsp90 being ubiquitously expressed, GA has a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec J. Med. Chem. 2004, 47, 3865-3873). Furthermore the ATPase activity of Hsp90 is elevated in cancer cells and is an indication of the increased level of stress in these cells. Hsp90 gene amplification has also been reported to occur in the later stages of cancer (Jolly and Morimoto JNCI Vol. 92, No. 19, 1564-1572, 2000).

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

There is some evidence that Hsp90 is found primarily within "activated" multichaperone complexes in the tumour cells as opposed to "latent" complexes in normal cells. One component of the multichaperone complex is the cdc37 co-chaperone. Cdc37 binds Hsp90 at the base of the ATP binding site and could affect the off rates of inhibitors bound to Hsp90 in the "activated" state (Roe et. al., Cell 116, (2004), pp. 87-98). The client protein bound to the Hsp90-Hsp70 form of the chaperone complex is believed to be more susceptible to ubiquitination and targeting to the proteasome for degradation. E3 ubiquitin ligases have been identified with chaperone interacting motifs and one of these (CHIP) was shown to promote the ubiquitination and degradation of Hsp90 client proteins (Connell et al., 2001. Xu et al., 2002).

Hsp90 Client Proteins

The number of reported Hsp90 client proteins now exceeds 100. Since many of its client proteins are involved in cell signalling proliferation and survival, Hsp90 has received major interest as an oncology target. Two groups of client proteins, cell signalling protein kinases and transcription factors, in particular suggest Hsp90 regulation may have potential benefit as an anticancer therapy.

Hsp90 protein kinase client proteins implicated in cell proliferation and survival include the following:

c-Src

Cellular Src (c-Src) is a receptor tyrosine kinase, required for mitogenesis initiated by multiple growth factor receptors, including the receptors for epidermal growth factor receptor (EGFR), platelet-derived growth factor receptor (PDGFR), colony stimulating factor-1 (CSF-1R), and the basic fibroblast growth factor (bFGFR). C-Src is also overexpressed and activated in many of the same human carcinomas that overexpress EGFR and ErbB2. Src is also required for the maintenance of normal bone homeostasis through its regulation of osteoclast function.

p185erbB2

ErbB2 (Her2/neu) is a receptor tyrosine kinase overexpressed in a variety of malignancies including breast, ovarian, prostate, and gastric cancers. ErbB2 was originally identified as an oncogene and inhibition of Hsp90 results in the polyubiquitination and degradation of erbB2.

Polo Mitotic Kinase

Polo-like kinases (Plks) are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase.

Akt (PKB)

Akt is involved in pathways that regulate cell growth by stimulating cell proliferation and suppressing apoptosis. Hsp90 inhibition by ansamycins results in a reduction in the Akt half life through ubiquitination and proteasomal degradation. Binding of cdc37 to Hsp90 is also required for the down-regulation of Akt. Following ansamycin treatment cancer cells arrest in the G2/M phase of the cell cycle 24 hours after treatment and proceed to apoptosis 24-48 hours later. Normal cells also arrest 24 hours after ansamycin treatment, but do not proceed on to apoptosis.

c-Raf, B-RAF, Mek

The RAS-RAF-MEK-ERK-MAP kinase pathway mediates cellular responses to growth signals. RAS is mutated to an oncogenic form in approximately 15% of human cancers. The three RAF genes are serine/threonine kinases that are regulated by binding RAS.

EGFR

The epidermal growth factor receptor (EGFR) is implicated in cell growth, differentiation, proliferation, survival, apoptosis, and migration. Overexpression of EGFR has been found in many different cancers and activating mutations of its kinase domain appear to be pathogenic in a subset of adenocarcinomas of the lung.

Flt3

FMS-like tyrosine kinase 3 (FLT3) is a receptor tyrosine kinase involved in cell proliferation, differentiation and apoptosis. Flt3 activation also leads to the activation of phosphatidylinositol 3-kinase (PI3K) and RAS signal-transduction cascades.

c-Met c-met is a receptor tyrosine kinase which binds hepatocyte growth factor (HGF) and regulates both cell motility and cell growth. c-met is overexpressed in tumours, including thyroid, stomach, pancreatic and colon cancer. HGF is also detected around the tumours, including liver metastases. This suggests that c-met and HGF play an important role in invasion and metastasis.

Cdk1, Cdk2, Cdk4, Cdk6

Cdk1, Cdk2, Cdk4, and Cdk6 drive the cell cycle. The activity of CDKs is regulated by their binding to specific subunits such as cyclins, inhibitory and assembly factors. The substrate specificity and timing of CDK activities is dictated by their interaction with specific cyclins. Cdk4/cyclin D and Cdk6/cyclin D are active in the G1 phase, Cdk2/cyclin E and Cdk2/cyclin A in S phase, and Cdc2/cyclin A and Cdc2/cyclin B in G2/M phase.

Cyclin-dependent kinase type 4 (CDK4), plays a key role in allowing cells to traverse G1 to S-phase transition of the cell cycle and is constitutively activated in many human cancers. The CDK4 activator, cyclin D1, is overexpressed and a CDK4 inhibitor, p16, is deleted in a variety of human tumours.

Cdk1/Cdk2 inhibitors have been developed which reversibly block normal cells in either the G1/S-phase or at the G2/M border. G2/M arrest is generally less well tolerated by the cells and consequently, they undergo apoptotic cell death. Since Hsp90 also is known to affect cell survival pathways this effect may be further amplified with an Hsp90 inhibitor.

Wee-1

The Wee-1 protein kinase carries out the inhibitory phosphorylation of CDC2 on tyrosine 15 (Tyr15). This is required for activation of the G2-phase checkpoint in response to DNA damage.

Hsp90 transcription factors implicated in cell proliferation and survival include the following:

Mutant p53

P53 is a tumour suppressor protein that causes cell cycle arrest and induces apoptosis. P53 is mutated in approximately half of all cancers. Mutant p53 associates with Hsp90 and is down-regulated in cancer lines treated with Hsp90 inhibitors, while wild type p53 levels were unaffected.

Progesterone Receptor/Estrogen Receptor/Androgen Receptor

Approximately 70% of post-menopausal women who develop breast cancer have tumours that express the estrogen receptor. The first line treatment of these patients is directed at preventing signalling through this pathway and thus inhibiting tumour growth. This can be done by ovarian ablation, treatment with gonadotrophin releasing hormone agonists, aromatase inhibition or treatment with specific agonists which bind to the estrogen receptor but prevent further signalling. Ultimately patients develop resistance to these interventions often as a consequence of crosstalk between the estrogen receptor and growth factor receptors located on the cell membrane. In the unliganded state estrogen receptors are complexed with Hsp90 which facilitates hormone binding. Following binding to the mature receptor Hsp90 complex the liganded receptor can bind to hormone-response elements (HREs) within the regulatory regions of target genes involved in maintaining cell proliferation. Inhibition of Hsp90 initiates proteosomal degradation of the estrogen receptor thus preventing further growth signalling via this pathway. Prostate cancers are hormone-dependent malignancies that respond to therapeutic interventions which reduce circulating levels of testosterone or prevent testosterone binding to the androgen receptor. Although patients initially respond to these treatments most subsequently develop resistance via restoration of signalling via the androgen receptor. Prior to ligand binding the androgen receptor exists in a complex with Hsp90 and other co-chaperones including p23 and immunophilins. This interaction maintains the androgen receptor in a high-affinity ligand binding conformation. Inhibition of Hsp90 leads to proteosomal degradation of the androgen receptor and other co-chaperones which may sensitise the tumour to further hormonal therapies.

Mutated steroid hormone receptors that have arisen for example during anti-hormone therapy and which might be resistant to such therapies are likely to have a greater dependence on HSP90 for their stability and hormone binding function.

Hif-1a

Hypoxia inducible factor-1a (HIF-1a) is a transcription factor that controls the expression of genes which play a role in angiogenesis. HIF-1a is expressed in the majority of metastases and is known to associate with Hsp90. Ansamycin treatment of renal carcinoma cell lines leads to the ubiquitination and proteasomal degradation of HIF-1a.

Hsp90 inhibitors are capable of affecting a large number of targets significant to signal transduction in tumour cell proliferation. Signal transduction inhibitors which regulate the activities of a single target, may not be as efficacious due to signalling pathway redundancy and the rapid development of resistance.

By regulating multiple targets involved in cell signalling and cell proliferation HSP90 inhibitors may prove beneficial in the treatment of a wide spectrum of proliferative disorders.

ZAP70

ZAP-70, a member of the Syk-ZAP-70 protein tyrosine kinase family, is normally expressed in T cells and natural killer cells and has a critical role in the initiation of T-cell signaling. However, it is also expressed aberrantly in approximately 50% of cases of CLL, usually in those cases with unmutated B-cell receptor genes. The mutational status of immunoglobulin heavy-chain variable-region ($IgV_H$) genes in the leukemic cells of chronic lymphocytic leukemia (CLL) is an important prognostic factor. The expression of ZAP-70 in CLL cells correlates with $IgV_H$ mutational status, disease progression, and survival. ZAP-70 positive CLL is more aggressive than ZAP-70 negative CLL indicating that ZAP-70 may be a key driver of malignancy in this disease. ZAP-70 is physically associated with HSP90 in B-CLL lymphoblasts thus the inhibition of Hsp90 may sensitise these cells to existing chemotherapy or monoclonal antibody therapy.

HSP90 is conserved across evolution being found in bacteria (e.g. HTPG in *E. coli*) and yeast (e.g. HSC82 and HSP82). Although clients have not been formally identified for the *E. coli* form, in yeast and all higher organisms the HSP90 family has been shown to function as a chaperone for many essential proteins as described above.

Neuropathic Diseases and Vain

Cdk5 is a member of the Cdk family of serine/threonine kinases, most of which are key regulators of the cell cycle. Cdk5 activity is regulated through association with its neuron-specific activators, p35 and p39. Recent evidence suggests that CDK5 can phosphorylate tau protein and a number of other neuronal proteins such as NUDE-1, synapsin1, DARPP32 and the Munc18/Syntaxin1A complex. The evidence also suggests that aberrant Cdk5 activity induced by the conversion of p35 to p25 plays a role in the pathogenesis of neurodegenerative diseases such as Alzheimer's disease (AD), amyotrophic lateral sclerosis (ALS) and Niemann's Pick type-C disease (NPD). Abnormal hyperphosphorylation of tau after A $β_{1-42}$ treatment destabilizes microtubules, contributing to neurite degeneration and the formation of paired helical filaments (PHFs) containing neurofibrillary tangles (NFTs), one of the principal lesions of AD. It has further been found that cdk5 is necessary for correct neuronal development The p35 protein which acts as a regulator of CDK5 activity has recently been identified as a client protein for HSP90 and therefore the activity of CDK5 can be regulated by changes in the level and activity of HSP90. Thus inhibition of HSP90 can lead to loss of p35, an inhibition of CDK5, a reduction of phosphorylated tau protein in susceptible individuals and will bring benefit to sufferers of Alzheimers Disease.

Additionally inhibition of HSP90 using known agents has been shown to reduce the accumulation of tau protein aggregates in cellular systems in vitro. (Dickey et al Curr Alzheimer Res. 2005 April; 2(2):231-8).

Cdk5 has also been shown to have a role in mediating pain signalling. Both Cdk5 and p35 have been shown to be expressed in nociceptive neurons. In p35 knockout mice, which show substantially reduced Cdk5 activity, the response to painful thermal stimuli is delayed (Pareek, T. K., et al., Proceedings of the National Academy of Sciences., 103:791-796 (2006). Additionally administration of the cyclin-dependent kinase 5 (Cdk5) inhibitor roscovitine has been shown to attenuate the formalin-induced nociceptive responses in rats (Wang, Cheng-haung, et al., Acta Pharmacologica Sinica., 26:46-50 (2005). Activation of calpain is calcium dependent and is known to affected by activation of the NMDA receptor calcium channel (Amadoro, G; Proceedings of the National Academy of Sciences of the United States of America, 103, 2892-2897 (2006)). NMDA receptor antagonists are know to be clinically effective against neuropathic pain conditions (Christoph, T; et al., Neuropharmacology, 51, 12-17 (2006)). This efficacy may be linked to the effect of NMDA receptor related calcium influx on calpain activity and its subsequent effect on the activity of Cdk5. As such compounds modulating Cdk5 activity are expected to be useful for the treatment or prevention of pain and thus modulation of the CDK5 regulator p35 by HSP90 inhibition could lead to inhibition of CDK5.

It is desirable to have an agent for the palliative treatment of pain, i.e. the direct relief of pain in addition to the relief of pain as the result of amelioration of the underlying disease or medical condition, which is the cause of the pain.

Stroke

Various Cdk's (especially Cdk's 4, 5 & 6) have been shown to be involved with or mediate neuronal death following hypoxic or ischemic insult (Rashidan, J.; et al.; Proceedings of the National Academy of Sciences., 102: 14080-14085 (2005). Furthermore the Cdk inhibitor flavopiridol has been shown to significantly reduce neuronal death in a rat model of focal cerebral ischemia (Osuga, H.; et al.; Proceedings of the National Academy of Sciences., 97:10254-10259 (2000). Cdk5 inhibitors have been shown to have protective effects in both necrotic and apoptotic paradigms of neuronal cell death (Weishaupt, J.; et al.; Molecular and Cellular Neuroscience., 24:489-502 (2003).

Stroke is a cerebrovascular event, which occurs when the normal bloodflow to the brain is disrupted, and the brain receives too much or too little blood. Stroke is one of the leading causes of death worldwide, and is also one of the most common causes of neurologic disability.

Ischemic stroke, which is the most common type of stroke, results from insufficient cerebral circulation of blood caused by obstruction of the inflow of arterial blood. Normally, adequate cerebral blood supply is ensured by a system of arteries within the brain. However, various disorders, including inflammation and atherosclerosis, can cause a thrombus, i.e., a blood clot that forms in a blood vessel. The thrombus may interrupt arterial blood flow, causing brain ischemia and consequent neurologic symptoms. Ischemic stroke may also be caused by the lodging of an embolus (an air bubble) from the heart in an intracranial vessel, causing decreased perfusion pressure or increased blood viscosity with inadequate cerebral blood flow. An embolus may be caused by various disorders, including atrial fibrillation and atherosclerosis.

A second type of stroke, hemorrhagic stroke, involves a hemorrhage or rupture of an artery leading to the brain. Hemorrhagic stroke results in bleeding into brain tissue, including the epidural, subdural, or subarachnoid space of the brain. A hemorrhagic stroke typically results from the rupture of an arteriosclerotic vessel that has been exposed to arterial hypertension or to thrombosis.

One opportunity for intervention in stroke is the prevention or reduction of risk of stroke in patients at risk for stroke. There are many known risk factors for stroke, including vascular inflammation, atherosclerosis, arterial hypertension, diabetes, hyperlipidemia and atrial fibrillation. At risk patients have been treated with agents to control blood pressure or manage blood lipid level, and have been treated with antiplatelet agents (such as clopidrogel) and anticoagulants. A second opportunity is the treatment of acute stroke. However, current pharmacologic therapies for treating acute stroke are limited to restoring blood flow within a narrow therapeutic time window of less than three hours after stroke. There remains a need for agents which are effective within a longer therapeutic time window. Another opportunity is recovery or restoration after the acute stroke period, i.e. the reduction or prevention of secondary cell damage in the penumbra. There remains a need for agents which are effective in reducing or preventing secondary cell damage after stroke.

It would be desirable to obtain a single pharmaceutical agent which can be used in more than one of the above-mentioned opportunities for treating stroke. Such an agent may be administered to patients at risk for stroke, and also may be administered to patients suffering from acute stroke, or patients undergoing treatment for recovery or restoration after the acute stroke period. Such an agent may also target more than one distinct mechanism in the biochemical cascade of stroke.

HSP90 Inhibitors as Anti-Fungal, Anti-Protozoal and Anti-Parasitic Agents

Fungal infections have become a major cause for concern in recent years due to the limited number of antifungal agents available, and the increasing incidence of species that are resistant to established antifungal agents such as the azoles. In addition, the growing population of immunocompromised patients (e.g. patients such as organ transplant patients, cancer patients undergoing chemotherapy, burn patients, AIDS patients, or patients with diabetic ketoacidosis) has given rise to an increase in the incidence of opportunistic fungal infections by fungal agents such as *Candida, Cryptoccocus* and *Aspergillus* species and, on occasion, *Fusarium, Trichosporon* and *Dreschlera* species.

Consequently, there is a need for new anti-fungal agents that can be used to treat the growing numbers of patients with fungal infections and in particular infections due to fungi that have become resistant to existing antifungal drugs.

Infection by a range of pathogens is associated with an antibody response to HSP90. For example in *Candida albicans* infected patients the 47 kDa C-terminal fragment of HSP90 is an immunodominant epitope. Furthermore this antibody response is associated with good prognosis suggesting a protective effect against infection. Recombinant antibodies to an epitope in this polypeptide are also protective against infection in mouse models of invasive candidiasis. (See Mathews et al *Antimicrobial Agents and Chemotherapy* 2003 vol 47, 2208-2216 and references therein). Likewise surface expressed HSP90 serves as an antigen in Chagas' disease, ascariasis, leishmaniasis, toxoplamosis and infection due to *Schistosoma mansoni* and it has been postulated that antibodies to HSP90 convey protection against plamodium infection and Malaria.

Mycograb (NeuTec Pharma/Novartis) is a human recombinant monoclonal antibody against heat shock protein 90 that is being developed as a treatment for candida and has shown significant responses in early trials. Furthermore, the natural product HSP90 inhibitors Geldanamycin, Herbimycin and Radicicol were originally identified by their antifungal activity. Key essential proteins have been identified as HSP90 clients in several human pathogens (see Cowen and Lindquist, Science. 2005 Sep. 30; 309(5744):2175-6.)

Thus HSP90 can play an important role in the growth of pathogens such as *Candida* species, and HSP90 inhibitors can be useful as treatments for a range of infectious diseases including candidiasis.

It has also been found that Hsp90 increases the capacity of fungi to develop antifungal drug resistance (see Cowen L E, Lindquist S. "Hsp90 potentiates the rapid evolution of new traits: drug resistance in diverse fungi". *Science.* 2005 Sep. 30; 309 (5744):2185-9). Therefore, co-administration of an Hsp90 inhibitor with an antifungal drug may enhance the efficacy of the antifungal drug and reduce resistance by preventing the emergence of resistant phenotypes.

HSP90 Inhibitors and the Treatment of Hepatitis C and Other Viral Diseases

Infection of a host cell with viral RNA/DNA results in a substantial redirection of cellular protein synthesis towards key viral proteins encoded by the viral nucleic acid. The increased protein synthetic burden places a stress on the cell as a consequence of increased demand for energy and synthetic precursors. Upregulation of heat shock proteins is frequently a consequence of viral infection at least in part due to this stress. One function of the HSP induction may be to assist in the stabilization and folding of the high levels of 'foreign' protein generated in preparation for virus replication. In particular recent work has suggested that HSP90 is required for stable production of functional NS2/3 protease in Hepatitis C(HCV) replicon infected cells. HSP 90 inhibitors have also been demonstrated to block viral replication in in vitro systems. (Nagkagawa, S, Umehara T, Matsuda C, et al Biochem. Biophys. Res Commun. 353 (2007) 882-888; Waxman L, Witney, M et al PNAS 98 (2001) 13931-13935).

Heat Shock Proteins and Antitumour Drug Resistance

It has long been recognized that the native tertiary conformation of any given polypeptide is determined by its primary (amino acid) sequence. However, as explained above, it is now clear that the proper folding of many proteins in vivo requires the assistance of heat-shock proteins (Hsps) acting as molecular chaperones. While this chaperone function is important to normal cellular function under all conditions, it becomes crucial in cells which are stressed (for example by heat, hypoxia or acidosis).

Such conditions typically prevail in tumour cells, which exist in a hostile host environment. The upregulation of Hsps often seen in such cells is therefore likely to represent a mechanism by which malignant cells maintain the integrity of their proteomes under conditions which compromise protein folding. Thus, modulators or inhibitors of stress proteins in general (and Hsp90 in particular) represent a class of chemotherapeutics with the unique ability to inhibit multiple aberrant signaling pathways simultaneously. They can therefore exert antitumour effects whilst eliminating (or reducing the incidence of) resistance relative to other treatment paradigms.

Moreover, therapeutic anticancer interventions of all types necessarily increase the stresses imposed on the target tumour cells. In mitigating the deleterious effects of such stresses, Hsps are directly implicated in resisting the effects of cancer drugs and treatment regimens. Thus, modulators or inhibitors of stress protein function in general (and Hsp90 in particular) represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

WO 99/29705 (Glycomed et al) discloses a class of glycomimetic compounds having a number of possible uses including the treatment of cancer. One compound specifically disclosed in WO 99/29705 is the compound 2-(2-hydroxy-benzoyl)-1,2,3,4-tetrahydro-isoquinoline-3-carboxylic acid.

Our earlier application, PCT/GB2006/001382 discloses a class of hydroxybenzamide compounds having Hsp90 inhibiting activity.

SUMMARY OF THE INVENTION

The invention provides compounds having Hsp90 inhibiting or modulating activity for use in treating, alleviating or preventing certain cdk5 mediated diseases and conditions.

Accordingly, in a first aspect, the invention provides the use of a compound for the manufacture of a medicament for the treatment of pain, wherein the compound is a compound of the formula (I):

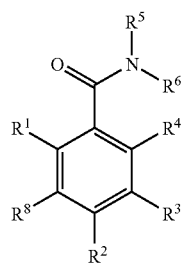

or salts, tautomers, solvates and N-oxides thereof; wherein:
$R^1$ is hydroxy or hydrogen;
$R^2$ is hydroxy; methoxy or hydrogen; provided that at least one of $R^1$ and $R^2$ is hydroxy;
$R^3$ is selected from hydrogen; halogen; cyano; $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group —(O)$_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbyl-amino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
or $R^3$ and $R^4$ together form a monocyclic carbocyclic or heterocyclic ring of 5 to 7 ring members;
$R^5$ and $R^6$ together with the nitrogen atom to which they are attached form a bicyclic heterocyclic group having 8 to 12 ring members of which up to 5 ring members are heteroatoms selected from oxygen, nitrogen and sulphur; wherein the bicyclic heterocyclic group is optionally substituted by one or more substituents $R^{10}$;
$R^8$ is selected from hydrogen and fluorine; and
$R^{10}$ is selected from:
halogen;
hydroxy;
trifluoromethyl;
cyano;
nitro;
carboxy;
amino;
mono- or di-$C_{1-4}$ hydrocarbylamino;
carbocyclic and heterocyclic groups having from 3 to 12 ring members; and
a group $R^a$—$R^b$; wherein:
$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and
$R^b$ is selected from hydrogen; carbocyclic and heterocyclic groups having from 3 to 12 ring members; and $C_{1-12}$ hydrocarbyl (such as $C_{1-10}$ hydrocarbyl) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), and carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, $SO_2$, $NR^c$, $X^1C(X^2)$, $C(X^2)X^1$ or $X^1C(X^2)X^1$;
$R^c$ is selected from $R^b$, hydrogen and $C_{1-4}$ hydrocarbyl; and
$X^1$ is O, S or $NR^c$ and $X^2$ is =O, =S or =$NR^c$.

In another aspect, the invention provides the use of a compound of the formula (I) or a sub-group thereof for the manufacture of a medicament for the prophylaxis or treatment of stroke.

In a further aspect, the invention provides the use of a compound of the formula (I) or a subgroup thereof for the manufacture of a medicament for use as a neuroprotective agent.

In other aspects, the invention provides:
A compound of the formula (I), (II), (III), (IV), (V), (VI), (VIa), (VII), (VIIa) or (VIIb) or any sub-groups or examples thereof as defined herein for use in the treatment of pain.
A compound of the formula (I), (II), (III), (IV), (V), (VI), (VIa), (VII), (VIIa) or (VIIb) or any sub-groups or examples thereof as defined herein for use in the reduction or elimination of pain in a patient (e.g. a mammal such as a human) suffering from pain.
The use of a compound of the formula (I), (II), (III), (IV), (V), (VI), (VIa), (VII), (VIIa) or (VIIb) or any sub-groups or examples thereof as defined herein for the manufacture of a medicament for use in the reduction or elimination of pain in a patient (e.g. a mammal such as a human) suffering from pain.
The use of a compound of the formula (I), (II), (III), (IV), (V), (VI), (VIa), (VII), (VIIa) or (VIIb) or any sub-groups or examples thereof as defined herein for the manufacture of a medicament for the treatment of any one or more of nociception, somatic pain, visceral pain, acute pain, chronic pain, hyperalgesia, allodynia, post operative pain, pain due to hypersensitivity, headache, inflammatory pain (rheumatic, dental, dysmenorrhea or infection), neurological pain, musculoskeletal pain, cancer related pain or vascular pain.
A compound of the formula (I), (II), (III), (IV), (V), (VI), (VIa), (VII), (VIIa) or (VIIb) or any sub-groups or examples thereof as defined herein for use in treating any one or more of nociception, somatic pain, visceral pain, acute pain, chronic pain, hyperalgesia, allodynia, post operative pain, pain due to hypersensitivity, headache, inflammatory pain (rheumatic, dental, dysmenorrhea or infection), neurological pain, musculoskeletal pain, cancer related pain or vascular pain.

A method of treating pain in a patient such as a mammal (e.g. human), which method comprises administering to the patient a therapeutically effective amount of a compound of the formula (I), (II), (III), (IV), (V), (VI), (VIa), (VII), (VIIa) or (VIIb) or any sub-groups or examples thereof as defined herein.

A method for the reduction or elimination of pain in a patient (e.g. a mammal such as a human) suffering from pain, which method comprises administering to the patient an effective pain-reducing or pain-eliminating amount of a compound of the formula (I), (II), (III), (IV), (V), (VI), (VIa), (VII), (VIIa) or (VIIb) or any sub-groups or examples thereof as defined herein.

A method for the treatment of any one or more of nociception, somatic pain, visceral pain, acute pain, chronic pain, hyperalgesia, allodynia, post operative pain, pain due to hypersensitivity, headache, inflammatory pain (rheumatic, dental, dysmenorrhea or infection), neurological pain, musculoskeletal pain, cancer related pain or vascular pain, which method comprises administering to the patient a therapeutically effective amount of a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of stroke.

A method for the prophylaxis or treatment of stroke in a patient such as a mammal (e.g. human), which method comprises administering to the patient a therapeutically effective amount of a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use as a neuroprotective agent.

A method of preventing or reducing neuronal damage in a patient suffering from stroke, which method comprises administering to the patient an effective neuroprotective amount of a compound of the formula (I), (II), (III), (IV), (V), (VI), (VIa), (VII), (VIIa) or (VIIb) or any sub-groups or examples thereof as defined herein.

The use of a compound of the formula (I), (II), (III), (IV), (V), (VI), (VIa), (VII), (VIIa) or (VIIb) or any sub-groups or examples thereof as defined herein for the manufacture of a medicament for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A compound of the formula (I), (II), (III), (IV), (V), (VI), (VIa), (VII), (VIIa) or (VIIb) or any sub-groups or examples thereof as defined herein for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation.

A method for the prevention or reduction of risk of stroke in patients at risk for stroke, for example a patient exhibiting any one or more risk factors selected from vascular inflammation, atherosclerosis, arterial hypertension, diabetes, hyperlipidemia and atrial fibrillation, which method comprises administering to the patient an effective therapeutic amount of compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of a disease state or condition mediated by a cyclin dependent kinase 5.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by a cyclin dependent kinase 5.

A method for the prophylaxis or treatment of a disease state or condition mediated by a cyclin dependent kinase 5, which method comprises administering to a subject in need thereof a compound of the formula (I), (II), (III), (IV), (V), (VI), (VIa), (VII), (VIIa) or (VIIb) or any sub-groups or examples thereof as defined herein.

A method for alleviating or reducing the incidence of a disease state or condition mediated by a cyclin dependent kinase 5, which method comprises administering to a subject in need thereof a compound of the formula (I), (II), (III), (IV), (V), (VI), (VIa), (VII), (VIIa) or (VIIb) or any sub-groups or examples thereof as defined herein.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by cdk5 or p35.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by cdk5 or p35, said disease state or condition being other than Alzheimer's disease, Huntington's disease or Creutzfeldt-Jakob disease.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition mediated by cdk5 or p35, said disease state or condition being other than a neurodegenerative disease.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a disease state or condition characterised by elevated levels of cdk5 or p35.

A compound of the formula (I), (II), (III), (IV), (V), (VI), (VIa), (VII), (VIIa) or (VIIb) or any sub-groups or examples thereof as defined herein for use in the prophylaxis or treatment of a disease state or condition mediated by cdk5 or p35, said disease state or condition being other than Alzheimer's disease, Huntington's disease or Creutzfeldt-Jakob disease.

A compound of the formula (I), (II), (III), (IV), (V), (VI), (VIa), (VII), (VIIa) or (VIIb) or any sub-groups or examples thereof as defined herein for use in the prophylaxis or treatment of a disease state or condition mediated by cdk5 or p35, said disease state or condition being other than a neurodegenerative disease.

A compound of the formula (I), (II), (III), (IV), (V), (VI), (VIa), (VII), (VIIa) or (VIIb) or any sub-groups or examples thereof as defined herein for use in the prophylaxis or treatment of a disease state or condition characterised by elevated levels of cdk5 or p35.

A method of prophylaxis or treatment of a disease state or condition mediated by cdk5 or p35, said disease state or condition being other than Alzheimer's disease, Huntington's disease or Creuzfeldt-Jacob disease, which method comprises administering to a patient in need thereof a therapeutically effective amount of a compound of the formula (I), (II), (III), (IV), (V), (VI), (VIa), (VII), (VIIa) or (VIIb) or any sub-groups or examples thereof as defined herein.

A method of prophylaxis or treatment of a disease state or condition mediated by cdk5 or p35, said disease state or condition being other than a neurodegenerative disease, which method comprises administering to a patient in need thereof a therapeutically effective amount of a compound of the formula (I), (II), (III), (IV), (V), (VI), (VIa), (VI), (VIa) or (VIIb) or any sub-groups or examples thereof as defined herein.

A method of prophylaxis or treatment of a disease state or condition characterised by elevated levels of cdk5 or p35, which method comprises administering to a patient in need thereof a therapeutically effective amount of a compound of the formula (I), (II), (III), (IV), (V), (VI), (VIa), (VI), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of a neuropathy, such as a peripheral neuropathy, other than Alzheimer's disease, Huntington's disease or Creutzfeldt-Jakob disease.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a neuropathy, such as a peripheral neuropathy, other than Alzheimer's disease, Huntington's disease or Creuzfeldt-Jacob disease.

A method of prophylaxis or treatment of a neuropathy, such as a peripheral neuropathy, other than Alzheimer's disease, Huntington's disease or Creuzfeldt-Jacob disease, which method comprises administering to a patient in need thereof a therapeutically effective amount of a compound of the formula (I), (II), (III), (IV), (V), (VI), (VIa), (VII), (VIIa) or (VIIb) or any sub-groups or examples thereof as defined herein.

In another aspect, the invention provides compounds having Hsp90 inhibiting or modulating activity for use as anti-fungal, anti-protozoal or anti-parasitic agents.

More particularly, the invention provides a compound of the formula (I) or salts, tautomers, solvates and N-oxides thereof for use as an anti-fungal, anti-protozoal or anti-parasitic agent (other than for use against *Plasmodium falciparum*).

Compounds of the present invention have antifungal activity, anti-protozoal activity and anti-parasitic activity.

In particular, compounds of the invention are useful in treating infection by pathogenic fungi, protozoa and parasites where infection by the pathogen is normally associated with an antibody response to HSP90.

In one embodiment, the invention provides compounds of the formula (I) and sub-groups thereof as defined herein for use as anti-fungal agents.

Examples of fungi include those that are pathogenic in man and other animals, for example:

*Candida* species such as *Candida albicans* and *Candida tropicalis*;

*Cryptococcus* species such as *Cryptococcus neoformans* and Cryptococcal meningitis;

*Aspergillus* species such as *Aspergillus fumigatus*, *Aspergillus flavus* and *Aspergillus niger*;

*Microsporum* species such as *Microsporum canis* and *Microsporum gypseum*;

*Epidermophyton* species;

*Trichophyton* species such as *Trichophyton equinum*, *Trichophyton mentagrophytes* and *Trichophyton rubrum*;

*Epidermophyton floccosum*;

*Exophiala werneckii*;

*Fusarium* species such as *Fusarium solani*;

*Sporothrix schenckii*;

*Penicillium* species such as *Penicillium rubrum*;

*Altermaria* species;

*Ceratocystis pilifera*;

*Chrysosporium pruinosum*;

*Helminthsporium* species;

*Paecilomyces variotti*;

yeasts, for example *Saccharomyces cerevisiae* and *Pityrosporum* species such as *Pityrosporum orbiculare* and *Pityrosporum ovale*;

*Histoplasma* species such as *Histoplasma capsulatum*;

*Coccidiodes* species;

*Paracoccidioides* species; and

*Blastomyces* species.

In another embodiment, the invention provides compounds of the formula (I) and sub-groups thereof as defined herein for use as anti-protozoal agents.

Examples of protozoa include:

*Trypanosoma cruzi*;

*Leishmania* species; for example the *L. donovani* complex (*L. donovani*, *L. infantum*, and *L. chagasi*); the *L. mexicana* complex (3 main species—*L. mexicana*, *L. amazonensis*, and *L. venezuelensis*); *L. tropica*; *L. major*; *L. aethlopica*; and the subgenus Viannia with four main species (*L.* (*V.*) *braziliensis, L.* (*V.*) *guyanensis, L.* (*V.*) *panamensis*, and *L.* (*V.*) *peruviana*);

*Toxoplasma gondii*; and

*Tichomonas vaginalis*.

In a further embodiment, the invention provides compounds of the formula (I) and sub-groups thereof as defined herein for use as anti-parasitic agents.

Examples of parasites include parasitic worms such as parasitic roundworms such as *Ascaris lumbricoides*;

parasitic flatworms such as the parasitic trematode worms, e.g. *Schistosoma mansoni*

The invention also provides inter alia:

A compound of the formula (I), (II), (III), (IV), (V), (VI), (VIa), (VII), (VIIa) or (VIIb) or any sub-groups or examples thereof as defined herein for use in the prophylaxis or treatment of a fungal, protozoal or parasitic disease state or condition (other than a disease state or condition due to *Plasmodium falciparum*), for example a disease state or condition characterised by an antibody response to Hsp90.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a fungal, protozoal or parasitic disease state or condition (other than a disease state or condition due to *Plasmodium falciparum*), for example a disease state or condition characterised by an antibody response to Hsp90.

A method for the prophylaxis or treatment of a fungal, protozoal or parasitic disease state or condition (other than a disease state or condition due to *Plasmodium falciparum*), for example a disease state or condition characterised by an antibody response to Hsp90, which method comprises administering to a subject in need thereof a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in the prophylaxis or treatment of a fungal disease state or condition, for example a disease state or condition characterised by an antibody response to Hsp90.

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of a fungal disease state or condition, for example a disease state or condition characterised by an antibody response to Hsp90.

A method for the prophylaxis or treatment of a fungal disease state or condition, for example a disease state or condition characterised by an antibody response to Hsp90, which method comprises administering to a subject in need thereof a compound of the formula (I), (II), (III), (IV), (V), (VI), (VIa), (VII), (VIIa) or (VIIb) or any sub-groups or examples thereof as defined herein.

A compound of the formula (I), (II), (III), (IV), (V), (VI), (VIa), (VII), (VIIa) or (VIIb) or any sub-groups or examples thereof as defined herein for use in preventing, arresting or reversing the infection of an animal (such as a mammal, e.g. a human) by pathogenic fungi.

The use of a compound of the formula (I), (II), (III), (IV), (V), (VI), (VIa), (VII), (VIIa) or (VIIb) or any sub-groups or examples thereof as defined herein for the manufacture of a medicament for preventing, arresting or reversing the infection of an animal (such as a mammal, e.g. a human) by pathogenic fungi.

A method for preventing, arresting or reversing the infection of an animal (such as a mammal, e.g. a human) by pathogenic fungi, which method comprises administering to a subject in need thereof a compound of the formula (I), (II), (III), (IV), (V), (VI), (VIa), (VII), (VIIa) or (VIIb) or any sub-groups or examples thereof as defined herein.

A compound as defined herein for any of the uses and methods set forth above, and as described elsewhere herein.

The use of a compound as defined herein for the manufacture of a medicament for the prophylaxis or treatment of any of the disease states or conditions described herein.

A combination of a compound of the formula (I), (II), (III), (IV), (V), (VI), (VIa), (VII), (VIIa) or (VIIb) or any sub-groups or examples thereof as defined herein with an ancillary compound which is an antifungal agent (e.g. an azole antifungal agent).

A pharmaceutical composition comprising a compound of the formula (I), (II), (III), (IV), (V), (VI), (VIa), (VII), (VIIa) or (VIIb) or any sub-groups or examples thereof as defined herein with an ancillary compound which is an antifungal agent (e.g. an azole antifungal agent).

A compound of the formula (I), (II), (III), (IV), (V), (VI), (VIa), (VI), (VIIa) or (VIIb) or any sub-groups or examples thereof as defined herein for use in preventing, reducing or reversing the development of resistance to an anti-fungal agent, anti-protozoal agent or anti-parasitic agent (preferably an anti-fungal agent) co-administered therewith.

The use of a compound of the formula (I), (II), (III), (IV), (V), (VI), (VIa), (VII), (VIIa) or (VIIb) or any sub-groups or examples thereof as defined herein for the manufacture of a medicament for coadministration with an anti-fungal agent, anti-protozoal agent or anti-parasitic agent (preferably an anti-fungal agent) to prevent, reduce or reverse the development of resistance to the anti-fungal agent, anti-protozoal agent or anti-parasitic agent.

A method of preventing or reducing development of resistance to an anti-fungal agent in a patient (e.g. a human patient), which method comprises administering to the patient a combination of an anti-fungal agent, anti-protozoa agent or anti-parasitic agent (preferably an anti-fungal agent) and a compound of the formula (I), (II), (III), (IV), (V), (VI), (VIa), (VII), (VIIa) or (VIIb) or any sub-groups or examples thereof as defined herein.

A method for the prophylaxis or treatment (or alleviation or reduction of the incidence) of a disease state or condition mediated by Hsp90, which method comprises administering to a subject in need thereof a combination of a compound of the formula (I), (II), (III), (IV), (V), (VI), (VIa), (VII), (VIIa) or (VIIb) or any sub-groups or examples thereof as defined herein with an anti-fungal, anti-protozoal or anti-parasitic drug, wherein the disease state or condition mediated by Hsp90 is the development of resistance to the anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoal or anti-parasitic drug; (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject in need thereof a combination of a compound of the formula (I), (II), (III), (IV), (V), (VI), (VIa), (VI), (VIIa) or (VIIb) or any sub-groups or examples thereof as defined herein with the said anti-fungal, anti-protozoal or anti-parasitic drug.

A method for the treatment of a fungal, protozoal or parasitic disease or condition, which method comprises administering to a subject in need thereof a combination of a compound of the formula (I), (II), (III), (IV), (V), (VI), (VIa), (VII), (VIIa) or (VIIb) or any sub-groups or examples thereof as defined herein with an anti-fungal, anti-protozoa or anti-parasitic drug, which method is characterized by the absence of drug resistance.

A method for the prophylaxis or treatment (or alleviation or reduction of the incidence) of a disease state or condition mediated by Hsp90 in a subject undergoing treatment with an anti-fungal, anti-protozoal or anti-parasitic drug, which method comprises administering to the subject a compound of the formula (I), (II), (III), (IV), (V), (VI), (VIa), (VII), (VIa) or (VIIb) or any sub-groups or examples thereof as defined herein, wherein the disease state or condition mediated by Hsp90 is the development of resistance to said anti-fungal, anti-protozoal or anti-parasitic drug.

A method for: (i) sensitizing fungal, protozoal or parasite cells to an anti-fungal, anti-protozoal or anti-parasitic drug; (ii) alleviating or reducing the incidence of resistance to an anti-fungal, anti-protozoa or anti-parasitic drug (iii) reversing resistance to an anti-fungal, anti-protozoal or anti-parasitic drug; (iv) potentiating the activity of an anti-fungal, anti-protozoal or anti-parasitic drug; (v) delaying or preventing the onset of resistance to an anti-fungal, anti-protozoal or anti-parasitic drug, which method comprises administering to a subject undergoing treatment with said ancillary compound a compound of the formula (I), (II), (III), (IV), (V), (VI), (VIa), (VII), (VIIa) or (VIIb) or any sub-groups or examples thereof as defined herein.

A method for the treatment of a fungal, protozoal or parasitic disease in a subject undergoing treatment with an anti-fungal, anti-protozoal or anti-parasitic drug, which method comprises administering to a subject in need thereof compound of the formula (I), (II), (III), (IV), (V), (VI), (VIa), (VII), (VIIa) or (VIIb) or any sub-groups or examples thereof as defined herein, which method is characterized by the absence of drug resistance e.g. to said anti-fungal, anti-protozoal or anti-parasitic drug).

In another aspect, the invention provides compounds having Hsp90 inhibiting or modulating activity for use as anti-viral agents. More particularly, the invention provides:

The use of a compound of the formula (I), (II), (III), (IV), (V), (VI), (VIa), (VI), (VIIa) or (VIIb) or any sub-groups or examples thereof as defined herein for the manufacture of a medicament for the prophylaxis or treatment of a viral infection (or viral disease).

A method for the prophylaxis or treatment of a viral infection (or viral disease), which method comprises administering to a subject in need thereof a compound of the formula (I), (II), (III), (IV), (V), (VI), (VIa), (VII), (VIIa) or (VIIb) or any subgroups or examples thereof as defined herein.

A compound of the formula (I), (II), (III), (IV), (V), (VI), (VIa), (VII), (VIIa) or (VIIb) or any sub-groups or examples thereof as defined herein for use in blocking or inhibiting viral replication in a host organism (e.g. an animal such as a mammal (e.g. human)).

The use of a compound of the formula (I), (II), (III), (IV), (V), (VI), (VIa), (VII), (VIIa) or (VIIb) or any subgroups or examples thereof as defined herein for the manufacture of a medicament for use in blocking or inhibiting viral replication in a host organism (e.g. an animal such as a mammal (e.g. human)).

A method of blocking or inhibiting viral replication in a host organism (e.g. an animal such as a mammal (e.g. human)), which method comprises administering to the host organism a compound of the formula (I), (II), (III), (IV), (V), (VI), (VIa), (VII), (VIIa) or (VIIb) or any sub-groups or examples thereof as defined herein.

The invention further provides:

A combination of a compound of the formula (I), (II), (III), (IV), (V), (VI), (VIa), (VII), (VIIa) or (VIIb) or any sub-groups or examples thereof as defined herein with an ancillary compound which is an antiviral agent.

A pharmaceutical composition comprising a compound of the formula (I), (II), (III), (IV), (V), (VI), (VIa), (VII), (VIIa) or (VIIb) or any sub-groups or examples thereof as defined herein and an ancillary compound which is an antiviral agent.

In a further aspect, the invention provides a compound of the formula (I), (II), (III), (IV), (V), (VI), (VIa), (VII), (VIIa) or (VIIb) or any sub-groups or examples thereof as defined herein for the prophylaxis or treatment of atherosclerosis.

The invention further provides:

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of atherosclerosis.

A method for the prophylaxis or treatment of atherosclerosis, which method comprises administering to a subject in need thereof a compound of the formula (I), (II), (III), (IV), (V), (VI), (VIa), (VII), (VIIa) or (VIIb) or any sub-groups or examples thereof as defined herein.

In a further aspect, the invention provides a compound of the formula (I), (II), (III), (IV), (V), (VI), (VIa), (VII), (VIIa) or (VIIb) or any sub-groups or examples thereof as defined herein for the prophylaxis or treatment of Ewing's sarcoma.

The invention further provides:

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of Ewing's sarcoma.

A method for the prophylaxis or treatment of Ewing's sarcoma, which method comprises administering to a subject in need thereof a compound of the formula (I), (II), (III), (IV), (V), (VI), (VIa), (VII), (VIIa) or (VIIb) or any sub-groups or examples thereof as defined herein.

In a further aspect, the invention provides a compound of the formula (I), (II), (III), (IV), (V), (VI), (VIa), (VII), (VIIa) or (VIIb) or any sub-groups or examples thereof as defined herein for the prophylaxis or treatment of lupus erythematosus.

The invention further provides:

The use of a compound of the formula (I), (II), (III), (IV), (V), (VI), (VIa), (VII), (VIIa) or (VIIb) or any sub-groups or examples thereof as defined herein for the manufacture of a medicament for the prophylaxis or treatment of lupus erythematosus.

A method for the prophylaxis or treatment of lupus erythematosus, which method comprises administering to a subject in need thereof a compound of the formula (I), (II), (III), (IV), (V), (VI), (VIa), (VII), (VIIa) or (VIIb) or any sub-groups or examples thereof as defined herein.

General Preferences and Definitions

In this section, as in all other sections of this application, unless the context indicates otherwise, references to a compound of formula (I) includes all subgroups of formula (I) as defined herein, including formulae (II), (III), (IV), (V), (VI), (VIa), (VII), (VIIa) and (VIIb) and the term 'subgroups' includes all preferences, embodiments, examples and particular compounds defined herein. Such compounds may be referred to for convenience as "compounds of the invention" or, in the singular, "a compound of the invention".

Moreover, a reference to a compound of formula (I), (II), (III), (IV), (V), (VI), (VIa), (VII), (VIIa) or (VIIb) and sub-groups thereof includes ionic forms, salts, solvates, isomers, tautomers, N-oxides, esters, prodrugs, isotopes and protected forms thereof, as discussed below:—preferably, the salts or tautomers or isomers or N-oxides or solvates thereof:—and more preferably, the salts or tautomers or N-oxides or solvates thereof.

The following general preferences and definitions shall apply to each of $R^1$ to $R^8$, $R^{10}$, $R^a$, $R^b$, $R^c$, $X^1$ and $X^2$ and their various sub-groups, sub-definitions, examples and embodiments unless the context indicates otherwise.

As used herein, the term 'treatment' and the related terms "treat" and "treating" refer to both prophylactic or preventative treatment as well as curative or palliative treatment of pain. Thus, the term encompasses situations where pain is already being experienced by a subject or patient, as well as situations where pain is not currently being experienced but is expected to arise. The term "treatment", "treat", "treating" and related terms also cover both complete and partial pain reduction or prevention. Thus, for example, the compounds of the invention may prevent existing pain from worsening, or they reduce or even eliminate pain. When used in a prophylactic sense, the compounds may prevent any pain from developing or they may lessen the extent of pain that may develop.

As used herein, the term "modulation", as applied to the activity of the heat shock protein Hsp90, is intended to define a change in the level of biological activity of the heat shock protein. Thus, modulation encompasses physiological changes which effect an increase or decrease in the relevant heat shock protein activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of heat shock protein activity. Thus, modulation may imply elevated/suppressed expression or over- or under-expression of the heat shock protein, including gene amplification (i.e. multiple gene copies) and/or increased or decreased expression by a transcriptional effect, as well as hyper- (or hypo-) activity and (de)activation of the heat shock protein (including (de)activation) by mutation(s). The terms "modulated", "modulating" and "modulate" are to be interpreted accordingly.

As used herein, the term "mediated", as used e.g. in conjunction with the heat shock protein as described herein (and applied for example to various physiological processes, diseases, states, conditions, therapies, treatments or interventions) is intended to operate limitatively so that the various processes, diseases, states, conditions, treatments and interventions to which the term is applied are those in which heat shock protein Hsp90 plays a biological role. In cases where the term is applied to a disease, state or condition, the biological role played by heat shock protein Hsp90 may be direct or indirect and may be necessary and/or sufficient for the manifestation of the symptoms of the disease, state or condition (or its aetiology or progression). Thus, heat shock protein Hsp90 activity (and in particular aberrant levels of heat shock protein Hsp90 activity, e.g. Hsp90 over-expression) need not necessarily be the proximal cause of the disease, state or condition: rather, it is contemplated that the heat shock protein Hsp90 mediated diseases, states or conditions include those having multifactorial aetiologies and complex progressions in which Hsp90 is only partially involved. In cases where the term is applied to treatment, prophylaxis or intervention (e.g. in the "Hsp90-mediated treatments" and "Hsp90-mediated prophylaxis" of the invention), the role played by Hsp90 may be direct or indirect and may be necessary and/or sufficient for the operation of the treatment, prophylaxis or outcome of the intervention. Thus, a disease state or condition mediated by Hsp90 includes the development of resistance to any particular cancer drug or treatment (including in particular resistance to one or more of the signalling inhibitors described herein).

As used herein, the term "modulation", as applied to the activity of cyclin dependent kinase 5 (CDK5), is intended to define a change in the level of biological activity of the kinase(s). Thus, modulation encompasses physiological changes which effect an increase or decrease in the relevant kinase activity. In the latter case, the modulation may be described as "Inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of cyclin dependent kinase 5 (CDK5), or at the level of enzyme (e.g. cyclin dependent kinase 5 (CDK5) activity (for example by allosteric mechanisms, competitive inhibition, active-site inactivation, perturbation of feedback inhibitory pathways etc.). Thus, modulation may imply elevated/suppressed expression or over- or under-expression of the cyclin dependent kinase 5 (CDK5) including gene amplification (i.e. multiple gene copies) and/or increased or decreased expression by a transcriptional effect, as well as hyper-(or hypo-) activity and (de)activation of the cyclin dependent kinase 5 (CDK5) including (de)activation) by mutation(s). The terms "modulated", "modulating" and "modulate" are to be interpreted accordingly.

As used herein, the term "mediated", as used e.g. in conjunction with the cyclin dependent kinase 5 (CDK5) as described herein (and applied for example to various physiological processes, diseases, states, conditions, therapies, treatments or interventions) is intended to operate limitatively so that the various processes, diseases, states, conditions, treatments and interventions to which the term is applied are those in which cyclin dependent kinase 5 (CDK5) plays a biological role. In cases where the term is applied to a disease, state or condition, the biological role played by cyclin dependent kinase 5 (CDK5) may be direct or indirect and may be necessary and/or sufficient for the manifestation of the symptoms of the disease, state or condition (or its aetiology or progression). Thus, cyclin dependent kinase 5 (CDK5) activity (and in particular aberrant levels of cyclin dependent kinase 5 (CDK5) activity, e.g. cyclin dependent kinase 5 (CDK5) over-expression) need not necessarily be the proximal cause of the disease, state or condition: rather, it is contemplated that the CDK5-mediated diseases, states or conditions include those having multifactorial aetiologies and complex progressions in which CDK5. In cases where the term is applied to treatment, prophylaxis or intervention (e.g. in the "CDK5-mediated treatments" of the invention), the role played by CDK5 may be direct or indirect and may be necessary and/or sufficient for the operation of the treatment, prophylaxis or outcome of the intervention.

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
- compositions (e.g. unitary formulations) comprising the two or more compounds/agents in admixture (for example within the same unit dose);
- compositions comprising material in which the two or more compounds/agents are chemically/physicochemically linked (for example by crosslinking, molecular agglomeration or binding to a common vehicle moiety);
- compositions comprising material in which the two or more compounds/agents are chemically/physicochemically co-packaged (for example, disposed on or within lipid vesicles, particles (e.g. micro- or nanoparticles) or emulsion droplets);
- pharmaceutical kits, pharmaceutical packs or patient packs in which the two or more compounds/agents are co-packaged or co-presented (e.g. as part of an array of unit doses);

Examples of non-physically associated combined compounds/agents include
- material (e.g. a non-unitary formulation) comprising at least one of the two or more compounds/agents together with instructions for the extemporaneous association of the at least one compound to form a physical association of the two or more compounds/agents;
- material (e.g. a non-unitary formulation) comprising at least one of the two or more compounds/agents together with instructions for combination therapy with the two or more compounds/agents;
- material comprising at least one of the two or more compounds/agents together with instructions for administration to a patient population in which the other(s) of the two or more compounds/agents have been (or are being) administered;
- material comprising at least one of the two or more compounds/agents in an amount or in a form which is specifically adapted for use in combination with the other(s) of the two or more compounds/agents.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Any references to formula (I) herein shall also be taken to refer to and any sub-group of compounds within formula (I) and any preferences and examples thereof unless the context requires otherwise.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, for example 5 to 7, and preferably 5 or 6 ring members. Examples of bicyclic groups are those containing 8, 9, 10, 11 and 12 ring members, and more usually 9 or 10 ring members.

The term "bicyclic" as used herein refers to groups that have two rings joined together in such as way that at least one ring member is shared by both rings. Thus, the bicyclic group can be a fused ring (two ring members shared by both rings), spirocyclic (one ring member shared by both rings) or a bridged ring (three or more ring members shared by both rings).

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic)

ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The terms "fully saturated" and "saturated" refer to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of heteroaryl groups are monocyclic and bicyclic groups containing from five to twelve ring members, and more usually five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
d) a pyrazole ring fused to a 5- or 6-membered ring containing 1 or 2 ring heteroatoms;
e) a pyrazine ring fused to a 5- or 6-membered ring containing 1 or 2 ring heteroatoms;
f) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

One sub-group of bicyclic heteroaryl groups consists of groups (a) to (e) and (g) to (o) above.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzofuranyl, benzothienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzofuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1, 2, 3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heterocylic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), In one sub-set of heterocyclic groups, the heterocyclic groups contain cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic sulphones (e.g. as in sulpholane and sulpholene), cyclic sulphoxides, cyclic sulphonamides and combinations thereof (e.g. thiomorpholine).

Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine.

One preferred sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Another sub-set of non-aromatic heterocyclic groups consists of pyrrolidine, piperidine, morpholine, thiomorpholine, thiomorpholine S,S-dioxide, piperazine and N-alkyl piperazines such as N-methyl piperazine.

One particular sub-set of heterocyclic groups consists of pyrrolidine, piperidine, morpholine and N-alkyl piperazines (e.g. N-methyl piperazine), and optionally thiomorpholine.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carbocyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged ring systems include bicyclo[2.2.1]heptane, aza-bicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$—$R^b$ wherein $R^a$ is a bond, O, CO, $X^1C(X^2)$, $C(X^2)X^1$, $X^1C(X^2)X^1$, S, SO, SO$_2$, NR$^c$, SO$_2$NR$^c$ or NR$^c$SO$_2$; and $R^b$ is selected from hydrogen, carbocyclic and heterocyclic groups having from 3 to 12 ring members, and a $C_{1-12}$ hydrocarbyl group (such as a $C_{1-10}$ hydrocarbyl group) optionally substituted by one or more substituents selected from hydroxy, oxo, halogen, cyano, nitro, carboxy, amino, mono- or di-$C_{1-8}$ non-aromatic hydrocarbylamino (e.g. mono- or di-$C_{1-4}$ hydrocarbylamino), carbocyclic and heterocyclic groups having from 3 to 12 ring members and wherein one or more carbon atoms of the $C_{1-12}$ hydrocarbyl group (or $C_{1-10}$ hydrocarbyl group) may optionally be replaced by O, S, SO, SO$_2$, NR$^c$, $X^1C(X^2)$, $C(X^2)X^1$ or $X^1C(X^2)X^1$;

$R^c$ is selected from $R^b$, hydrogen and $C_{1-4}$ hydrocarbyl; and $X^1$ is O, S or NR$^c$ and $X^2$ is =O, =S or =NR$^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I), such further substituent groups $R^{10}$ may include carbocyclic or heterocyclic groups, which are typically not themselves further substituted. In another sub-group of compounds of the formula (I), the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 11, or 10, or 9, or 8, or 7, or 6, or 5 non-hydrogen atoms.

Where the carbocyclic and heterocyclic groups have a pair of substituents on the same or adjacent ring atoms, the two substituents may be linked so as to form a cyclic group. Thus, two adjacent groups $R^{10}$, together with the carbon atoms or heteroatoms to which they are attached may form a 5-membered heteroaryl ring or a 5- or 6-membered non-aromatic carbocyclic or heterocyclic ring, wherein the said heteroaryl and heterocyclic groups contain up to 3 heteroatom ring members selected from N, O and S. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group.

Examples of such linked substituent groups include:

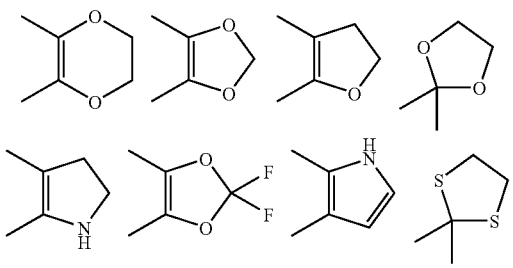

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkenyl groups. Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds of the formula (I) unless the context indicates otherwise.

The prefix "$C_{x-y}$" (where x and y are integers) as used herein refers to the number of carbon atoms in a given group. Thus, a $C_{1-4}$ hydrocarbyl group contains from 1 to 4 carbon atoms, and a $C_{3-6}$ cycloalkyl group contains from 3 to 6 carbon atoms, and so on.

The term "acyclic hydrocarbyl" (e.g. as in "acyclic $C_{1-5}$ hydrocarbyl") as used herein refers to non-cyclic hydrocarbyl groups and in particular to alkyl, alkenyl and alkynyl groups as defined herein.

The term "mono- or di-$C_{1-5}$ hydrocarbylamino" as used herein refers to a monosubstituted or disubstituted amine group bearing either one or two hydrocarbyl substituent groups that each contain from 1 to 5 carbon atoms.

Preferred non-aromatic hydrocarbyl groups are saturated groups such as alkyl and cycloalkyl groups.

Generally by way of example, the hydrocarbyl groups can have up to ten carbon atoms (and more typically up to eight carbon atoms), unless the context requires otherwise. Within the sub-set of hydrocarbyl groups having 1 to 10 carbon atoms, particular examples are $C_{1-8}$ hydrocarbyl groups or $C_{1-8}$ hydrocarbyl groups, such as $C_{1-4}$ hydrocarbyl groups (e.g. $C_{1-3}$ hydrocarbyl groups or $C_{1-2}$ hydrocarbyl groups or $C_{2-3}$ hydrocarbyl groups or $C_{2-4}$ hydrocarbyl groups), specific examples being any individual value or combination of values selected from $C_1$, $C_2$, $C_3$, $C_4$, $C_5$, $C_8$, $C_7$, $C_8$, $C_9$ and $C_{10}$ hydrocarbyl groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups or $C_{2-3}$ alkyl groups or $C_{2-4}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 10 carbon atoms, more typically 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 10 carbon atoms, more typically 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 10 carbon atoms, more typically 3 to 8 carbon atoms, and particular examples are C cycloalkenyl groups.

Examples of alkynyl groups include, but are not limited to, ethynyl and 2-propynyl (propargyl) groups. Within the sub-set of alkynyl groups having 2 to 10 carbon atoms, more typically 2 to 8 carbon atoms, particular examples are $C_{2-6}$ alkynyl groups, such as $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

The terms $C_{1-12}$ hydrocarbyl, $C_{1-10}$ hydrocarbyl and $C_{1-8}$ hydrocarbyl as used herein encompasses alkyl, alkenyl, alkynyl, cycloalkyl, cycloalkenyl, phenyl, benzyl and phenylethyl groups wherein the preferences for and examples of each of the aforesaid groups are as defined above. Within this definition, particular hydrocarbyl groups are alkyl, cycloalkyl, phenyl, benzyl and phenylethyl (e.g. 1-phenylethyl or 2-phenylethyl) groups, one subset of hydrocarbyl groups consisting of alkyl and cycloalkyl groups and in particular $C_{1-4}$ alkyl and cycloalkyl groups such as methyl, ethyl, n-propyl, isopropyl, n-butyl, isobutyl, tert-butyl, cyclopropyl and cyclobutyl.

The term $C_{1-5}$ hydrocarbyl as used herein encompasses alkyl, alkenyl, alkynyl, cycloalkyl and cycloalkenyl groups wherein the preferences for and examples of the aforesaid groups are as defined above. Within this definition, particular $C_{1-5}$ hydrocarbyl groups are saturated $C_{1-5}$ hydrocarbyl groups, namely alkyl and cycloalkyl groups, such as methyl, ethyl, n-propyl, isopropyl, n-butyl, isobutyl, tert-butyl, n-pentyl, 3-methylbutyl, 2-methylbutyl, pent-2-yl, pent-3-yl, 3-methylbut-2-yl, 2,2-dimethylpropyl, cyclopropyl, cyclobutyl, cyclopentyl, cyclopropylmethyl, cyclopropylethyl, cyclobutylmethyl, methylcyclopropyl, ethylcyclopropyl, dimethylcyclopropyl, methylcyclobutyl.

Also within the scope of the term $C_{1-5}$ hydrocarbyl as used herein are unsaturated $C_{1-5}$ hydrocarbyl groups, i.e. alkene, cycloalkene and alkyne groups such as vinyl, 1-propenyl, isopropenyl, 1-butenyl, 2-butenyl, 1-pentenyl, 2-pentenyl, allyl, methylallyl, dimethylallyl, acetylenyl, propargyl, cyclobutenyl and cyclopentenyl.

The term $C_{1-4}$ hydrocarbyl as used herein encompasses alkyl, alkenyl, alkynyl, cycloalkyl and cycloalkenyl groups wherein the preferences for and examples of the aforesaid groups are as defined above. Within this definition, particular $C_{1-4}$ hydrocarbyl groups are alkyl and cycloalkyl groups, such as methyl, ethyl, n-propyl, isopropyl, n-butyl, isobutyl, tert-butyl, cyclopropyl and cyclobutyl.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members, more usually 3, 4, 5 or 6 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members, more usually 5 to 6 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom. Thus, in an oxa-$C_{4-6}$ cycloalkyl group, there will be from 3 to 5 carbon ring members and an oxygen ring member. For example, an oxa-cyclohexyl group is a tetrahydropyranyl group.

The definition "$R^a$—$R^b$" as used herein, either with regard to substituents present on a carbocyclic or heterocyclic moiety, or with regard to other substituents present at other locations on the compounds of the formula (I), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, $NR^cC(O)O$, OC(S)O, SC(S)O, $NR^cC(S)O$, $OC(NR^c)O$, $SC(NR^c)O$, $NR^cC(NR^c)O$, OC(O)S, SC(O)S, $NR^cC(O)S$, OC(S)S, SC(S)S, $NR^cC(S)S$, $OC(NR^c)S$, $SC(NR^c)S$, $NR^cC(NR^c)S$, $OC(O)NR^c$, $SC(O)NR^c$, $NR^cC(O)NR^c$, $OC(S)NR^c$, $SC(S)NR^c$, $NR^cC(S)NR^c$, $OC(NR^c)NR^c$, $SC(NR^c)NR^c$, $NR^cC(NR^cNR^c$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-10}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-10}$ hydrocarbyl group, examples of hydrocarbyl groups $R^a$—$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), $C_{1-10}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When $R^a$ is $SO_2NR^c$, $R^b$ can be, for example, hydrogen or an optionally substituted $C_{1-10}$ hydrocarbyl group, or a carbocyclic or heterocyclic group. Examples of $R^a$—$R^b$ where $R^a$ is $SO_2NR^c$ include aminosulphonyl, $C_{1-4}$alkylaminosulphonyl and di-$C_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$—$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-10}$ hydrocarbyl group, or a carbocyclic or heterocyclic group. Examples of $R^a$—$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for $R^1$ to $R^{10}$ $R^1$ & $R^2$ $R^1$ is hydroxy or hydrogen; and $R^2$ is hydroxy, methoxy or hydrogen; provided that at least one of $R^1$ and $R^2$ is hydroxy.

Preferably, $R^1$ is hydroxy or hydrogen; and $R^2$ is hydroxy or hydrogen; provided that at least one of $R^1$ and $R^2$ is hydroxy.

In one embodiment, $R^1$ is hydroxy and $R^2$ is hydrogen or methoxy, preferably hydrogen.

In another embodiment, $R^1$ is hydrogen and $R^2$ is hydroxy.

In a further embodiment, $R^1$ is hydroxy and $R^2$ is hydroxy or methoxy.

In a preferred embodiment, $R^1$ and $R^2$ are both hydroxy.

$R^8$ $R^8$ is selected from hydrogen and fluorine. Preferably $R^8$ is hydrogen.

$R^3$ $R^3$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members.

In one sub-group of compounds, $R^3$ is selected from hydrogen, halogen, cyano, $C_{1-5}$ hydrocarbyl and $C_{1-5}$ hydrocarbyloxy; wherein the $C_{1-5}$ hydrocarbyl moiety in each instance is optionally substituted by one or more substituents selected from hydroxy, halogen, $C_{1-2}$ alkoxy and amino.

In another sub-group of compounds, $R^3$ is selected from halogen (e.g. chlorine or bromine), $C_{1-5}$ alkyl and $C_{3-4}$ cycloalkyl.

More typically, $R^3$ is selected from hydrogen, chlorine, $C_{1-5}$ hydrocarbyl and $C_{1-5}$ hydrocarbyloxy.

Particular groups $R^3$ include hydrogen, $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

A further subgroup of substituents $R^3$ consists of $C_{1-5}$ alkyl, $C_{2-5}$ alkenyl and $C_{3-4}$ cycloalkyl groups, preferably secondary alkyl and alkenyl groups such as isopropyl, sec-butyl, tert-butyl, 1,2-dimethylallyl and 1,2-dimethylpropyl, or cycloalkyl groups such as cyclopropyl.

When only one of $R^1$ and $R^2$ is hydroxy, $R^3$ may be other than hydrogen.

In one particular embodiment, $R^1$ and $R^2$ are both hydroxy and $R^3$ is hydrogen.

In a further particular embodiment, $R^3$ is selected from isopropyl and tert-butyl.

In one general embodiment, $R^3$ is other than halogen.

In another general embodiment, $R^3$ may be other than fluorine.

In a further general embodiment, $R^3$ may be other than fluorine or methoxy.

$R^4$

In one embodiment, $R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$alkylamino, and aryl and heteroaryl groups of 5 to 12 ring members.

In one sub-group of compounds, $R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbylamino, wherein the $C_{1-5}$ hydrocarbyl moiety in each instance is optionally substituted by one or more substituents selected from hydroxy, halogen, $C_{1-2}$ alkoxy and amino.

Within this sub-group, $R^4$ is more typically selected from hydrogen, methoxy, halogen (e.g. fluorine or chlorine), cyano; hydroxy; amino and $C_{3-6}$ cycloalkyl.

More particularly, $R^4$ can be selected from a sub-set $R^{4a}$ wherein the sub-set $R^{4a}$ consists of hydrogen, methoxy, fluorine and chlorine.

Preferably $R^4$ is hydrogen.

In another embodiment, $R^3$ and $R^4$ together form a carbocyclic or heterocyclic ring of 5 to 7 ring members. The carbocyclic and heterocyclic groups can be any of the groups listed above in General Definitions and Preferences section but one particular group is a group wherein $R^3$ and $R^4$ together with the phenyl ring form a dihydrobenzofuran group.

Particular examples of the phenyl ring containing the moieties $R^1$, $R^2$, $R^3$ and $R^4$ are as set out in Table 1. The point of attachment to the carbonyl group is indicated by means of an asterisk.

TABLE 1

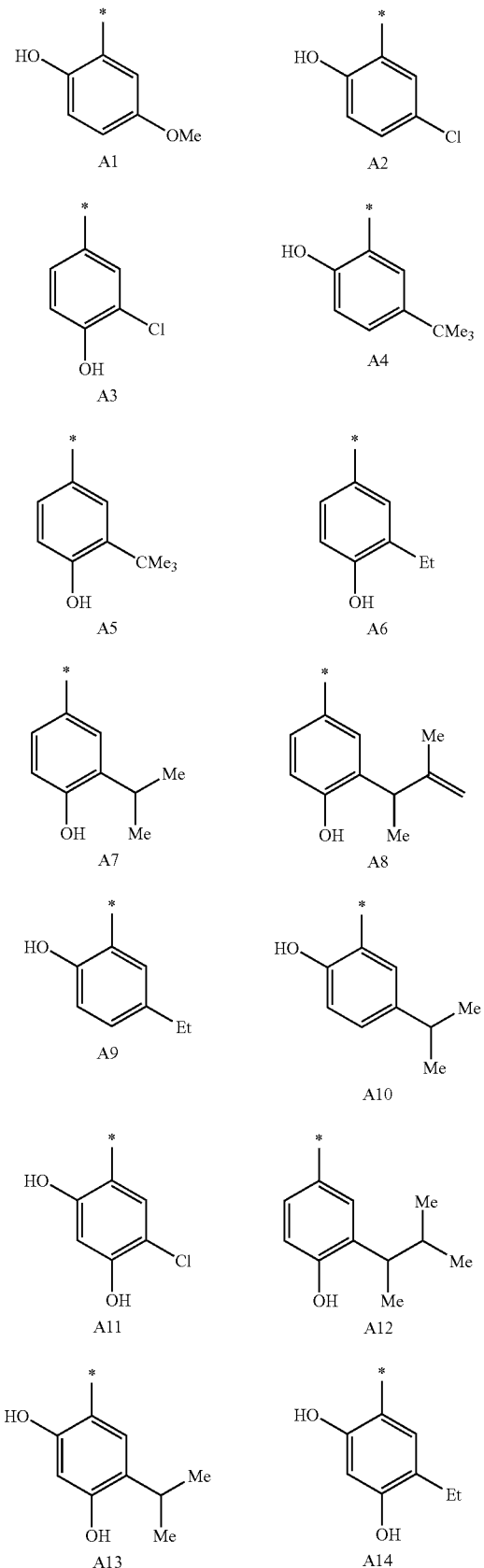
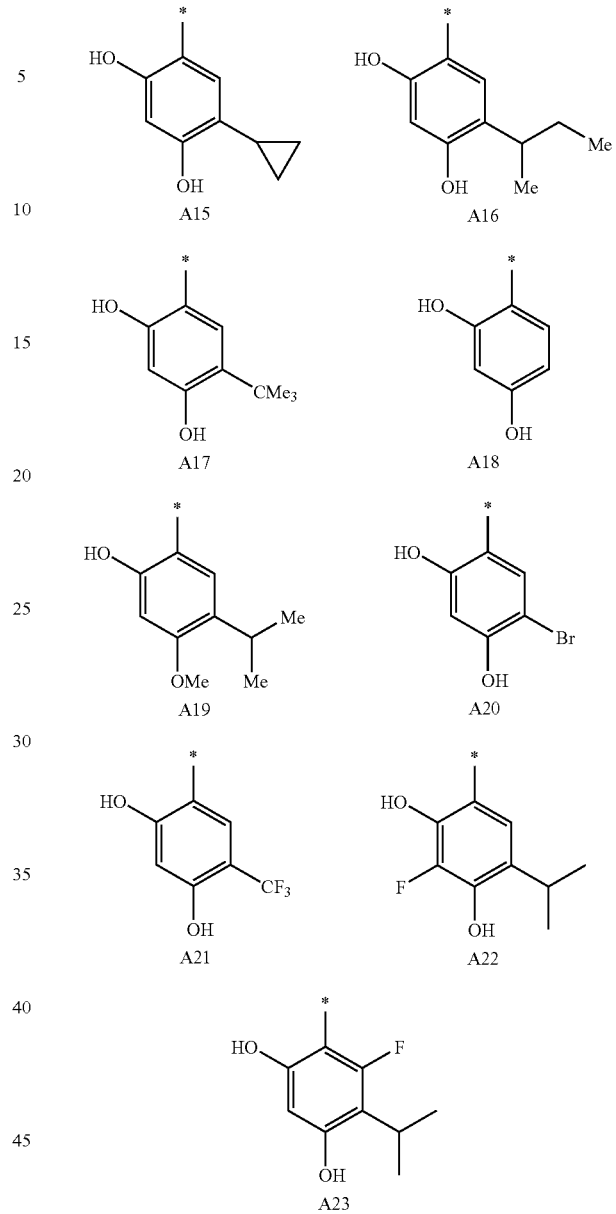

In one embodiment, the phenyl moiety is selected from groups A1 to A21.

In another embodiment, the phenyl moiety is selected from groups A1 to A18.

Preferred phenyl moieties include groups A5, A7, A11, A13, A14, A15, A16, A17 and A18.

Particularly preferred phenyl moieties are A5, A7, A13, A14 and A17.

Particularly preferred phenyl moieties are A11 and A13.

One particularly preferred phenyl moiety is group A13.

$R^5$ & $R^8$ $R^5$ and $R^6$ together with the nitrogen atom to which they are attached form a bicyclic heterocyclic group having up to 12 ring members of which up to 5 ring members are heteroatoms selected from oxygen, nitrogen and sulphur.

The bicyclic groups can be any of the groups listed above in the General Preferences and Definitions section or listed below in the Particular and Preferred Sub-groups section, and such groups may be unsubstituted or substituted by one or more substituents $R^{10}$ as defined herein.

The bicyclic heterocyclic group is typically a fused ring bicyclic group or a spirocyclic group and more typically is a fused ring bicyclic group. Particular fused ring systems of interest in the context of the invention are 5.6 and 6.6 fused ring systems. In the bicyclic heterocyclic groups, one of the rings may be a heterocyclic ring and the other may be a carbocyclic ring, or both rings may be heterocyclic.

In one sub-group of compounds, one of the rings of the bicyclic heterocyclic group is non-aromatic and other is aromatic. Preferably the nitrogen atom of the group $NR^5R^6$ forms part of the non-aromatic ring. Particular examples of such groups are dihydroindole, dihydroisoindol, tetrahydroquinoline and tetrahydroisoquinoline groups.

More particular examples of such groups are dihydroindole, dihydroisoindol, tetrahydroquinoline and tetrahydroisoquinoline groups, but wherein the tetrahydroisoquinoline group bears no substituent groups on the non-aromatic ring thereof.

The bicyclic heterocyclic rings are optionally substituted by one or more substituent groups $R^{10}$ as defined herein.

In one embodiment, the bicyclic heterocyclic ring is substituted by 1, 2 or 3 substituent groups $R^{10}$ as defined herein.

In another embodiment, the bicyclic heterocyclic ring is substituted by 1 or 2 substituent groups $R^{10}$ as defined herein.

The substituent group or groups $R^{10}$ may be attached to either or both of the two rings making up the bicyclic heterocyclic group. In one embodiment, the ring containing the nitrogen atom of the group $NR^5R^6$ does not bear any substituents $R^{10}$. In another embodiment, the ring containing the nitrogen atom of the group $NR^5R^6$ bears a substituent $R^{10}$ but the substituent is other than a carboxylic acid group.

In one sub-group of compounds, the bicyclic heterocyclic group is unsubstituted or is substituted by one, two or three (preferably one or two) substituents selected from a group $R^{10a}$ consisting of halogen, hydroxy, amino and a group $R^a$—$R^b$ where $R^a$ is selected from a bond, O, CO, C(O)O, C(O)NR$^c$, NR$^c$C(O), NR$^c$C(O)O, NR$^c$, SO, SO$_2$, SONR$^c$, and SO$_2$NR$^c$; and R$^b$ is selected from hydrogen; carbocyclic and heterocyclic groups having 5 or 6 ring members; and $C_{1-10}$ hydrocarbyl (e.g. $C_{1-8}$ hydrocarbyl such as $C_{1-8}$ alkyl or $C_{3-7}$ cycloalkyl) optionally substituted by one or more substituents selected from hydroxy, oxo, amino, mono- or di-$C_{1-8}$ non-aromatic hydrocarbylamino, (e.g. mono- or di-$C_{1-4}$ hydrocarbylamino), carboxy, and carbocyclic and heterocyclic groups having from 3 to 7 ring members, and wherein one or more of the carbon atoms of the $C_{1-8}$ hydrocarbyl group may optionally be replaced by O, S, C(O)O, C(O)NR$^c$ or NR$^c$.

Within this sub-group of compounds and sub-groups, preferences and examples thereof, where it is stated that one or more of the carbon atoms of the $C_{1-8}$ hydrocarbyl group may optionally be replaced by O, S, C(O)O, C(O)NR$^c$ or NR$^c$, the orientation of the ester and amide groups may be in either direction unless indicated to the contrary.

In the above sub-groups, when R$^b$ is a carbocyclic or heterocyclic group, the carbocyclic or heterocyclic group may be substituted by one or more substituents $R^{10}$ as defined herein. For example, when R$^b$ is a carbocyclic or heterocyclic group, the carbocyclic or heterocyclic group may be substituted by one or more substituents selected from $CO_2R^{14}$ wherein $R^{14}$ is hydrogen or $C_{1-6}$ alkyl;

$C_{1-4}$ alkyl optionally substituted by hydroxy or $C_{1-2}$ alkoxy; $C_{1-4}$ alkoxy optionally substituted by hydroxy or $C_{1-2}$ alkoxy; or a group [sol], CH$_2$[sol], C(O)[sol], OCH$_2$CH$_2$[sol] or OCH$_2$CH$_2$CH$_2$[sol] where [sol] is as defined below.

In a more particular sub-group, the bicyclic heterocyclic group is unsubstituted or is substituted by one, two or three (preferably one or two) substituents selected from a group $R^{10b}$ consisting of halogen, OH, NH$_2$, CH$_2$OH, CH$_2$NH$_2$, O—$C_{1-6}$-alkyl, NH—$C_{1-6}$alkyl, aryl, heteroaryl, $C_{3-7}$ cycloalkyl, heterocyclyl, O-heteroaryl, O—$C_{3-7}$ cycloalkyl, O-heterocycloalkyl, C(=O)$C_{1-6}$ alkyl, C(=O)OC$_{1-6}$ alkyl, C(=O)NH$_2$, C(=O)NHC$_{1-6}$alkyl, C(=O)N(C$_{1-6}$ alkyl)$_2$, NH(C$_{1-6}$alkyl), N(C$_{1-6}$alkyl)$_2$, NC(=O)C$_{1-6}$alkyl, C$_6$ aryl, OC$_6$ aryl, C(=O)C$_6$aryl, C(=O)OC$_6$aryl, C(=O)NH$_2$, C(=O)NHC$_6$aryl, C(=O)N(C$_6$ aryl)$_2$, NH(C$_6$ aryl), N(C$_6$ aryl)$_2$, NC(=O)C$_6$ aryl, C$_{5-6}$ heterocyclyl, OC$_{5-8}$ heterocyclyl, C(=O)C$_{5-6}$ heterocyclyl, C(=O)OC$_{5-6}$heterocyclyl, C(=O)NHC$_{5-6}$ heterocyclyl, C(=O)N(C$_{5-6}$ heterocyclyl)$_2$, NH(C$_{5-6}$ heterocyclyl), N(C$_{5-6}$ heterocyclyl)$_2$, NC(=O)C$_{5-6}$ heterocyclyl, C(=O)NHC$_{1-6}$ alkyl, C$_{5-6}$ aryl, S(=O)C$_{1-6}$ alkyl, S(=O)N—C$_{1-6}$ alkyl and SO$_2$N—C$_{1-6}$ alkyl; and a group [sol], CH$_2$[sol] or OCH$_2$CH$_2$[sol] where [sol] is selected from the following groups

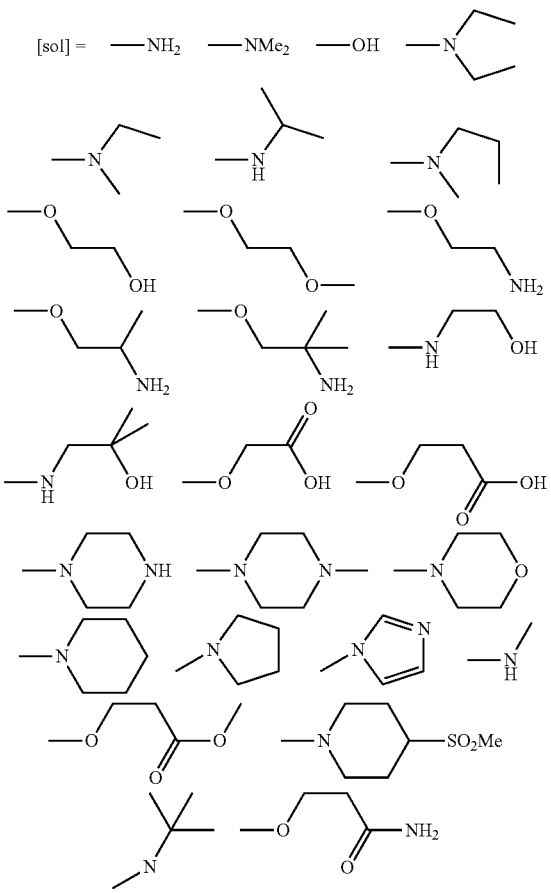

In another sub-group of compounds, the bicyclic ring is unsubstituted or is substituted by 1, 2 or 3 (e.g. 1 or 2, for example 1) groups $R^{10c}$ where $R^{10c}$ is a group [sol], CH$_2$ [sol] or OCH$_2$CH$_2$[sol] where [sol] is selected from the following groups

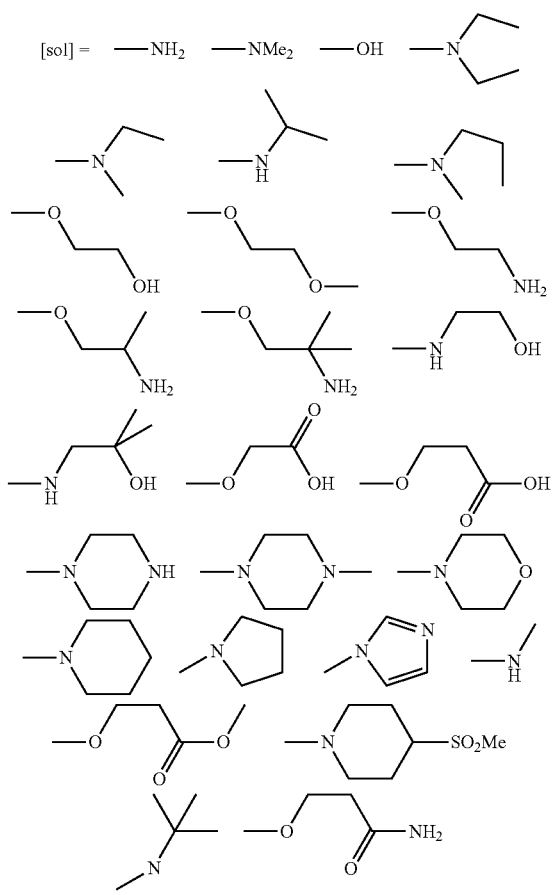

and wherein (i) $R^{10c}$ is optionally further selected from a group $OCH_2CH_2CH_2[sol]$ and/or (ii) [sol] is further selected from $NHR^{11}$ wherein $R^{11}$ is $COR^{12}$ or $R^{12}$ and $R^{12}$ is $C_{1-4}$ alkyl, aryl or aryl-$C_{1-4}$ alkyl.

In another sub-group of compounds, the bicyclic ring is unsubstituted or is substituted by one or two substituents $R^{10cc}$ where $R^{10cc}$ is selected from:

halogen;

$CO_2R^{14}$ wherein $R^{14}$ is hydrogen or $C_{1-6}$ alkyl;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group [sol], $CH_2[sol]$, $C(O)[sol]$, $OCH_2CH_2[sol]$ or $OCH_2CH_2CH_2[sol]$ where [sol] is selected from the following groups

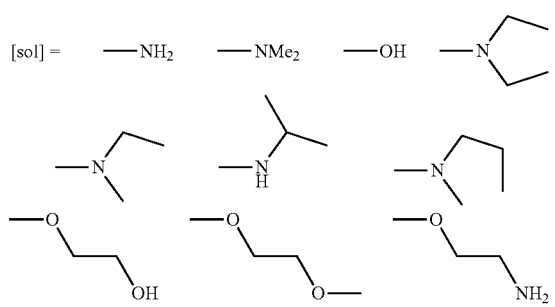

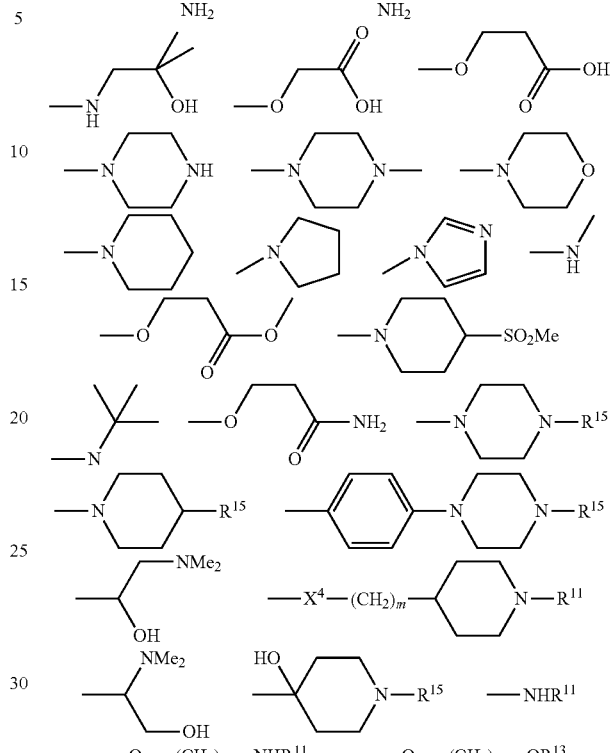

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In a further sub-group of compounds, the bicyclic ring is unsubstituted or is substituted by one or two substituents $R^{10ccc}$ where $R^{10ccc}$ is selected from:

a group [sol] or $CH_2[sol]$ where [sol] is selected from the following groups:

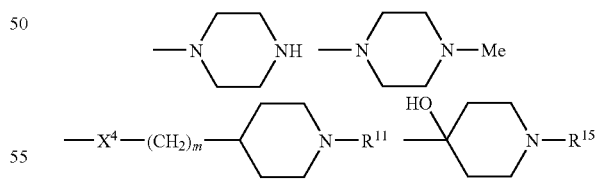

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In another sub-group of compounds, where $R^{10b}$ or $R^{10c}$ or $R^{10cc}$ is a group [sol], $CH_2[sol]$, $OCH_2CH_2[sol]$ or $OCH_2CH_2CH_2[sol]$ and [sol] contains a primary or secondary amine group, the primary or secondary amine group can be derivatised to form an acyl derivative such as an amide, carbamate or urea. For example, the amine group can be derivatised to form a carbamate such as a $C_{1-4}$alkyloxycarbonylamino group, or a benzyloxycarbonylamino group.

In one sub-group of compounds, $R^5$ and $R^6$ together with the nitrogen atom to which they are attached form an optionally substituted dihydroisoindole group wherein the optional substituents are selected from groups $R^{10}$, $R^{10a}$, $R^{10b}$, $R^{10c}$ and $R^{10cc}$ and sub-groups and examples thereof as defined herein.

Particular examples of the group $NR^6R^6$ are shown in Table 2. The point of attachment to the carbonyl group is shown by means of an asterisk.

TABLE 2

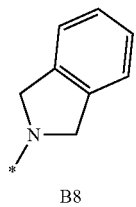

B8

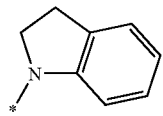

B13

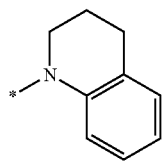

B14

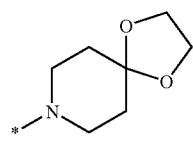

B20

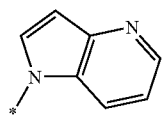

B26

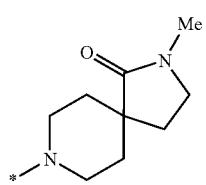

B29

TABLE 2-continued

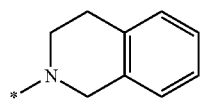

B30

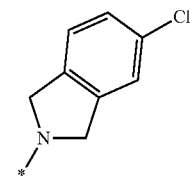

B35

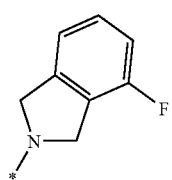

B36

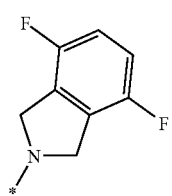

B37

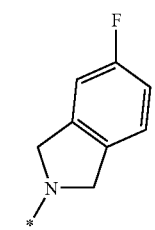

B38

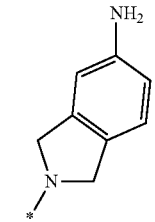

B39

TABLE 2-continued
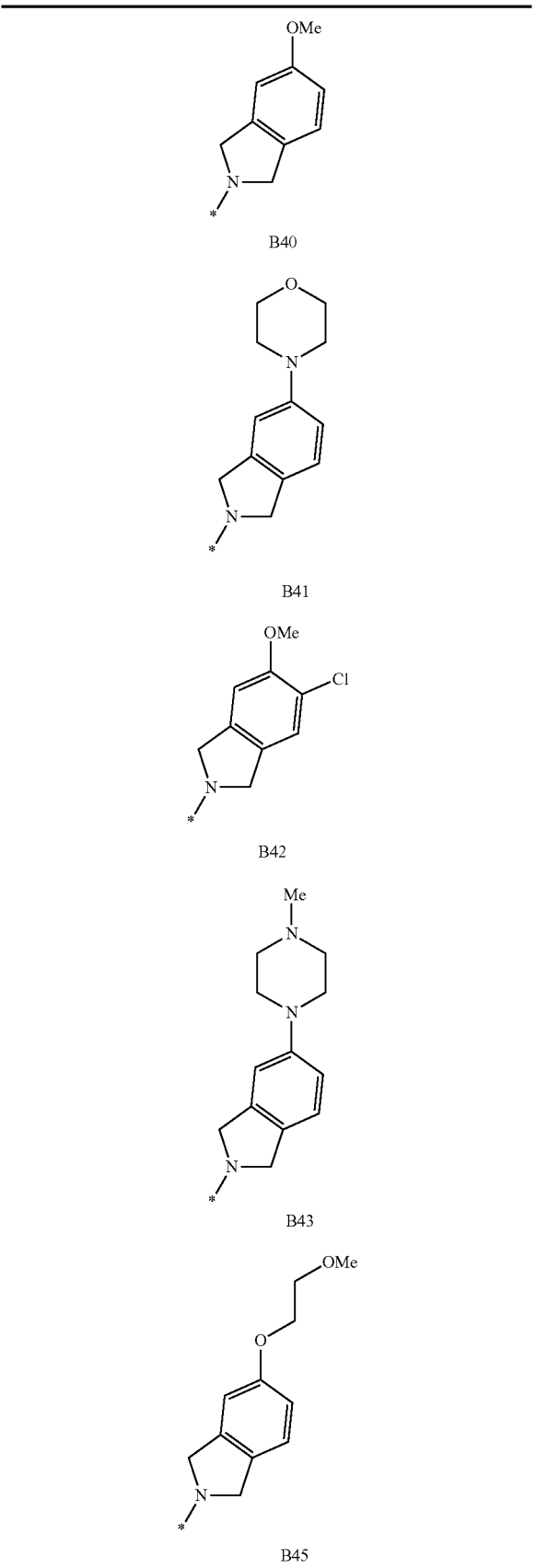
B40
B41
B42
B43
B45
TABLE 2-continued
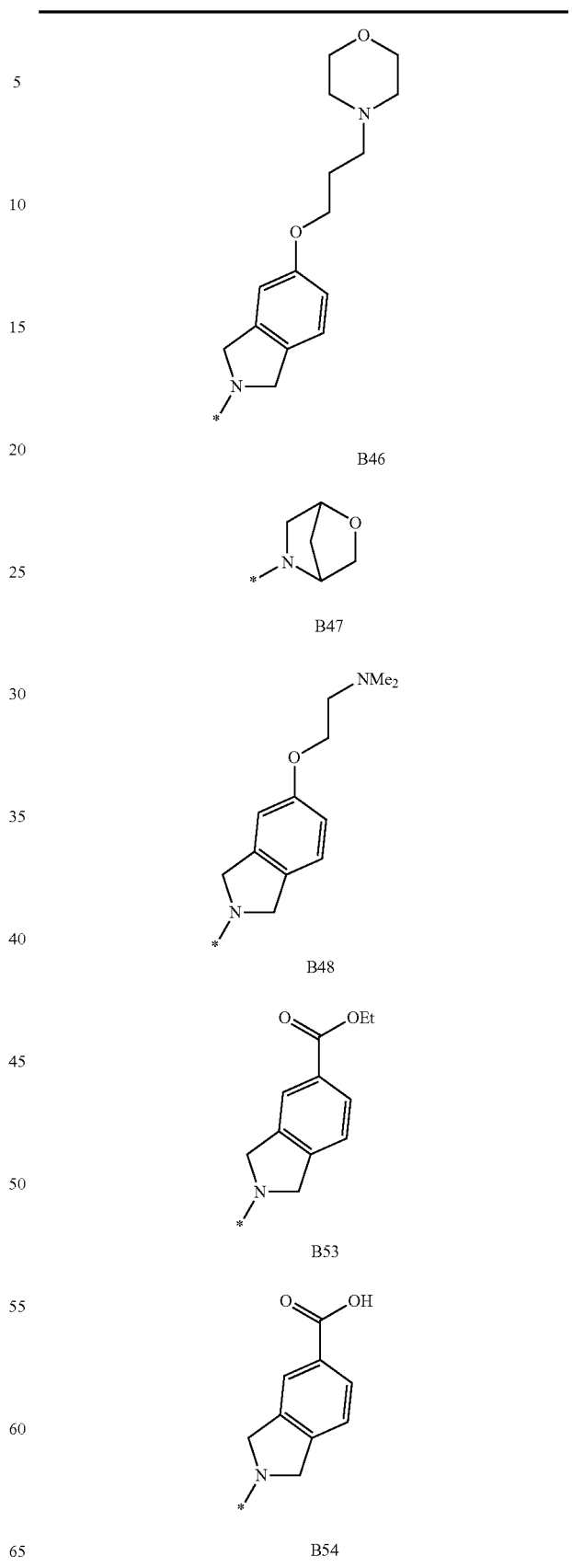
B46
B47
B48
B53
B54

TABLE 2-continued
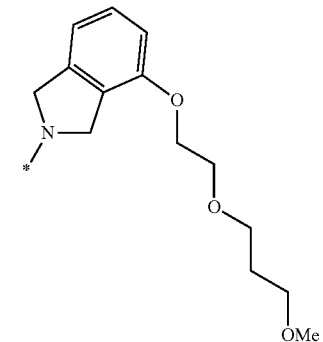
B55
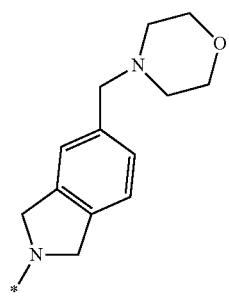
B56
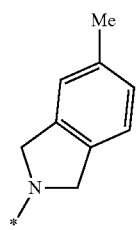
B57
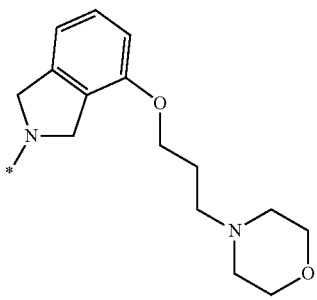
B58
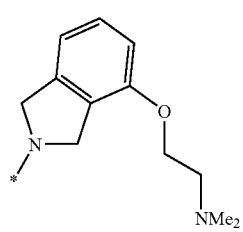
B59
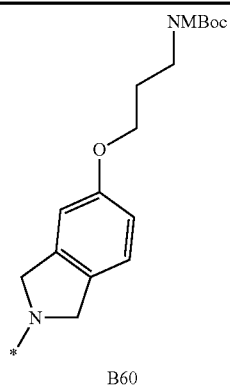
B60
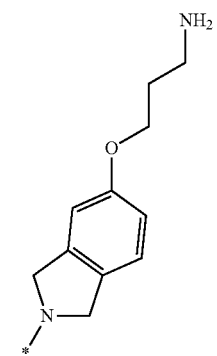
B61
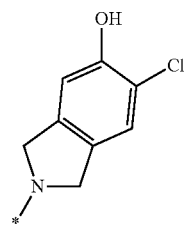
B62
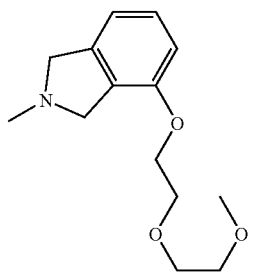
B71
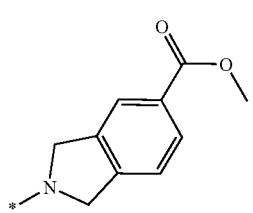
B72

TABLE 2-continued
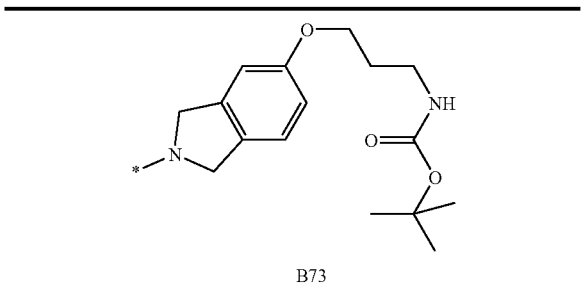
B73
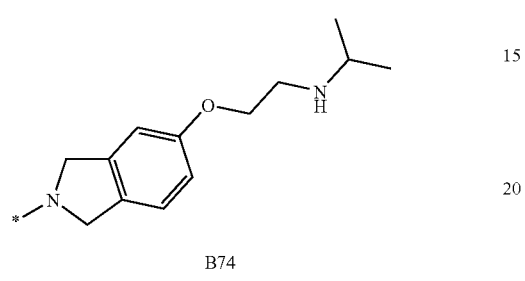
B74
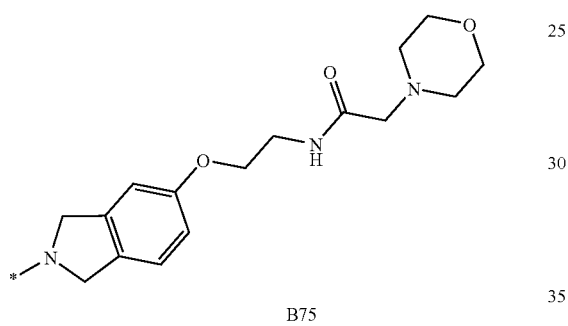
B75
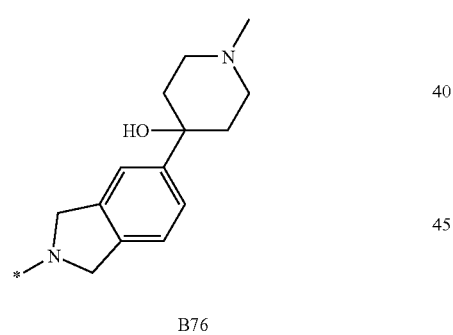
B76
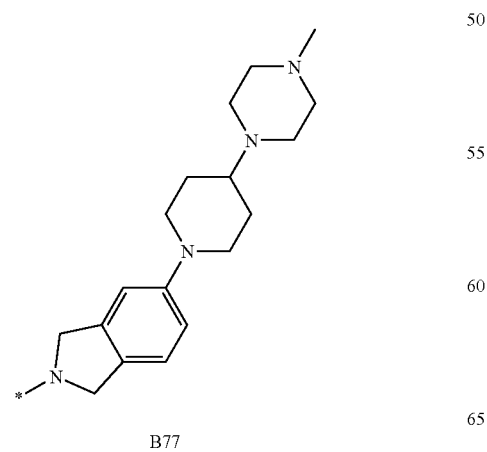
B77
TABLE 2-continued
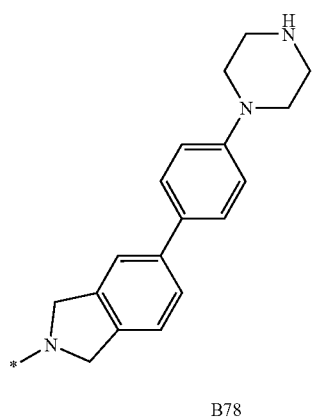 [SMILES: "B78" ; *N1Cc2ccc(-c3ccc(N4CCNCC4)cc3)cc2C1]
B78
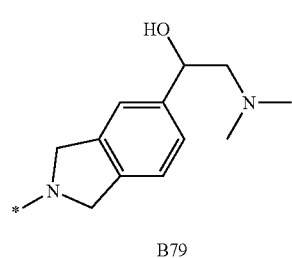 [SMILES: "B79" ; *N1Cc2ccc(C(O)CN(C)C)cc2C1]
B79
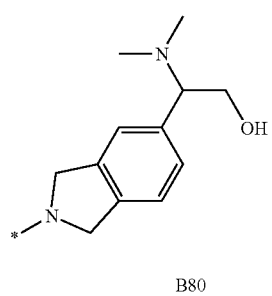 [SMILES: "B80" ; *N1Cc2ccc(C(CO)N(C)C)cc2C1]
B80
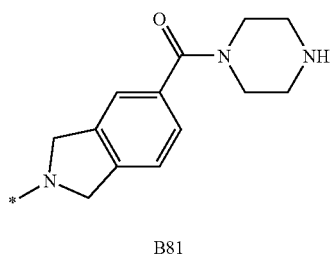 [SMILES: "B81" ; *N1Cc2ccc(C(=O)N3CCNCC3)cc2C1]
B81
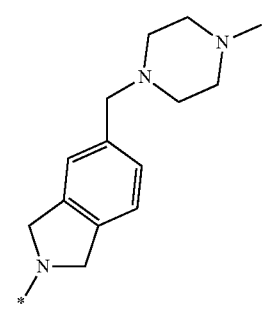
B82

TABLE 2-continued
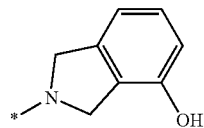
B83
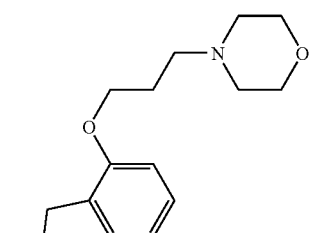
B84
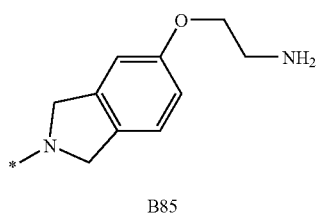 [SMILES: "B85" ; *N1Cc2ccc(OCCN)cc2C1]
B85
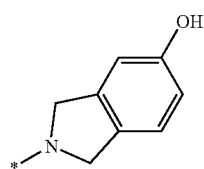
B86
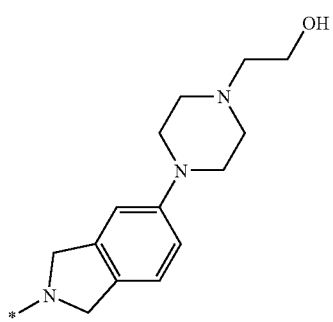
B87
TABLE 2-continued
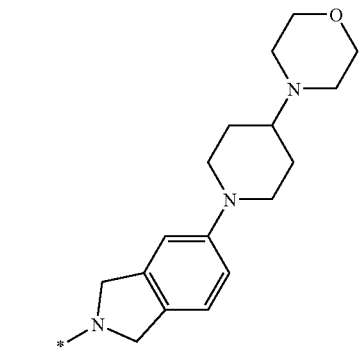
B88
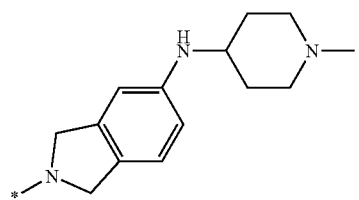
B89
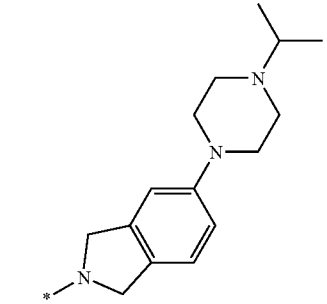
B90
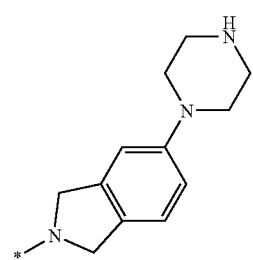
B91
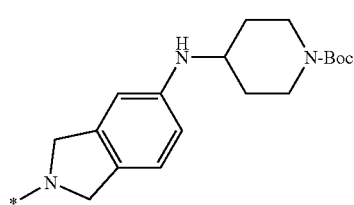
B92

TABLE 2-continued
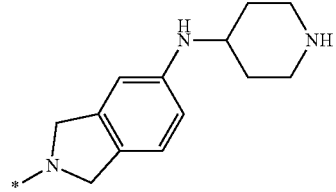
B93
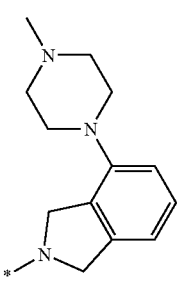
B94
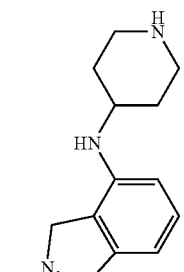
B95
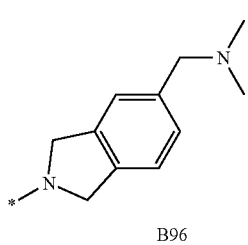 [SMILES: "B96" ; *N1Cc2ccc(CN(C)C)cc2C1]
B96
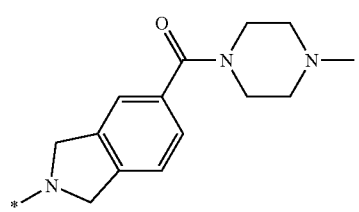
B97
TABLE 2-continued
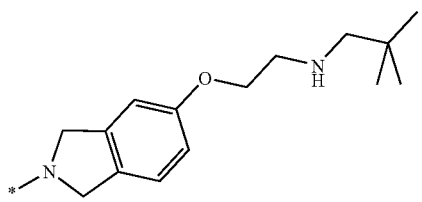
B98
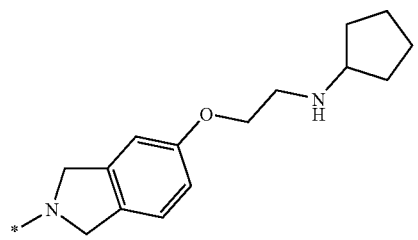
B99
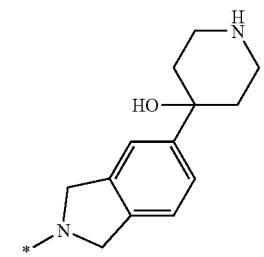
B100
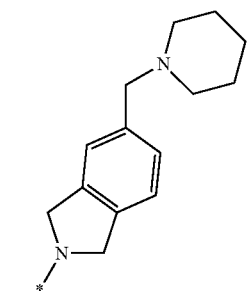
B101
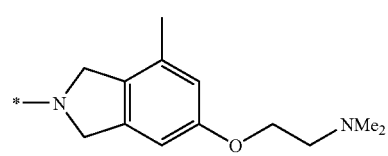
B102
One set of preferred groups $NR^5R^6$ consists of or includes groups B8 and B30.
Another preferred group $NR^5R^6$ is group B8.
A further set of preferred groups $NR^5R^6$ consists of groups B8, B35, B36, B37, B38, B39, B40, B41, B42, B43, B45, B46, B48, B53, B54, B55, B55, B57, B58, B59, B60, B61 and B62.

A further set of preferred groups $NR^5R^6$ consists of groups B8, B35, B36, B37, B38, B39, B40, B41, B42, B43, B45, B46, B48, B53, B54, B55, B56, B57, B58, B59, B60, B61 and B62

Another set of preferred groups consists of B8, B35, B36, B37, B38, B39, B40, B41, B42, B43, B45, B46, B48, B53, B54, B55, B56, B57, B58, B59, B60, B61, B62, B71, B72, B74, B75, B76, B77, B78, B79, B80, 881, B82, B83, B85, B86, B87, B93, B94, B95, B97, B98, B99, B100 and B100.

A further sub-set of groups $NR^5R^6$ consists of B43, B46, B48, B76, B82, B89, B91 and B96. Within this sub-set, more preferred groups are groups B43, B46, B48, B76, B82, B89 and B91, with B76, B82 and B89 being particularly preferred.

Particular and Preferred Subgroups

One sub-group of compounds for use in the invention can be represented by the general formula (II):

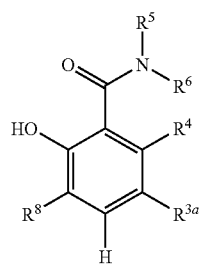

(II)

or salts, tautomers, solvates and N-oxides thereof; wherein:
$R^{3a}$ is selected from hydrogen, halogen, cyano, $C_{1-5}$ hydrocarbyl and $C_{1-5}$ hydrocarbyloxy;
wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
or $R^{3a}$ and $R^4$ together form a monocyclic carbocyclic or heterocyclic ring of 5 to 7 ring members;
$R^5$ and $R^6$ together with the nitrogen atom to which they are attached form a bicyclic group having up to 12 ring members (e.g. 8-12 ring members or 9-10 ring members) of which up to 5 ring members are heteroatoms selected from oxygen, nitrogen and sulphur; and
$R^6$ is selected from hydrogen and fluorine.

Another sub-group of compounds for use in the invention can be represented by the formula (III):

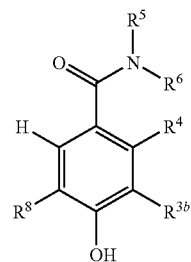

(III)

or salts, tautomers, solvates and N-oxides thereof; wherein:
$R^{3b}$ is selected from hydrogen, halogen, cyano, $C_{1-5}$ hydrocarbyl and $C_{1-5}$ hydrocarbyloxy;
wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
or $R^{3b}$ and $R^4$ together form a monocyclic carbocyclic or heterocyclic ring of 5 to 7 ring members;
$R^5$ and $R^6$ together with the nitrogen atom to which they are attached form a bicyclic group having from up to 12 ring members (e.g. 8-12 ring members or 9-10 ring members) of which up to 5 ring members are heteroatoms selected from oxygen, nitrogen and sulphur; and
$R^8$ is selected from hydrogen and fluorine.

A further sub-group of compounds for use in the invention can be represented by the formula (IV):

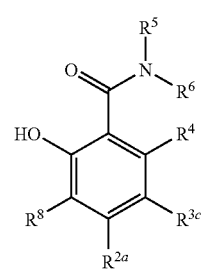

(IV)

or salts, tautomers, solvates and N-oxides thereof; wherein:
$R^{2a}$ is selected from hydroxy and methoxy (and is preferably hydroxy);
$R^{3c}$ is selected from hydrogen, halogen, cyano, $C_{1-5}$ hydrocarbyl and $C_{1-5}$ hydrocarbyloxy; wherein the $C_{1-5}$ hydrocarbyl and $C_{1-5}$ hydrocarbyloxy moieties are each optionally substituted by one or more substituents selected from hydroxy, halogen, $C_{1-2}$ alkoxy, amino, mono- and di-$C_{1-2}$ alkylamino, and aryl and heteroaryl groups of 5 to 12 ring members;
$R^4$ is selected from hydrogen; a group —$(O)_n$—$R^7$ where n is 0 or 1 and $R^7$ is an acyclic $C_{1-5}$ hydrocarbyl group or a monocyclic carbocyclic or heterocyclic group having 3 to 7 ring members; halogen; cyano; hydroxy; amino; and mono- or di-$C_{1-5}$ hydrocarbyl-amino, wherein the acyclic $C_{1-5}$ hydrocarbyl group and the mono and di-$C_{1-5}$ hydrocarbylamino moieties in each instance are optionally substituted by one or more substituents selected from hydroxy, halogen, $C_{1-2}$ alkoxy, amino, mono- and di-$C_{1-2}$alkylamino, and aryl and heteroaryl groups of 5 to 12 ring members;

or $R^{3c}$ and $R^4$ together form a monocyclic carbocyclic or heterocyclic ring of 5 to 7 ring members;

$R^5$ and $R^6$ together with the nitrogen atom to which they are attached form a bicyclic group having up to 12 ring members (e.g. 8-12 ring members or 9-10 ring members) of which up to 5 ring members are heteroatoms selected from oxygen, nitrogen and sulphur; and $R^8$ is selected from hydrogen and fluorine.

Within formulae (II), (III) and (IV), particular sub-groups of compounds are those wherein $NR^5R^6$ forms a bicyclic ring of up 10 ring members (e.g. 9 or 10 ring members, preferably 9 ring members) of which up to 5 ring members are heteroatoms selected from O, N and S, the monocyclic or bicyclic ring being optionally substituted by up to three substituent groups $R^{10}$, $R^{10a}$, $R^{10c}$, $R^{10cc}$ and $R^{10cc}$ as defined herein, more typically up to two substituents, for example up to one substituent.

More particular substituents for the bicyclic heterocyclic group $NR^5R^6$ are those forming part of a sub-group $R^{10d}$ which consists of the members of sub-group $R^{10c}$ and fluoro, chloro, bromo, trifluoromethyl, difluoromethoxy, trifluoromethoxy, cyano, methyl, ethyl, cyclopropyl, hydroxy, methylsulphonyl, amino, methylamino, dimethylamino, methoxy, ethoxy, hydroxymethyl, hydroxyethyl, ethoxycarbonyl, methoxycarbonyl, aminocarbonyl, oxo, methoxymethyl, carboxy, phenyl, $C_{1-2}$ alkoxycarbonyl, aminocarbonyl, acetyl, methylsulphonyl and pyridyl. Within this sub-group, one sub-set of substituents includes methyl, ethyl, chloro, fluoro, hydroxy, methylsulphonyl, amino, methylamino, dimethylamino, cyano, methoxy, ethoxy, hydroxymethyl, cyclopropyl, hydroxyethyl, ethoxycarbonyl, methoxycarbonyl, aminocarbonyl, oxo, methoxymethyl and acetyl.

For example, $NR^5R^6$ can form a 5.6 or 6.6 fused bicyclic ring of 9 or ten ring members of which 1 to 3 are heteroatoms, the bicyclic ring being optionally substituted by one or more substituents $R^{10}$ or $R^{10a}$ or $R^{10b}$ or $R^{10c}$ or $R^{10cc}$ or $R^{10d}$ and sub-groups (sub-sets) and examples thereof as defined herein.

Within this sub-group, examples of fused bicyclic rings are those in which a non-aromatic ring such as a pyrrolidine, piperidine, piperazine or morpholine ring is fused to a 6-membered aryl or heteroaryl ring such as a benzene or pyridine ring, and wherein a nitrogen atom present in the non-aromatic ring is bonded to the carbonyl group in formulae (II), (III) or (IV).

Particular fused bicyclic rings include dihydroindole, dihydroisoindole, tetrahydroquinoline and tetrahydroisoquinoline, and aza-analogues thereof in which one or two carbon ring members in the aromatic ring are replaced by nitrogen.

One sub-group of bicyclic heterocyclic groups formed by $NR^5R^6$ consists of dihydroisoindole optionally substituted by one or more (e.g. 1, 2 or 3) optional substituents selected from groups $R^{10}$, $R^{10a}$, $R^{10b}$ and $R^{10c}$ or $R^{10cc}$ and or $R^{10d}$ and sub-groups (sub-sets) and examples thereof as defined herein.

Preferred compounds are those wherein the group $R^{3a}$ or $R^{3b}$ or $R^{3c}$ is selected from hydrogen, halogen and $C_{1-5}$ alkyl; wherein the $C_{1-5}$ alkyl moiety in each instance is optionally substituted by one or more substituents selected from hydroxy, halogen, $C_{1-2}$ alkoxy and amino.

More preferably, the group $R^{3a}$ or $R^{3b}$ or $R^{3c}$ is hydrogen or a C alkyl group optionally substituted by one or more substituents selected from hydroxy, halogen, $C_{1-2}$ alkoxy and amino. In particular, the group $R^{3a}$ or $R^{3b}$ or $R^{3c}$ is selected from hydrogen and isopropyl, sec-butyl, tert-butyl and 1,2-dimethylpropyl groups.

Another sub-group of compounds for use in the invention is represented by formula (V):

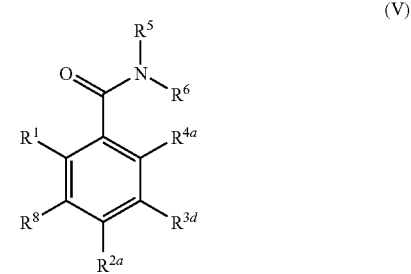

(V)

or salts, tautomers, solvates and N-oxides thereof;

wherein $R^1$ is hydrogen or hydroxy; $R^{2a}$ is hydroxy or methoxy; provided that at least one of $R^1$ and $R^{2a}$ is hydroxy; $R^{3d}$ is selected from ethyl and secondary and tertiary alkyl groups of 3 to 6 carbon atoms; $R^{4a}$ is selected from hydrogen, fluorine, chlorine and methoxy; and $R^5$, $R^6$ and $R^8$ are as defined herein; provided that when $R^1$ and $R^2$ are both hydroxy, then $R^{3d}$ can additionally be selected from hydrogen.

In one embodiment, when $R^1$ and $R^2$ are both hydroxy, $R^{3d}$ is hydrogen.

In another embodiment, $R^{3d}$ is ethyl or a secondary or tertiary alkyl group. Particularly preferred alkyl groups $R^{3d}$ are ethyl, isopropyl and tert-butyl, and in particular isopropyl.

Within formulae (II) to (V), preferred groups $NR^5R^6$ are dihydroisoindole groups which may be substituted or unsubstituted by one, two or three groups $R^{10}$, $R^{10a}$ or $R^{10b}$ or $R^{10c}$ or $R^{10cc}$ or $R^{10d}$ and sub-groups (sub-sets) and examples thereof as defined herein but, in one particular embodiment, are unsubstituted.

Another preferred sub-set of compounds can be represented by formula (VI):

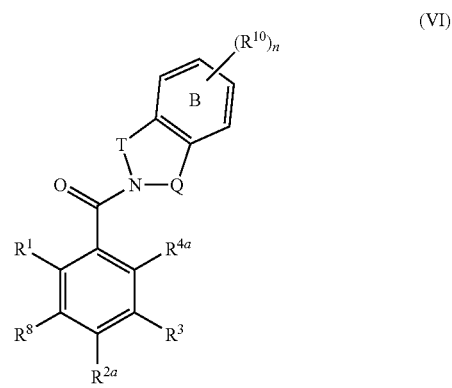

(VI)

or salts, tautomers, solvates and N-oxides thereof;

wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10})_j$ and Q is a group $(CHR^{10})_k$ where j and k are each 0, 1, 2 or 3 provided that the sum of j and k is 2 or 3; n is 0, 1, 2 or 3 and $R^3$, $R^{4a}$, $R^8$ and $R^{10}$ are as defined herein.

Another preferred sub-set of compounds can be represented by formula (VIa):

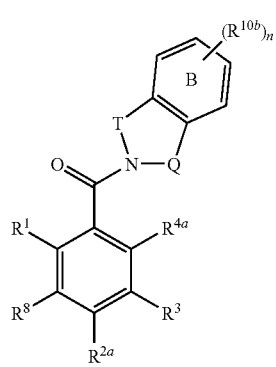
(VIa)

or salts, tautomers, solvates and N-oxides thereof;

wherein $R^1$ is hydroxy or hydrogen; $R^{2a}$ is hydroxy or methoxy (preferably hydroxy) provided that at least one of $R^1$ and $R^{2a}$ is hydroxy, ring B is an aromatic ring containing up to two (and preferably 0 or 1) nitrogen heteroatom ring members; T is a group $(CHR^{10b})_j$ and Q is a group $(CHR^{10b})_k$ where j and k are each 0, 1, 2 or 3 provided that the sum of j and k is 2 or 3; n is 0, 1, 2 or 3 and $R^3$, $R^{4a}$, $R^8$ and $R^{10b}$ are as defined herein.

In one sub-group of compounds within formula (VI) or formula (VIa), $R^1$ is hydrogen.

In another subgroup of compounds within formula (VI) or formula (VIa), $R^1$ is hydroxy.

In formula (VI), examples of the bicyclic group:

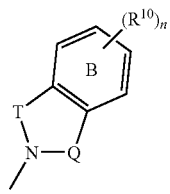

include the groups C1 to C6 below.

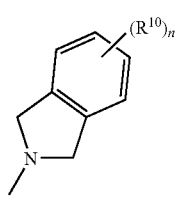
C1

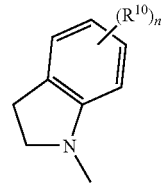
C2

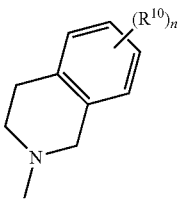
C3

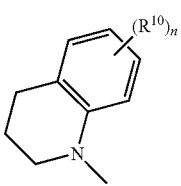
C4

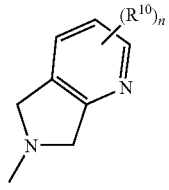
C5

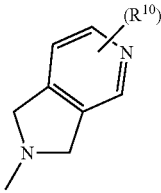
C6

Preferred Groups are Groups C1, C5 and C6

In the groups C1 to C6, the moiety $R^{10}$ can be a group $R^{10}$ as hereinbefore defined or can be a group $R^{10b}$, $R^{10c}$, $R^{10cc}$ or $R^{10ccc}$ as defined herein. In each case, n is preferably 1, 2 or 3, and more preferably is 1 or 2, e.g. 1.

A currently preferred group is group C1.

Within formula (VI), one particular group of compounds can be represented by the formula (VII):

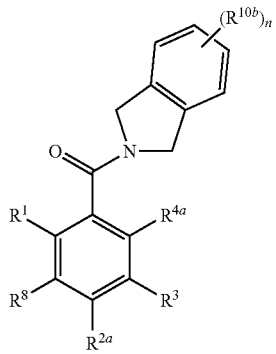
(VII)

or salts, tautomers, solvates and N-oxides thereof;
wherein $R^1$, $R^{2a}$, $R^3$, $R^{4a}$, $R^8$ and $R^{10b}$ are as defined herein and n is 0, 1 2 or 3 (more preferably 0, 1 or 2, e.g. 0 or 1), and provided that at least one of $R^1$ and $R^{2a}$ is hydroxy.

Within formulae (VI) and (VI), the substituent $R^3$ is preferably a group $R^{3d}$ as defined herein and/or the substituent $R^{10b}$ is either absent (n=0) or is selected from groups $R^{10c}$ and $R^{10d}$ and sub-groups (sub-sets) and examples thereof as defined herein. Preferably $R^1$ and $R^{2a}$ are both hydroxy.

One particular group of compounds for use in the invention within formula (VII) is represented by the formula (VIIa):

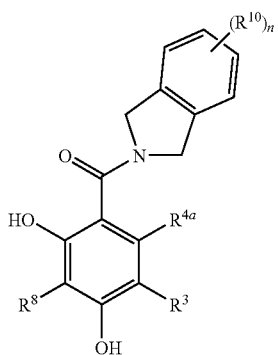

(VIIa)

or salts, tautomers, solvates and N-oxides thereof;
wherein $R^3$ is selected from hydrogen, halogen, $C_{1-5}$ alkyl, $C_{2-5}$ alkenyl and $C_{3-4}$ cycloalkyl groups;
$R^{4a}$ is selected from hydrogen, fluorine, chlorine and methoxy; $R^8$ is hydrogen or fluorine; n is 0, 1 2 or 3; and $R^{10}$ is as defined herein.

Within formula (VIIa), $R^{10}$ can be selected from, for example, one, two or three groups $R^{10a}$ or $R^{10b}$ or $R^{10c}$ or $R^{10cc}$ or $R^{10d}$ and sub-groups (sub-sets) and examples thereof as defined herein.

One preferred group of compounds within formula (VII) for use in the invention is represented by the formula (VIIb):

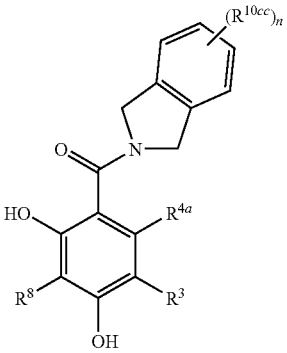

(VIIb)

or salts, tautomers, solvates and N-oxides thereof;
wherein $R^3$ is selected from hydrogen, halogen, $C_{1-5}$ alkyl, $C_{2-5}$ alkenyl and $C_{3-4}$ cycloalkyl groups;
$R^{4a}$ is selected from hydrogen, fluorine, chlorine and methoxy; $R^8$ is hydrogen or fluorine; n is 0, 1 2 or 3; and $R^{10cc}$ is selected from:

halogen;
$CO_2R^{14}$ wherein $R^{14}$ is hydrogen or $C_{1-6}$ alkyl;
$C_{1-4}$ alkyl optionally substituted by hydroxy or $C_{1-2}$ alkoxy;
$C_{1-4}$ alkoxy optionally substituted by hydroxy or $C_{1-2}$ alkoxy; or
a group [sol], $CH_2$[sol], $C(O)$[sol], $OCH_2CH_2$[sol] or $OCH_2CH_2CH_2$[sol] where [sol] is selected from the following groups

[sol] =

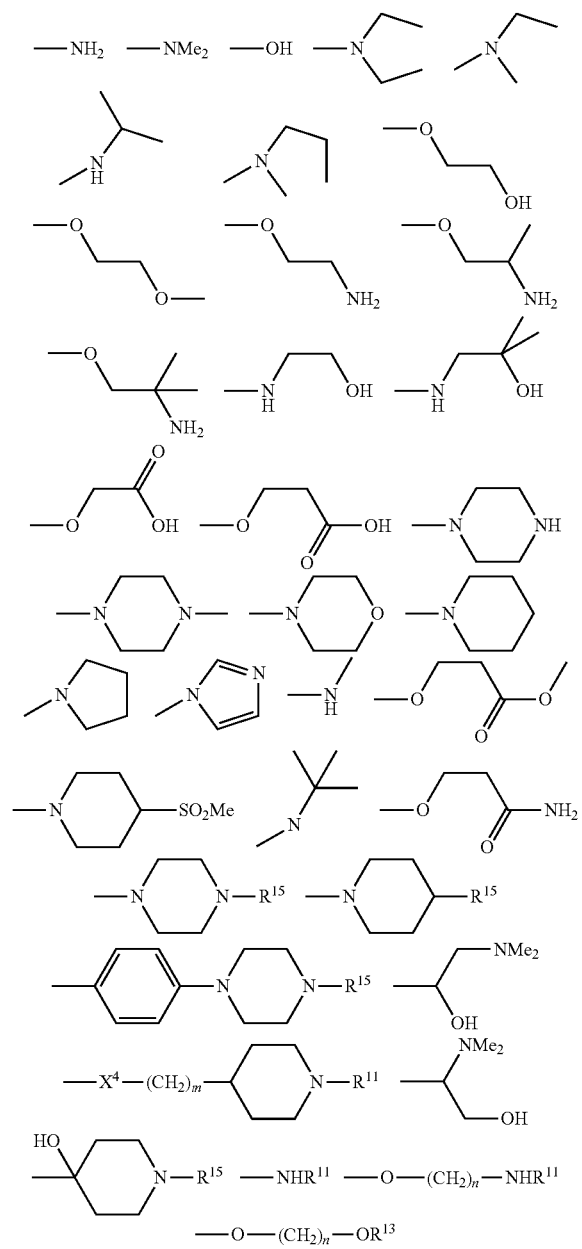

wherein $X^4$ is NH or O, m is 0 or 1, n is 1, 2 or 3, $R^{11}$ is hydrogen, $COR^{12}$, $C(O)OR^{12}$ or $R^{12}$; $R^{12}$ is $C_{1-6}$ alkyl, $C_{3-6}$ cycloalkyl, aryl, aryl-$C_{1-6}$ alkyl or $CH_2R^{15}$; and $R^{15}$ is selected from hydrogen, $C_{1-6}$ alkyl, $C_{3-6}$ cycloalkyl, hydroxy-$C_{1-6}$ alkyl, piperidine, N—$C_{1-6}$ alkylpiperazine, piperazine, morpholine, $COR^{13}$ or $C(O)OR^{13}$; and $R^{13}$ is $C_{1-6}$ alkyl.

In a further embodiment, the compound can be an aza- or diaza-analogue of the compounds of formulae (VI), (VII) and (VIIa) as defined herein wherein one or two of the carbon atoms of the benzene ring attached to the five membered ring is replaced by nitrogen.

For example, the group:

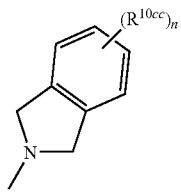

in the compound of formula (VIIa)
may be replaced by:

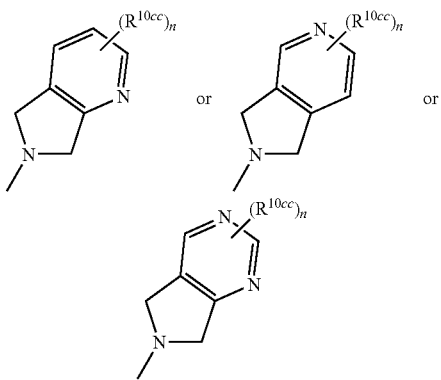

In each of formulae (VI), (VIa), (VII), (VIIa) and (VIIb) and subgroups thereof as defined herein, n is preferably 1, 2 or 3, and more preferably is 1 or 2. In one embodiment, n is 1.

Specific compounds for use in the invention include:
(5-chloro-2-hydroxy-phenyl)-(1,3-dihydro-isoindol-2-yl)-methanone;
(3-tert-butyl-4-hydroxy-phenyl)-(2,3-dihydro-indol-1-yl)-methanone;
(3-tert-butyl-4-hydroxy-phenyl)-(3,4-dihydro-2H-quinolin-1-yl)-methanone;
(3,4-dihydro-1H-isoquinolin-2-yl)-(4-hydroxy-3-isopropyl-phenyl)-methanone;
(1,3-dihydro-isoindol-2-yl)-(2,4-dihydroxy-5-isopropyl-phenyl)-methanone;
(3-tert-butyl-4-hydroxy-phenyl)-(1,4-dioxa-8-aza-spiro[4.5]dec-8-yl)-methanone;
(3-tert-butyl-4-hydroxy-phenyl)-(1,3-dihydro-isoindol-2-yl)-methanone;
(3-tert-butyl-4-hydroxy-phenyl)-pyrrolo[3,2-b]pyridin-1-yl-methanone;
8-(3-tert-butyl-4-hydroxy-benzoyl)-2-methyl-2,8-diaza-spiro[4.5]decan-1-one;
(1,3-dihydro-isoindol-2-yl)-(4-hydroxy-3-isopropyl-phenyl)-methanone;
(3-tert-butyl-4-hydroxy-phenyl)-(3,4-dihydro-1H-isoquinolin-2-yl)-methanone;
(1,3-dihydro-isoindol-2-yl)-(5-ethyl-2,4-dihydroxy-phenyl)-methanone;
(5-cyclopropyl-2,4-dihydroxy-phenyl)-(1,3-dihydro-isoindol-2-yl)-methanone;
(5-sec-butyl-2,4-dihydroxy-phenyl)-(1,3-dihydro-isoindol-2-yl)-methanone;
(1,3-dihydro-isoindol-2-yl)-(2,4-dihydroxy-phenyl)-methanone;
(5-chloro-1,3-dihydro-isoindol-2-yl)-(2,4-dihydroxy-5-isopropyl-phenyl)-methanone;
[5-(3-amino-propoxy)-1,3-dihydro-isoindol-2-yl]-(2,4-dihydroxy-5-isopropyl-phenyl)-methanone;
(5-bromo-2,4-dihydroxy-phenyl)-(1,3-dihydro-isoindol-2-yl)-methanone;
(1,3-dihydro-isoindol-2-yl)-(2,4-dihydroxy-5-trifluoromethyl-phenyl)-methanone;
(2,4-dihydroxy-5-isopropyl-phenyl)-[4-[2-(2-methoxy-ethoxy)-ethoxy]-1,3-dihydro-isoindol-2-yl]methanone;
(2,4-dihydroxy-5-isopropyl-phenyl)-[4-(2-dimethylamino-ethoxy)-1,3-dihydro-isoindol-2-yl]-methanone;
(24-dihydroxy-5-isopropyl-phenyl)-[4-(3-morpholin-4-yl-propoxy)-1,3-dihydro-isoindol-2-yl]methanone;
(3-sec-butyl-4-hydroxy-phenyl)-(1,3-dihydro-isoindol-2-yl)-methanone;
(5-tert-butyl-2,4-dihydroxy-phenyl)-(1,3-dihydro-isoindol-2-yl)-methanone;
(5-chloro-2,4-dihydroxy-phenyl)-(1,3-dihydro-isoindol-2-yl)-methanone;
(1,3-dihydro-isoindol-2-yl)-(2-hydroxy-5-isopropyl-4-methoxy-phenyl)-methanone;
(4,7-difluoro-1,3-dihydro-isoindol-2-yl)-(2,4-dihydroxy-5-isopropyl-phenyl)-methanone;
(2,4-dihydroxy-5-isopropyl-phenyl)-(5-fluoro-1,3-dihydro-isoindol-2-yl)-methanone;
(1,3-dihydro-isoindol-2-yl)-(3-fluoro-2,4-dihydroxy-5-isopropyl-phenyl)-methanone;
(1,3-dihydro-isoindol-2-yl)-(2-fluoro-4,6-dihydroxy-3-isopropyl-phenyl)-methanone;
(2,4-dihydroxy-5-isopropyl-phenyl)-(4-fluoro-1,3-dihydro-isoindol-2-yl)-methanone hydrochloride;
(5-chloro-6-methoxy-1,3-dihydro-iso-indol-2-yl)-(2,4-dihydroxy-5-isopropyl-phenyl)-methanone;
(2,4-dihydroxy-5-isopropyl-phenyl)-[5-(2-methoxy-ethoxy)-1,3-dihydro-isoindol-2-yl]-methanone;
(2,4-dihydroxy-5-isopropyl-phenyl)-[5-(3-morpholin-4-yl-propoxy)-1,3-dihydro-isoindol-2-yl]-methanone;
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-(2-oxa-5-aza-bicyclo[2.2.1]hept-5-yl)-methanone;
(3,4-dihydro-1H-isoquinolin-2-yl)-(2,4-dihydroxy-5-isopropyl-phenyl)-methanone;
(5-amino-1,3-dihydro-isoindol-2-yl)-(2,4-dihydroxy-5-isopropyl-phenyl)-methanone;
(2,4-dihydroxy-5-isopropyl-phenyl)-(5-methoxy-1,3-dihydroisoindol-2-yl)-methanone;
(2,4-dihydroxy-5-isopropyl-phenyl)-(5-morpholin-4-yl-1,3-dihydro-isoindol-2-yl)-methanone;
(2,4-dihydroxy-5-isopropyl-phenyl)-[5-(4-methyl-piperazin-1-yl)-1,3-dihydro-isoindol-2-yl]-methanone;
2-(2,4-dihydroxy-5-isopropyl-benzoyl)-2,3-dihydro-1H-isoindole-5-carboxylic acid methyl ester;
2-(2,4-dihydroxy-5-isopropyl-benzoyl)-2,3-dihydro-1H-isoindole-5-carboxylic acid;
(2,4-dihydroxy-5-isopropyl-phenyl)-(5-morpholin-4-ylmethyl-1,3-dihydro-isoindol-2-yl)-methanone;
{3-[2-(2,4-dihydroxy-5-isopropyl-benzoyl)-2,3-dihydro-1H-isoindol-5-yloxy]-propyl}-carbamic acid tert-butyl ester;
(2,4-dihydroxy-5-isopropyl-phenyl)-(5-methyl-1,3-dihydro-isoindol-2-yl)-methanone;

(2,4-dihydroxy-5-isopropyl-phenyl)-[5-(2-isopropylamino-ethoxy)-1,3-dihydro-isoindol-2-yl]-methanone;
N-{2-[2,4-dihydroxy-5-isopropyl-benzoyl)-2,3-dihydro-1H-isoindol-5-yloxy]-ethyl}-2-morpholin-4-yl-acetamide;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-{5-[4-(4-methyl-piperazin-1-yl)-piperidin-1-yl]-1,3-dihydro-isoindol-2-yl}-methanone;
(2,4-dihydroxy-5-isopropyl-phenyl)-[5-(4-piperazin-1-yl-phenyl)-1,3-dihydro-isoindol-2-yl]-methanone;
2,4-dihydroxy-5-isopropyl-phenyl)-[5-(1-dimethylamino-2-hydroxy-ethyl)-1,3-dihydro-isoindol-2-yl]-methanone;
dihydroxy-5-isopropyl-phenyl)-[5-(2-dimethylamino-1-hydroxy-ethyl)-1,3-dihydro-isoindol-2-yl]-methanone;
(2,4-dihydroxy-5-isopropyl-phenyl)-[5-(piperazine-1-carbonyl)-1,3-dihydro-isoindol-2-yl]-methanone hydrochloride;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[4-(3-morpholin-4-yl-propoxy)-1,3-dihydro-isoindol-2-yl]methanone;
[5-(2-amino-ethoxy)-1,3-dihydro-isoindol-2-yl]-(2,4-dihydroxy-5-isopropyl-phenyl)-methanone;
(2,4-dihydroxy-5-isopropyl-phenyl)-(5-hydroxy-1,3-dihydro-isoindol-2-yl)-methanone;
(2,4-dihydroxy-5-isopropyl-phenyl)-{5-[4-(2-hydroxy-ethyl)-piperazin-1-yl]-1,3-dihydro-isoindol-2-yl}-methanone;
(2,4-dihydroxy-5-isopropyl-phenyl)-[5-(4-morpholin-4-yl-piperidin-1-yl)-1,3-dihydro-isoindol-2-yl]-methanone;
(2,4-dihydroxy-5-isopropyl-phenyl)-[5-(1-methyl-piperidin-4-ylamino)-1,3-dihydro-isoindol-2-yl]-methanone;
(2,4-dihydroxy-5-isopropyl-phenyl)-[5-(4-isopropyl-piperazin-1-yl)-1,3-dihydro-isoindol-2-yl]-methanone;
(2,4-dihydroxy-5-isopropyl-phenyl)-(5-piperazin-1-yl-1,3-dihydro-isoindol-2-yl)-methanone;
4-[2-(2,4-Dihydroxy-5-isopropyl-benzoyl)-2,3-dihydro-1H-isoindol-5-ylamino]-piperidine-1-carboxylic acid tert-butyl ester;
(2,4-dihydroxy-5-isopropyl-phenyl)-[5-(piperidin-4-ylamino)-1,3-dihydro-isoindol-2-yl]-methanone;
(2,4-dihydroxy-5-isopropyl-phenyl)-[4-(4-methyl-piperazin-1-yl)-1,3-dihydro-isoindol-2-yl]-methanone;
(2,4-dihydroxy-5-isopropyl-phenyl)-[4-(piperidin-4-ylamino)-1,3-dihydro-isoindol-2-yl]-methanone;
(2,4-dihydroxy-5-isopropyl-phenyl)-(5-dimethylaminomethyl-1,3-dihydroisoindol-2-yl)-methanone;
(2,4-dihydroxy-5-isopropyl-phenyl)-[5-(4-methyl-piperazine-1-carbonyl)-1,3-dihydro-isoindol-2-yl]-methanone;
(2,4-dihydroxy-5-isopropyl-phenyl)-{5-[2-(2,2-dimethyl-propylamino)-ethoxy]-1,3-dihydro-isoindol-2-yl}methanone;
[5-(2-cyclopentylamino-ethoxy)-1,3-dihydro-isoindol-2-yl]-(2,4-dihydroxy-5-isopropyl-phenyl)-methanone;
(2,4-dihydroxy-5-isopropyl-phenyl)-(5-piperidin-1-ylmethyl-1,3-dihydro-isoindol-2-yl)-methanone;
(2,4-dihydroxy-5-isopropyl-phenyl)-[5-(4-hydroxypiperidin-4-yl)-1,3-dihydro-isoindol-2-yl]-methanone;
(5-chloro-2,4-dihydroxy-phenyl)-[5-(4-methyl-piperazin-1-yl)-1,3-dihydro-isoindol-2-yl]methanone;
(5-chloro-6-hydroxy-1,3-dihydro-isoindol-2-yl)-(2,4-dihydroxy-5-isopropyl-phenyl)-methanone;
(2,4-dihydroxy-5-isopropyl-phenyl)-[5-(4-methyl-piperazin-1-yl)-1,3-dihydro-isoindol-2-yl]-methanone;
(5-chloro-2,4-dihydroxy-phenyl)-[5-(4-methyl-piperazin-1-yl)-1,3-dihydro-isoindol-2-yl]methanone;
(2,4-dihydroxy-5-isopropyl-phenyl)-[5-(2-dimethylamino-ethoxy)-7-methyl-1,3-dihydro-isoindol-2-yl]-methanone;
and salts, solvates, N-oxides and tautomers thereof.

Preferred individual compounds of the formula (I) for use in the invention are:
(2,4-dihydroxy-5-isopropyl-phenyl)-[5-(2-dimethylamino-ethoxy)-1,3-dihydro-isoindol-2-yl]-methanone;
(2,4-dihydroxy-5-isopropyl-phenyl)-[5-(4-methyl-piperazin-1-yl)-1,3-dihydro-isoindol-2-yl]-methanone;
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone;
(2,4-dihydroxy-5-isopropyl-phenyl)-[5-(1-methyl-piperidin-4-ylamino)-1,3-dihydro-isoindol-2-yl]-methanone;
(2,4-dihydroxy-5-isopropyl-phenyl)-(5-piperazin-1-yl-1,3-dihydro-isoindol-2-yl)-methanone;
(2,4-dihydroxy-5-isopropyl-phenyl)-(5-dimethylaminomethyl-1,3-dihydroisoindol-2-yl)-methanone;
or salts, solvates, N-oxides and tautomers thereof.

Particularly preferred individual compounds for use in the invention are:
(2,4-dihydroxy-5-isopropyl-phenyl)-[5-(4-hydroxy-1-methyl-piperidin-4-yl)-1,3-dihydro-isoindol-2-yl]-methanone;
(2,4-dihydroxy-5-isopropyl-phenyl)-[5-(4-methyl-piperazin-1-ylmethyl)-1,3-dihydro-isoindol-2-yl]-methanone; and
(2,4-dihydroxy-5-isopropyl-phenyl)-[5-(1-methyl-piperidin-4-ylamino)-1,3-dihydro-isoindol-2-yl]-methanone;
or salts, solvates or tautomers thereof.

For the avoidance of doubt, it is to be understood that each general and specific preference, embodiment and example of the group $R^1$ may be combined with each general and specific preference, embodiment and example of the groups $R^2$ and/or $R^3$ and/or $R^4$ and/or $R^4$ and/or $R^5$ and/or $R^6$ and/or $R^{10}$ and/or Q and/or T and/or sub-groups thereof as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

In one embodiment, the formulae (I), (II), (III), (IV), (V), (VI), (VIa), (VII), (VIa) or (VIIb) and sub-groups thereof may be as defined herein but may optionally exclude the compound 2-(2-hydroxy-benzoyl)-1,2,3,4-tetrahydro-isoquinoline-3-carboxylic acid and salts and optionally N-oxides and/or esters and/or tautomers and/or prodrugs and/or protected forms thereof.

Salts, Solvates, Tautomers, Isomers, N-Oxides, Esters, Prodrugs and Isotopes

A reference to a compound of the formulae (I) and sub-groups thereof also includes ionic forms, salts, solvates, isomers, tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof.

Many compounds of the formula (I) can exist in the form of salts, for example acid addition salts or, in certain cases salts of organic and inorganic bases such as phenolate, carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic [which may be referred to elsewhere herein simply as L-lactic acid], (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

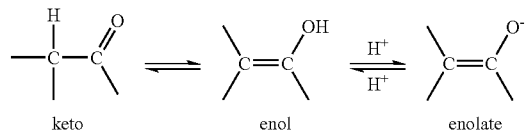

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and i isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds for use in the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

In one general embodiment, formula (I) and sub-formulae, sub-groups, preferences and examples thereof do not cover esters such as carboxylic acid esters and acyloxy esters.

In one particular embodiment, formula (I) and sub-formulae, sub-groups, preferences and examples thereof do not cover esters of hydroxy compounds wherein $R^2$ is hydroxy and the ester is formed with the hydroxy group $R^2$.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is:
$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

One preferred compound of the formula (I) is the compound of formula ((VIII):

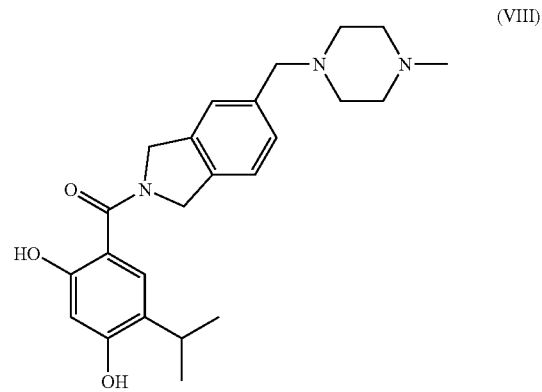 [SMILES: CC(C)c1cc(C(=O)N2Cc3ccc(CN4CCN(C)CC4)cc3C2)c(O)cc1O]

which has the chemical name (2,4-dihydroxy-5-isopropyl-phenyl)-[5-(4-methyl-piperazin-1-ylmethyl)-1,3-dihydro-isoindol-2-yl]-methanone.

Acid Addition salts of 2,4-dihydroxy-5-isopropyl-phenyl)-[5-(4-methyl-piperazin-1-ylmethyl)-1,3-dihydro-isoindol-2-yl]-methanone The 2,4-dihydroxy-5-isopropyl-phenyl)-[5-(4-methyl-piperazin-1-ylmethyl)-1,3-dihydro-isoindol-2-yl]-methanone may be presented in the form of an acid addition salt.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), aspartic (e.g. L-aspartic), benzenesulphonic, benzoic, 4-acetamidobenzoic, butanoic, camphoric (e.g. (+) camphoric), camphor-sulphonic, (+)-(1S)-camphor-10-sulphonic, capric, caproic, caprylic, carbonic, cinnamic, citric, cyclamic, dodecanoic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, isobutyric, lactic (e.g. (+)-L-lactic and (±)-DL-lactic), laurylsulphonic, lactobionic, maleic, malic, (−)-L-malic, malonic, (±)-DL-mandelic, methanesulphonic, mucic, naphthalenesulphonic (e.g. naphthalene-2-sulphonic and naphthalene-1,5-disulphonic), 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, toluenesulphonic (e.g. p-toluenesulphonic), undecylenic, valeric acids and xinafoic acids.

Particular acid addition salts are the salts formed with hydrochloric acid, lactic acid (e.g. L-lactic acid) or sulphuric acid.

A preferred salt is the salt formed with lactic acid, i.e. the lactate salt and in particular the L-lactate salt.

The acid addition salts are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19.

In the solid state, the acid addition salts can be crystalline or amorphous or a mixture thereof.

In one embodiment, the salts are amorphous.

In an amorphous solid, the three dimensional structure that normally exists in a crystalline form does not exist and the positions of the molecules relative to one another in the amorphous form are essentially random, see for example Hancock et al. J. Pharm. Sci. (1997), 86, 1).

In another embodiment, the acid addition salts are substantially crystalline.

The acid addition salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound of formula (VIII) with the appropriate acid in water or in an organic solvent, or in a mixture of the two.

For example, the acid addition salt can be prepared by forming a solution of (2,4-dihydroxy-5-isopropyl-phenyl)-[5-(4-methyl-piperazin-1-ylmethyl)-1,3-dihydro-isoindol-2-yl]-methanone free base in a solvent (typically an organic solvent) or mixture of solvents, and treating the solution with an acid to form a precipitate of the acid addition salt.

The acid may be added as a solution in a solvent which is miscible with the solvent in which the free base is dissolved. The solvent in which the free base is initially dissolved may be one in which the acid addition salt thereof is insoluble. Alternatively, the solvent in which the free base is initially dissolved may be one in which the acid addition salt is at least partially soluble, a different solvent in which the acid addition salt is less soluble subsequently being added such that the salt precipitates out of solution.

In an alternative method of forming an acid addition salt, (2,4-dihydroxy-5-isopropyl-phenyl)-[5-(4-methyl-piperazin-1-ylmethyl)-1,3-dihydro-isoindol-2-yl]-methanone is dissolved in a solvent comprising a volatile acid and optionally a co-solvent, thereby to form a solution of the acid addition salt with the volatile acid, and the resulting solution is then concentrated or evaporated to isolate the salt. An example of an acid addition salt that can be made in this way is the acetate salt.

The salt is typically precipitated from the organic solvent as it is formed and hence can be isolated by separation of the solid from the solution, e.g. by filtration.

One acid salt can be converted to the free base and optionally to another acid addition salt by methods well known to the skilled person. For example, the free base can be formed by passing the salt solution through a column containing an amine stationary phase (e.g. a Strata-NH2 column). Alternatively, a solution of the acid addition salt in water can be treated with sodium bicarbonate to decompose the salt and precipitate out the free base. The free base may then be combined with another acid by one of the methods described above or elsewhere herein.

Acid addition salts have a number of advantages over the corresponding free base. For example, they will enjoy one or more of the following advantages over the free base in that they:

will be more soluble and hence will be better for i.v. administration (e.g. by infusion)
will have better stability (e.g. improved shelf life);
will have better thermal stability;
will be less basic and therefore better for i.v. administration;
will have advantages for production;
will have improved solubility in aqueous solution;
will have better physicochemical properties;
may have improved anti-cancer activity; and
may have an improved therapeutic index.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition' for example for a period of six months or more, more usually twelve months or more, for example eighteen months or more. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

The terms "non-hygroscopic" and "non-hygroscopicity" and related terms as used herein refer to substances that absorb less than 5% by weight (relative to their own weight) of water when exposed to conditions of high relative humidity, for example 90% relative humidity, and/or do not undergo changes in crystalline form in conditions of high humidity and/or do not absorb water into the body of the crystal (internal water) in conditions of high relative humidity.

Crystalline Forms of 2,4-dihydroxy-5-isopropyl-phenyl)-[5-(4-methyl-piperazin-1-ylmethyl)-1,3-dihydro-isoindol-2-yl]-methanone In another preferred embodiment, the compound of formula (VIII) i.e. (2,4-dihydroxy-5-isopropyl-phenyl)-[5-(4-methyl-piperazin-1-ylmethyl)-1,3-dihydro-isoindol-2-yl]-methanone, or an acid addition salt thereof, is presented in substantially crystalline form.

By "substantially crystalline" is meant that the compound of formula (VIII) or its acid addition salt are from 50% to 100% crystalline, and more particularly the compound of formula (VIII) or its acid addition salts may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

More preferably the compound of formula (VIII) or its acid addition salts are those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

The crystalline forms, in the solid state, can be solvated (e.g. hydrated) or non-solvated (e.g. anhydrous).

In one embodiment, the crystalline forms are non-solvated (e.g. anhydrous).

The term "anhydrous" as used herein does not exclude the possibility of the presence of some water on or in the salt (e.g. a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the crystalline forms are solvated. Where the crystalline forms are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

The crystalline forms described herein, individual crystals thereof and their crystal structures form further aspects of the invention.

The crystalline forms and their crystal structures can be characterised using a number of techniques including single crystal X-ray crystallography, X-ray powder diffraction (XRPD), differential scanning calorimetry (DSP) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to conventional methods, such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

Alternatively, the crystalline structure of a compound can be analysed by the solid state technique of X-ray Powder Diffraction (XRPD). XRPD can be carried out according to conventional methods such as those described herein and in introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle ($2\theta$) and interplanar spacing (d) parameters of an X-ray diffraction spectrum. These are related by Bragg's equation, $n\lambda = 2d \sin \theta$, (where n=1; $\lambda$=wavelength of the cathode used; d=interplanar spacing; and $\theta$=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of $2\theta \pm 0.2°$. The peaks mean main peaks and include peaks not larger than medium at diffraction angles other than those stated above.

The compound of formula (VIII) and its acid addition salts exist in a number of different crystalline forms and these are described in more detail in our co-pending International patent application number PCT/GB2007/ . . . claiming priority from GB 0620259.2 and U.S. provisional patent application Ser. No. 60/829,243, both filed on 12 Oct. 2006.

Particular crystalline salts of interest are the L-lactate salts described below.

Crystalline forms of the salts formed between (2,4-dihydroxy-5-isopropyl-phenyl)-[5-(4-methyl-piperazin-1-ylmethyl)-1,3-dihydro-isoindol-2-yl]-methanone and L-lactic acid The lactic acid salts of the compound of formula (VIII) exist in one unstable form (FL3) and two stable forms (FL1 and FL2).

Form FL1

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle ($2\theta/°$) peak at 16.81.

Preferably, the XRPD pattern also exhibits diffraction angle (2θ/°) peaks at 6.53, 13.10, 14.13, 14.40, 17.22, 18.65, 19.52, 19.82, 22.33, 22.84 and 23.09.

More preferably, the XRPD pattern further exhibits diffraction angle (2θ/°) peaks at 6.18, 8.39, 11.08, 15.21, 16.21, 20.49, 20.76, 21.13, 22.02, 23.94, 25.19, 26.41, 26.95 and 27.81.

Most preferably, the XRPD pattern is substantially as shown in FIG. 1 herein.

Form FL1 can be prepared by suspending (2,4-dihydroxy-5-isopropyl-phenyl)-[5-(4-methyl-piperazin-1-ylmethyl)-1,3-dihydro-isoindol-2-yl]-methanone free base in a mixture of ethanol and EtOAc (e.g. in a volume ratio of 3:5); adding L-lactic acid to the mixture (e.g. wherein the L-lactic acid is in the form of a solution in ethanol); clarifying the mixture (e.g. by heating until clear and/or filtering off any remaining solid); stirring the clarified mixture with seeding and removing crystallised form FL1, e.g. by filtration.

Form FL2

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 22.34.

Preferably, the XRPD pattern also exhibits diffraction angle (2θ/°) peaks at 8.03, 10.71, 11.98, 13.13, 15.39, 16.09, 16.61, 17.26, 18.17, 18.82, 20.40, 21.01, 21.53, 22.34, 22.56, 23.71 and 27.70.

More preferably, the XRPD pattern further exhibits diffraction angle (2θ/°) peaks at 24.30, 24.65, 26.56 and 28.29.

Figure 2:
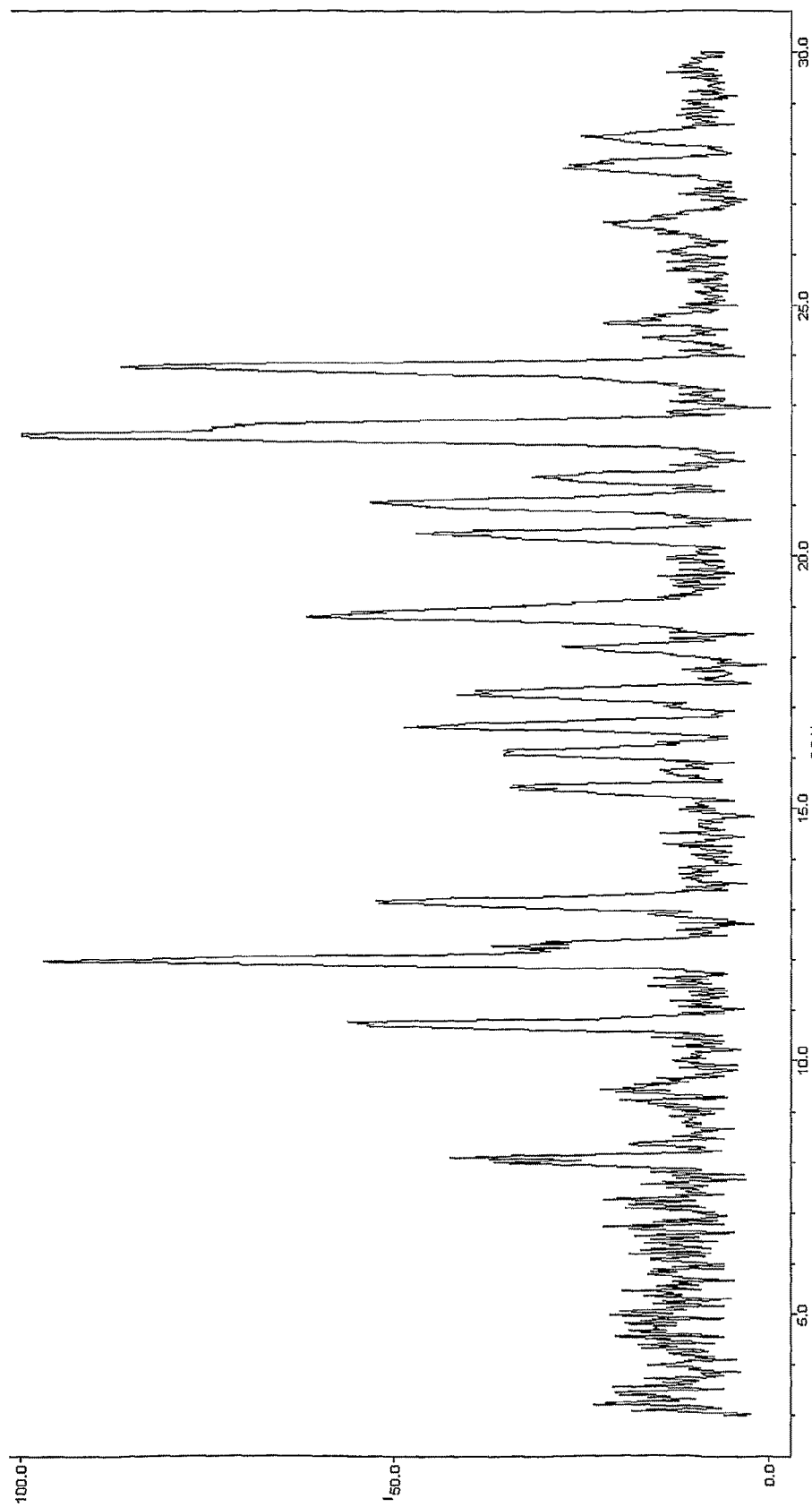

Most preferably, the XRPD pattern is substantially as shown in FIG. 2 herein.

Figure 3:
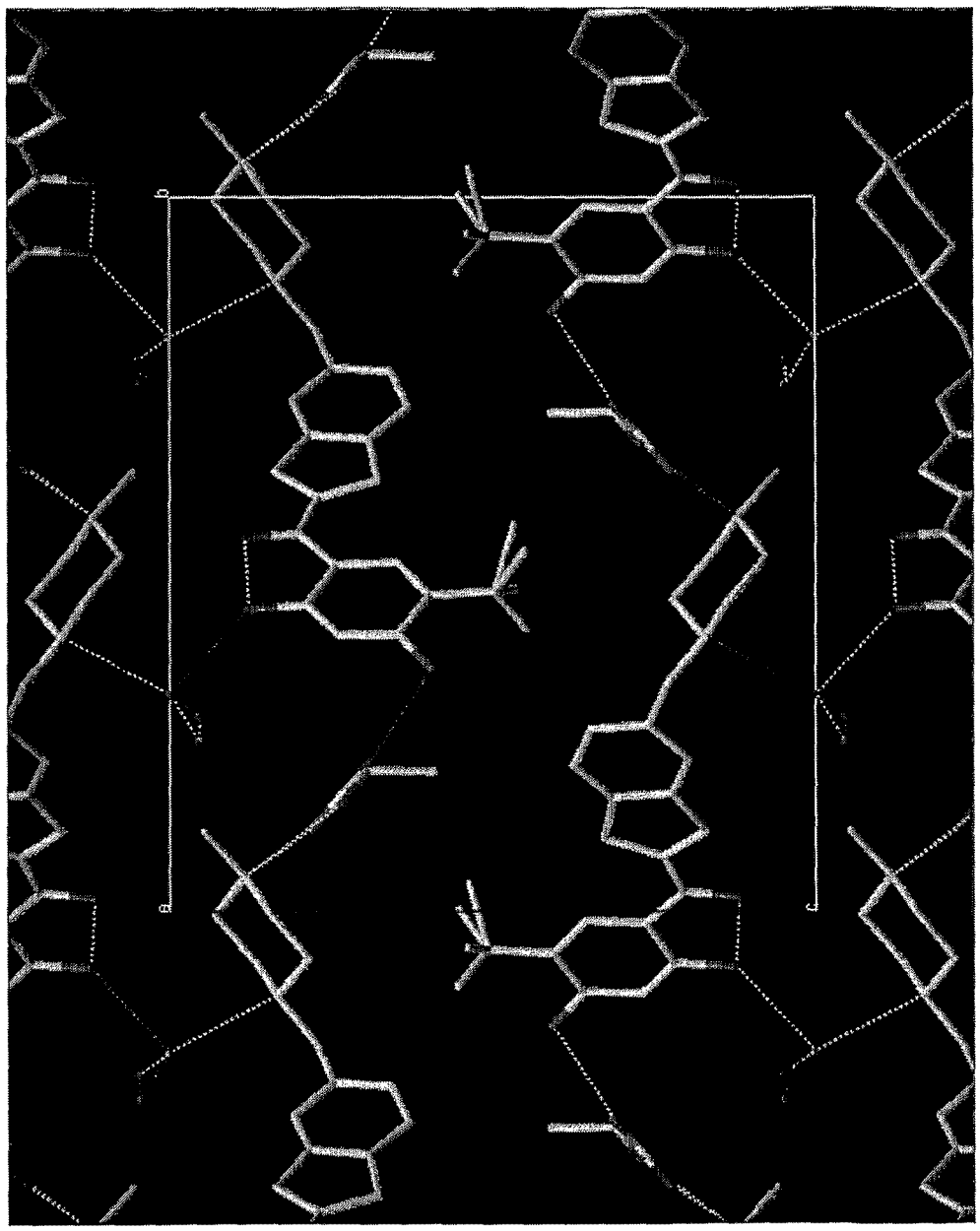

From X-ray crystallography studies, it has been found that form FL2 has a crystal structure that belongs belong to the monoclinic space group $P2_1$ and has crystal lattice parameters at 293 K a=5.8 b=16.6, c=14.9 Å, β=98 α=γ=90°. The crystal packing diagram is shown in FIG. 3 herein.

Accordingly, in another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate which is crystalline and:
(a) has a crystal structure as set out in FIG. 3; and/or
(b) has a crystal structure as defined by the coordinates in Table EX85B(ii) herein; and/or
(c) has crystal lattice parameters at 293 K a=5.8 b=16.6, c=14.9 Å, β=98 α=γ=90°; and/or
(d) has a crystal structure that belongs belong to a monoclinic space group such as $P2_1$.

Crystalline form FL2 is a stable hydrate which is nominally a trihydrate since there are three crystal; water positions in the asymmetric unit but they are not 100% occupied at room temperature and humidity. Form FL2 may be used for the preparation of solid pharmaceutical compositions. Accordingly, in another aspect, the invention provides combinations comprising a solid pharmaceutical composition containing 2,4-dihydroxy-5-isopropyl-phenyl)-[5-(4-methyl-piperazin-1-ylmethyl)-1,3-dihydro-isoindol-2-yl]-methanone L-lactate in crystalline form FL2 as defined herein.

Form FL2 can be prepared by precipitation from a saturated aqueous methanolic solution using acetone as the anti-solvent. More particularly, crystalline form FL2 can be prepared by a method which comprises forming saturated solution of form FL1 in methanol:water (preferably in a 9:1 ratio) and then adding acetone to precipitate form FL2.

Form FL3

In another embodiment, the combination of the invention comprises (2,4-dihydroxy-5-isopropyl-phenyl)-[5-(4-methyl-piperazin-1-ylmethyl)-1,3-dihydro-isoindol-2-yl]-methanone L-lactate salt in a crystalline form characterised by an XRPD pattern having a diffraction angle (2θ/°) peak at 5.53.

Preferably, the XRPD pattern also exhibits diffraction angle (2θ/°) peaks at 11.07, 13.16, 16.69, 17.17, 18.00, 18.49, 19.28, 21.05, 22.47 and 22.84.

More preferably, the XRPD pattern further exhibits diffraction angle (2θ/°) peaks at 8.36, 13.85, 19.79, 20.34, 21.47, 21.93, 24.56, 26.28, 27.06, 27.47 and 29.11.

Figure 4:
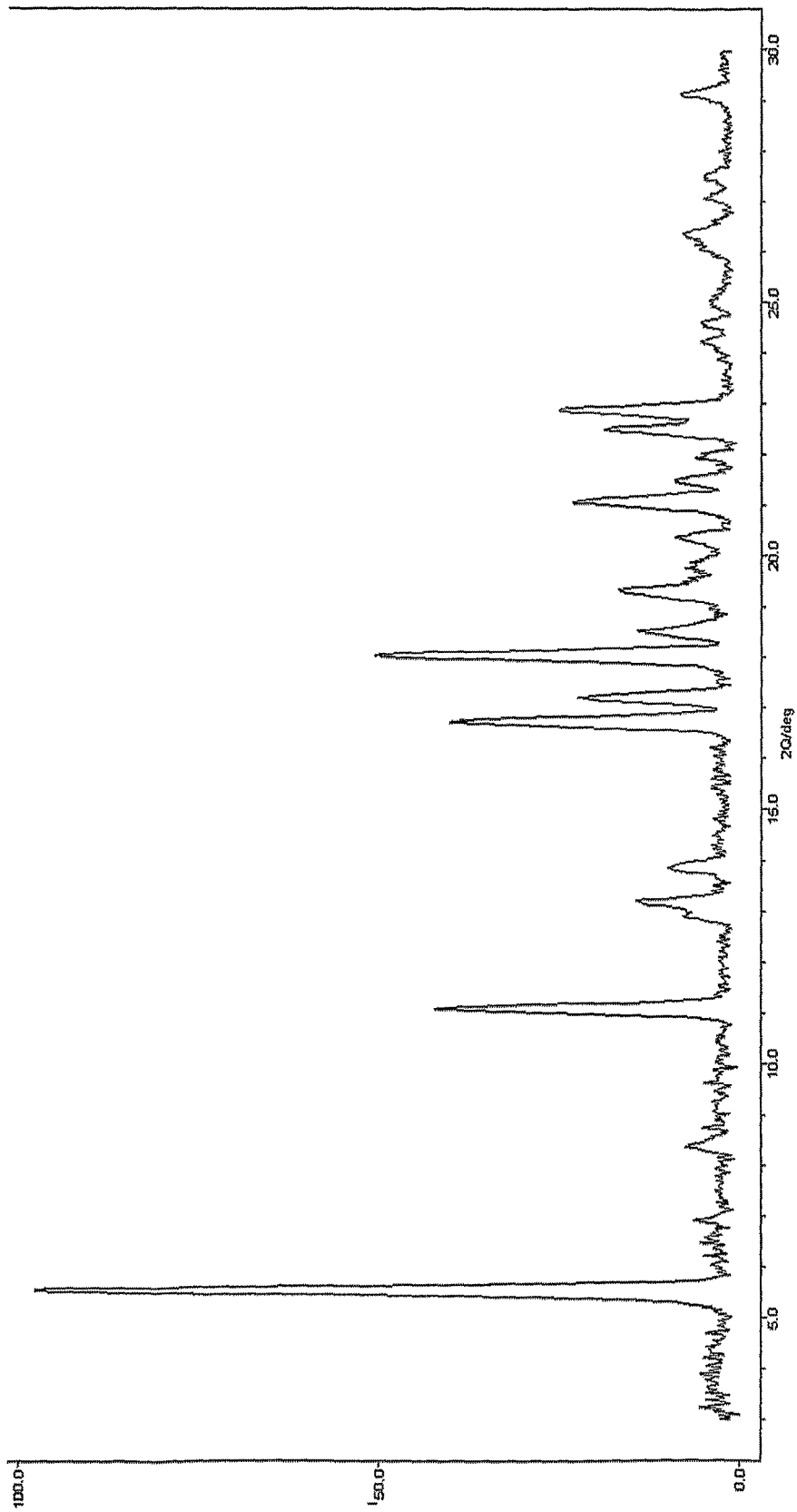

Most preferably, the XRPD pattern is substantially as shown in FIG. 4 herein.

Form FL3 is an unstable form that can be made by precipitation from a saturated THF solution using heptane as the anti-solvent. Accordingly, in another aspect, the invention provides a method for preparing crystalline form FL3, which method comprises forming a saturated solution of form FL1 in THF and then adding heptane to precipitate form FL3.

Biological Activity and Therapeutic Uses

The compounds of the formulae (I) and sub-groups thereof are inhibitors of Hsp90. The activity of the compounds as inhibitors of Hsp90 can be measured using the assays set forth in the examples below, for example the isothermal titration calorimetry (ITC) experiments described in Example 80. The level of activity exhibited by a given compound in the ITC assay can be defined in terms of the $K_d$ value, and preferred compounds of the present invention are compounds having a $K_d$ value of less than 1 micromolar, more preferably less than 0.1 micromolar.

Treatment of Pain and Stroke

As described above in the introductory part of this application, the p35 protein which acts as a regulator of CDK5 activity is a client protein for HSP90 and therefore the activity of CDK5 can be regulated by changes in the level and activity of HSP90. Thus, inhibition of HSP90 can lead to loss of p35, an inhibition of CDK5. Accordingly, the compounds of the present invention, which are inhibitors of HSP90, will be useful in preventing, treating or alleviating diseases and conditions mediated by p35 and CDK5.

For example, as a consequence of their activity in modulating or inhibiting HSP90, they will be useful for treating pain or conditions such as stroke.

Pain

The range of pain sensations experienced and multiple mechanisms involved make a precise definition of pain difficult, therefore in the present invention the term "pain" is used in the broadest sense to describe a spectrum of conditions including nociceptive pain, arising from tissue damage or inflammation, pain related to noxious stimuli, acute pain, chronic pain, and neuropathic pain. In the present description the terms "treatment" or "treat" refer to both prophylactic or preventative treatment as well as curative or palliative treatment of pain, in particular anti-nociceptive and anti-allodynic treatment of pain.

Examples of types of pain for which the compounds of the present invention will be useful in treating include nociception, somatic pain, visceral pain, acute pain, chronic pain, hyperalgesia, allodynia, post operative pain, pain due to hypersensitivity, headache, inflammatory pain (rheumatic, dental, dysmenorrhea or infection), neurological pain, musculoskeletal pain, cancer related pain or vascular pain.

In one embodiment, the pain may be other than cancer pain.

In another embodiment, the pain may be cancer pain, For example, the cancer pain may be cancer pain resulting from structural damage, periosteal irritation, and nerve entrapment which is the most common complication of both benign and metastatic bone disease, and presents a significant problem in both hospital and community practice (Coleman, 1997, Cancer 80; 1588-1594). In another embodiment the cancer related pain is pain associated with cancer therapy, e.g. postchemotherapy syndromes, chronic postsurgical pain syndromes, post radiation syndromes or bone cancer pain.

One subgroup of types of pain includes nociception, somatic pain, visceral pain, acute pain, chronic pain, hyperalgesia, allodynia, post operative pain, pain due to hypersensitivity, headache, inflammatory pain (rheumatic, dental, dysmenorrhea or infection), neurological pain, musculoskeletal pain or vascular pain.

The pain may be pain associated with a disease or pathological condition in a mammal.

Therefore in one embodiment of the invention is used for the direct treatment of pain in diseases and medical conditions.

Acute pain is that generally short lived with a specific origin e.g. soft tissue damage/trauma (including post surgical pain), inflammation or infection, usually with no persistent psychological reaction. Acute pain can be modulated by analgesics or treatment of the underlying condition e.g. antibiotics to treat infection.

Chronic pain is a more complex condition involving persistent pain over long periods with, sometimes with no apparent cause and with no apparent biological purpose. Chronic pain can often have psychological consequences. Common causes of chronic pain include low-back pain, headache, pain associated with cancer, arthritis pain and fibromyalgia or myofascial pain.

Neuropathic pain is distinct from "normal" or nociceptive pain, usually results from neurological dysfunction and has a complex and variable etiology. It is often characterised by hyperalgesia (lowered pain threshold and enhanced perception) and allodynia (innocuous thermal or mechanical stimuli causing a perception of pain). Neuropathic pain often fails to respond to the same drugs as nociceptive conditions and is therefore more difficult to treat. Neuropathic pain can arise whenever nerves are damaged by trauma or amputation, disease (herpes zoster, diabetes, cancer), or chemical injury (e.g. as a side effect of drug treatment with nucleotide anti-HIV or some antineoplastic drugs). Examples would include monoradiculopathies, trigeminal neuralgia, post herpetic neuralgia, complex regional pain syndromes and peripheral neuropathies.

Peripheral neuropathy is a neurodegenerative condition affecting peripheral nerves usually manifesting as one or a combination of motor, sensory, sensorimotor, or autonomic dysfunction. Peripheral neuropathies can result from disease e.g. diabetes (diabetic neuropathy), alcoholism, acquired immunodeficiency syndrome (AIDS), drug therapies e.g. treatment with cytostatics or genetic predisposition (e.g. Metachromatic leukodystrophy). Peripheral neuropathies are often accompanied by pain conditions.

In addition, the compounds of formula (I) can be used inter alia in the treatment of pain conditions such as acute and chronic pain (as well as, but not limited to, pain associated with cancer, surgery, arthritis, dental surgery, trauma, musculo-skeletal injury or disease, visceral diseases) and migraine headache. Additionally the painful conditions can be neuropathic; examples of such conditions are post-herpetic neuralgia, diabetic neuropathy, drug-induced neuropathy, HIV-mediated neuropathy, sympathetic reflex dystrophy or causalgia, fibromyalgia, myofacial pain, entrapment neuropathy, phantom limb pain and trigeminal neuralgia. Neuropathic conditions include central pain related to stroke, multiple sclerosis, spinal cord injury, arachnoiditis, neoplasms, syringomyelia, Parkinson's disease and epilepsy.

Another sub-group of pain conditions includes all of the pain conditions listed in the preceding paragraph other than cancer pain, i.e. pain associated with cancer.

The present invention is particularly applicable to the palliative treatment of pain, i.e. the direct relief of pain in addition to the relief of pain as the result of amelioration of the underlying disease or medical condition, which is the cause of the pain. Thus, advantageously the invention provides methods and uses for the direct analgesic or acute treatment of pain.

The ability of the compounds in treating pain conditions may be tested using a variety of well known techniques. Examples of such techniques include observations of spontaneous pain (i.e. gait analysis/spontaneous foot lifting/weight bearing), evoked elements (e.g. heat (Hargreaves test and hot plate test), cold (application of acetone), paw pressure test (Randal Siletoe test) or mechanical (von Frey hairs) stimuli or rat tail clip test) or similar/equivalent assays, in test species exposed to the test compound in comparison to appropriate controls.

These models could be further modified to improve sensitivity or to test inflammatory pain behaviour by injection of an inflammatory agent (formalin, carageenan, capsaicin, complete Freud's adjuvant, or incomplete Freud's adjuvant) given intra-plantar or intra-articular prior to testing. Activity of the compounds in neuropathic pain conditions could be evaluated using the "Chung" model of peripheral neuropathy (Kim S H, Chung J M., *Pain* 1992; 50: 355-363). In vivo electro-physiological single cell recordings or nerve fibre recordings could be employed to measure spontaneous and evoked firing rates. Immunohistochemical evidence e.g. staining for substance P, cGRP, galanin, or other relevant substances might also be used.

The activity of the compounds in treating pain arises from their activity as HSP90 inhibitors and hence their ability to inhibit of cyclin dependent kinase 5 (CDK5

Stroke

The compounds of formula (I) may also be used to treat patients suffering from stroke or at risk of suffering from stroke.

Where a patient is suffering from stroke, the compounds of the invention may be administered to provide a neuroprotective effect to prevent or reduce the extent of damage to brain issue.

For example, the compounds of the invention may be used to treat ischemic stroke, which is the most common type of stroke, and which results from insufficient cerebral circulation of blood caused by obstruction of the inflow of arterial blood.

The ischemic stroke may be caused by, for example, a thrombus, i.e., a blood clot that forms in a blood vessel. The thrombus may interrupt arterial blood flow, causing brain ischemia and consequent neurologic symptoms. The thrombus may be one which arises as a result of inflammation or atherosclerosis.

Ischemic stroke may also be caused by the lodging of an embolus (an air bubble) from the heart in an intracranial vessel, causing decreased perfusion pressure or increased blood viscosity with inadequate cerebral blood flow. An embolus may be caused by various disorders, including atrial fibrillation and atherosclerosis.

The compounds of the invention may also be used to treat hemorrhagic stroke, which is a form of stroke involving a hemorrhage or rupture of an artery leading to the brain. Hemorrhagic stroke results in bleeding into brain tissue, including the epidural, subdural, or subarachnoid space of the brain. A hemorrhagic stroke typically results from the rupture of an arteriosclerotic vessel that has been exposed to arterial hypertension or to thrombosis.

During acute ischemic stroke, i.e., the period from the cerebrovascular event up to 24 hours after the event, the arterial occlusion results in an immediate infracted core of brain tissue, where cerebral blood flow is significantly reduced, for example to less than 20% of the normal blood flow. The infracted core suffers irreversible damage due to significant cell death. The length of time that ischemia persists, and the severity of the ischemia, contribute to the extent of injury. An area around the infracted core, known as the ischemic penumbra, suffers a delayed and less severe infarct. For example, during acute stroke the penumbra may have a reduction in blood flow of from about 20-40% of normal blood flow. It is envisaged that compounds of the invention will be useful in reducing neuronal cell death due to ischemia.

The compounds of the invention are also useful for the prevention or reduction of risk of stroke in patients at risk for stroke. For example, the patients may exhibit any one or more risk factors selected from vascular inflammation, atherosclerosis, arterial hypertension, diabetes, hyperlipidemia and atrial fibrillation.

The compounds of the invention may be administered to facilitate recovery or restoration after an acute stroke period, for example through the reduction or prevention of secondary cell damage in the penumbra.

The usefulness of the compounds of formula (I) arises from their ability to inhibit HSP90 and consequently modulate (e.g. inhibit) cdk5 kinase activity which has been shown to be involved with or mediate neuronal death following hypoxic or ischemic insult.

By virtue of their activity as HSP90 inhibitors and their consequent effect on cdk5 activity, the compounds of the invention will also be useful in treating other neuropathies, e.g. peripheral neuropathies. However, excluded from the methods and uses of the invention are Alzheimer's disease, Creutzfeldt-Jakob disease and Huntington's disease. In one general embodiment, the neuropathy may be other than a neurodegenerative disease or condition.

Treatment of Fungal Diseases and Conditions

As described above in the introductory part of this application, compounds having Hsp90 inhibitory activity have been found to exhibit potent anti-fungal activity and prevent the development of resistance to anti-fungals and in particular Hsp90 dependent resistance to anti-fungals. Moreover, it has been found that inhibition of Hsp90 activity can reduce the development of resistance to commonly used anti-fungal drugs such as the azoles. It is therefore envisaged that the compounds of the invention will be useful in the prophylaxis or treatment of a range of fungal diseases and conditions and will also be useful, when coadministered with other anti-fungal drugs such as the azoles, in enhancing the activity of the anti-fungal drugs.

The antifungal activity of the compounds of the present invention may be evaluated by determining the minimum fungistatic (inhibition) concentration (m.i.c.). This test is usually performed by preparing a series of plates or tubes containing a suitable nutrient medium, each plate or tube also containing a different concentration of the test compound and then inoculating the medium with the fungal species. After an incubation period the plates are examined visually for the presence or absence of fungal growth. The m.i.c. is the minimum concentration required to prevent fungal growth.

The compounds may be used in animal medicine (for example in the treatment of mammals such as humans).

Fungal infections in animals against which the compounds of the present invention may be used include:

Superficial mycoses—i.e. fungal infections limited to the outermost layers of the skin and hair;

Cutaneous mycoses—i.e. fungal infections that extend deeper into the epidermis but are typically restricted to the keratinized layers of the skin, hair, and nails;

Subcutaneous mycoses—i.e. fungal infections involving the dermis, subcutaneous tissues, muscle, and fascia;

Systemic mycoses due to primary pathogens (these typically originate primarily in the lungs and may spread to other organ systems); and Systemic mycoses due to opportunistic pathogens (infections of patients with immune deficiencies who would otherwise not be infected).

Particular examples of fungal disease states for which compounds of the present invention may be used include:

Dermatophyte infections such as tinea versiColour (a superficial fungal infection of the skin), tinea pedis (Athletes' Foot), tinea capitis (superficial fungal infection on the head), tinea barbae (fungal infection of bearded areas), tinea corporis (fungal infection of smooth skin areas).

Mucosal Candidiasis such as Oral Candidiasis, esophagitis and Vaginal candidiasis.

Invasive or deep organ candidiasis (e.g., fungemia, endocarditis, and endophthalmitis).

Crytpococcal infections such as Cryptococcal meningitis.

Histoplasmosis.

Blastomycosis, a fungal infection of the lungs and occasionally the skin.

Invasive Fungal Infections in patients with weakened immune systems or under treatment with anti-cancer or anti-AID drugs, for example Invasive Candidiasis and Invasive Aspergillosis.

Aspergilloses such as Allergic Bronchopulmonary Aspergillosis.

Aspergilloma.

Intertrigo infections (fungal infections occurring in folds of skin e.g. between the toes or fingers, in the underarm area, or in the groin area).

Maduramycosis (fungal invasion of the tissue of the foot, also known as madura foot).

Coccidioidomycosis.

Mucormycosis.

Blastomycosis

Geotrichosis.

Chromoblastomycosis.

Conidlosporosis.

Histoplasmosis.

Rhinosporidosis.

Nocaidiosis.

Para-actinomycosis.

Penicilliosis.

Monoliasis.

Sporotrichosis.

Fungal infections of particular interest are Candidiasis and Aspergillosis.

Compounds of the present invention also have anti-protozoal activity and anti-parasitic activity. The antiprotozoal activity of the compounds of the present invention may be assessed by conventional methods, for example by determining the minimum inhibition concentration (m.i.c.) or 50% inhibition level ($IC_{50}$).

Examples of protozoal and parasitic diseases or conditions for which the compounds of the invention may prove useful include:

Chagas disease ((trypanosomiasis)—an infection caused by the parasite *Trypanosoma cuzi.*

Ascariasis—a human disease caused by the parasitic roundworm *Ascaris lumbricoides.*

Leishmaniasis—a disease caused by parasites of the genus *Leishmania.*

Toxoplasmosis—a parasitic disease caused by the protozoan *Toxoplasma gondii.*

Schistosomiasis (Bilharzia)—a disease caused by the parasite *Schistoma mansoni.*

Trichomoniasis—a sexually transmitted disease caused by the parasitic protozoan *Trichomonas vaginalis.*

Anti-Viral Activity

As discussed above in the introductory sections of this application, infection of a host cell with viral RNA/DNA results in a substantial redirection of cellular protein synthesis towards key viral proteins encoded by the viral nucleic acid, and this frequently gives rise to upregulation of heat shock proteins. It is believed that one function of the HSP induction may be to assist in the stabilization and folding of the high levels of 'foreign' protein generated in preparation for virus replication and it has been shown (Nagkagawa et al.) that HSP 90 inhibitors can block viral replication. Accordingly, the compounds of the invention are useful in combating viral infections, for example by blocking or inhibiting viral replication.

Examples of viral infections that may be treated with the compounds of the invention include infections due to any one or more of the following viruses:

Picornaviruses such as rhinoviruses (common cold virus), Coxsackie virus (e.g. Coxsackie B virus); and foot and mouth disease virus;

Hepatitis viruses such as hepatitis A virus (HAV), hepatitis B virus (HBV), hepatitis C virus (HCV), hepatitis D virus (HDV) and hepatitis E virus (HEV), Coronaviruses (e.g. common cold virus and Severe acute respiratory syndrome (SARS) to virus)

Adenoviruses such as Human Adenoviruses (a cause of respiratory and conjunctival infections);

Astroviruses (a cause of flu-like symptoms);

Flaviviruses such as the Yellow Fever virus;

Orthomyxoviruses such as influenza viruses (e.g. influenza A, B and C viruses);

Parainfluenza viruses;

Respiratory syncytial virus;

Enteroviruses such as Poliovirus (Poliomyelitis virus);

Paramyxoviruses such as the Measles (rubeola) virus, mumps virus, respiratory syncytial virus (RSV) and canine distemper virus (CDV);

Togaviruses such as the Rubella (German Measles) virus and Sindbis virus;

Herpes viruses such as:

Herpes simplex virus (HSV), for example HSV-1 which causes fever blisters (cold sores), gingivostomatitis, herpes keratitis, eczema herpeticum and HSV encephalitis); and HSV-2 which causes genital lesions, neonatal infections, HSV meningitis, HSV proctitis;

Varicella zoster virus (VZV), which causes chickenpox, congenital varicella syndrome and shingles;

Epstein-Barr Virus (EBV), which causes infectious mononucleosis, Burkitt's lymphoma and nasopharyngeal cancer;

Cytomegalovirus (CMV), e.g. human cytomegalovirus (HCMV);

Human herpes virus 6 (HHV6), which causes exanthum subitum or roseola infantum

Human herpes virus 8 (HHV-8) or Kaposi's sarcoma-associated herpes virus (KSHV), which is found in the saliva of many AIDS patients and associated with Kaposi's sarcoma;

Papovaviridae such as polyoma virus and human papilloma virus (HPV);

Parvoviruses;

Poxviruses such as Variola virus (human smallpox virus);

Rhabdoviruses such as rabies virus and vesicular stomatitis virus (RSV); and

Retroviruses such as Human immunodeficiency virus (HIV) which is responsible for acquired immune deficiency syndrome (AIDS); and Human T-lymphotrophic virus (HTLV).

Particular viral infections against which the compounds of the invention may be used include herpes virus, pox virus, Epstein-Barr virus, Sindbis virus, adenovirus, HIV (for prevention of AIDS development in HIV-infected individuals), HPV, HCV and HCMV viruses.

The viral infection may be other than an infection with hepatitis C virus (HCV).

The activity of the compounds of the invention as agents for blocking or preventing viral replication in host organisms or host cells can be determined in accordance with standard procedures well known to the skilled person.

The compounds of the invention may be used as the sole antiviral agent or they may be used in conjunction with other anti-viral agents such as acyclovir, ganciclovir, oseltamivir (Tamiflu®) and zanamavir (Relenza®), amantidine, rimantadine, adefovir dipivoxil, interferons (e.g. interferon alfa-2b and pegylated interferon alfa-2a), lamivudine, entecavir, ribavirin, famciclovir, valcicylovir, valacyclovir, azidothymidine (AZT-Retrovir®), atazanavir, fosamprenavir, lamivudine, lamivudine+abacavir, tenofovir disoproxil fumarate, tenofovir disoproxil fumarate+emtricitabine, tipranavir, nelfinavir, indinavir, raltegravir, ritonavir, lopinavir+ritonavir, darunavir, amprenavir, enfuvirtide, saquinavir, hydroxyurea, VGV-1 and anti-viral vaccines.

Atherosclerosis

It is known that inflammatory and immune cells play a central role in the initiation and progression of human atherosclerosis (Riganò et al., *Ann. N.Y. Acad. Sci.*, 2007, 1107:1-10) and it has been proposed that Hsp90 acts as an autoantigen in carotid atherosclerosis. Riganò et al. found specific antibodies and cells against Hsp90 in the sera of 60% of patients tested who were suffering from carotid atherosclerotic plaques but no specific antibodies and T cells against Hsp90 in the sera of healthy patients. Therefore, the Hsp90 inhibitors of the invention should be useful in the treatment or prevention of atherosclerosis.

Ewing's sarcoma

Ewing's sarcoma, also known as primitive neuroectodermal tumour, is a cancer affecting bone or soft tissue, and most commonly occurs in the pelvis, femur, humorous and the ribs. Ewing's sarcoma occurs most frequently in male teenagers and is the result of a translocation between chromosomes 11 and 22, which fuses the EWS gene of chromosome 22 to the FLI1 gene of chromosome 11 (see May et al., *Proc. Natl. Acad. Sci.* 1993, 90:5752-5756). It is envisaged that the proteins expressed by the fused EWS-FL11 gene will function as client proteins of Hsp90 and that inhibition of Hsp90 will therefore provide a means of preventing or treating the sarcoma.

Lupus Erythematosus

Increased expression of Hsp90 has been observed in patients suffering from the autoimmune disease lupus erythematosus (see Cid et al., *J. Neuroimmunol.*, 2007, 184 (1-2): 2236). It is therefore envisaged that inhibition of Hsp90 will provide a means for treating or preventing this disease.

hERG Activity

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. Nature, 345 (6277):672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. Cell, 81:299-307, and Trudeau, M. C., Warmke, J. W., Ganetzky, B., and Robertson, G. A. (1995). HERG, a Human Inward Rectifier in the Voltage-Gated Potassium Channel Family. Science, 269:92-95.

The elimination of hERG blocking activity remains an important consideration in the development of any new drug.

It has been found that many compounds of the formula (I) have low hERG activity and a good separation between Hsp90 inhibitory activity and hERG activity.

Preferred compounds of the formula (I) have mean $IC_{50}$ values against hERG that are greater than 30 times, or greater than 40 times, or greater than 50 times the $IC_{50}$ values of the compounds in cellular proliferation assays. Preferred compounds of the formula (I) have mean $IC_{50}$ values against hERG that are greater than 5 µM, more particularly greater than 10 µM, and more preferably greater than 15 µM. Some compounds of the invention have mean $IC_{50}$ values against hERG that are greater than 50 µM.

Methods for the Preparation of Compounds of the Formula (I)

In this section, as in all other sections of this application unless the context indicates otherwise, references to Formula (I) also include all sub-groups and examples thereof as defined herein. Where a reference is made to a group $R^1$, $R^2$, $R^3$, $R^4$, $R^5$, $R^6$, $R^{10}$ or any other "R" group, the definition of the group in question is as set out above and as set out in the following sections of this application unless the context requires otherwise.

Compounds of the formula (I) can be prepared in accordance with synthetic methods well known to the skilled person. For example, compounds of the formula (I) can be prepared by reaction of a compound of the formula (X):

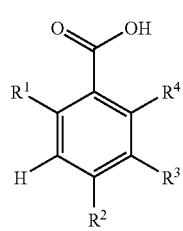

or an activated and/or protected form thereof, with an amine of the formula $HNR^5R^6$ under conditions suitable for forming an amide bond, and thereafter where necessary removing any protecting groups and optionally converting one compound of the formula (I) to another compound of the formula (I).

The amines of the formula $HNR^5R^6$ are either commercially available or can be made using methods well known to the skilled person, see for example, *Advanced Organic Chemistry, by Jerry March*, 4th edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

The carboxylic acid (X) can be converted to an amide of the formula (I) by first forming an acid chloride by treatment of the carboxylic acid with thionyl chloride, or by reaction with oxalyl chloride in the presence of a catalytic amount of dimethyl formamide, or by reaction of a potassium salt of the acid with oxalyl chloride. The acid chloride can then be reacted with the amine $HNR^5R^6$ in the presence of a non-interfering base such as triethylamine. The reaction may be carried out at around room temperature in a polar solvent such as dioxan.

As an alternative to using the acid chloride method described above, the carboxylic acid (X) can be converted to the amide (I) by reaction with the amine $HNR^5R^6$ in the presence of amide coupling reagents of the type commonly used in the formation of amide or peptide linkages. Examples of such reagents include 1,1'-carbonyldiimidazole (CDI), 1,3-dicyclohexylcarbodiimide (DCC) (Sheehan et at, *J. Amer. Chem. Soc.* 1955, 77, 1067), 1-ethyl-3-(3'-dimethylaminopropyl)-carbodiimide (referred to herein either as EDC or EDAC but also known in the art as EDCI and WSCDI) (Sheehan et al, *J. Org. Chem.*, 1961, 26, 2525), uronium-based coupling agents such as O-(7-azabenzotriazol-1-yl)-N,N,N'N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Bar.*, 103, 708, 2024-2034). Preferred coupling reagents include EDC (EDAC) and DCC in combination with HOAt or HOBt.

One particular coupling reagent comprises EDC in combination with HOBt.

A preferred coupling agent is 1,1'-carbonyldiimidazole (CDI).

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example 1 in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Illustrative routes to the compounds of formula (I) are described in more detail below.

Compounds of the formula (I) in which the benzoyl moiety is derived from a 2-hydroxy-5-substituted benzoic acid can be prepared by the sequence of reactions shown in Scheme 1.

The starting material for the synthetic route shown in Scheme 1 is 5-chloro-2-hydroxy benzoic acid, which can be obtained commercially. Conversion to the acid chloride is carried out by heating with thionyl chloride. The acid chloride may be used either in situ and reacted with various amines, or can be isolated as a stable white solid. Other simple 2-hydroxy-5-substituted benzoic acids may be used in this procedure to synthesise other amides of 2-hydroxy-5-substituted benzoic acids.

Scheme 1: 5-Chloro-2-hydroxybenzoic acid amides

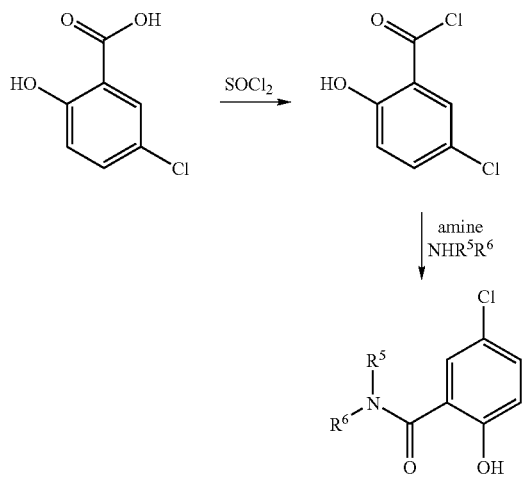

Compounds of formula (I) can also be made according to the method shown in Scheme 2. The starting material for the synthetic route shown in Scheme 2 is 4-ethyl anisole, which can be obtained commercially. Conversion to the carboxylic acid can be carried out by lithiation at low temperature, followed by quenching of the resulting anion with solid carbon dioxide. The carboxylic acid may be coupled with various amines, using standard amide coupling reagents of the type commonly used in the formation of peptide linkages as described above.

Deprotection of the methyl ether can be effected using boron tribromide (e.g. by the method described in *Synthesis* 1991, 469) to give the compound of formula (I). The method illustrated in Scheme 2 can be used to prepare other simple 2-hydroxy-5-substituted benzoic acids which can then be coupled to an appropriate amine to give the compounds of formula (I). The process of coupling intermediates acids with amines, anilines or amino-heterocyclic compounds, followed by removal of any protecting groups, is straightforward and is suitable for the synthesis of large combinatorial libraries of molecules, useful for this invention. Examples of combinatorial libraries are described in *Solid-Phase Synthesis and Combinatorial Technologies* by Pierfausto Seneci. Wiley-Interscience, New York. 2000. xii+637 pp. ISBN 0471331953).

Scheme 2

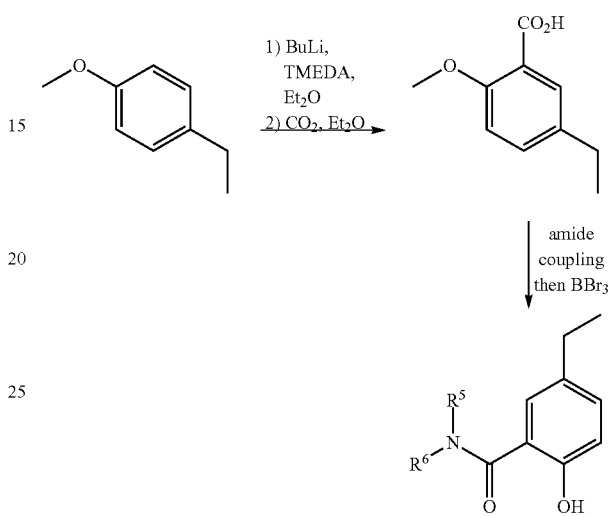

Compounds of the Formula (I) can also be made according to the methods described in Scheme 3. The starting material 3-tert-butyl-4-hydroxybenzoic acid (X=tert-butyl) is commercially available and can be coupled using the amide coupling agents (as outlined above) with a broad range of amines of the formula $HNR^5R^6$ to give compounds of the invention. The other starting material illustrated in Scheme 3,3-isopropyl-4-hydroxybenzoic acid (X=isopropyl), can be prepared according to a modification of a literature procedure using carbon tetrachloride and copper powder in a Friedel-Crafts type reaction, in which the intermediate species is hydrolysed to the carboxylic acid (*J Chem Soc, Chem Commun* 1985, 1134). The Friedel Crafts method can be used to prepare other simple 2-hydroxy-3-substituted benzoic acids.

Scheme 3: 3-Alkyl-4-hydroxybenzoic acid amides

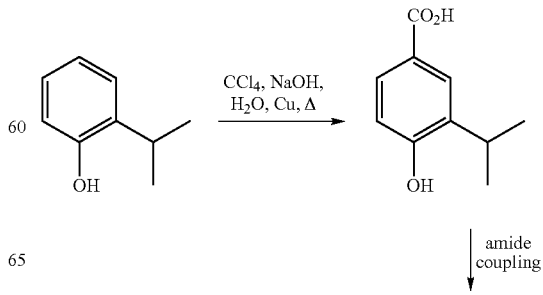

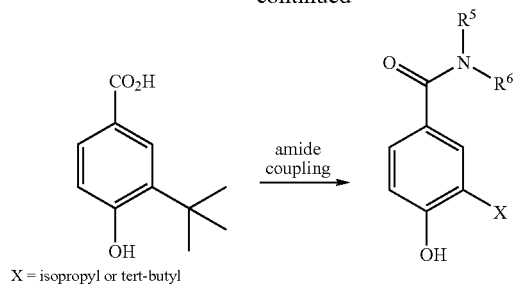

X = isopropyl or tert-butyl

Compounds of the formula (I) can also be made according to the method described in Scheme 4. 2,4-Dihydroxy-5-isopropyl-benzoic acid amides can be prepared by amide coupling using coupling reagents (as outlined above) from a bi-benzyl ether protected intermediate, shown in the scheme, followed by catalytic hydrogenation using hydrogen gas and palladium on carbon. The benzoic acid intermediate itself is made by Friedel-Crafts acylation of 2,4-dihydroxybenzoic acid methyl ester (from commercial sources) using a literature procedure (*J. Ind. Chem. Soc.*, 1953, 30, 269). Typically, Friedel-Crafts acylation of a phenol is carried out by treatment of the phenol with an acylating agent (such as an acid chloride or acid anhydride) in the presence of a Lewis acid catalyst (such as boron trifluoride or aluminium chloride) either at room temperature or at more elevated temperatures (60-120° C.). As an alternative to a direct Friedel-Crafts acylation, the 4-hydroxy group of the 2,4-dihydroxybenzoic acid methyl ester can be O-acylated using an acid anhydride such as acetic anhydride in the presence of a base such as 4-dimethylaminopyridine (4-DMAP) to give a 2-hydroxy-4-acyloxy-benzoic acid methyl ester. Treatment of the 2-hydroxy-4-acyloxy-benzoic acid methyl ester with trifluoromethanesulphonic acid in the presence of an acyl chloride such as acetyl chloride then gives the 2,4-dihydroxy-5-acylbenzoic acid methyl ester.

Benzyl protection of the phenol groups, the Wittig reaction of the ketone to the olefin and ester hydrolysis (saponification) can be carried out under standard conditions, well known to those skilled in the art of organic synthesis (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8). For example, the Wittig reaction can be carried out in an inert polar solvent (such as tetrahydrofuran) and can involve treatment of an aldehyde or ketone with a phosphorus ylide species that may be prepared by the reaction of a phosphonium salt with a base (such as butyl lithium or potassium tert-butoxide). The ester hydrolysis to the carboxylic acid is usually carried out by treatment with an aqueous alkali metal hydroxide such sodium hydroxide. The saponification reaction may be carried out using an organic co-solvent such as an alcohol (e.g. methanol) and the reaction mixture is typically heated to a non-extreme temperature, for example up to about 50-60° C.

It is to be understood that other 2,4-dihydroxy-5-substituted benzoic acids could be made using this procedure to synthesise different examples of compounds of formula 1 not specifically exemplified herein.

In Scheme 4, as an alternative to the use of the Wittig reagent MePPH$_3$Br to form the olefin (XXVI), the ketone (XXV) can be reacted with methyl magnesium bromide under standard Grignard reaction conditions to give an intermediate hydroxy compound which is then dehydrated to the olefin by reaction with a suitable reagent such as sodium acetate and acetic acid.

The intermediate compound 2,4-bis-benzyloxy-5-isopropenyl-benzoic acid (XXVII) and its precursor compounds (XXV) and (XXVI) shown in Scheme 4 are believed to be novel and, as such, each of the compounds represents a further aspect of the invention.

The 2,4-bis-benzyloxy-5-isopropenyl-benzoic acid amides (XXVIII) are also believed to be novel and also form a further aspect of the invention.

Scheme 4: 2,4-Dihydroxy-5-isopropyl-benzoic acid amides

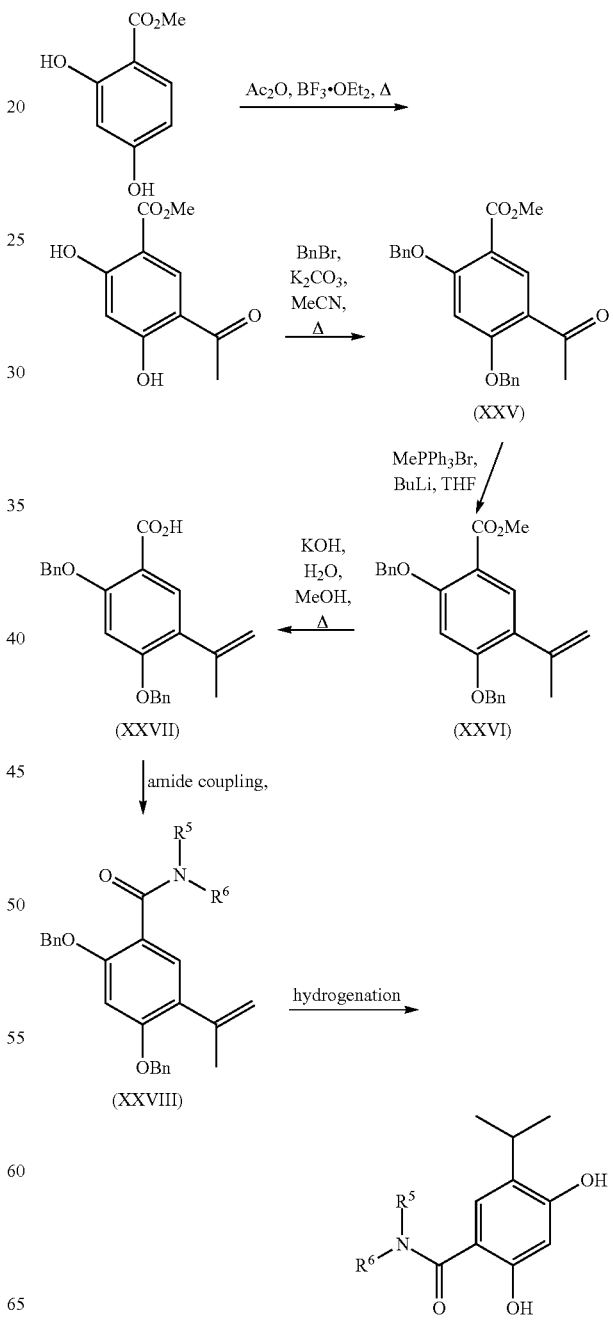

The intermediate compound 2,4-bis-benzyloxy-5-isopropenyl-benzoic acid (XXVII) in Scheme 4 can be made using a variety of methods well known to the skilled person. For example, compound (XXVII) can be made by the synthetic route illustrated in Scheme 4A.

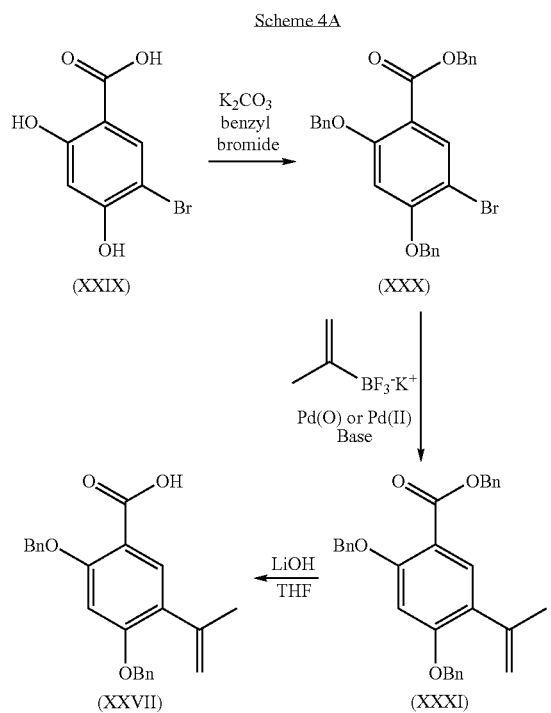

As shown in Scheme 4A, 5-bromo-2,4-dihydroxybenzoic acid is benzylated using benzyl bromide in the presence of a base such as potassium carbonate to give the bis-benzyloxy-bromobenzoic acid benzyl ester (XXX). The ester (XXX) is then reacted with potassium isoprenyl trifluoroborate in the presence of a palladium (0) or palladium (II) compound and a base to give the isopropenyl-bis benzyl ester (XXXI). The palladium compound can be a palladium (0) compound such as $Pd(PPh_3)_4$ or a palladium (II) compound such as [1,1'-bis(diphenyl-phosphino)ferrocene]dichloropalladium(II). The base can be an organic base such as n-butylamine or an inorganic base such as a metal carbonate, e.g. caesium carbonate. The reaction with potassium isoprenyl trifluoroborate is typically carried out at reflux temperature for a prolonged period, for example 15 hours or more. The resulting isopropenyl bis-benzyloxy ester (XXXI) is then hydrolysed to give the carboxylic acid (XXVII) using, for example, an alkali metal hydroxide such as lithium hydroxide, typically with heating to a non-extreme temperature.

Compounds of the formula (I) can also be made according to the route illustrated in Scheme 5. 4-Hydroxy-3-(1',2'-dimethyl-propyl)-benzoic acid amides can be prepared by amide coupling using standard coupling agents (as outlined above) from the alkyl substituted acid. The olefinic acid itself can be prepared by Claisen rearrangement of a precursor ether, as shown in the scheme, by thermal rearrangement in anisole, followed by saponification, which in this case can yield more than one isomer of the olefin, the major one being shown in the scheme. Such Claisen reactions are well known in the literature, e.g. see *J. Chem. Soc, Perkin Trans 1* 1981, 897. The ether itself can be prepared by simple alkylation of commercially available 4-hydroxy benzoic acid ethyl ester. The alkylation and saponification reactions are simple modifications that can be carried out under various conditions (for example see, *Advanced Organic Chemistry*, by Jerry March, 4$^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)). It is to be understood that other 4-hydroxy-3-substituted benzoic acids could be made using this procedure to synthesise different examples of compounds of formula 1 not specifically exemplified herein.

Scheme 5: 4-Hydroxy-3-(1',2'-dimethyl-propyl)-benzoic acid amides

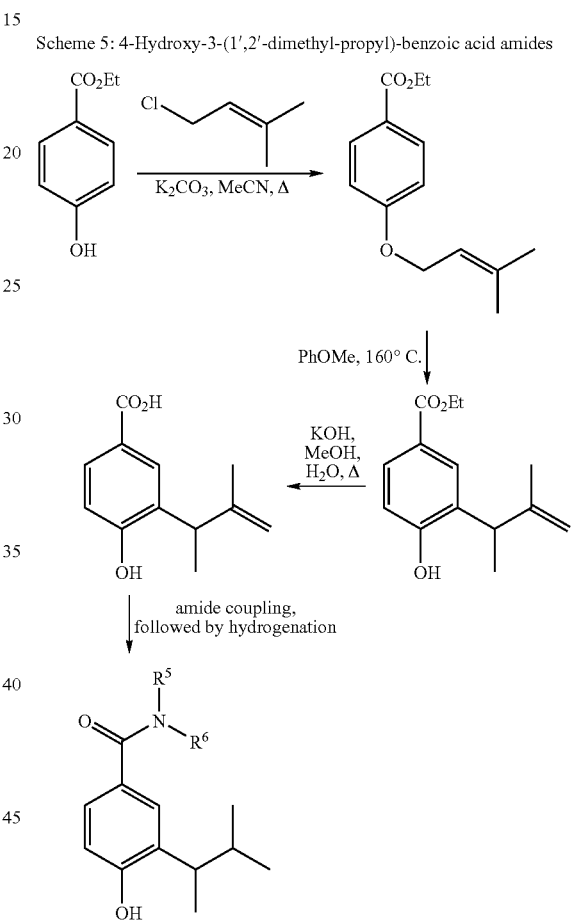

Compounds of the formula (I) can also be made according to the method shown in Scheme 6. 2,4-Dihydroxy-5-bromobenzoic acid is used as the starting material, which is commercially available. Simple protection and deprotection gives the benzoic acid precursor (for example see, *Advanced Organic Chemistry*, by Jerry March, 4$^{th}$ edition, 119, Wiley Interscience, New York; *Fiesers'Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)), which can be used in amide coupling reactions with a range of amines (as outlined above). These precursor amides can be subjected to Suzuki cross coupling procedures to make alkyl substituted compounds. A broad range of Suzuki coupling conditions are described in the literature, and the ones used here were taken from *J. Am. Chem. Soc.* 2003, 11148. Suzuki coupling chemistry is also broadly applicable to synthesis of alkyl-aryl and aryl-aryl compounds. The Suzuki reaction is typically carried out in the presence of a palladium catalyst such as bis(tri-t-butyl-phosphine)-palladium and a base (e.g. a carbonate such as potassium carbonate). The reaction may be carried out in an aqueous solvent system, for example aqueous ethanol, and the reaction mixture is typically subjected to heating, for example to a temperature in excess of 100° C. Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid. The final products of the reaction sequence illustrated in Scheme 6 are formed by catalytic hydrogenation (as outlined above) to remove the benzyl protecting groups and to reduce the olefin, formed in the Suzuki reaction to the alkyl substituent. It is to be understood that other 2,4-dihydroxy-5-substituted benzoic acids could be made using this procedure to synthesise different examples of compounds of formula I not specifically exemplified herein.

Scheme 6: 2,4-Dihydroxy-5-(alkyl)-benzoic acid amides

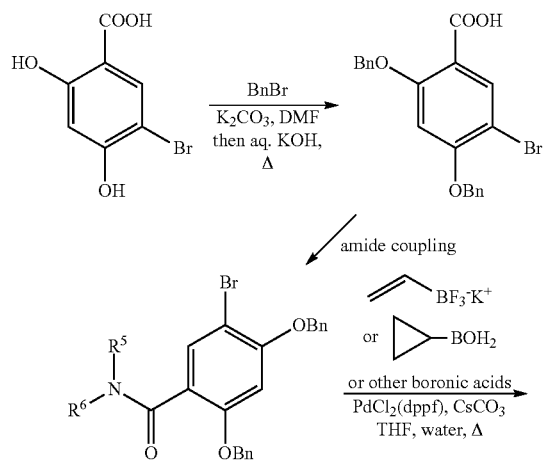

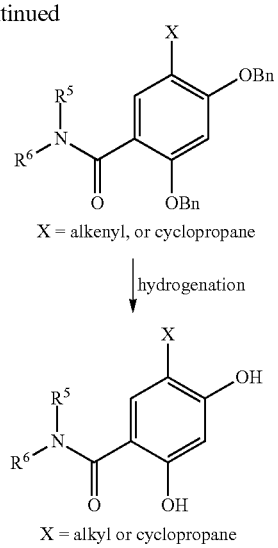

Compounds of the formula (I) wherein $NR^5R^6$ is an optionally substituted isoindoline group, for example as in compounds of the formulae (VII) and (VIIa), can be prepared by the methods illustrated in Scheme 7, or methods analogous thereto.

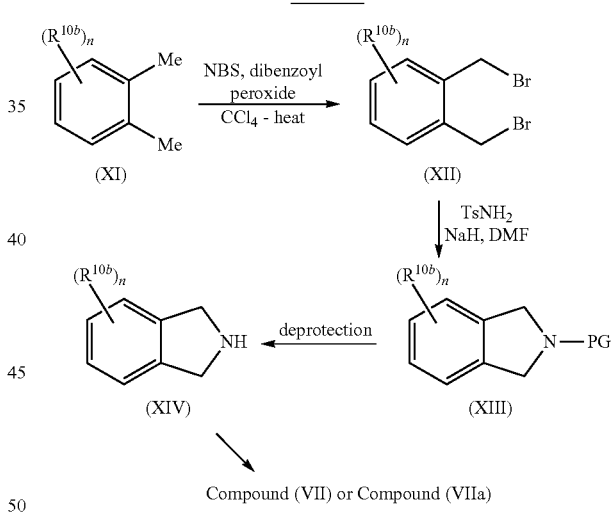

As shown in Scheme 7, an optionally substituted 1,2-dimethylbenzene ($X^1$) is heated with N-bromosuccinimide in the presence of dibenzoyl peroxide to give the dibromo-compound (XII). The reaction is typically carried out in carbon tetrachloride with heating at reflux. The dibromo-compound (XII) is then reacted with a compound $PG-NH_2$ where PG is a protecting group such as tosyl or para-methoxybenzyl in the presence of a base such as a metal hydride (e.g. sodium hydride), when PG is a tosyl group, or an alkali metal carbonate (e.g. sodium carbonate), when PG is para-methoxybenzyl. The protecting group PG can then be removed to give the amine (XIV). Thus, for example, a tosyl group can be removed by heating with a mixture of phenol, hydrobromic acid and propanoic acid, whereas a para-methoxybenzyl group can be removed in standard manner using trifluoroacetic acid and anisole. The amine (XIV) is then coupled with a carboxylic acid of the formula (X) as described above.

In a variation on the reaction sequence of Scheme 7, one or more functional groups $R^{10b}$ present in the protected isoindoline (XIII) or the deprotected isoindoline compound (XIV) can be converted into other groups $R^{10b}$. For example, where the group $R^{10b}$ in compound (XIV) is a nitro group, it can be reduced to give the corresponding amino group, for example by catalytic hydrogenation in the presence of a palladium on charcoal catalyst. In a further example, when $R^{10b}$ in the compound (XIII) is an ester group (e.g. $CO_2Me$), it can be hydrolysed to give a carboxylic acid which can then be reacted with an amine such as morpholine to give the corresponding amide. Further functional group interconversions may subsequently be carried out (for example reduction of the amide to the corresponding aminomethyl compound with lithium aluminium hydride) before removal of the protecting group PG. Alternatively, the ester group can be reduced to a hydroxymethyl group which may then be converted to an aldehyde, and the aldehyde group may subsequently be used as a substrate for further conversions, for example a reductive amination reaction with an amine such as morpholine, piperidine or N-methyl piperazine.

A variation on the route illustrated in Scheme 7 is shown in Scheme 7A

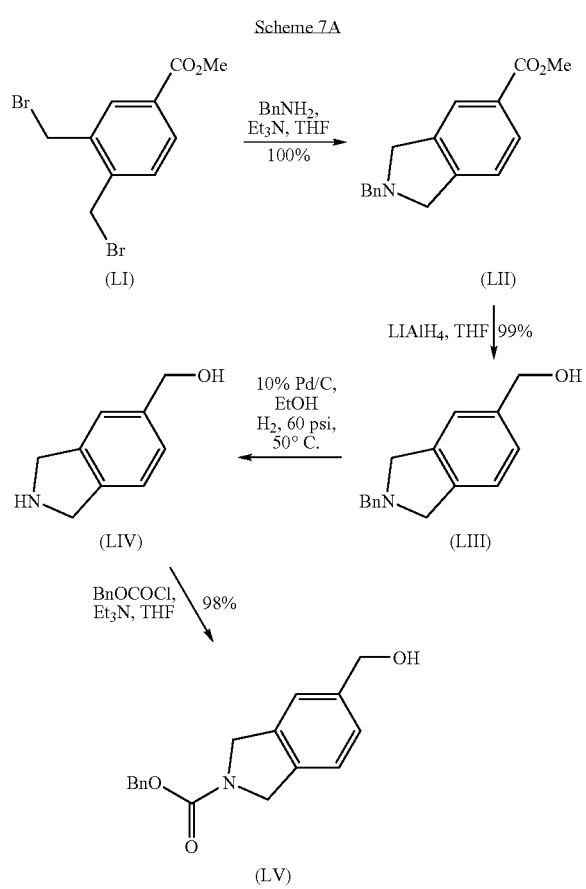

In Scheme 7A, the commercially available bis-bromomethyl benzoic acid ester ((LI) is reacted with benzylamine in a polar aprotic solvent such as tetrahydrofuran (THF) in the presence of a non-interfering base such as triethylamine to give the N-benzyl dihydroisoindole intermediate (LII). The ester group in intermediate (LII) is then reduced to the corresponding alcohol using lithium aluminium hydride in THF to give the hydroxymethyldihydroisoindole intermediate (LII). Debenzylation of the hydroxymethyldihydroisoindole intermediate (II) is then carried out by hydrogenation over palladium on charcoal catalyst in an alcohol (e.g. ethanol) solvent at a mildly elevated temperature (e.g. up to about 50°) to give the intermediate (LIV). Intermediate (LIV) is then converted to intermediate (LV) by reaction with a reagent suitable for introducing a benzyloxycarbonyl ("Z") group onto the nitrogen atom of the dihydroisoindole ring. For example, the intermediate (LIV) can be reacted with benzyl chloroformate in a polar non-protic solvent such as THF in the presence of a non-interfering base such as triethylamine to give intermediate (LV).

An alternative synthesis of the isoindoline compound (XIV) is shown in Scheme 8.

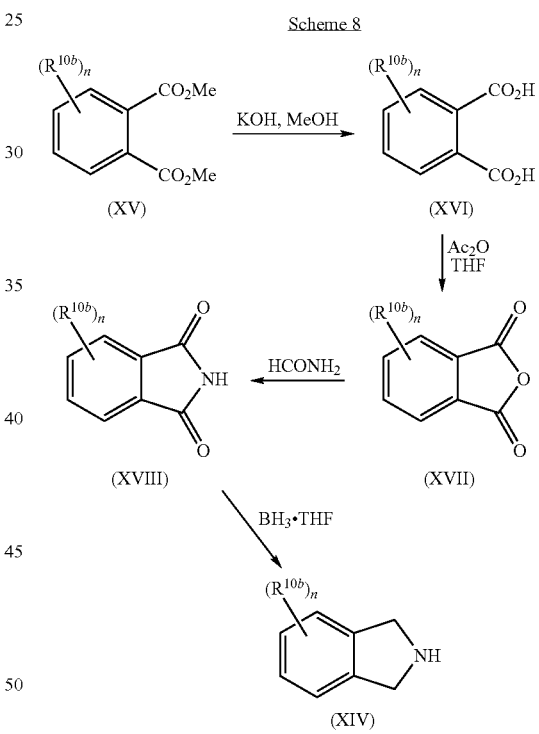

The starting material for Scheme 8 is the ortho diester (XV) which is hydrolysed to the corresponding dicarboxylic acid (XVI) using an alkali metal hydroxide such as potassium hydroxide before being subjected to cyclisation to the phthalic anhydride (XVII) by reaction with acetic anhydride. The phthalic anhydride (XVII) can be converted to the corresponding phthalimide (XVIII) by reaction with formamide at an elevated temperature (e.g. approximately 210° C.). The phthalimide (XVIII) can then be reduced to the isoindoline (XIV) using a suitable reducing agent such as borane in tetrahydrofuran.

Isoindoline intermediate compounds can also be prepared be prepared by the synthetic route shown in Scheme 9.

Scheme 9

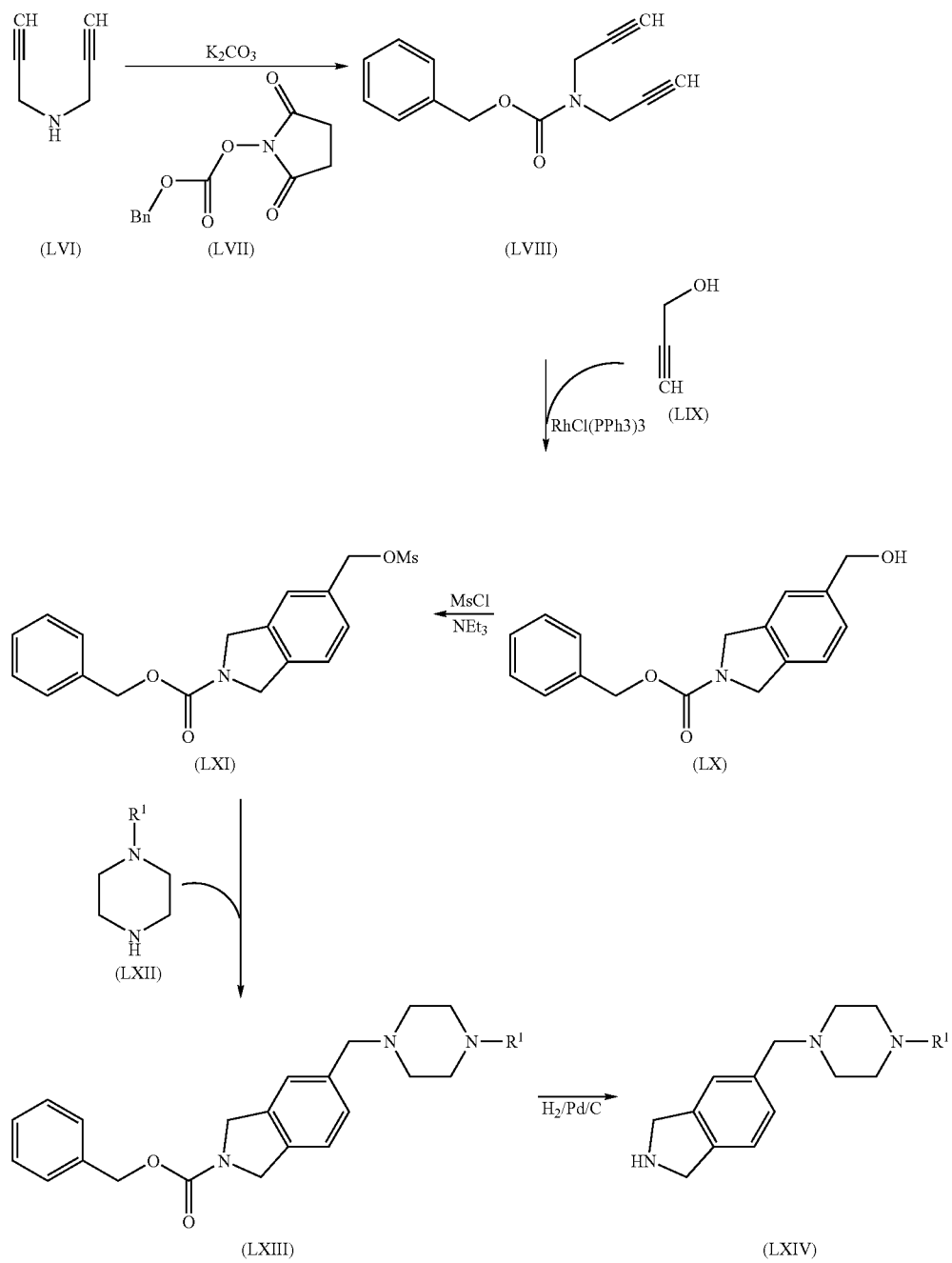

In Scheme 9, the dipropargylamine (LVI) is reacted with N-(benzyloxycarbonyloxy) succinimide (LVII) in ethyl acetate in the presence of potassium carbonate to give the Z-protected dipropargylamine (LVIII) (the term "Z" referring to a benzyloxycarbonyl group). As an alternative to N-(benzyloxycarbonyloxy) succinimide, benzyl chloroformate may be used to introduce the benzyloxycarbonyl protecting group. Compound (LVIII) is then reacted with propargyl alcohol (LIX) in the presence of Wilkinson's catalyst in a 2+2+2 cycloaddition reaction to give the Z-protected isoindoline (LX). The hydroxymethyl group on the isoindoline (LX) is then converted to a mesyloxy group by reaction with methanesulphonyl chloride in a polar solvent such as THF in the presence of a non-interfering base such as triethylamine to give the mesyl compound (LXI). The mesyl compound (LXI) is reacted with alkylpiperazine (LXII) in acetone solution to give the Z-protected isoindoline (LXIII). Removal of the benzyloxycarbonyl group to give the unprotected isoindoline compound (LXIV) is then accomplished by hydrogenation over a palladium on charcoal catalyst.

A variation on the reaction sequence shown in Scheme 9 is illustrated in Scheme 9A.

Scheme 9A

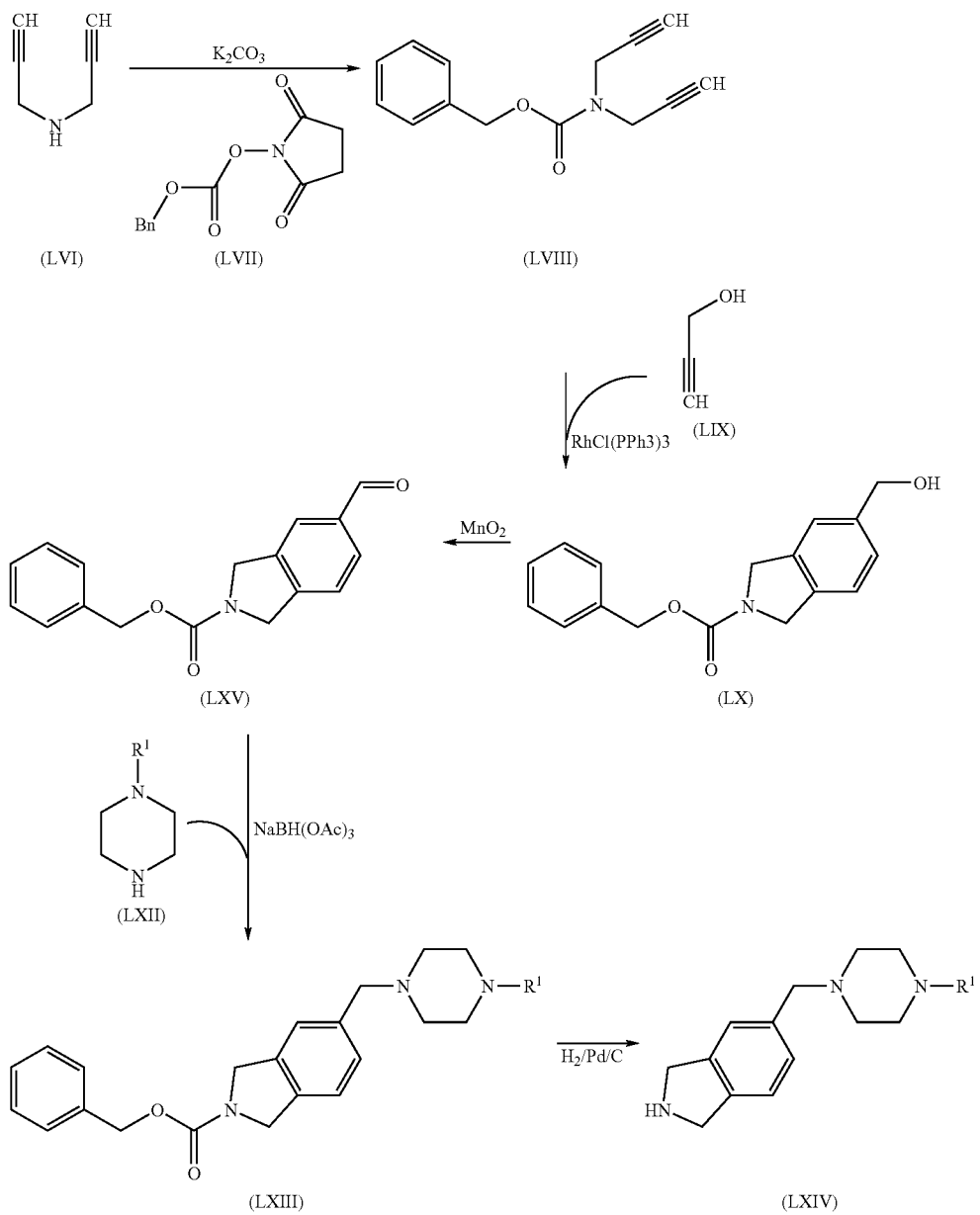

In Scheme 9A, rather than being converted to the mesylate (LXI), the hydroxymethylindoline (LX) is oxidised to the corresponding aldehyde (LXV) using manganese dioxide in dichloromethane, and the aldehyde is then converted to a compound of the formula (LXIII) by reaction with a compound of the formula (LXII) under reductive amination conditions, e.g. in the presence of sodium triacetoxyborohydride. The Z-group is then removed by hydrogenation as described above in respect of Scheme 9 to give the intermediate (LXIV).

Compounds of the formula (VIIb) as defined herein can be prepared by the reaction of a compound of the formula (XIX) or a protected derivative thereof with a compound of the formula (XX):

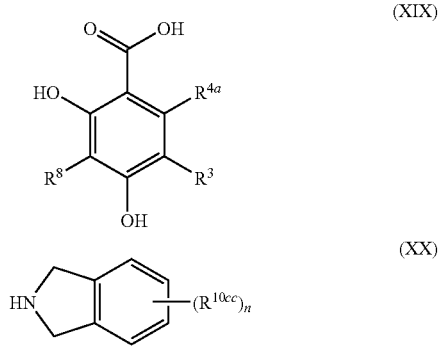

wherein n, $R^3$, $R^{4a}$, $R^8$ and $R^{10cc}$ are as defined herein, under amide forming conditions as described above and in the examples.

Within formula (XX), particular intermediates of the invention can be represented by the formula (XXI):

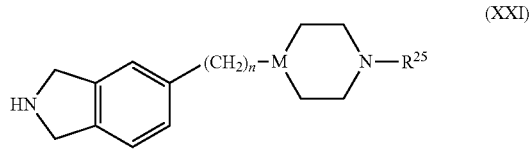

(XXI)

wherein n is 0 or 1; M is N or CHOH and $R^{25}$ is hydrogen or methyl; provided that when n is 0 and $R^{25}$ is methyl, then M is CHOH.

Particular intermediates within formula (XXI) are the compounds (XXII), (XXIII) and (XXIV) below.

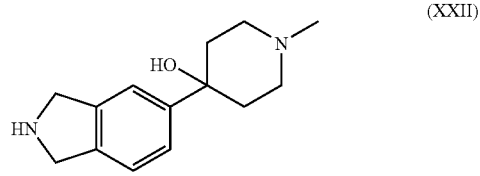

(XXII)

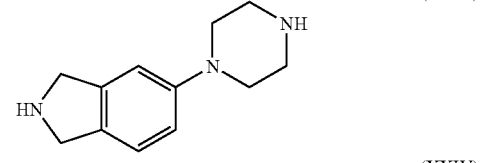

(XXIII)

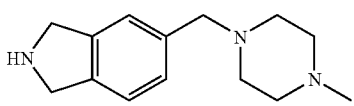

(XXIV)

The intermediates of formula (XXI) can be made by methods well known to the skilled person or methods analogous thereto. For example, intermediate XXII can be prepared by lithium-halogen exchange of a suitably N-protected 5-bromoisoindoline, quenching with 1-methyl-4-piperidone and subsequent deprotection. Intermediate XXII can be prepared by Buchwald palladium coupling of 4-BOC-piperazine and a suitably N-protected 5-bromoisoindoline followed by subsequent deprotection. One method of preparation for intermediate XXIV is from a suitably N-protected isoindoline-5-carboxylic acid, Weinreb amide formation, reduction to the aldehyde, followed by reductive amination and subsequent deprotection.

Once formed, where the substituent groups permit, one compound of the formula (I), or a protected form thereof, can be converted into another compound of the formula (I).

For example, when $R^1$ and $R^2$ are both protected hydroxy groups (e.g. benzyloxy groups), and $R^3$ is bromine, the bromine atom can be replaced by trifluoromethyl by reaction with a trifluoroacetate salt (e.g. sodium trifluoroacetate), and copper (I) iodide in a polar solvent such as dimethylformamide.

In another procedure, compounds of the formula (I) wherein $R^8$ is fluorine can be prepared from compounds of the formula (I) where $R^8$ is hydrogen by electrophilic fluorination. Electrophilic fluorination can be carried out using a fluorinating agent such as 1-(chloromethyl)-4-fluoro-1,4-diazoniabicyclo[2.2.2]octane bis(tetrafluoroborate) or similar N-fluoro-diazonia compounds.

In a further procedure, compounds of the formula (I) wherein $R^1$ and $R^2$ are both hydroxy groups can be monomethylated to give a compound where one of $R^1$ and $R^2$ is a methoxy group by reaction with one equivalent of a methylating agent such as dimethylsulphate. The methylation reaction is typically carried out in a polar solvent such as acetonitrile in the presence of a base, for example an alkali metal carbonate such as potassium carbonate. Analogous methylation reactions may also be carried out on intermediate compounds containing two phenolic hydroxy groups.

Many of the procedures described below and used in this synthesis are well known to those skilled in the art, and examples of alkylations, acylations, functional group interconversions and reagents and conditions for carrying out such conversions can be found in, for example, *Advanced Organic Chemistry*, by Jerry March, 4th edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8).

As well as the specific examples, and the methods of preparation outlined below, it is understood that modification to the routes described would allow synthesis of many further examples of compounds claimed in Formula 1. For example, alternative benzoic acid starting materials with differing or additional substitution patterns could be prepared.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc). When the hydroxy group is a phenolic hydroxy group, for example in compounds of the formula (I) wherein $R^1$ and/or $R^2$ are hydroxy, a preferred protecting group is a benzyl group.

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_6$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl)

and methanesulphonyl (mesyl) groups and benzyl groups such as a para-methoxybenzyl (PMB) group. A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$alkyl ester; or a $C_{5-20}$ aryl-$C_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O) CH$_3$).

Methods of Purification

The compounds may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Alternatively, normal phase preparative LC based methods might be used in place of reverse phase methods. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's p$K_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (I) or acid addition salt thereof. Lyophilisation refers to the procedure of freeze-drying a composition. Freeze-drying and lyophilisation are therefore used herein as synonyms. A typical process is to solubilize the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one embodiment of the invention, the pharmaceutical composition is in a form suitable for i.v. administration, for example by injection or infusion.

In another embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

For fungal, protozoal and parasitic diseases and conditions where the infection takes place in the skin or a mucosal surface, topical compositions may be of particular benefit.

Compositions for topical use include ointments, creams, suspensions, lotions, powders, solutions, pastes, sprays, patches, gels, liquid drops, aerosols, oils and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Thus, unit-dose suppositories or pessaries may be prepared by admixture of the active ingredient with one or more conventional solid carriers, for example coca butter, and shaping the resulting mixture. Further examples of moldable waxy materials include polymers such as high molecular weight polyalkylene glycols, e.g. high molecular weight polyethylene glycols.

Alternatively, in the case of vaginal administration, the formulation may be presented as a tampon impregnated with the active ingredients and optionally one or more excipients or diluents. Other formulations suitable for rectal and vaginal administration include creams, gels, foams, pastes and sprays.

Further examples of topical compositions include dressings such as bandages and adhesive plasters impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 micrograms, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

Treatment of Pain and Stroke

The compounds of formula (I) may be used to treat pain conditions in patients. Prior to treatment, a diagnosis of the pain condition will be carried out by someone skilled in the art. This could include obtaining history and characteristics of the pain, physical examination of the patient and any appropriate diagnostic tests. Once the type of pain has been determined, a compound of formula (I) may be administered in an amount effective to treat the pain.

As stated above, the terms "treatment" and "treat" in the context of pain include both prophylactic and palliative treatment. Thus, the compounds of formula (I) may be used in a prophylactic sense to prevent the onset of pain or to prevent pain from worsening, or they may be used to reduce or eliminate pain in a patient suffering from pain.

The compounds may also be used to treat or reduce the effects of stroke as described above. For example, the compounds may be used as neuroprotective agents to prevent or reduce the damage to brain tissue following a stroke. They may also be administered to patients exhibiting one or more risk factors indicative of a possible stroke.

Thus, the compounds of formula (I) are typically administered to a subject in need of such administration, for example a human or animal patient, preferably a human.

The compounds are typically administered in amounts that are therapeutically or prophylactically useful and which generally are non-toxic. However, in certain situations (for example in the case of extreme pain or pain associated with a terminal condition), the benefits of administering the compounds may outweigh the disadvantages of any toxic effects or side effects, in which case it may be considered desirable to administer the compound in amounts that are associated with a degree of toxicity.

The compounds of the invention may be administered over a prolonged term to maintain beneficial therapeutic effects or may be administered for a short period only. Alternatively they may be administered in a pulsatile or continuous manner.

A typical daily dose of the compound of formula (I), whether administered topically or systemically, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required.

Ultimately, however, the quantity of compound administered and the type of composition used will be commensurate with the nature of the disease or physiological condition being treated and will be at the discretion of the physician.

A typical daily dose of the compound of formula (I), whether administered topically or systemically, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compounds may be administered once or more than once each day depending on the severity and type of pain.

Ultimately, however, the quantity of compound administered and the type of composition used will be commensurate with the nature of the disease or physiological condition being treated and will be at the discretion of the physician.

Accordingly, a person skilled in the art would know through their common general knowledge the dosing regimes to use.

The compounds of formula (I) can be administered as a sole therapeutic agent or in combination with other therapeutic agents. For example, the compounds can be administered in a combination together with one or more other therapeutic agents useful for treating pain. Examples include other anti-nociceptive compounds, non-steroidal anti-inflammatories (NSAID's), opioids, GABA analogues, narcotic analgesics, local anesthetics, NMDA antagonists, neuroleptic agents, anti-convulsants, anti-spasmodics, anti depressants or muscle relaxants and/or excipients/formulations to treat the pain conditions described.

Treatment of Fungal, Protozoal, Viral and Parasitic Diseases

It is envisaged that the compounds of the formula (I) and sub-groups as defined herein will be useful in the prophylaxis or treatment of a range of fungal, protozoal and parasitic disease states or conditions mediated by Hsp90 client proteins. Examples of such disease states and conditions are set out above. For example, compounds of the invention may be administered to human patients suffering from, or at risk of infection by one or more fungal, protozoal or parasitic species.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively, they may be administered in a pulsatile or continuous manner in accordance with persistent intermittent dosing.

For topical administration, pessaries will typically be inserted into the vagina singly or in twos or threes, generally once or twice daily. It is often convenient to administer pessaries nightly. Vaginal creams, gels, foams or ointments will generally be administered one to four times daily and, similarly, it may be found convenient to apply the medicament at night. Application of a cream is often assisted by means of an applicator.

Often, a cream will be administered in conjunction with another form of the medicament, for example, a tampon or pessary. Combinations such as these are within the scope of the present invention.

Tampons will usually be administered once daily although in certain cases it may prove necessary to increase the frequency of administration.

The duration of treatment generally will be between one and fourteen days although longer periods may be required in some instances.

A typical daily dose of the compound of formula (I), whether administered topically or systemically, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more ancillary compounds for treatment of a particular disease state, and in particular with other anti-fungal, anti-protozoal, antiviral or anti-parasitic agents, and most particularly with other anti-fungal agents.

Examples of other anti-fungal agents that may be administered together (whether concurrently or at different time intervals) with the compounds of the formula (I) include, but are not limited to:

anti-fungal azoles such as fluconazole, ketoconazole, itraconazole, butoconazole, clotrimazole, miconazole, oxiconazole, econazole, mebendazole, bifonazole, fenticonazole, isoconazole, sertaconazole, sulconazole, thiabendazole, tiaconazole, ravuconazole, posaconazole and voriconazole;

Polyene antibiotics such as nystatin, amphotericin B, natamycin, rimocidin, filipin and pimaricin;

Allylamines such as terbinafine, amorolfine, naftifine, butenafine, echinocandin, anidulafungin, caspofungin and micafungin;

Flucytosine;

Griseofulvin;

Fluocinonide; and

Gentian Violet

Examples of other anti-viral agents that may be administered with the compounds of the invention include acyclovir, ganciclovir, oseltamavir (Tamiflu®) and zanamavir (Relenza®), amantidine, rimantadine, adefovir dipivoxil, interferons (e.g. Interferon alfa-2b and pegylated interferon alfa-2a), lamivudine, entecavir, ribavirin, famciclovir, valcicylovir, valacyclovir, azidothymidine (AZT-Retrovir®), atazanavir, fosamprenavir, lamivudine, lamivudine+abacavir, tenofovir disoproxil fumarate, tenofovir disoproxil fumarate+emtricitabine, tipranavir, nelfinavir, indinavir, raltegravir, ritonavir, lopinavir+ritonavir, darunavir, amprenavir, enfuvirtide, saquinavir, hydroxyurea, VGV-1 and antiviral vaccines.

For the case of Hsp90 inhibitors combined with other therapies, the two or more treatments may be given in individually varying dose schedules and via different routes.

Where the compound is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

A person skilled in the art would know through his or her common general knowledge the dosing regimes and combination therapies to use.

Methods of Diagnosis

Prior to administration of a compound, a patient may be screened to determine whether a fungal, protozoal, viral or parasitic disease or condition from which the patient is or may be suffering is one which would be susceptible to treatment with a compound having activity against Hsp90.

For example, a biological sample taken from a patient may be analysed to establish the presence of a fungal, protozoal, viral or parasitic infection either by culture or direct microscopy. Active infection may also be diagnosed on the basis of an immune response which can be measured in the patient's blood. Thus, the compounds of the invention may be used to treat members of a sub-population of patients who have been diagnosed as suffering from a fungal, protozoal, viral or parasitic infection.

EXAMPLES

The invention will now be illustrated, but not limited, by reference to the specific embodiments described in the following examples.

In the examples, the following abbreviations may be used.
AcOH acetic acid
BOC tert-butyloxycarbonyl
Bn benzyl
CDI 1,1-carbonyldiimidazole
DMAW90 Solvent mixture: DCM: MeOH, AcOH, $H_2O$ (90:18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether
h hour(s)
HOAt 1-hydroxyazabenzotriazole
HOBt 1-hydroxybenzotriazole
MeCN acetonitrile
MeOH methanol
min. minutes
P.E. petroleum ether
r.t. room temperature
$SiO_2$ silica
TBTU N,N,N',N'-tetramethyl-O-(benzotriazol-1-yl)uronium tetrafluoroborate
THF tetrahydrofuran Proton magnetic resonance ($^1H$ NMR) spectra were recorded on a Bruker AV400 instrument operating at 400.13 MHz, in DMSO-dB or MeOH-$d_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

In the examples, the compounds prepared were characterised by liquid chromatography and mass spectroscopy using the system and operating conditions set out below. Where atoms with different isotopes are present and a single mass quoted, the mass quoted for the compound is the monoisotopic mass (i.e. $^{35}Cl$; $^{79}Br$ etc.). Different systems were used, as described below, and these were equipped with, and were set up to run under, closely similar operating conditions. The operating conditions used are also described below.

System Description:
System 1 (Analytical System):
HPLC System: Waters 2795
Mass Spec Detector: Micromass Platform LC
PDA Detector: Waters 2996 PDA
System 2 (Preparative and Analytical System):
HPLC System: Waters Fractionlynx system
Mass Spec Detector: Waters ZQ
PDA Detector: Waters 2996 PDA
System 3 (Preparative and Analytical System):
HPLC System: Agilent 1100 system
Mass Spec Detector: LC/MSD
UV Detector: Agilent MWD
Operating Conditions:
Acidic Analytical Conditions:
Eluent A: $H_2O$ (0.1% Formic Acid)
Eluent B: $CH_3CN$ (0.1% Formic Acid)
Gradient: 5-95% eluent B over 3.5 minutes (over 15 minutes w/column 2)
Flow: 0.8 ml/min
Column 1: Phenomenex Synergi 4μ MAX-RP 80A, 2.0×50 mm
Column 2: Phenomenex Synergi 4μ MAX-RP 80A, 2.0×150 mm
Basic Analytical Conditions:
Eluent A: $H_2O$ (10 mM $NH_4HCO_3$ buffer adjusted to pH=9.2 with $NH_4OH$)
Eluent B: $CH_3CN$
Gradient: 5-95% eluent B over 3.5 minutes
Flow: 0.8 ml/min
Column: Phenomenex Gemini 5μ 2.0×50 mm
MS conditions (Waters Systems):
Capillary voltage: 3.6 kV (3.40 kV on ES negative)
Cone voltage: 25 V
Source Temperature: 120° C.
Scan Range: 125-800 amu
Ionisation Mode: ElectroSpray Positive, Negative or Positive & Negative
MS Conditions (Agilent Systems):
Capillary voltage: 4000 V (3500 V on ES Negative)
Fragmentor/Gain: 150/1
Drying gas Temp/flow: 350° C./13.0 $Lmin^{-1}$
Nebuliser pressure: 50 psig
Scan Range: 125-800 amu
Ionisation Mode: ElectroSpray Positive or Negative The starting materials for each of the Examples are commercially available unless otherwise specified.

A. General Synthetic Methods

In the following general methods, the volumes stated may vary according to the scale of the reaction, as will be apparent to the skilled person.

Method A1
Amide Coupling (Acid Chloride Method)

A mixture of a carboxylic acid (1 equivalent) and thionyl chloride (1.5 equivalents) in benzene (or toluene) was stirred and held at reflux for 2 hours. Excess amine was added dropwise to the hot solution and the mixture stirred at room temperature for 15 minutes. Alternatively, the acid chloride could be isolated by evaporation and then re-dissolved in a 9:1 mixture of dichloromethane: triethylamine and the amine then added and the mixture stirred under nitrogen at room temperature for 1-18 hours. In either case, the mixture was diluted with ethyl acetate and extracted successively with water, saturated aqueous sodium bicarbonate and 2M hydrochloric acid. The organic layer was reduced to dryness in vacuo and the pure products were obtained either by trituration with ethyl acetate or by column chromatography on silica (eluting with mixtures of ethyl acetate in petroleum ether) or in a few cases by preparative HPLC/MS.

Method A2
Amide Coupling (EDC, HOBt Method)

A stirred solution of the acid (1 equivalent) in dichloromethane (10 ml) was treated successively with N-ethyl-N'-(3-dimethylaminopropyl)carbodiimide hydrochloride (1.2 equivalents), 1-hydroxybenzotriazole (1.2 equivalents) and the amine (1.5 equivalents) and the mixture was stirred at room temperature overnight. The mixture was washed successively with 2M hydrochloric acid and 2M sodium hydroxide, the organic layer was separated and the solvent removed in vacuo to afford the products. The products were either obtained pure or were purified by column chromatography on silica (eluting with mixtures of ethyl acetate in petroleum ether or methanol in ethyl acetate as appropriate).

Method A3
Anisole or benzyl ether dealkylation (BBr$_3$ Method)

A stirred solution of the anisole or benzyl ether (1 equivalent) in dichloromethane at 0° C. was treated dropwise with a 1M solution of boron tribromide in dichloromethane (1.5 equivalents per group to be deprotected) and the mixture was stirred for 2 hours. The reaction was quenched by the addition of water and saturated aqueous sodium bicarbonate, the organic layer was separated and the solvent was removed in vacuo. The pure products were obtained either by trituration with diethyl ether or ethyl acetate or by column chromatography on silica (eluting with mixtures of ethyl acetate in petroleum ether).

Method A4
Amide Coupling (EDC, HOAt Method)

A stirred solution of the acid (1 equivalent) in dimethylformamide (5 ml) was treated successively with N-ethyl-N'-(3-dimethylaminopropyl)carbodiimide hydrochloride (1.2 equivalents), 1-hydroxy-7-aza-benzotriazole (1.2 equivalents) and the amine (1.5 equivalents) and the mixture was stirred at room temperature overnight. DMF was evaporated and crude dissolved in EtOAc and was washed successively with saturated sodium bicarbonate, the organic layer was separated and the solvent removed in vacuo. The products were either obtained pure or were purified by column chromatography on silica (eluting with mixtures of ethyl acetate in petroleum ether or methanol in ethyl acetate as appropriate).

Method A5
Hydrogenation

A stirred solution of protected derivative (1 equivalent) and a catalytic amount of 10% palladium on carbon (typically 30-50 mg) in ethanol (5-10 ml), methanol (5-10 ml) or methanol/DCM (3 ml/3 ml) was stirred at room temperature under an atmosphere of hydrogen for 2-16 hours. The catalyst was removed by filtration, washed with methanol (5 ml) and the solvent removed in vacuo to afford the products. Some required purification by flash chromatography, eluting typically with ether.

Method A6
Suzuki Coupling

The aryl bromide (1 equivalent, typically 0.5 mmol), boronic acid or potassium vinyl trifluoroborate derivative (1.2 equivalents) and caesium carbonate (3 equivalents) were dissolved in THF (10 ml) under nitrogen. 1,1'-Bis(diphenylphosphino)ferrocene] palladium(II) dichloride (0.1 equivalent) was added and then water (1 ml). The mixture begins to darken until black. The mixture was then heated at reflux under nitrogen until the reaction is complete (845 hrs). The mixture was cooled, diluted with DCM and magnesium sulphate added. The mixture was filtered and the solvent evaporated. The resulting residues were purified by flash chromatography in pet. ether/ether mixtures, and generally gave product in good yield (~60-80%).

Method A7
Resorcinol Mono-O-Methylation

Dimethyl sulphate (1 equivalent) was added to a stirred solution of the resorcinol (1 equivalent) and potassium carbonate (2.2 equivalents) in acetonitrile (10 ml per mmol of substrate) and the mixture was stirred at room temperature for 16 hours. The solvent was removed in vacuo, the residue partitioned between dichloromethane and water, the organic layer separated and the solvent removed in vacuo. The pure products were obtained either after column chromatography on silica (eluting with mixtures of petroleum ether and ethyl acetate) or by preparative HPLC/MS.

Method A8
Electrophilic Aromatic Fluorination 1-(Chloromethyl)-4-fluoro-1,4-diazoniabicyclo[2.2.2]octane bis(tetrafluoroborate) (1 equivalent) was added to a solution of the substrate (1 equivalent) in acetonitrile (15 ml per mmol of substrate) and the mixture was stirred at room temperature for 16 hours. The solvent was removed in vacuo and the residue was partitioned between ethyl acetate and water. The organic layer was separated and reduced to dryness in vacuo. The pure products were obtained either after column chromatography on silica (eluting with mixtures of petroleum ether and ethyl acetate) or by preparative HPLC/MS.

B. Synthesis of Carboxylic Acid Intermediates

Preparation B1

4-Hydroxy-3-isopropylbenzoic acid

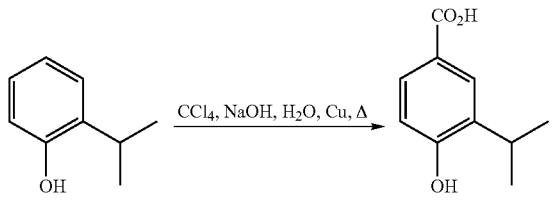

Carbon tetrachloride (28 ml, 0.26 mol) and copper powder (1.0 g) were added to a stirred solution of 2-isopropylphenol (27.2 g, 0.2 mol) in 50% aqueous sodium hydroxide (120 ml) and the mixture was held at reflux for 16 hours. Upon cooling the mixture was acidified to pH 2 or below by the addition of concentrated hydrochloric acid and was extracted with ethyl acetate. The organic layer was extracted with a saturated aqueous solution of sodium bicarbonate and the aqueous layer acidified to pH 2 or below by the very careful addition of concentrated hydrochloric acid. The solution was extracted with ethyl acetate, the organic layer was washed with water, separated and the solvent removed in vacuo to afford 4-hydroxy-3-isopropylbenzoic acid (12.5 g, 35%) as a bright red solid that was used without further purification. $^1$H NMR (DMSO-$d_6$) 12.36 (1H, br s), 10.13 (1H, br s), 7.73 (1H, d), 7.63 (1H, dd), 6.85 (1H, d), 3.22 (1H, m), 1.19 (6H, d). MS: [M–H]$^+$ 179.

Alternatively, if required, the crude product may be purified using a three step procedure involving di-benzylation [according to the conditions outlined below in Preparation B5 for the synthesis of methyl 5-acetyl-2,4-bis-benzyloxybenzoate (BnBr, K$_2$CO$_3$, MeCN, reflux)], column chromatography on silica to remove highly coloured impurities (eluting with 3-5% ethyl acetate in petroleum ether) and catalytic hydrogenation [according to Method A5 outlined above (10% Pd/C, EtOH, H$_2$)] to afford 4-hydroxy-3-isopropylbenzoic acid as a colourless solid.

Preparation B2

5-Ethyl-2-methoxybenzoic acid

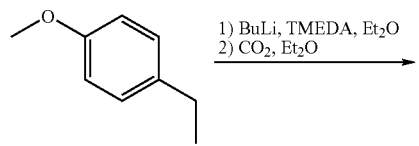

n-Butyl lithium (2.5M in hexanes, 38.5 ml, 100.0 mmol) was added dropwise under a nitrogen atmosphere to a stirred solution of 4-ethylanisole (11.7 g, 86.0 mmol) and N,N,N',N'-tetramethylethylenediamine (10 ml, 88.0 mmol) in anhydrous diethyl ether (100 ml) and the mixture was stirred and held at 30° C. for 16 hours. The mixture was cooled and poured slowly in to a mixture of excess solid carbon dioxide in anhydrous diethyl ether. Upon warming to room temperature the mixture was made basic by the addition of 2M sodium hydroxide, the aqueous layer was separated and acidified to pH 2 or below by the addition of concentrated hydrochloric acid. The mixture was extracted with diethyl ether, the organic layer separated and the solvent removed in vacuo to afford 5-ethyl-2-methoxybenzoic acid (5.7 g, 37%) as a pale yellow oil. $^1$H NMR (DMSO-$d_6$) 12.50 (1H, br s), 7.48 (1H, d), 7.33 (1H, dd), 7.03 (1H, d), 2.56 (2H, q), 1.17 (3H, q). MS: [M+H]$^+$ 181.

Preparation B3

2,4-Bis-benzyloxy-5-chloro-benzoic acid

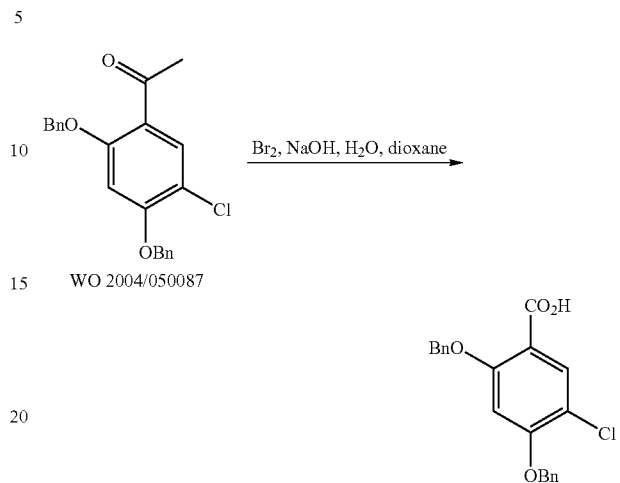

WO 2004/050087

1-(2,4-Bis-benzyloxy-5-chloro-phenyl)-ethanone [prepared as per WO 2004/0500087] (1.10 g, 3.0 mmol) was added to a stirred solution of sodium hydroxide (1.20 g, 30.0 mmol) in water (10 ml) and dioxane (10 ml). Bromine (1.44 g, 9.0 mmol) was added dropwise and the mixture stirred at room temperature for 3 hours. The dioxane was removed by evaporation in vacuo and the mixture acidified to pH 2 or below by the addition of 2M hydrochloric acid. The mixture was extracted with ethyl acetate, the organic layer separated and the solvent removed in vacuo to afford 2,4-bis-benzyloxy-5-chloro-benzoic acid (900 mg, 81%) as a pale yellow solid. $^1$H NMR (DMSO-$d_6$) 12.58 (1H, br s), 7.77 (1H, s), 7.55-7.30 (10H, m), 7.11 (1H, s), 5.31 (2H, s), 5.27 (2H, s). MS: [M+H]$^+$ 369.

Preparation B4

3-(1,2-Dimethyl-allyl)-4-hydroxy-benzoic acid

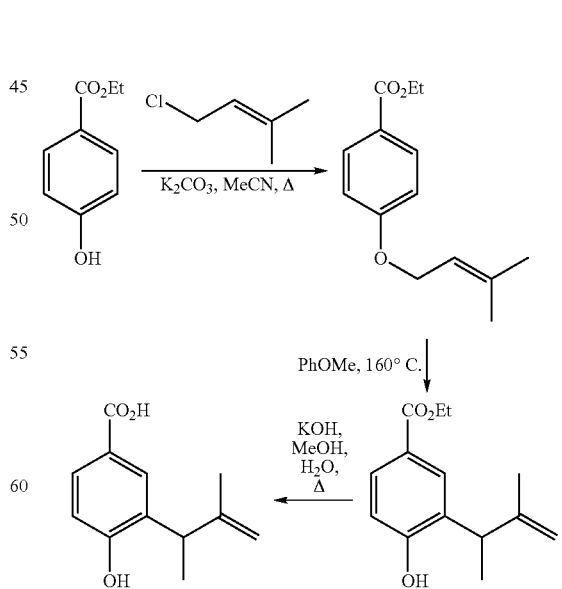

Ethyl 4-hydroxybenzoate (1.66 g, 10.0 mmol) and anhydrous potassium carbonate (2.07 g, 15.0 mmol) in acetonitrile (30 ml) was treated with 3-methyl-2-butenyl chloride (1.35 ml, 12.0 mmol) and the mixture was stirred and held at reflux for 3 hours. Upon cooling the solvent was removed in vacuo and the mixture partitioned between dichloromethane and water. The organics were separated and the solvent removed in vacuo to afford ethyl 4-(3-methyl-but-2-enyloxy)-benzoate (2.23 g, 95%) as a pale yellow liquid which was used without further purification. $^1$H NMR (DMSO-$d_6$) 7.89 (2H, d), 7.04 (2H, d), 5.44 (1H, t), 4.62 (2H, d), 4.28 (2H, q), 1.77 (3H, s), 1.73 (3H, s), 1.31 (3H, t). MS: [M+H]$^+$ 235.

Ethyl 4-(3-methyl-but-2-enyloxy)-benzoate (2.23 g, 9.53 mmol) was dissolved in anisole (8 ml) and the mixture stirred and held at reflux for 4 days. The solvent was removed in vacuo and the residue subjected to column chromatography on silica. Elution with 20% ethyl acetate in petroleum ether afforded ethyl 3-(1,2-dimethyl-allyl)-4-hydroxy-benzoate (600 mg, 27%) as a Colourless solid. $^1$H NMR (DMSO-$d_6$) 10.32 (1H, br s), 7.67 (1H, dd), 7.62 (1H, s), 6.90 (1H, d), 4.90 (1H, s), 4.85 (1H, s), 4.25 (2H, q), 3.75 (1H, q), 1.61 (3H, s), 1.30 (3H, t), 1.26 (3H, d). MS: [M+H]$^+$ 235.

Ethyl 3-(1,2-dimethyl-allyl)-4-hydroxy-benzoate (600 mg, 2.56 mmol) was dissolved in methanol (20 ml), a solution of potassium hydroxide (560 mg, 10.0 mmol) in water (10 ml) was added and the mixture was stirred and held at reflux for 16 hours. Upon cooling the methanol was removed in vacuo and the solution acidified to pH 2 or below by the addition of 2M hydrochloric acid. The solution was extracted with dichloromethane, the organic layer was separated and the solvent was removed in vacuo to afford 3-(1,2-dimethyl-allyl)-4-hydroxy-benzoic acid (270 mg, 51%) as a colourless gum. $^1$H NMR (DMSO-$d_6$) 12.38 (1H, br s), 10.22 (1H, br s), 7.63 (2H, m), 6.88 (1H, d), 4.90 (1H, s), 4.87 (1H, s), 3.75 (1H, q), 1.60 (3H, s), 1.28 (3H, d). MS: [M−H]$^+$ 205.

Preparation B5

2,4-Bis-benzyloxy-5-isopropenyl-benzoic acid

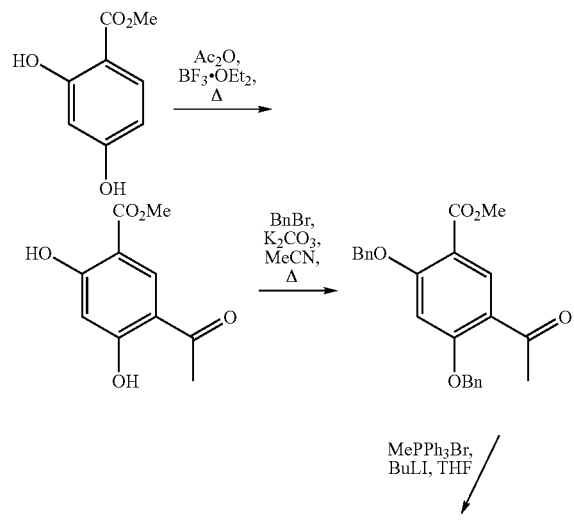

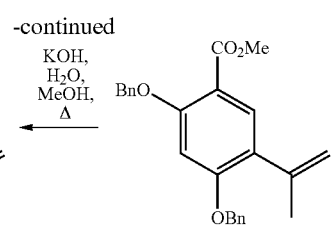

Acetic anhydride (3.06 g, 30.0 mmol) was added to methyl 2,4-dihydroxybenzoate (5.04 g, 30.0 mmol) in boron trifluoride diethyl etherate (7.6 ml) and the mixture was stirred and held at reflux for 3 hours and then allowed to cool to room temperature. Water (80 ml) was added and the mixture stirred at room temperature for 30 minutes. The resulting yellow solid was removed by filtration and sucked as dry as possible under vacuum. The solid was dissolved in dichloromethane and was washed with water, the organic layer was separated and the solvent removed in vacuo to afford methyl 5-acetyl-2,4-dihydroxybenzoate as a bright yellow solid (2.62 g, 42%) which was used without further purification. $^1$H NMR (DMSO-$d_6$) 12.58 (1H, s), 11.22 (1H, s), 8.33 (1H, s), 6.45 (1H, s), 3.90 (3H, s), 2.62 (3H, s). MS: [M+H]$^+$ 211.

Methyl 5-acetyl-2,4-dihydroxybenzoate (2.62 g, 12.48 mmol) was dissolved in acetonitrile (40 ml), anhydrous potassium carbonate (4.93 g, 35.7 mmol) was added and the stirred mixture was treated with benzyl bromide (5.09 g, 29.75 mmol) and held at reflux for 3 hours. Upon cooling the solvent was removed in vacuo and the mixture partitioned between water and dichloromethane. The organic layer was separated and the solvent removed in vacuo to afford methyl 5-acetyl-2,4-bis-benzyloxybenzoate (3.48 g, 71%) as a colourless solid which was dried at 50° C. in a vacuum oven and used without further purification. $^1$H NMR (DMSO-$d_6$) 8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]$^+$ 391.

A stirred suspension of methyltriphenylphosphonium bromide (1.96 g, 5.5 mmol) in anhydrous tetrahydrofuran (20 ml) at 0° C. under a nitrogen atmosphere was treated dropwise with n-butyl lithium (1.6 M in hexanes, 3.5 ml, 5.5 mmol) and the resulting bright yellow solution was stirred at 0° C. for 30 minutes. A solution of methyl 5-acetyl-2,4-bis-benzyloxybenzoate (1.95 g, 5.00 mmol) in anhydrous tetrahydrofuran (20 ml) was added dropwise and the resulting mixture was allowed to warm to room temperature and was stirred for 16 hours. Methanol (10 ml) was added and the solvent was removed in vacuo. The residues were partitioned between dichloromethane and water, the organic layer was separated and the solvent removed in vacuo to afford a brown gum that was purified by column chromatography on silica. Elution with 7% ethyl acetate in petroleum ether afforded methyl 2,4-bis-benzyloxy-5-isopropenyl-benzoate as a colourless solid (700 mg, 36%). $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]$^+$ 389.

Methyl 2,4-bis-benzyloxy-5-isopropenyl-benzoate (700 mg, 1.80 mmol) was dissolved in methanol (20 ml), a solution of potassium hydroxide (286 mg, 5.1 mmol) in water (4 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford 2,4-bis-benzyloxy-5-isopropenyl-benzoic acid (600 mg, 89%) as a colourless solid. $^1$H NMR (DMSO-d$_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]$^+$ 375.

Preparation B6

2,4-Bis-benzyloxy-5-bromo-benzoic acid

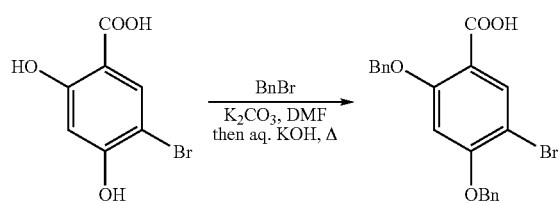 [SMILES: O=C(O)c1cc(Br)c(O)cc1O ; "BnBr" ; O=C(O)c1cc(Br)c(OCc2ccccc2)cc1OCc1ccccc1]

2,4-dihydroxy-5-bromobenzoic acid (5.16 g, 22.15 mmol) was dissolved in DMF (40 ml) and potassium carbonate (12.2 g) and benzyl bromide (8 ml) were sequentially added. The mixture was stirred at room temperature for 18 hours under nitrogen. An aqueous solution of potassium hydroxide (2 g) in water (25 ml) was then added, followed by methanol (50 ml) and the mixture heated to reflux with vigorous stirring for 24 hours. The mixture was then allowed to cool, was poured into 1N HCl (250 ml) and was then extracted with ether and then DCM. The combined organic layers were dried over magnesium sulphate and the solvent evaporated in vacuo. The resulting solid material was washed with P.E. and then Et$_2$O (3×50 ml) to yield pure product (5.2 g, 56%). $^1$H NMR (MeOH-d$_4$) 8.06 (1H, s), 7.51-7.30 (10H, m), 6.85 (1H, s), 5.22 (2H, s), 5.20 (2H, s). MS: [M+H]$^+$ 413.

Preparation B7

Synthesis of (Z)-4-benzyloxy-3-(1-methyl-propenyl)-benzoic acid

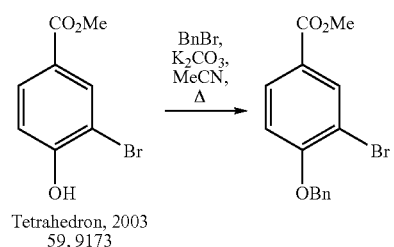

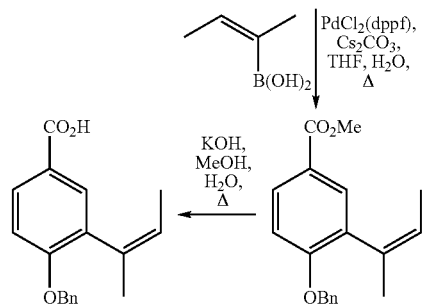

Methyl 3-bromo-4-hydroxybenzoate [prepared as per *Tetrahedron*, 2003, 59, 9173] (3.47 g, 15.0 mmol) was dissolved in acetonitrile (50 ml), anhydrous potassium carbonate (3.11 g, 22.5 mmol) was added and the stirred mixture was treated with benzyl bromide (3.08 g, 18.0 mmol) and held at reflux for 5 hours. Upon cooling the solvent was removed in vacuo and the mixture partitioned between water and dichloromethane. The organic layer was separated, the solvent removed in vacuo and the residue subjected to column chromatography on silica. Elution with 10% ethyl acetate in petroleum ether afforded methyl 4-benzyloxy-3-bromobenzoate (3.6 g, 75%) as a colourless solid. $^1$H NMR (DMSO-d$_6$) 8.12 (1H, d), 7.96 (1H, dd), 7.51 (2H, m), 7.43 (2H, t), 7.35 (2H, m), 5.32 (2H, s), 3.84 (3H, s).

Methyl 4-benzyloxy-3-bromobenzoate (1.61 g, 5.0 mmol), caesium carbonate (4.89 g, 15.0 mmol), (E)-2-buten-2-yl boronic acid (600 mg, 6.0 mmol) and [1,1'-bis(diphenylphosphino)ferrocenyl]palladium (II) chloride (204 mg, 0.25 mmol) were dissolved in anhydrous tetrahydrofuran (100 ml), water (10 ml) was added and the mixture was stirred and held at reflux under an atmosphere of nitrogen for 16 hours. Upon cooling the solvent was removed in vacuo and the mixture partitioned between dichloromethane and water. The organic layer was separated, the solvent removed in vacuo and the residue subjected to column chromatography on silica. Elution with 5% ethyl acetate in petroleum ether afforded methyl (Z)-4-benzyloxy-3-(1-methyl-propenyl)-benzoate (600 mg, 41%) as a colourless solid. $^1$H NMR (DMSO-d$_6$) 7.88 (1H, dd), 7.59 (1H, d), 7.40 (4H, m), 7.34 (1H, m), 7.23 (1H, d), 5.57 (1H, q), 5.21 (2H, s), 3.82 (3H, s), 1.94 (3H, s), 1.38 (3H, d).

Methyl (Z)-4-benzyloxy-3-(1-methyl-propenyl)-benzoate (592 mg, 2.0 mmol) was dissolved in methanol (20 ml), a solution of potassium hydroxide (336 mg, 6.0 mmol) in water (7 ml) was added and the mixture was stirred and held at reflux for 3 hours. Upon cooling the solvent was removed in vacuo and the mixture acidified to pH 2 or below by the addition of 2M hydrochloric acid. The mixture was extracted with dichloromethane, the organic layer was separated and the solvent removed in vacuo to afford (Z)-4-benzyloxy-3-(1-methyl-propenyl)-benzoic acid (460 mg, 82%) as a colourless solid. $^1$H NMR (DMSO-d$_6$) 7.85 (1H, dd), 7.57 (1H, d), 7.40 (4H, m), 7.34 (1H, m), 7.18 (1H, d), 5.57 (1H, q), 5.21 (2H, s), 1.96 (3H, s), 1.40 (3H, d). MS: [M+H]$^+$ 283.

Preparation B8

Synthesis of 2,4-bis-benzyloxy-5-tert-butyl-benzoic acid

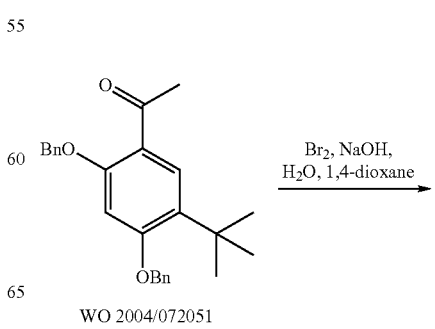

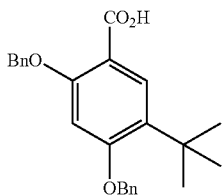

1-(2,4-Bis-benzyloxy-5-tert-butyl-phenyl)-ethanone [prepared as per WO 2004/072051] (2.02 g, 5.2 mmol) was dissolved in 1,4-dioxane (30 ml), a solution of sodium hydroxide (2.08 g, 52.0 mmol) in water (30 ml) was added and the mixture was stirred and treated dropwise with bromine (0.8 ml, 15.6 mmol). The resulting mixture was stirred at room temperature for 16 hours. The 1,4-dioxane was removed in vacuo and the mixture acidified to pH 2 or below by the addition of 2M hydrochloric acid. The mixture was extracted with ethyl acetate, the organic layer was separated, the solvent removed in vacuo and the residue subjected to column chromatography on silica. Elution with 30% ethyl acetate in petroleum ether afforded 2,4-bis-benzyloxy-5-tert-butyl-benzoic acid (1.6 g, 79%) as a pale yellow oil. $^1$H NMR (DMSO-d) 12.18 (1H, br s), 7.69 (1H, s), 7.52 (4H, t), 7.45-7.33 (6H, m), 6.93 (1H, s), 5.24 (2H, s), 5.23 (2H, s), 1.32 (9H, s). MS: [M+H]$^+$ 391.

Preparation B9

Synthesis of
2,4-bis-benzyloxy-5-isopropenyl-benzoic acid

Alternative Synthesis

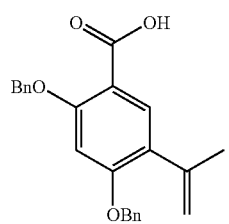

Step 1: Synthesis of
2,4-bis-benzyloxy-5-bromo-benzoic acid benzyl
ester

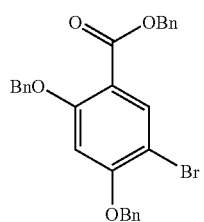 [SMILES: O=C(OCc1ccccc1)c1cc(Br)c(OCc2ccccc2)cc1OCc1ccccc1]

To a 10 L jacketed vessel, fitted with a flange lid containing stirrer, thermometer and dropping funnel, was charged acetone (2.5 L) followed by 5-bromo-2,4-dihydroxybenzoic acid (100 g, 0.43 mol) and potassium carbonate (356 g, 2.58 mol). To the stirring mixture at ambient was added benzyl bromide (185 mL, 1.55 mol) at a rate of ~20 ml/min. The mixture was heated at 60° C. for 18 h and then taken to 45° C. Water (1.5 L) was added and the mixture stirred for 30 min. The mixture was extracted with EtOAc (2×1 L) and the combined organic portions reduced in vacuo. To the residue was added Et$_2$O (200 mL) and petroleum ether (1 L), the mixture stirred for 30 min and the solid formed collected by filtration and dried in vacuo to give the title compound (197.2 g) as a white solid.

Step 2: Synthesis of Potassium Isopropenyl
Trifluoroborate

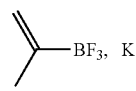

To a solution of 2-bromopropene (20 mL, 225 mmol) in anhydrous THF (250 mL) stirring under a N$_2$ atmosphere at −78° C. was added over 30 mins n-BuLi (2.5M in hexanes) (100 mL, 250 mmol) and the mixture stirred for 30 mins. To the mixture at −78° C. was slowly added triethyl borate (58 mL, 340 mmol) at a rate to ensure that the temperature of the reaction mixture did not exceed −65° C. The resulting solution was then stirred at −78° C. for 30 mins, allowed to slowly warm to ambient and stirred for a further 90 mins. Potassium hydrogen fluoride (105 g, 1.35 mol) was added to the mixture followed by water (250 mL). The mixture was stirred at ambient for 14 h and then reduced to dryness.

The procedure was repeated as above and following reduction to dryness the two residues were combined for further work-up.

To the combined residues was added acetone (800 mL), the mixture stirred for 1 h and then filtered. The solid collected was washed with acetone (200 mL) and the combined filtrates reduced in vacuo to give a solid. This solid was triturated with Et$_2$O (250 mL) and then dried in vacuo to give the title compound (28.2 g) as a white solid.

Step 3: Synthesis of
2,4-bis-benzyloxy-5-isopropenyl-benzoic acid
benzyl ester

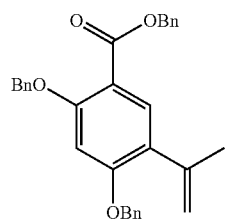

To a mixture of 2,4-bis-benzyloxy-5-bromo-benzoic acid benzyl ester (42.9 g, 85.7 mmol), potassium isopropenyl trifluoroborate (14.0 g, 95.2 mmol) and caesium carbonate (83.8 g, 257.1 mmol) in THF (800 mL) was added Pd(PPh$_3$)$_4$ (2.0 g) followed by water (150 mL). The mixture was heated at reflux for 72 h then allowed to cool to ambient. The mixture was reduced in vacuo to remove THF and then partitioned between water (500 mL) and EtOAc (300 mL).

The organic portion was washed with brine, dried (MgSO₄), filtered and reduced in vacuo to give the title compound (40.9 g) as a brown oil.

Step 3A

Alternative Synthesis of 2,4-bis-benzyloxy-5-isopropenyl-benzoic acid benzyl ester

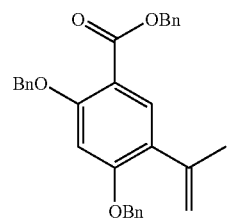 [SMILES: C=C(C)c1cc(C(=O)OCc2ccccc2)c(OCc2ccccc2)cc1OCc1ccccc1]

A mixture of 2,4-bis-benzyloxy-5-bromo-benzoic acid benzyl ester (10.0 g, 20 mmol), potassium isopropenyl trifluoroborate (4.0 g, 27.2 mmol) and n-butylamine (6.0 mL, 60 mmol) in 2-propanol/water (2:1, 200 mL) was purged with N₂ for 5 minutes. To this mixture was added [1,1'-bis(diphenyl-phosphino)ferrocene]dichloropalladium (II) (816 mg, 1.09 mmol) and the mixture was heated at reflux for 20 h. The mixture was allowed to cool to ambient then diluted with water (400 mL) and extracted with EtOAc (2×300 mL). The combined organic extracts were washed with 1M aqueous HCl, brine, dried (MgSO₄), filtered through a plug of Celite and the filtrate reduced in vacuo to give the title compound (11.1 g) as a brown gum.

Step 4: Synthesis of 2,4-bis-benzyloxy-5-isopropenyl-benzoic acid

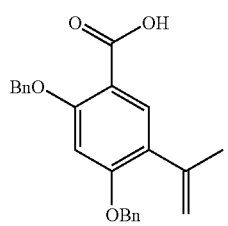 [SMILES: C=C(C)c1cc(C(=O)O)c(OCc2ccccc2)cc1OCc1ccccc1]

To a solution of 2,4-bis-benzyloxy-5-isopropenyl-benzoic acid benzyl ester (40.8 g, 87.9 mmol) in THF-MeOH-water (3:1:1, 300 mL total) was added lithium hydroxide (8.42 g, 352 mmol). The mixture was heated at 50° C. for 16 h, allowed to cool to ambient and then diluted with water (300 mL). The mixture was taken to pH~1 using conc. HCl (~30 mL) and then extracted with EtOAc (2×200 mL). The combined organic extracts were washed with brine, dried (MgSO₄), filtered and reduced in vacuo. The solid residue was taken up in P.E-MeOH (9:1, 300 mL total), the slurry stirred for 1 h at ambient and the solid collected by filtration. The solid was dried in vacuo to give the title compound (26.8 g) as an off-white solid. ¹H NMR (400 MHz, DMSO-d₆) 12.30 (s, 1H), 7.61 (s, 1H), 7.53 (d, J=7.0 Hz, 2H), 7.47-7.31 (m, 8H), 6.94 (s, 1H), 5.23 (d, J=14.0 Hz, 4H), 5.08 (d, J=9.0 Hz, 2H), 2.04 (s, 3H).

Preparation B10

2,4-Bis-benzyloxy-5-isopropyl-benzoic acid

Step 1

Preparation of 1-(2-4-Bis-benzyloxy-phenyl)-ethanone

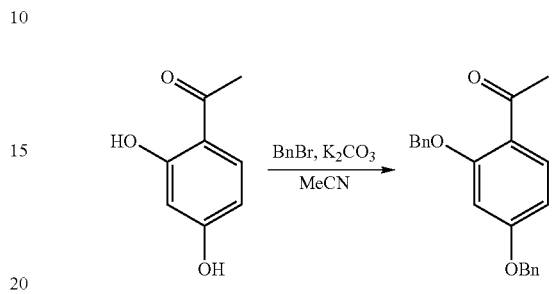

Material Inputs:

| S. No. | Item | Quantity | Eq. |
|---|---|---|---|
| 1. | 1,3 Dihydroxy acetophenone | 50 g | 1 |
| 2. | Benzyl bromide | 97 ml | 3 |
| 3. | Acetonitrile | 750 ml | 15 times |
| 4. | Potassium carbonate | 115 g | 3 |

1,3 Dihydroxy acetophenone (50 g) was placed in a 2 L single neck RB flask equipped with a reflux condenser and a guard tube. Acetonitrile (750 ml), potassium carbonate (115 g) and benzyl bromide (97 ml) were added and the mixture was heated at reflux (90° C.) for 16 hours. On completion, the acetonitrile was removed under reduced pressure. Water (200 ml) was added to the reaction mixture which was then extracted with ethyl acetate (500 ml). The organic layer was separated and dried over sodium sulphate. The solvent was removed under reduced pressure to give a residue which was washed n-hexane (600 ml) to give the product.

| | |
|---|---|
| Quantity of the product obtained: | 105.1 g |
| Yield | 96.24% |
| Nature | Solid |
| Colour | Brown |

Step 2

Preparation of 24-Bis-benzyloxy-1-isopropenylbenzene

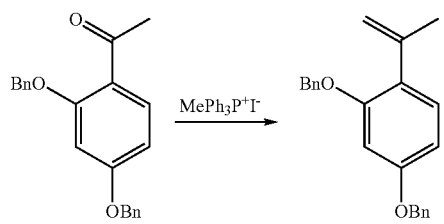 [SMILES: CC(=O)c1ccc(OCc2ccccc2)cc1OCc1ccccc1 ; C=C(C)c1ccc(OCc2ccccc2)cc1OCc1ccccc1]

119

Material Inputs:

| S. No. | Item | Quantity | Eq. |
|---|---|---|---|
| 1. | Compound of Step 1 | 20 g | 1 |
| 2. | n-BuLi (1.6 M) | 92.6 ml | 2.3 |
| 3. | Methyl-triphenylphosphonium iodide | 53.4 g | 2.2 |
| 4. | THF | 200 ml | 10 times |

Methyl-triphenylphosphonium iodide (53.4 g) and THF (100 ml) were introduced into a 1 L 3-neck RB flask equipped with an addition funnel and an inlet for nitrogen atmosphere and the mixture was cooled to 0° C. n-BuLi (92.6 ml) was added dropwise to the reaction mixture over a period of 15 min at 0° C. The reaction mixture was stirred for 10 min at 0° C. and further stirred at RT for 30 min. 1-(2-4-Bis-benzyloxy-phenyl)-ethanone (20 g) in THF (100 ml) was added dropwise to the reaction mixture over a period of 10 min at 0° C. and the reaction mixture was stirred overnight at RT. The progress of the reaction was monitored by TLC (10% EtOAc/n-hexane, product $R_f$~0.9). On completion, methanol (~100 ml) was added to the reaction mixture and the solvent was removed under reduced pressure to give a residue. n-Hexane (1 L) was added to the residue which was refluxed (75° C.) for 30 min. before filtering the mixture was through a Celite bed and washing the bed with n-hexane (500 ml). The solvent was removed under reduced pressure to give a residue, which was further purified by column chromatography (SiO$_2$ 2% EtOAc/n-hexane).

| Quantity of the product obtained: | 12.5 g |
|---|---|
| Yield | 63.13% |
| Nature | Liquid. |
| Colour | Colorless |

Step 3

4-Isopropyl-benzene-1,3-diol

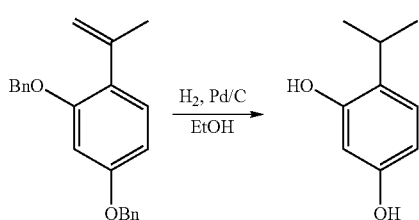

Material Inputs:

| S. No. | Item | Quantity | Eq. |
|---|---|---|---|
| 1. | 2-4-Bis-benzyloxy-1-isopropenylbenzene | 12.5 g | 1 |
| 2. | Ethanol | 125 ml | 10 times |
| 3. | 20% Palladium hydroxide | 2 g | |

To a mixture of 2-4-bis-benzyloxy-1-isopropenylbenzene (12.5 g) in ethanol (125 ml) in a 500 ml hydrogenation flask was added 20% palladium hydroxide (2 g). The reaction mixture was hydrogenated at 80 psi for 36 h. The progress of the reaction was monitored by TLC (10% EtOAc/n-hexane, product $R_f$~0.1). On completion, the reaction mixture was filtered through a bed of Celite and the bed was washed with ethanol (300 ml). The solvent was removed under reduced pressure to give a crude product, which was used as such for the next step.

| Quantity of the product obtained | 5.8 g (crude) |
|---|---|
| Nature | Solid. |
| Colour | Colourless. |

Step 4

1-(2,4-Dihydroxy-5-isopropyl-phenyl)-ethanone

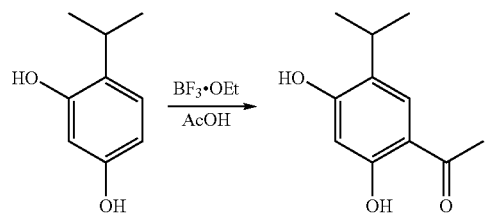

Material Inputs:

| S. No. | Item | Quantity | Eq. |
|---|---|---|---|
| 1. | 4-Isopropyl-benzene-1,3-diol | 5.8 g | 1 |
| 2. | Boron trifluoride etherate | 28.7 ml | 6 |
| 3. | Acetic acid | 4.55 ml | 2 |

4-isopropyl-benzene-1,3-diol (5.8 g) and boron trifluoride etherate (28.7 ml) were introduced into a 250 ml single neck RB flask equipped with a reflux condenser and an inlet for nitrogen atmosphere stirred at RT for 10 min. Acetic acid (4.55 ml) was added to the reaction mixture and stirred at 90° C. for 16 h. On completion, 10% sodium acetate (300 ml) was added to the reaction mixture which was stirred at RT for 4 hours. The reaction mixture was then extracted with ethyl acetate (300 ml) and washed with saturated sodium bicarbonate (100 ml) and the organic layer was dried over sodium sulphate. The reaction was monitored by TLC (10% EtOAc/n-hexane, product $R_f$~0.5). The solvent was removed under reduced pressure to give a residue, which was further purified by column chromatography (SiO$_2$, 10% EtOAc/n-hexane).

| Quantity of the product obtained | 3.2 g |
|---|---|
| Yield | 43.24% |
| Nature | Solid. |
| Colour | Colourless |

Step 5

1-(2,4-Bis-benzyloxy-5-isopropyl-phenyl)-ethanone

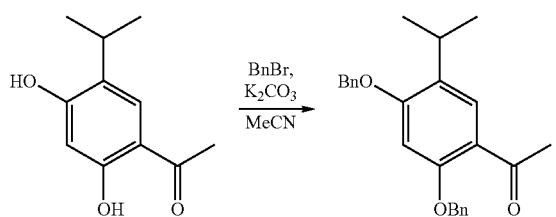

Material Inputs:

| S. No. | Item | Quantity | Eq. |
|---|---|---|---|
| 1. | 1-(2,4-Dihydroxy-5-isopropyl-phenyl)-ethanone | 3.2 g | 1 |
| 2. | Benzyl bromide | 5.89 ml | 3 |
| 3. | Potassium carbonate | 6.82 g | 3 |
| 4. | Acetonitrile | 60 ml | 20 times |

To a mixture of 1-(2,4-dihydroxy-5-isopropyl-phenyl)-ethanone (3.2 g), acetonitrile (60 ml) and potassium carbonate (10.6 g) in a a 250 ml single neck RB flask equipped with a reflux condenser and a guard tube was added benzyl bromide (9.1 ml). The reaction mixture was refluxed (90° C.) for 16 h. The progress of the reaction was monitored by TLC (10% EtOAc/n-hexane, product $R_f$~0.5). On completion, acetonitrile was removed under reduced pressure. Water (100 ml) was added to the residue obtained and the resulting mixture was extracted with ethyl acetate (200 ml). The organic layer was dried over sodium sulphate. The solvent was removed under reduced pressure to give a residue to which n-hexane (150 ml) was added to give the product.

| | |
|---|---|
| Quantity of the product obtained | 5.1 g |
| Yield | 83.6% |
| Nature | Solid. |
| Colour | Colourless |

Step 6

2,4-Bis-benzyloxy-5-isopropyl-benzoic acid

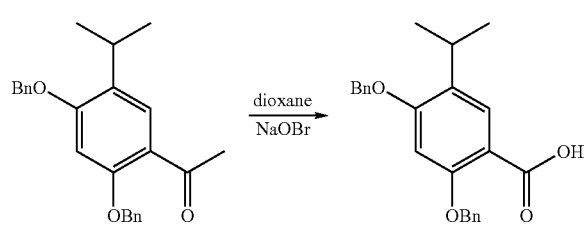

Material Inputs:

| S. No. | Item | Quantity |
|---|---|---|
| 1. | 1-(2,4-Bis-benzyloxy-5-isopropyl-phenyl)-ethanone | 7 g |
| 2. | Sodium hypobromide | 13 g in water 100 ml |
| 3. | Dioxane | 100 ml |

Procedure:

A mixture of a mixture of 1-(2,4-Bis-benzyloxy-5-isopropyl-phenyl)-ethanone (7 g) in dioxane (100 ml) in a 500 ml single neck RB flask equipped with a guard tube was cooled to 10° C. and sodium hypobromide [13 g in water (100 ml)] was added. The reaction mixture was stirred overnight at RT. The progress of the reaction was monitored by TLC (30% EtOAc/n-hexane, product $R_f$~0.5). On completion, sodium bisulphite (7 g) was added to the reaction mixture which was cooled to 0° C. The reaction mixture was then acidified with HCl (~10 ml) to pH~2, extracted with ethyl acetate (100 ml) and washed with water (25 ml). The organic layer was dried over sodium sulphate, and the solvent was removed under reduced pressure to give a residue, which was further purified by column chromatography ($SiO_2$, 10% EtOAc/n-hexane).

| | |
|---|---|
| Quantity of the product obtained | 3.4 g |
| Yield | 48.3% |
| Nature | Solid. |
| Colour | Colourless. |

C. Synthesis of Isoindoline Intermediates

Preparation C1

Synthesis of 4,7-difluoroisoindoline

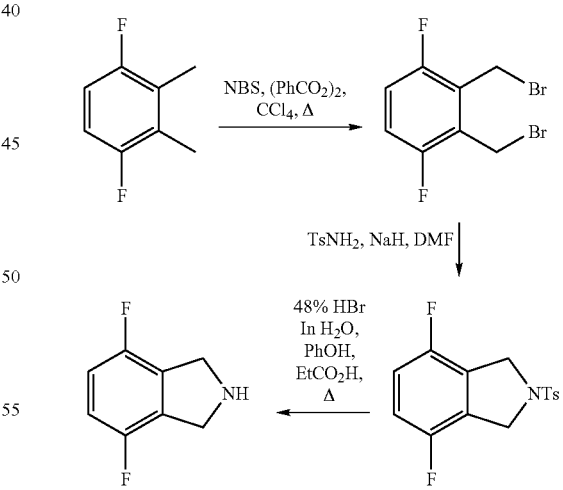

A mixture of 1,4-difluoro-2,3-dimethylbenzene (4.26 g, 30.0 mmol), N-bromosuccinimide (10.68 g, 60.0 mmol) and dibenzoyl peroxide (75 wt % in water, 120 mg) in carbon tetrachloride (50 ml) was stirred and held at reflux for 16 hours. Upon cooling to room temperature the mixture was filtered, the solids washed with carbon tetrachloride (10 ml), the organic extracts combined and the solvent removed in vacuo to afford 2,3-bis-bromomethyl-1,4-difluorobenzene (9.0 g, 100%) as a pale yellow liquid that solidified upon standing. $^1$H NMR (DMSO-$d_6$) 7.36 (2H, dd), 4.78 (4H, s).

A solution of 4-toluenesulphonamide (2.44 g, 14.28 mmol) in N,N-dimethylformamide (10 ml) was added dropwise to a vigorously stirred suspension of sodium hydride (1.2 g, 60 wt % in mineral oil, 30.0 mmol) in anhydrous N,N-dimethylformamide (60 ml). The mixture was stirred at room temperature for 1 hour, at 110° C. for 1 hour and was then cooled to 60° C. and a solution of 2,3-bis-bromomethyl-1,4-difluorobenzene (4.28 g, 14.28 mmol) in N,N-dimethylformamide (30 ml) was added dropwise. The mixture was stirred at 60° C. for 1 hour and then at room temperature for 16 hours. The solvent was removed in vacuo and the residue partitioned between dichloromethane and 1M hydrochloric acid. The organic layer was separated, washed with 5% aqueous potassium carbonate solution, the organics were separated and the solvent removed in vacuo. The residue was rinsed with diethyl ether, filtered and the solids sucked dry under reduced pressure to afford 4,7-difluoro-2-(toluene-4-sulfonyl)isoindoline (2.46 g, 56%) as a pale tan solid. $^1$H NMR (DMSO-$d_6$) 7.82 (2H, d), 7.43 (2H, d), 7.15 (2H, dd), 4.66 (4H, s), 2.36 (3H, s). MS: [M+H]$^+$ 310.

A mixture of 4,7-difluoro-2-(toluene-4-sulfonyl)isoindoline (2.36 g, 7.64 mmol), phenol (2.36 g, 25.11 mmol), 48% hydrogen bromide in water (20 ml) and propionic acid (4 ml) was stirred and held at reflux for 6 hours. Upon cooling to room temperature water (50 ml) was added and the mixture extracted with diethyl ether (2×100 ml). The aqueous layer was basified by the addition of 2M sodium hydroxide and was extracted with diethyl ether (3×100 ml). The combined extracts were evaporated to dryness in vacuo to afford 4,7-difluoroisoindoline (586 mg, 50%) as a brown oil that solidified upon standing. $^1$H NMR (DMSO-$d_6$) 7.06 (2H, dd), 4.12 (4H, s). MS: [M+H]$^+$ 156.

Preparation C2

Synthesis of 5-hydroxyisoindoline hydrobromide

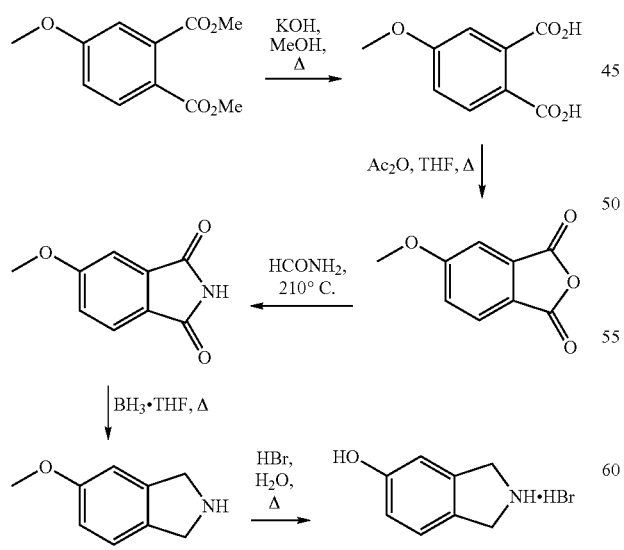

A solution of dimethyl 4-methoxyphthalate (36.75 g, 0.16 mol) in methanol (100 ml) was treated with a solution of potassium hydroxide (28.0 g, 0.5 mol) in water (50 ml) and the mixture was stirred and held at reflux for 4 hours. Upon cooling to room temperature the methanol was removed in vacuo and the mixture acidified to pH 2 or below by the addition of 5M hydrochloric acid. The solid material was filtered off, washed with water and sucked dry under reduced pressure overnight to afford 4-methoxyphthalic acid (31.8 g, 99%) as an off white solid. $^1$H NMR (DMSO-$d_6$) 12.90 (2H, br s), 7.74 (1H, d), 7.12-7.05 (2H, m), 3.84 (3H, s). MS: [M+H]$^+$ 197.

Acetic anhydride (40 ml) was added to a mixture of 4-methoxyphthalic acid (30.8 g, 0.16 mol) in anhydrous tetrahydrofuran (150 ml) and the mixture was stirred and held at reflux for 4 hours. Upon cooling to room temperature the solvent was removed in vacuo to afford 4-methoxyphthalic anhydride (27.8 g, 99%) as an off white solid. $^1$H NMR (DMSO-$d_6$) 8.02 (1H, d), 7.59 (1H, d), 7.49 (1H, dd), 3.97 (3H, s). MS: [M+H]$^+$ 179.

A mixture of 4-methoxyphthalic anhydride (27.8 g, 0.16 mol) and formamide (175 ml) was stirred and held at 210° C. for 5 hours and was then allowed to cool to room temperature overnight. The solid material was filtered off, washed sequentially with water (100 ml), 50% aqueous acetone (50 ml) and diethyl ether (200 ml) and sucked dry under reduced pressure to afford 4-methoxyphthalimide (21.3 g, 77%) as a pale yellow solid. $^1$H NMR (DMSO-$d_6$) 11.15 (1H, br s), 7.74 (1H, d), 7.33-7.28 (2H, m), 3.92 (3H, s).

A stirred solution of 4-methoxyphthalimide (21.3 g, 0.12 mol) in anhydrous tetrahydrofuran (425 ml) at 0° C. was treated dropwise with a solution of borane in tetrahydrofuran (1M, 340 ml, 0.34 mol) and the resulting mixture was stirred and held at reflux for 16 hours. The mixture was cooled to 0° C., methanol (150 ml) was added dropwise followed by 5M hydrochloric acid (150 ml) and the mixture was stirred and held at reflux for 3 hours. Upon cooling to room temperature the organic solvent was removed in vacuo, the mixture was diluted with water (750 ml) and was extracted with dichloromethane (3×750 ml). The aqueous layer was basified to pH 12 or above by the addition of 5M sodium hydroxide, extracted with dichloromethane (3×750 ml) and the combined extracts were evaporated to dryness in vacuo to afford 5-methoxyisoindoline (8.34 g, 47%) as a brown oil. $^1$H NMR (DMSO-$d_6$) 7.13 (1H, d), 6.84 (1H, d), 6.74 (1H, dd), 4.05 (2H, s), 4.01 (2H, s), 3.73 (3H, s). MS: [M+H]$^+$ 150.

5-Methoxyisoindoline (8.34 g, 55.97 mmol) in 48% aqueous hydrobromic acid (100 ml) was stirred and held at reflux for 16 hours. Upon cooling to room temperature the solvent was removed in vacuo to afford 5-hydroxyisoindoline hydrobromide (11.32 g, 93%) as a tan solid. $^1$H NMR (DMSO-$d_6$) 9.63 (1H, br s), 9.32 (2H, br s), 7.18 (1H, d), 6.79 (1H, d), 6.76 (1H, dd), 4.42 (2H, t), 4.38 (2H, t). MS: [M+H]$^+$ 136.

Preparation C3

Synthesis of 5-chloro-2,3-dihydro-1H-isoindole

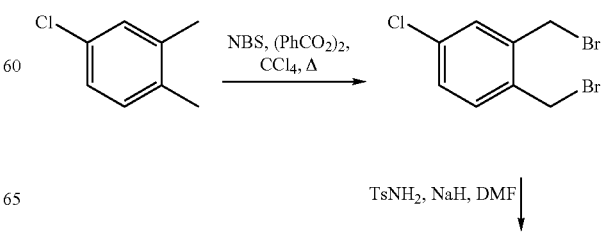

TsNH$_2$, NaH, DMF

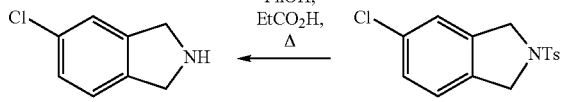

A mixture of 3,4-dimethylchlorobenzene (10 g, 71.1 mmol), N-bromosuccinimide (25 g, 142.2 mmol), and benzoyl peroxide (0.147 g, 0.6 mmol), was refluxed in 80 ml of carbon tetrachloride for 18 hours. After cooling, the insoluble material was filtered off and washed with a small amount of carbon tetrachloride. The filtrate and the washings were combined and concentrated under reduced pressure to obtain 20 g of 1,2-bis-bromomethyl-4-chloro-benzene as a pale yellow oil product as a major component.

To a suspension of 60% sodium hydride (3.0 g, 0.125 mmol) in mineral oil in 80 ml of anhydrous DMF (100 ml) was dropwise added a solution of para-toluene sulphonamide (5.6 g, 32.60 mmol) in 30 ml of DMF over 1 hour with vigorous stirring at room temperature. After the addition, the mixture was stirred for 1 hour at room temperature and another 1 hour heating at 90° C. To this mixture was added dropwise a solution of 1,2-bis-bromomethyl-4-chloro-benzene (4 g, 14.18 mmol) in 20 ml of anhydrous DMF at 60° C. and then stirred overnight at room temperature. The resultant mixture was poured onto ice and the resulting precipitate was collected by filtration. The precipitate was washed with 1N hydrochloric acid, 5% sodium carbonate and brine then dried (MgSO$_4$), filtered and evaporated to give 2.8 g of 5-Chloro-2-(toluene-4-sulphonyl)-2,3-dihydro-1H-isoindole as a pale yellow solid. MS: [M+H]$^+$ 308

1.0 g of 2-(p-toluensulphonyl)-5-chloroisoindoline and 1.0 g of phenol were added to a mixture of 8 ml of 48% hydrobromic acid and 1.4 ml of propionic acid, and then mixture was heated at reflux for 6 hours. The resultant reaction mixture was diluted with 10 ml of water and extracted twice with 50 ml of ethyl acetate. The water layer was basified with aqueous sodium hydroxide solution and extracted with ethyl acetate three times. The extract was concentrated and the crude product was diluted with 4N HCl/dioxane and stirred for 15 minutes before evaporating the HCl and then re-evaporating with toluene three times to give 0.3 g of 5-chloro-2,3-dihydro-1H-isoindole hydrochloride as a black solid. MS: [M+H]$^+$153-15

Preparation C4

Synthesis of 5-chloro-6-methoxy-2,3-dihydro-1H-isoindole

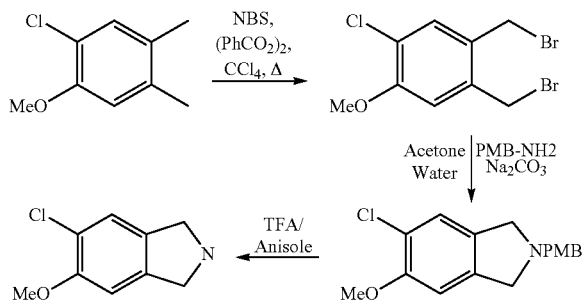

A mixture of 1-chloro-2-methoxy-4,5-dimethyl-benzene (3 g, 17.6 mmol), N-bromosuccinimide (6.3 g, 35.3 mmol), and benzoyl peroxide (0.100 g, 0.41 mmol) in carbon tetrachloride (40 ml) was heated at reflux for 18 hours. After cooling, the insoluble material was removed by filtration, washed with a small amount of carbon tetrachloride and the filtrate evaporated to give 1,2-bis-bromomethyl-4-chloro-5-methoxy-benzene as an oil product as a major component. MS: [M+H]$^+$ 329

A solution of 4-methoxybenzylamine (2.4 g, 17.6 mmol) in acetone (110 ml) was added dropwise to a mixture of 1,2-bis-bromomethyl-4-chloro-5-methoxy-benzene (assumed theoretical, 17.6 mmol) and Na$_2$CO$_3$ (12 g, 114 mmol) in acetone/water (10 ml:12.5 ml) then stirred at room temperature for 2 hours and concentrated in vacuo. The crude material was dissolved in ethyl acetate and extracted with 2N HCl. The aqueous layer was neutralized with sodium carbonate, extracted with ethyl acetate (×2), dried (MgSO$_4$) and evaporated under vacuum to give 5-chloro-6-methoxy-2-(4-methoxy-benzyl)-2,3-dihydro-1H-isoindole (0.8 g, 2.6 mmol) as a brown gum. MS: [M+H]$^+$ 304

A solution of 5-chloro-6-methoxy-2-(4-methoxy-benzyl)-2,3-dihydro-1H-isoindole (600 mg) and anisole (0.3 ml) in trifluoroacetic acid (6 ml) was heated at 180° C. (50 W) for 40 minutes in a CEM discover microwave synthesiser. The reaction mixture was evaporated and re-evaporated with toluene. The crude material was partitioned between DCM and water, the aqueous layer washed with DCM (×3) then evaporated and re-evaporated with toluene to give 5-chloro-6-methoxy-2,3-dihydro-1H-isoindole (256 mg) as green crystals. MS: [M+H]$^+$ 184

Preparation C5

Synthesis of 2,3-dihydro-1H-isoindol-5-ylamine trifluoroacetate

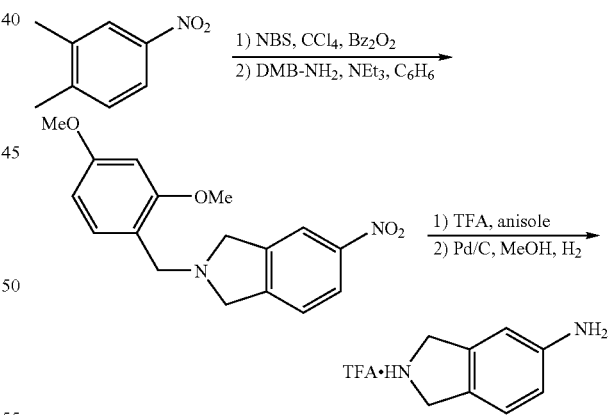

A solution of 4-nitro-o-xylene (15.1 g; 0.1 mol) in carbon tetrachloride (150 ml) was treated with N-bromosuccinimide (36 g; 0.2 mol) followed by benzoyl peroxide (1 g) then heated at reflux overnight. The reaction was allowed to cool to ambient temperature, filtered and the filtrate evaporated to give 32 g of crude 1,2-bis-bromomethyl-4-nitro-benzene as a mobile oil. The crude product was dissolved in benzene (200 ml) then treated dropwise over 30 minutes with a solution of 2,4-dimethoxybenzylamine (15 ml) and triethylamine (27.85 ml) in benzene (100 ml) then heated at 80° C. for 3 hours. The reaction was cooled, washed with water followed by saturated sodium bicarbonate. The organics were extracted with 2M HCl (2×150 ml) then combined aqueous basified with 2M NaOH and extracted with EtOAc (×2). The combined EtOAc layer was dried (MgSO$_4$), evaporated then purified by flash column chromatography eluting with EtOAc/P.E. (1:3-1, 2-1:1). Product containing fraction were combined and evaporated to give 10.15 g of 2-(2,4-dimethoxy-benzyl)-5-nitro-2,3-dihydro-1H-isoindole as a brown solid. $^1$H NMR (DMSO-d$_6$) 8.12 (2H, m), 7.50 (1H, d), 7.25 (1H, d), 6.55 (1H, d), 6.52 (1H, dd), 3.93 (4H, s), 3.80 (3H, s), 3.78 (2H, s), 3.75 (3H, s).

2-(2,4-dimethoxy-benzyl)-5-nitro-2,3-dihydro-1H-isoindole (13 g) in TFA (18 ml) was treated with anisole (6 ml) then heated in a CEM microwave synthesiser at 120° C. (30 Watts) for 20 minutes (carried out batch wise, 6 times). The reaction mixture was evaporated in vacuo and the residue partitioned between DCM and water. The water layer was separated, washed with DCM (×3) then evaporated and re-evaporated with toluene/MeOH (×3) to give 9.8 g of 5-nitro-2,3-dihydro-1H-isoindole trifluoroacetic acid salt as a beige solid. $^1$H NMR (DMSO-d$_6$) 9.85 (2H, br s), 8.32 (1H, d), 8.25 (1H, dd), 7.70 (1H, d), 4.68 (2H, s), 4.65 (2H, s).

A mixture of 5-nitro-2,3-dihydro-1H-isoindole trifluoroacetic acid salt (9.8 g) and 10% palladium on carbon (1 g) in methanol (75 ml) was hydrogenated at room temperature and pressure for 16 hours. The reaction was filtered through Celite™, the filtrate evaporated and re-evaporated with toluene to give 8.76 g of 2,3-dihydro-1H-isoindol-5-ylamine mono trifluoroacetic acid salt as a dark brown solid. $^1$H NMR (DMSO-d$_6$) 9.45 (2H, br s), 7.05 (1H, d), 6.60 (2H, m), 5.35 (2H, br s), 4.40 (2H, s), 4.30 (2H, s).

Preparation C6

Synthesis of
5-morpholin-4-ylmethyl-2,3-dihydro-1H-isoindole ditrifluoroacetate

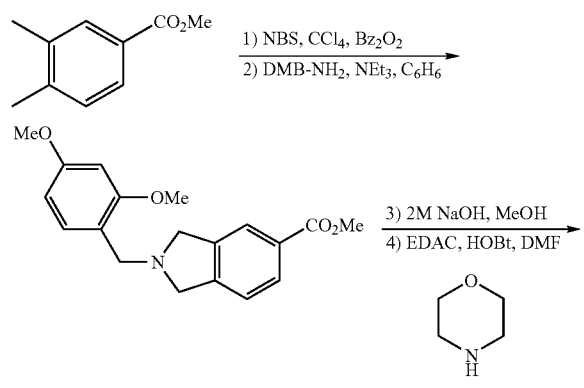

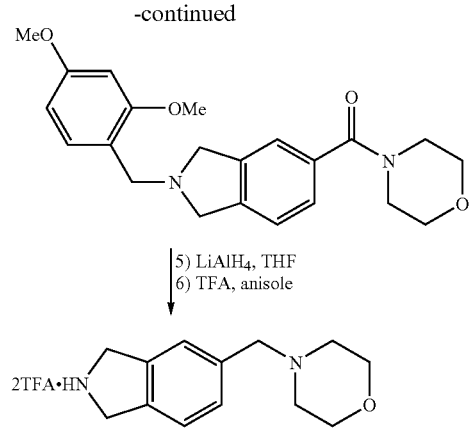

Steps 1 and 2 were carried out in a manner analogous to that described in Preparation C5 using methyl 3,4-dimethylbenzoate as the starting material.

A mixture of 2-(2,4-dimethoxybenzyl)-2,3-dihydro-1H-isoindole-5-carboxylic acid methyl ester (4.65 g; 14.2 mmol) and lithium hydroxide monohydrate (660 mg; 1.1 equiv.) in 4:1:1 THF-MeOH—H$_2$O (60 ml) was stirred at room temperature overnight. A further 170 mg of base were added and stirring continued for 7 hours. The reaction was evaporated then re-evaporated with MeOH/toluene (×2). A mixture of the crude 2-(2,4-dimethoxy-benzyl)-2,3-dihydro-1H-isoindole-5-carboxylic acid lithium salt (1.5 g; 4.7 mmol), morpholine (820 µl; 2 equiv.), EDAC (1.1 g; 1.2 equiv.) and HOBt (760 mg; 1.2 equiv.) in DMF (25 ml) was stirred at room temperature overnight then evaporated in vacuo. The residue was partitioned between EtOAc and saturated NaHCO$_3$, the EtOAc layer was separated, washed with brine, dried (MgSO$_4$) and evaporated. Purification by flash column chromatography (2% then 5% MeOH/DCM as eluant) gave 1.1 g of [2-(2,4-dimethoxybenzyl)-2,3-dihydro-1H-isoindol-5-yl]-morpholin-4-yl-methanone as a red/brown gum. $^1$H NMR (DMSO-d$_6$) 7.30-7.18 (4H, m), 6.56 (1H, d), 6.52 (1H, dd), 3.85 (4H, s), 3.78 (5H, m), 3.73 (3H, s).

A solution of [2-(2,4-dimethoxybenzyl)-2,3-dihydro-1H-isoindol-5-yl]-morpholin-4-yl-methanone (1.05 g; 2.75 mmol) in dry THF (20 ml) under a nitrogen atmosphere was treated with 1M lithium aluminium hydride solution then stirred at room temperature overnight. The reaction was quenched by the cautious addition of saturated sodium sulphate solution, then diluted with EtOAc (40 ml), filtered through Celite™ and evaporated. Purification by flash column chromatography (2% then 5% MeOH/DCM as eluant) gave 340 mg of 2-(2,4-dimethoxybenzyl)-5-morpholin-4-ylmethyl-2,3-dihydro-1H-isoindole as a pale brown gum.

A mixture of 2-(2,4-dimethoxybenzyl)-5-morpholin-4-ylmethyl-2,3-dihydro-1H-isoindole (340 mg) and anisole (350 µl) in trifluoroacetic acid (1.5 ml) was heated at 13° C. in a CEM microwave synthesiser for 1 hour then evaporated and re-evaporated with toluene. The residue was partitioned between DCM and water. The water layer was separated, washed with DCM (×3) then evaporated and re-evaporated with toluene/MeOH (×3) to give 422 mg of 5-morpholin-4-ylmethyl-2,3-dihydro-1H-isoindole ditrifluoroacetate as a brown gum. $^1$H NMR (DMSO-d$_6$) 10.30 (1H, br s), 9.60 (2H, br s), 7.55-7.45 (3H, m), 4.45 (4H, s), 4.45-4.30 (2H, m), 4.20-3.88 (2H, m), 3.70-3.55 (2H, m), 3.30-3.00 (4H, m).

Preparation C7

Synthesis of ethyl-2,3-dihydro-1H-isoindole-5-carboxylate trifluoroacetate

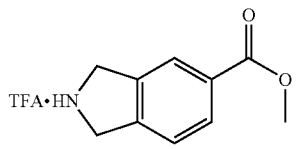

A solution of 2-(2,4-dimethoxy-benzyl)-2,3-dihydro-1H-isoindole-5-carboxylic acid methyl ester (215 mg) and anisole (200 μl) in 1 ml of TFA was heated at 140° C. for 30 minutes in a CEM discover microwave synthesiser. The reaction was partitioned between water and DCM, the water layer was separated, washed with DCM then evaporated and re-evaporated with toluene/MeOH (×2) to give 105 mg of the title compound. $^1$H NMR (DMSO-$d_6$) 9.70 (2H, br s), 8.02 (1H, s), 8.98 (1H, d), 7.57 (1H, d), 4.60 (2H, s), 4.56 (2H, s), 3.89 (3H, s).

Preparation C8

4-Hydroxy-2-(4-methoxy-benzyl)-isoindole-1,3-dione

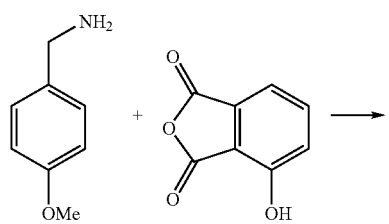

A mixture of 3-hydroxyphthalic anhydride (543 mg, 3.31 mmol), 4-methoxybenzylamine (0.43 mL, 3.31 mmol) and acetic acid (3 mL) was heated at 100° C. for 4 hours. The mixture was allowed to cool and diluted with water (20 mL). The white solid was collected by filtration, washed well with water and dried to give the title compound (760 mg, 81%). $^1$H NMR (DMSO-$d_6$) 11.03 (1H, s), 7.61 (1H, dd), 7.28 (1H, d), 7.23-7.19 (3H, m), 6.89-6.86 (2H, m), 4.63 (2H, s), 3.71 (3H, s). MS: [M–H$^+$] 282.

Preparation C9

4-Hydroxy-2-(2,4-dimethoxy-benzyl)-isoindole-1,3-dione

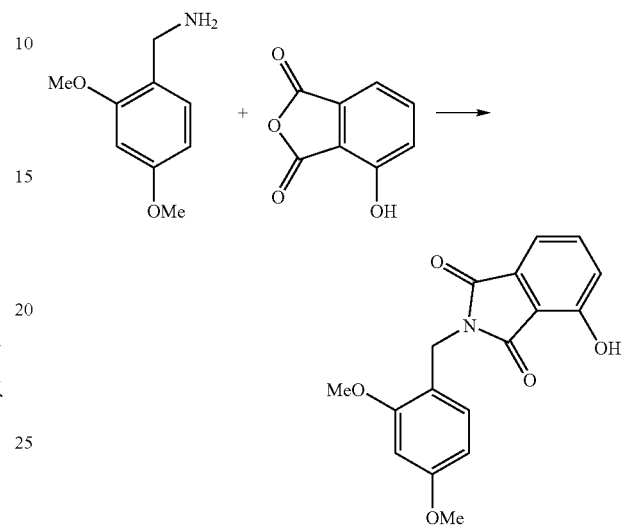

A mixture of 3-hydroxyphthalic anhydride (1.24 g, 7.6 mmol), 2,4-dimethoxybenzylamine (1.14 mL, 7.6 mmol) and acetic acid (5 mL) was heated at 80° C. for 24 hours. The mixture was allowed to cool and diluted with water (20 mL). The white solid was collected by filtration, washed well with water and dried to give the title compound (1.73 g, 73%). $^1$H NMR (DMSO-$d_6$) 11.00 (1H, s), 7.62 (1H, dd), 7.29 (1H, d), 7.21 (1H, d), 6.90 (1H, d), 6.56 (1H, d), 6.43 (1H, dd), 4.59 (2H, s), 3.79 (3H, s), 3.72 (3H, s). MS: [M–H$^+$] 314.

Preparation C10

2-(4-Methoxy-benzyl)-4-[2-(2-methoxy-ethoxy)-ethoxy]-isoindole-1,3-dione

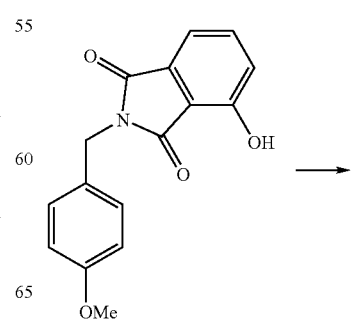

-continued

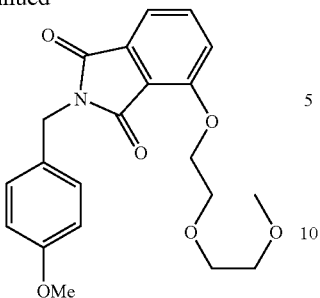

1-(2-Bromo-ethoxy)-2-methoxy-ethane (107 mg, 0.58 mmol) was added to a suspension of 4-hydroxy-2-(4-methoxy-benzyl)-isoindole-1,3-dione (150 mg, 0.53 mmol) and potassium carbonate (200 mg, 1.4 mmol) in DMF (2 mL). After 3.5 hours, a catalytic amount of potassium iodide was added. After a further 17 hours, the mixture was warmed to 60° C. After 3 hours, an additional amount of 1-(2-bromo-ethoxy)-2-methoxy-ethane (20 mg, 0.11 mmol) was added and the mixture maintained at 60° C. for a further 20 hours. The mixture was concentrated in vacuo then the residue was taken up in ethyl acetate and washed with potassium carbonate solution and brine. The organic phase was dried (MgSO$_4$) and concentrated to give the title compound as a yellow oil (149 mg, 73%). $^1$H NMR (methanol-d$_4$) 7.71 (1H, t), 7.43-7.40 (2H, m), 7.31-7.27 (2H, m), 6.87-6.83 (2H, m), 4.71 (2H, s), 4.37-4.34 (2H, m), 3.92-3.89 (2H, m), 3.77-3.74 (5H, m), 3.55-3.53 (2H, m), 3.33 (3H, s). MS: [M+H]$^+$ 386.

Preparation C11

2-(2,4-Dimethoxy-benzyl)-4-(2-dimethylamino-ethoxy)-isoindole-1,3-dione

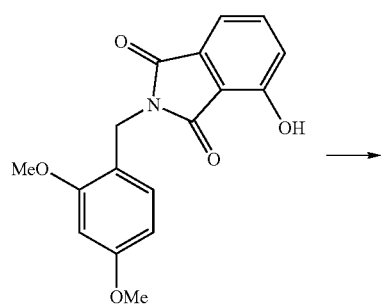

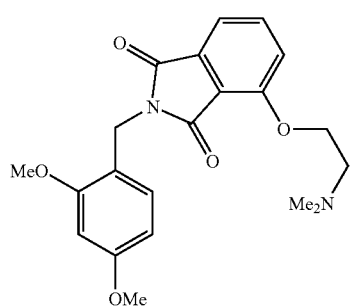

A mixture of 2-(2,4-dimethoxy-benzyl)-4-hydroxy-isoindole-1,3-dione (317 mg, 1.01 mmol), 2-dimethylaminoethyl chloride hydrochloride (160 mg, 1.11 mmol) and potassium carbonate (350 mg, 2.5 mmol) in DMF (4 mL) was heated at 60° C. for 18 hours. The mixture was concentrated in vacuo, taken up in ethyl acetate and extracted twice with 1N hydrochloric acid. The aqueous extracts were made basic with solid potassium carbonate and extracted with ethyl acetate (×2). The combined organic extracts were washed with brine, dried (MgSO$_4$) and concentrated to give the title compound (236 mg, 61%) as an off-white solid. $^1$H NMR (methanol-d$_4$) 7.73 (1H, t), 7.44-7.40 (2H, m), 7.02 (1H, d), 6.51 (1H, d), 6.42 (1H, dd), 4.72 (2H, s), 4.33 (2H, t), 3.80 (3H, s), 3.76 (3H, s), 2.87 (2H, t), 2.40 (6H, s). MS: [M+H]$^+$ 385.

Preparation C12

2-(2,4-Dimethoxy-benzyl)-4-(3-morpholin-4-yl-propoxy)-isoindole-1,3-dione

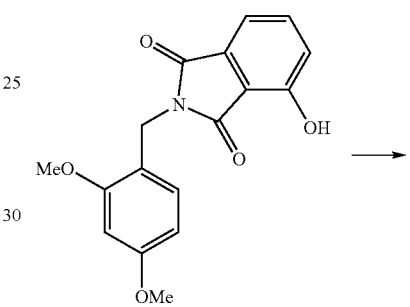

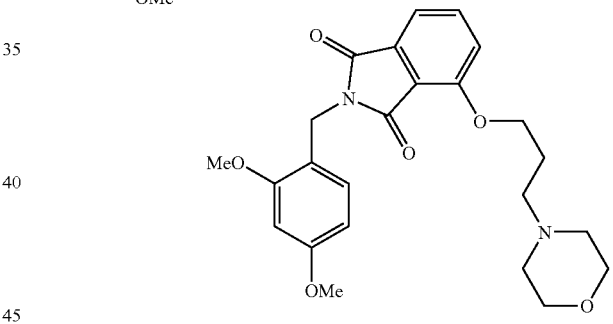

A mixture of 2-(2,4-dimethoxy-benzyl)-4-hydroxy-isoindole-1,3-dione (313 mg, 1.00 mmol), 4-(3-chloropropyl)morpholine (160 mg, 1.11 mmol) and potassium carbonate (350 mg, 2.5 mmol) in DMF (5 mL) was heated at 60° C. for 18 hours. The mixture was diluted with ethyl acetate and extracted twice with 1N hydrochloric acid. The aqueous extracts were made basic with solid potassium carbonate and extracted with ethyl acetate. The organic extract was washed with brine, dried (MgSO$_4$) and concentrated to give a yellow solid which was recrystallised from methanol/petrol then ethyl acetate/chloroform/petrol to give the title compound (298 mg, 68%) as an off-white solid. $^1$H NMR (methanol-d$_4$) 7.72 (1H, t), 7.41 (1H, d), 7.39 (1H, d), 7.02 (1H, d), 6.51 (1H, d), 6.43 (1H, dd), 4.72 (2H, s), 4.27 (2H, t), 3.81 (3H, s), 3.76 (3H, s), 3.68 (4H, t), 2.61 (2H, t), 2.50 (4H, m), 2.05 (2H, qn). MS: [M+H]$^+$ 441.

Preparation C13

2-(4-Methoxy-benzyl)-4-[2-(2-methoxy-ethoxy)-ethoxy]-2,3-dihydro-1H-isoindole

Preparation C14

2-(2,4-Dimethoxy-benzyl)-4-(2-dimethylamino-ethoxy)-2,3-dihydro-1H-isoindole

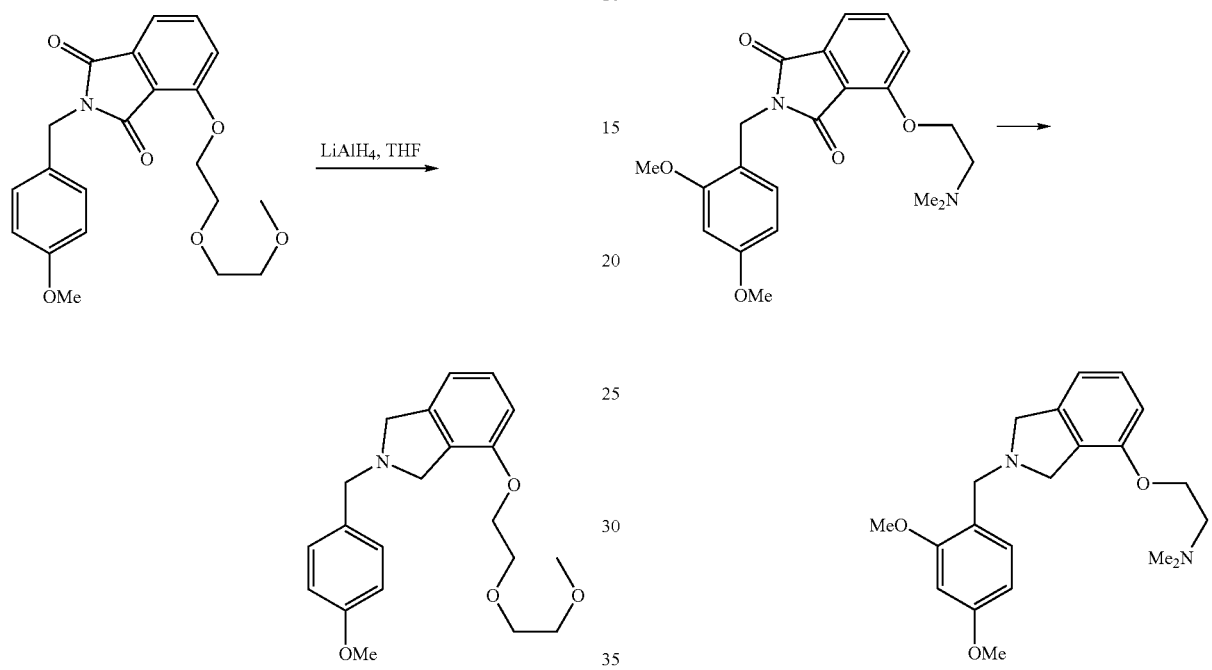

2-(4-Methoxy-benzyl)-4-[2-(2-methoxy-ethoxy)-ethoxy]-isoindole-1,3-dione (149 mg, 0.38 mmol) was treated with a 1M solution of lithium aluminium hydride in THF (5 mL, 5 mmol). The mixture was maintained at r.t. for 4 hours, 60° C. for 1 hour, then r.t. for a further 18 hours. The mixture was then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 15 minutes. The solids were removed by filtration, being well washed with ethyl acetate. Concentration of the filtrate gave a residue which was absorbed onto an SCX cartridge and washed with 5% methanol/dichloromethane then eluted with 10% 1M ammonia in methanol/dichloromethane to afford the title compound (134 mg, 97%). $^1$H NMR (methanol-$d_4$) 7.43-7.39 (2H, m), 7.27 (1H, t), 6.99-6.96 (2H, m), 6.90 (1H, d), 6.88 (1H, d), 4.33 (2H, s), 4.28 (2H, s), 4.23 (2H, s), 4.18-4.15 (2H, m), 3.85-3.79 (5H, m), 3.67-3.64 (2H, m), 3.54-3.51 (2H, m), 3.33 (3H, s). MS: [M+H]$^+$ 358.

2-(2,4-Dimethoxy-benzyl)-4-(2-dimethylamino-ethoxy)-isoindole-1,3-dione (201 mg, 0.52 mmol) was treated with a 1M solution of lithium aluminium hydride in THF (5 mL, 5 mmol). After 7.5 hours at r.t. a further portion of lithium aluminium hydride solution (5 mL, 5 mmol) was added and the mixture maintained for further 18 hours. The mixture was then cooled in ice and quenched by the dropwise addition of water (0.4 mL), 2N sodium hydroxide solution (0.8 mL) and water (0.8 mL). Magnesium sulfate was added, followed by ethyl acetate and then the mixture was stirred at r.t. for 1 hour. The solids were removed by filtration, being well washed with ethyl acetate. Concentration of the filtrate gave the title compound (192 mg, 103%) as a brown oil which was carried forward without further purification. $^1$H NMR (methanol-$d_4$) 7.24 (1H, d), 7.16 (1H, t), 6.82-6.78 (2H, m), 6.55 (1H, d), 6.51 (1H, dd), 4.12 (2H, t), 3.92 (4H, s), 3.86 (2H, s), 3.82 (3H, s), 3.80 (3H, s), 2.76 (2H, t), 2.33 (6H, s). MS: [M+H]$^+$ 357.

Preparation C15

2-(2,4-Dimethoxy-benzyl)-4-(3-morpholin-4-yl-propoxy)-2,3-dihydro-1H-isoindole

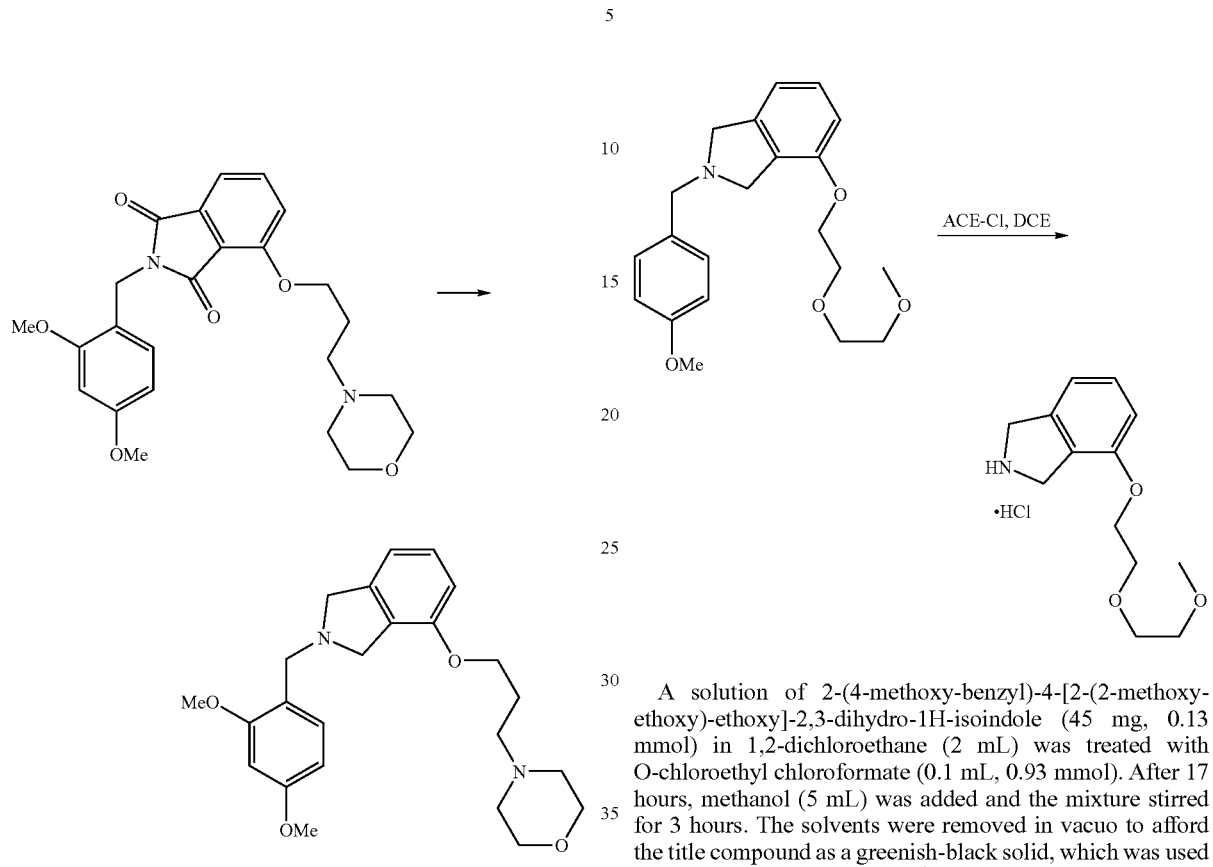

2-(2,4-Dimethoxy-benzyl)-4-(3-morpholin-4-yl-propoxy)-isoindole-1,3-dione (298 mg, 0.68 mmol) was treated with a 1M solution of lithium aluminium hydride in THF (5 mL, 5 mmol) and maintained at r.t. for 21 hours. The mixture was heated to 75° C. for 1 hour then cooled in ice and quenched by the dropwise addition of water (0.2 mL), 2N sodium hydroxide solution (0.4 mL) and water (0.4 mL). Magnesium sulfate was added, followed by ethyl acetate and then the mixture was stirred at r.t. for 1 hour. The solids were removed by filtration, being well washed with ethyl acetate. Concentration of the filtrate gave a crude product which was purified by flash chromatography on silica, eluting with 5% methanol in DCM. This afforded the title compound (233 mg, 83%) as a red oil. $^1$H NMR (methanol-$d_4$) 7.24 (1H, d), 7.15 (1H, t), 6.80 (1H, d), 6.78 (1H, d), 6.56 (1H, d), 6.52 (1H, dd), 4.05 (2H, t), 3.94 (2H, s), 3.88 (2H, s), 3.87 (2H, s), 3.83 (3H, s), 3.80 (3H, s), 3.70-3.68 (4H, m), 2.54-2.50 (2H, m), 2.49-2.47 (4H, m), 2.00-1.93 (2H, m). MS: [M+H]$^+$ 413.

Preparation C16

4-[2-(2-Methoxy-ethoxy)-ethoxy]-2,3-dihydro-1H-isoindole

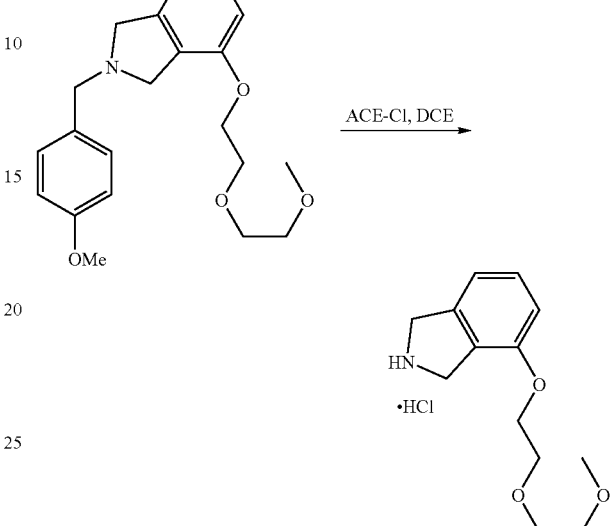

A solution of 2-(4-methoxy-benzyl)-4-[2-(2-methoxy-ethoxy)-ethoxy]-2,3-dihydro-1H-isoindole (45 mg, 0.13 mmol) in 1,2-dichloroethane (2 mL) was treated with O-chloroethyl chloroformate (0.1 mL, 0.93 mmol). After 17 hours, methanol (5 mL) was added and the mixture stirred for 3 hours. The solvents were removed in vacuo to afford the title compound as a greenish-black solid, which was used without further purification. $^1$H NMR (methanol-$d_4$) 7.36 (1H, t), 6.98 (2H, d), 4.60 (2H, s), 4.57 (2H, s), 4.23-4.21 (2H, m), 3.85-3.83 (2H, m), 3.69-3.67 (2H, m), 3.57-3.54 (2H, m), 3.36 (3H, s). MS: [M+H]$^+$ 238.

Preparation C17

[2-(2-(2,3-Dihydro-1H-isoindol-4-yloxy)-ethyl]-dimethyl-amine

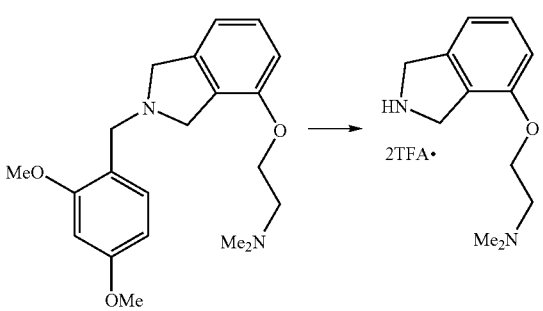 [SMILES: COc1ccc(CN2Cc3cccc(OCCN(C)C)c3C2)c(OC)c1 ; CN(C)CCOc1cccc2c1CNC2]

A solution of 2-(2,4-dimethoxy-benzyl)-4-(2-dimethyl-amino-ethoxy)-2,3-dihydro-1H-isoindole (170 mg, 0.48 mmol) in trifluoroacetic acid (0.5 mL) and anisole (0.5 mL) was heated at 150° C. under microwave irradiation for 10 minutes. The mixture was diluted with ethyl acetate and extracted twice with water. The combined aqueous extracts were concentrated to give the title compound as a purple oil (240 mg, including residual TFA and/or water). $^1$H NMR (methanol-$d_4$) 7.42 (1H, t), 7.07 (1H, d), 7.04 (1H, d), 4.64 (4H, br.s), 4.47-4.44 (2H, m), 3.65-3.63 (2H, m), 3.01 (6H, s). MS: [M+H]$^+$ 207.

Preparation C18

4-(3-Morpholin-4-yl-propoxy)-2,3-dihydro-1H-isoindole

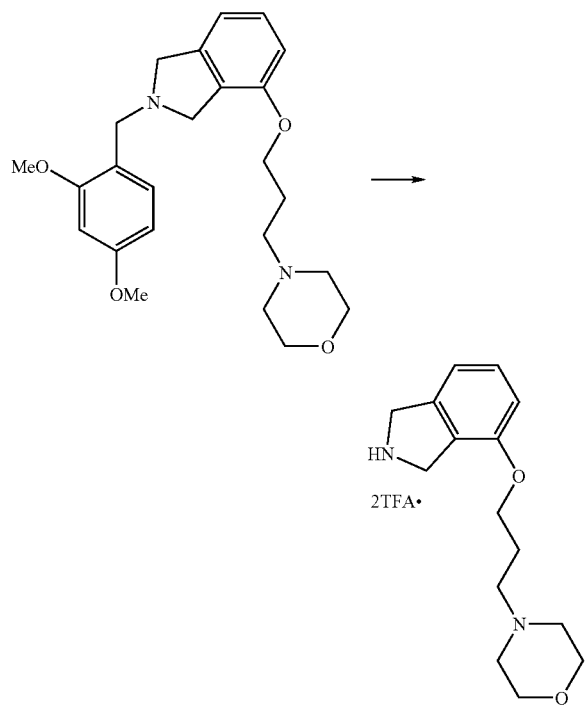

A solution of 2-(2,4-dimethoxy-benzyl)-4-(3-morpholin-4-yl-propoxy)-2,3-dihydro-1H-isoindole (233 mg, 0.56 mmol) in trifluoroacetic acid (1.0 mL) and anisole (0.5 mL) was heated at 150° C. under microwave irradiation for 10 minutes. The mixture was diluted with diethyl ether and extracted twice with water. The combined aqueous extracts were concentrated to give an oil which was dissolved in methanol and concentrated in vacuo to afford the title compound as a brown oil (348 mg, including residual TFA and/or water). $^1$H NMR (methanol-$d_4$) 7.40 (1H, t), 7.03 (1H, d), 6.99 (1H, d), 4.63 (2H, s), 4.59 (2H, s), 4.21 (2H, t), 4.14-4.04 (2H, m), 3.85-3.73 (2H, m), 3.61-3.52 (2H, m), 3.41-3.36 (2H, m), 3.25-3.13 (2H, m), 2.32-2.25 (2H, m). MS: [M+H]$^+$ 263.

Preparation C19

Synthesis of 4-bromo-2,3-dihydro-1H-isoindole trifluoroacetate

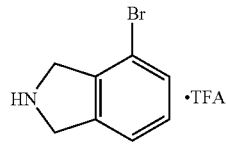

Prepared in a manner analogous to 5-nitro-2,3-dihydro-1H-isoindole (described in preparation C5). $^1$H NMR (DMSO-$d_6$) 9.73 (2H, br s), 7.60 (1H, d), 7.45 (1H, d), 7.35 (1H, t), 4.65 (2H, s), 4.55 (2H, s).

Preparation C20

Synthesis of 5-bromo-2,3-dihydro-1H-isoindole

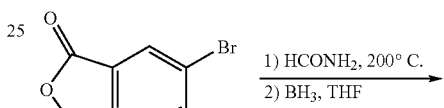

A mixture of 4-bromophthalic anhydride (25 g) in formamide (75 ml) was heated at 200° C. for 16 hours then allowed to cool to room temperature. The reaction mixture was diluted with water (200 ml), filtered, the filter cake was washed with water then diethyl ether and sucked dry to give 20.85 g of light mustard solid.

280 ml of 1M Borane-THF complex was added dropwise to a stirred solution of 4-bromophthalimide (20.85 g; 92.2 mmol) in anhydrous THF (200 ml) at 0° C. then heated at reflux overnight. The reaction was cooled to 0° C. then treated cautiously with methanol (100 ml) followed by 2M HCl (100 ml) then heated at reflux for 3 hours. The reaction mixture was cooled and the organics evaporated. The aqueous was diluted with water (100 ml) the extracted with DCM (×3). The aqueous was basified with 2M NaOH then extracted with DCM (×3). The combined DCM extracts were dried (MgSO$_4$), filtered and evaporated to give 6.99 g of 5-bromo-2,3-dihydro-1H-isoindole as a dark brown gummy solid. $^1$H NMR (DMSO-$d_6$) 7.45 (1H, s), 7.36 (1H, d), 7.20 (1H, d), 4.05 (4H, s).

Preparation C21

Synthesis of 2,3-dihydro-1H-isoindole-5-carboxylic acid methyl ester trifluoroacetate

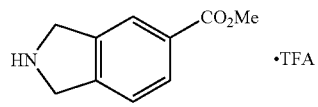

2-(2,4-Dimethoxybenzyl)-2,3-dihydro-1H-isoindole-5-carboxylic acid methyl ester (preparation C6, step 2 product) was deprotected in a manner analogous to 5-nitro-2,3-dihydro-1H-isoindole (described in preparation C5) to give the title compound. $^1$H NMR (DMSO-$d_6$) 9.70 (2H, br s), 8.00 (1H, s), 7.95 (1H, d), 7.57 (1H, d), 4.60 (4H, s), 2.88 (3H, s).

D. Synthesis of Benzylated Resorcinol Intermediates

Preparation D1

Synthesis of (2,4-bis-benzyloxy-5-isopropyl-phenyl)-[5-(2-methoxy-ethoxy)-1,3-dihydro-isoindol-2-yl]-methanone

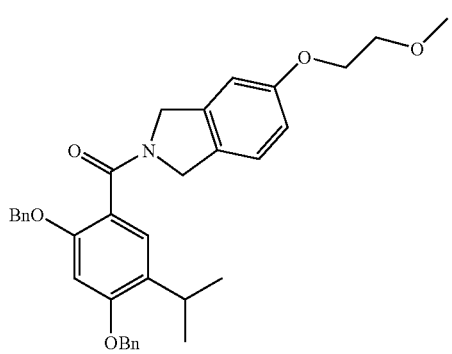 [SMILES: COCCOc1ccc2c(c1)CN(C(=O)c1cc(C(C)C)c(OCc3ccccc3)cc1OCc1ccccc1)C2]

(2,4-Bis-benzyloxy-5-isopropyl-phenyl)-(5-hydroxy-1,3-dihydro-isoindol-2-yl)-methanone (A2 from 2,4-bis-benzyloxy-5-isopropyl-benzoic acid (Preparation B10) and 5-hydroxyisoindoline) (100 mg, 0.2 mmol), 1-chloro-2-methoxy-ethane (23.6 mg, 0.25 mmol) and $K_2CO_3$ (34.5 mg, 0.25 mmol) in DMF (4 ml) were combined and stirred for 2 hours at room temperature. A further 0.25 mmol of 1-chloro-2-methoxy-ethane and $K_2CO_3$ was added then heated at 90° C. for 16 hours. Reaction cooled to room temperature and diluted with EtOAc then filtered. The filtrate was reduced in vacuo then purified by flash column chromatography, eluting with 100% petroleum ether to 100% ethyl acetate to afford 115 mg of the title compound as a colourless gel. MS: [M+H]$^+$ 552

Preparation D2

Synthesis of (2,4-bis-benzyloxy-5-isopropyl-phenyl)-[5-(3-morpholin-4-yl-propoxy)-1,3-dihydro-isoindol-2-yl]-methanone

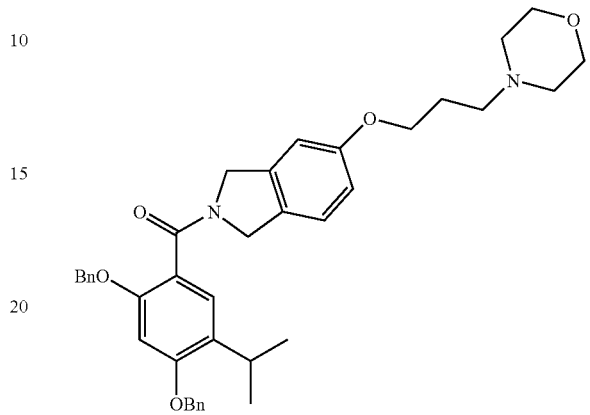

A mixture of (2,4-bis-benzyloxy-5-isopropyl-phenyl)-(5-hydroxy-1,3-dihydro-isoindol-2-yl)-methanone (100 mg, 0.2 mmol), 4-(3-chloropropyl)morpholine (82 mg, 0.5 mmol) and $K_2CO_3$ (104 mg, 0.75 mmol) in DMF (5 ml) was heated at 90° C. for 16 hours. The reaction mixture was diluted with EtOAc and filtered. The filtrate was reduced in vacuo and purified by flash column chromatography, eluting with 0-100% P.E./EtOAc then 0-10% MeOH/EtOAc to give the title compound as a colourless gel (90.1 mg). MS: [M+H]$^+$ 621.

Preparation D3

Synthesis of (2,4-bis-benzyloxy-5-isopropyl-phenyl)-[5-(2-dimethylamino-ethoxy)-1,3-dihydro-isoindol-2-yl]-methanone

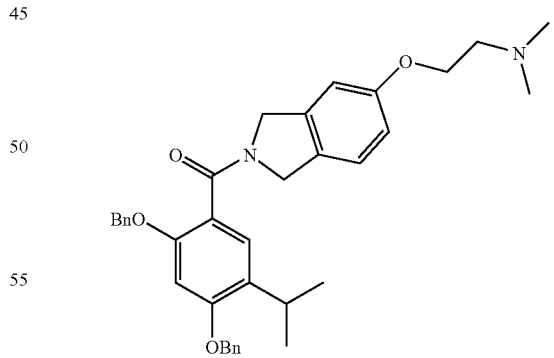

A mixture of (2,4-bis-benzyloxy-5-isopropyl-phenyl)-(5-hydroxy-1,3-dihydro-isoindol-2-yl)-methanone (100 mg, 0.2 mmol), 2-dimethylaminoethylchloride.HCl (72 mg, 0.5 mmol) and $K_2CO_3$ (173 mg, 1.25 mmol) in DMF (5 ml) was heated at 90° C. for 16 hours. Dilute reaction mixture with EtOAc and filtered. The reaction mixture was diluted with EtOAc and filtered. The filtrate was reduced in vacuo and purified by flash column chromatography, eluting 100%

DCM then 90% DMAW 90 to give the title compound as an off white gel (79 mg). MS: [M+H]⁺ 565

Preparation D4

Synthesis of 2,4-bis-benzyloxy-5-isopropyl-benzoyl chloride

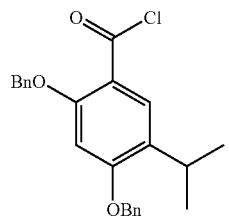 [SMILES: CC(C)c1cc(C(=O)Cl)c(OCc2ccccc2)cc1OCc1ccccc1]

2,4-Bis-benzyloxy-5-isopropyl-benzoic acid (Preparation B10) (0.2 g, 0.53 mmol) was dissolved in DCM (10 ml) and treated with oxalyl chloride (1.5 g, 12 mmol) and a catalytic amount of DMF. The reaction mixture was stirred at room temperature for 14 hours and the solvent was then removed in vacuo. The crude material was dissolved in toluene and evaporated. Crude 2,4-bis-benzyloxy-5-isopropyl-benzoyl chloride was obtained as an oil (200 mg).

Preparation D5

Synthesis of (2,4-bis-benzyloxy-5-isopropyl-phenyl)-(5-morpholin-4-yl-1,3-dihydro-isoindol-2-yl)-methanone

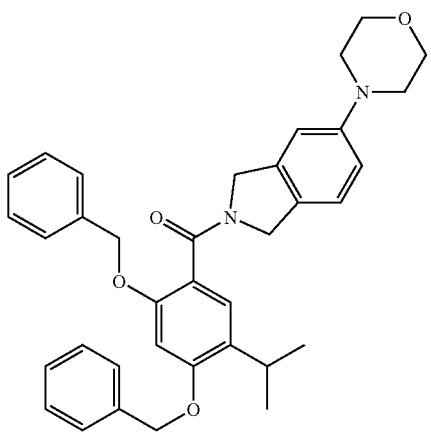 [SMILES: CC(C)c1cc(C(=O)N2Cc3ccc(N4CCOCC4)cc3C2)c(OCc2ccccc2)cc1OCc1ccccc1]

A solution of 2,4-bis-benzyloxy-5-isopropyl-benzoic acid (505 mg; 1.3 mmol) (Preparation B5), 5-nitroisoindoline, trifluoroacetate (360 mg; 1 equiv.), EDAC (300 mg; 1.2 equiv.), HOBt (210 mg; 1.2 equiv.) and NEt₃ (270 µl; 1.5 equiv.) in DMF (10 ml) was stirred at room temperature overnight then evaporated in vacuo. The residue was partitioned between EtOAc and 2M HCl, the EtOAc layer was separated, washed with saturated NaHCO₃, dried (MgSO₄) and evaporated. Purification by flash column chromatography (1:4 then 1:2 then 1:1 EtOAc/P.E. as eluant) gave 460 mg of (2,4-bis-benzyloxy-5-isopropyl-phenyl)-(5-nitro-1,3-dihydro-isoindol-2-yl)methanone. MS: [M+H]⁺ 523.

A solution of (2,4-bis-benzyloxy-5-isopropyl-phenyl)-(5-nitro-1,3-dihydro-isoindol-2-yl)methanone (460 mg; 0.88 mmol) in ethanol (25 ml) was treated with tin (II) chloride dihydrate (1 g; 5 equiv.) then heated at reflux overnight then evaporated in vacuo. The residue was partitioned between EtOAc and saturated NaHCO₃, the EtOAc layer was separated, dried (MgSO₄) and evaporated to give 380 mg of (5-amino-1,3-dihydro-isoindol-2-yl)-(2,4-bis-benzyloxy-5-isopropyl-phenyl)-methanone.

A mixture of (5-amino-1,3-dihydro-isoindol-2-yl)-(2,4-bis-benzyloxy-5-isopropyl-phenyl)-methanone (100 mg; 0.2 mmol), bis(2-chloroethyl)ether (30 µl; 1.1 equiv.), Hunig's base (125 µl; 3.5 equiv.) and tetrabutylammonium iodide (10 mg) in NMP (1 ml) was heated in a CEM microwave synthesiser at 150° C. for 30 minutes. A further 30 µl of Hunigs base and 125 µl of bis(2-chloroethyl)ether were added and heating repeated for the same time. The reaction mixture was partitioned between EtOAc and saturated NH₄Cl solution, the EtOAc layer was separated, washed with more saturated NH₄Cl solution, then brine, dried (MgSO₄) and evaporated. Purification by flash column chromatography (1:2 then 1:1 then 2:1 EtOAc/P.E. as eluant) gave 60 mg of (2,4-bis-benzyloxy-5-isopropyl-phenyl)-(5-morpholin-4-yl-1,3-dihydro-isoindol-2-yl)-methanone. MS: [M+H]⁺ 563.

Preparation D6

Synthesis of 2-(2,4-bis-benzyloxy-5-isopropyl-benzoyl)-2,3-dihydro-1H-isoindole-5-carboxylic acid

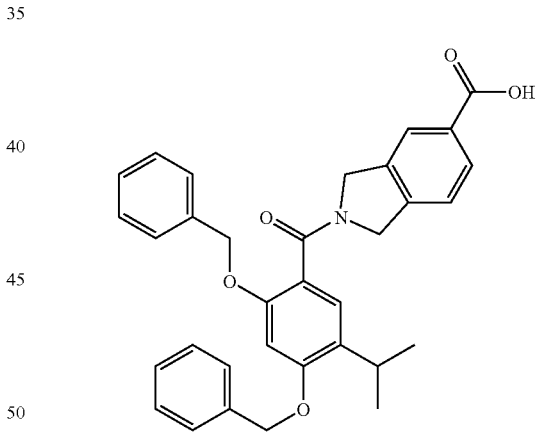

A solution of 2-(2,4-bis-benzyloxy-5-isopropyl-benzoyl)-2,3-dihydro-1H-isoindole-5-carboxylic acid methyl ester (390 mg) in methanol (10 ml) and 2M NaOH (10 ml) was heated at 50° C. for 48 hours then evaporated. The residue was acidified with 2M HCl, the solid collected by filtration, washed with water and sucked dry to give 255 mg of 2-(2,4-bis-benzyloxy-5-isopropyl-benzoyl)-2,3-dihydro-1H-isoindole-5-carboxylic acid as a white solid. [M+H]⁺ 520.

Examples

By following the methods described above, the compounds set out in the Table below were prepared.

| Example Number | Compound | Chemical Name | Method | NMR Data | MS |
|---|---|---|---|---|---|
| 1 | | (5-Chloro-2-hydroxy-phenyl)-(1,3-dihydro-isoindol-2-yl)-methanone | A1. From 5-chloro-2-hydroxy-benzoic acid and isoindoline | $^1$H NMR (MeOH-d$_4$) 7.20-7.42 (6 H, m), 6.92 (1 H, d), 4.94 (2 H, s), 4.74 (2 H, s) | MS: [M + H]$^+$ 274 |
| 2 | | (3-tert-Butyl-4-hydroxy-phenyl)-(2,3-dihydro-indol-1-yl)-methanone | A2. From 3-tert-butyl-4-hydroxy-benzoic acid and indoline | $^1$H NMR (DMSO-d$_6$) 7.56 (2 H, br m), 7.40 (1 H, s), 7.33 (1 H, d), 7.26 (1 H, d), 7.13 (1 H, t), 6.98 (1 H, t), 6.85 (1 H, d), 4.07 (2 H, t), 3.08 (2 H, t), 1.38 (9 H, s) | MS: [M + H]$^+$ 296 |
| 3 | | (3-tert-Butyl-4-hydroxy-phenyl)-(3,4-dihydro-2H-quinolin-1-yl)-methanone | A2. From 3-tert-butyl-4-hydroxy-benzoic acid and 1,2,3,4-tetrahydro-quinoline | $^1$NMR (DMSO-d$_6$) 11.05 (1 H, br s), 8.17 (1 H, d), 8.04 (2 H, m), 7.88 (1 H, d), 7.67 (1 H, t), 7.54 (1 H, t), 7.09 (1 H, d), 3.39 (1 H, m), 3.28 (1 H, m), 1.40 (9 H, s), 1.07 (3 H, m), 0.84 (1 H, m) | MS: [M + H]$^+$ 310 |
| 4 | | (3,4-Dihydro-1H-isoquinolin-2-yl)-(4-hydroxy-3-isopropyl-phenyl)-methanone | A2. From 3-isopropyl-4-hydroxy-benzoic acid and 1,2,3,4-tetrahydro-isoquinoline | $^1$H NMR (DMSO-d$_6$) 9.77 (1 H, br s), 7.24 (1 H, d), 7.17 (4 H, s), 7.18 (1 H, dd), 6.84 (1 H, d), 4.68 (2 H, s), 3.70 (2 H, br s), 3.23 (1 H, m), 2.87 (2 H, m), 1.18 (6 H, d) | MS: [M + H]$^+$ 296 |
| 5 | | (1,3-Dihydro-isoindol-2-yl)-(2,4-dihydroxy-5-isopropyl-phenyl)-methanone | A2 & A5. From 2,4-Bis-benzyloxy-5-isopropenyl-benzoic acid (B9) and isoindoline | $^1$H NMR (DMSO-d$_6$) 10.03 (1 H, s), 9.63 (1 H, s), 7.29 (4 H, br m), 7.03 (1 H, s), 6.40 (1 H, s), 4.77 (4 H, br s), 3.09 (1 H, m), 1.14 (6 H, d) | MS: [M + H]$^+$ 298 |

-continued

| Example Number | Compound | Chemical Name | Method | NMR Data | MS |
|---|---|---|---|---|---|
| 6 | | (3-tert-Butyl-4-hydroxy-phenyl)-(1,4-dioxa-8-aza-spiro[4.5]dec-8-yl)-methanone | A4. From 3-tert-butyl-4-hydroxy-benzoic acid and 4-piperidine ethylene ketal | $^1$H NMR (DMSO-d$_6$) 9.82 (1 H, s), 7.22 (1 H, s), 7.13 (1 H, dd), 6.82 (1 H, d), 3.91 (4 H, s), 3.52 (4 H, br m), 1.63 (4 H, bm), 1.37 (9 H, s) | MS: [M + H]$^+$ 320 |
| 7 | | (3-tert-Butyl-4-hydroxy-phenyl)-(1,3-dihydro-isoindol-2-yl)-methanone | A4. From 3-tert-butyl-4-hydroxy-benzoic acid and isoindoline | $^1$H NMR (DMSO-d$_6$) 9.82 (1 H, s), 7.41 (1 H, s), 7.38 (2 H, dd), 7.29 (3H, br m), 6.82 (1 H, d), 4.82 (4 H, br m), 1.37 (9 H, s) | MS: [M + H]$^+$ 296 |
| 8 | | (3-tert-Butyl-4-hydroxy-phenyl)-pyrrolo[3,2-b]pyridin-1-yl-methanone | A4. From 3-tert-butyl-4-hydroxy-benzoic acid and 1H-pyrrolo[3,2-b]pyridine | $^1$H NMR (DMSO-d$_6$) 8.57 (1 H, dd), 8.43 (1 H, d), 7.89 (1 H, dd), 7.63 (1 H, s), 7.56 (1 H, dd), 7.35 (1 H, m), 7.09 (1 H, d), 6.84 (1 H, dd), 1.37 (9 H, s) | MS: [M + H]$^+$ 295 |
| 9 | | 8-(3-tert-Butyl-4-hydroxy-benzoyl)-2-methyl-2,8-diaza-spiro[4.5]decan-1-one | A4. From 3-tert-butyl-4-hydroxy-benzoic acid and 4-spiro-[3-(N-methyl-2-pyrrolidinone] piperidine hydrochloride | $^1$H NMR (DMSO-d$_6$) 9.82 (1 H, s), 7.22 (1 H, s), 7.13 (1 H, dd), 6.82 (1 H, d), 3.98 (2 H, br m), 3.34 (2 H, s), 3.13 (2 H, m), 2.71 (3 H, s), 1.92 (2 H, t), 1.60 (2 H, m), 1.43 (2 H, m), 1.37 (9 H, s) | MS: [M + H]$^+$ 345 |
| 10 | | (1,3-Dihydro-isoindol-2-yl)-(4-hydroxy-3-isopropyl-phenyl)-methanone | A4. From 3-isopropyl-4-hydroxy-benzoic acid and isoindoline | $^1$H NMR (DMSO-d$_6$) 9.82 (1 H, s), 7.4 (2 H, s), 7.38 (1 H, dd), 7.30 (3 H, m), 6.82 (1 H, d), 4.82 (4 H, dd), 3.23 (1 H, m), 1.23 (6 H, s) | MS: [M + H]$^+$ 282 |

| Example Number | Compound | Chemical Name | Method | NMR Data | MS |
|---|---|---|---|---|---|
| 11 | | (3-tert-Butyl-4-hydroxy-phenyl)-(3,4-dihydro-1H-isoquinolin-2-yl)-methanone | A4. From 3-tert-butyl-4-hydroxy-benzoic acid and 1,2,3,4-tetrahydro isoquinoline | $^1$H NMR (DMSO-d$_6$) 7.22 (1 H, s), 7.13 (5 H, m), 6.82 (1 H, d), 4.70 (2 H, s), 3.75 (2 H, br s), 2.85 (2 H, t), 1.37 (9 H, s) | MS: [M + H]$^+$ 310 |
| 12 | | (1,3-Dihydro-isoindol-2-yl)-(5-ethyl-2,4-di-hydroxy-phenyl)-methanone | A2, A6 and A5. From 2,4-Bis-benzyloxy-5-bromo-benzoic acid, isoindoline and potassium vinyl trifluoroborate | $^1$H NMR (MeOH-d$_4$) 7.30 (4 H, s), 7.15 (1 H, s), 6.38 (1 H, s), 4.91 (4 H, s), 2.58 (2 H, q), 1.18 (3 H, t) | MS: [M + H]$^+$ 284 |
| 13 | | (5-Cyclopropyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and cyclopropane boronic acid | $^1$H NMR (DMSO-d$_6$) 7.40-7.23 (4 H, m), 6.73 (1 H, s), 6.40 (1 H, s), 4.75 (4 H, br s), 1.92 (1 H, m), 0.78 (2 H, m), 0.53 (2 H, m) | MS: [M + H]$^+$ 296 |
| 14 | | (5-sec-Butyl-2,4-dihydroxy-phenyl)-(1,3-dihydro-isoindol-2-yl)-methanone | A2, A6 and A5. From 2,4-Bis-benzyloxy-5-bromo-benzoic acid, isoindoline and 2-buten-2-yl boronic acid | $^1$H NMR (MeOH-d$_4$) 7.30 (4 H, s), 7.15 (1 H, s), 6.39 (1 H, s), 4.92 (1 H, s), 3.00 (4 H, s), 1.63 (1 H, q), 1.18 (2 H, m), 0.88 (3 H, t), (3 H, t) | MS: [M + H]$^+$ 312 |
| 15 | | (1,3-Dihydro-isoindol-2-yl)-(3-ethoxy-4-hydroxyphenyl)-methanone | Method A4. From 3-ethoxy-4-hydroxy-benzoic acid and isoindoline | $^1$H NMR (DMSO-d$_6$) 7.45 (1 H, br s), 7.30 (3 H, d), 7.18 (1 H, d), 7.08 (1 H, dd), 6.85 (1 H, d), 4.85 (4 H, s), 4.10 (2 H, q), 1.38 (3 H, t) | MS: [M + H]$^+$ 284 |

| Example Number | Compound | Chemical Name | Method | $^1$H NMR Data | MS |
|---|---|---|---|---|---|
| 16 | 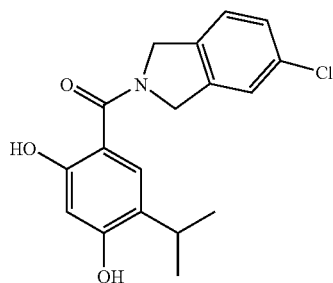 | (1,3-Dihydro-isoindol-2-yl)-(2,4-dihydroxy-phenyl)methanone | A2 and A5. From 2,4-Bis-benzyloxy-5-bromo-benzoic acid and isoindoline | $^1$H NMR (MeOH-d$_4$) 7.30 (5 H, m), 7.15 (1 H, s), 6.42 (1 H, s), 6.38 (1 H, s), 4.93 (4 H, s) | MS: [M + H]$^+$ 256 |

Example 17

Synthesis of (5-chloro-1,3-dihydro-isoindol-2-yl)-(2,4-dihydroxy-5-isopropyl-phenyl)-methanone

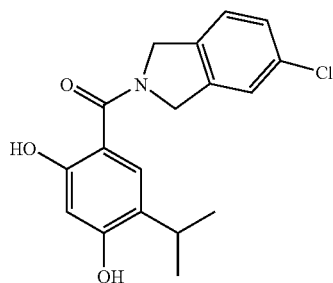 [SMILES: CC(C)c1cc(C(=O)N2Cc3ccc(Cl)cc3C2)c(O)cc1O]

A solution of 2,4-bis-benzyloxy-5-isopropyl-benzoic acid (Preparation B10) (0.451 g, 1.2 mmol), EDC (0.276 mg, 1.44 mmol), HOAt (0.196 mg, 1.44 mmol), triethylamine (0.5 ml, 3.6 mmol) and 5-chloro-2,3-dihydro-1H-isoindole (0.187 g, 1.2 mmol) (Preparation C3) in DMF (5 ml) was stirred at room temperature for 16 hours, then evaporated under vacuum. The crude material was dissolved in ethyl acetate and extracted twice with saturated NaHCO$_3$, organics washed with water three times, then evaporated under vacuum to give 0.5 g of 2,4-bis-benzyloxy-5-isopropyl-phenyl)-(5-chloro-1,3-dihydro-isoindol-2-yl)-methanone. MS: [M+H]$^+$ 512

Boron trichloride (1M in DCM) was added dropwise to a solution of 2,4-bis-benzyloxy-5-isopropyl-phenyl)-(5-chloro-1,3-dihydro-isoindol-2-yl)-methanone (0.5 g, 0.97 mmol) in dry DCM (10 ml) at 0° C. under nitrogen, then stirred for at 0° C. for 1 hour, warmed to room temperature and stirred for a further 3 hours. The reaction was quenched with ice, partitioned between DCM and water. The DCM layer was dried (MgSO$_4$), evaporated under vacuum, then purified by flash silica column chromatography eluting with 80% P.E.: EtOAc to give 0.1 g of (5-chloro-1,3-dihydro-isoindol-2-yl)-(2,4-dihydroxy-5-isopropyl-phenyl)-methanone as a white solid. MS: [M+H]$^+$ 332. $^1$H NMR (DMSO-d$_6$) 10.0 (1H, s) 9.60 (1H, s), 7.45 (1H, br s), 7.33 (2H, br s), 7.0 (1H, s), 6.4 (1H, s), 4.80 (4H, br s), 3.10 (1H, m), 1.15 (6H, d).

Example 18

Synthesis of [5-(3-amino-propoxy)-1,3-dihydro-isoindol-2-yl]-(2,4-dihydroxy-5-isopropyl-phenyl)-methanone hydrochloride

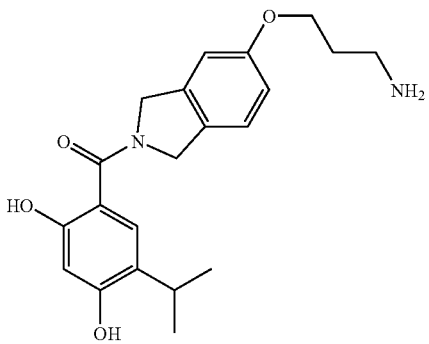 [SMILES: CC(C)c1cc(C(=O)N2Cc3ccc(OCCCN)cc3C2)c(O)cc1O]

A solution of {3-[2-(2,4-dihydroxy-5-isopropyl-benzoyl)-2,3-dihydro-1H-isoindol-5-yloxy]-propyl}carbamic acid tert-butyl ester (Example 46) (1 g) in EtOAc (10 ml) was treated with a saturated solution of HCl in EtOAC (20 ml) then stirred at room temperature for 2 hours. The reaction mixture was evaporated and re-evaporated with ethanol (×3). The title compound was isolated as a cream foam (840 mg). $^1$H NMR (DMSO-d6) 10.05 (1H, br s), 9.60 (1H, s), 7.88 (3H, br s), 7.30-7.18 (1H, m), 7.05 (1H, s), 7.00-6.85 (2H, m), 6.42 (1H, s), 4.75 (2H, br s) 4.70 (2H, br S), 4.05 (2H, t), 3.10 (1H, m), 3.00-2.95 (2H, m), 2.00 (2H, tt), 1.15 (6H, d). MS: [M+H]$^+$ 371.

Example 19

(5-Bromo-2,4-dihydroxy-phenyl)-(1,3-dihydro-isoindol-2-yl)-methanone

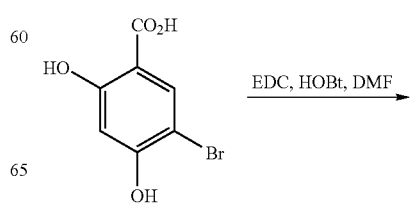

-continued

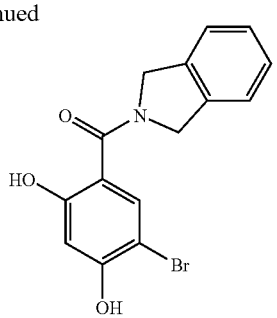

A solution of 5-bromo-2,4-dihydroxy-benzoic acid (520 mg, 2.33 mmol) in DMF (5 mL) was treated with 1-(3-dimethylaminopropyl)-3-ethylcarbodiimide hydrochloride (471 mg, 2.45 mmol) then HOBt (362 mg, 2.68 mmol). After 25 min, 2,3-dihydro-1H-isoindole (0.5 mL, 2.63 mmol) was added then the mixture was stirred at r.t. for 18 h. The solvent was removed in vacuo then the residue was taken up in ethyl acetate and washed with 1N hydrochloric acid, saturated sodium bicarbonate solution and brine then dried (MgSO$_4$) and concentrated. The residue was triturated with methanol to afford the title compound as a grey solid (328 mg, 44%). $^1$H NMR (DMSO-d$_6$) 10.45 (1H, s), 10.32 (1H, s), 7.36 (1H, br.s), 7.35 (1H, s), 7.28 (3H, br.s), 6.59 (1H, s), 4.77 (2H, br.s), 4.71 (2H, br.s). MS: [M+H]$^+$ 332/334.

Example 20

(1,3-Dihydro-isoindol-2-yl)-(2,4-dihydroxy-5-trifluoromethyl-phenyl)-methanone 20A. (2,4-Bis-benzyloxy-5-bromo-phenyl)-(1,3-dihydro-isoindol-2-yl)-methanone

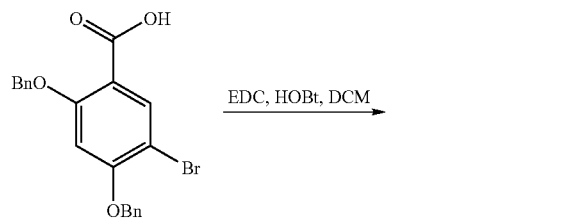

According to general method A2, 2,4-bis-benzyloxy-5-bromo-benzoic acid (1.02 g, 2.47 mmol) gave a residue which was purified by flash chromatography on silica (ethyl acetate/petrol gradient, 0-20%) to afford the title compound as a white crystalline solid (501 mg, 39%). $^1$H NMR (methanol-d$_4$) 7.52 (1H, s), 7.49-7.46 (2H, m), 7.42-7.37 (2H, m), 7.34 (t, 2H), 7.30-7.24 (4H, m), 7.23-7.20 (3H, m), 7.16 (1H, d), 6.94 (1H, s), 5.24 (2H, s), 5.16 (2H, s), 4.86 (2H, s), 4.60 (2H, s). MS: [M+H]$^+$ 514/516.

20B. (2,4-Bis-benzyloxy-5-trifluoromethyl-phenyl)-(1,3-dihydro-isoindol-2-yl)-methanone

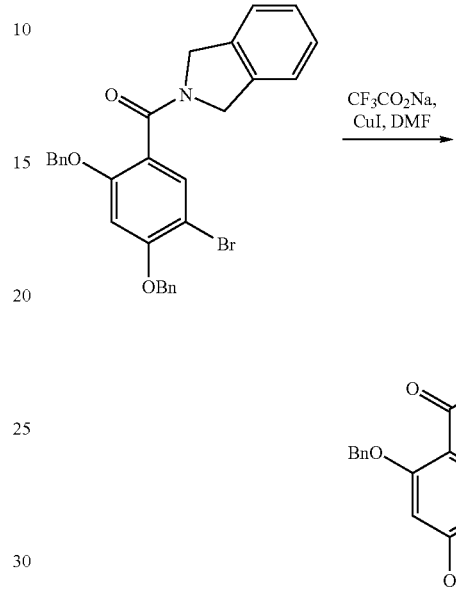

A mixture of (2,4-bis-benzyloxy-5-bromo-phenyl)-(1,3-dihydro-isoindol-2-yl)-methanone (491 mg, 0.95 mmol), sodium trifluoroacetate (649 mg, 4.8 mmol) and copper (I) iodide (364 mg, 1.91 mmol) were dried under vacuum (0.04 mbar) for 6 hours. The flask was flushed with nitrogen, DMF (5 mL) was added and the mixture heated at 150° C. for 17 hours. After cooling to r.t., the mixture was diluted with DCM (100 mL) and filtered through Celite, rinsing with DCM. The filtrate was concentrated to dryness and the residue was partially purified by flash chromatography on silica (ethyl acetate/petrol gradient, 0-20%). The purest fraction was recrystallised from methanol to afford the title compound as a white solid (140 mg, 29%). $^1$H NMR (methanol-d$_4$) 7.60 (1H, s), 7.48-7.44 (2H, m), 7.40 (2H, t), 7.37-7.21 (m, 9H), 7.17 (1H, d), 7.02 (1H, s), 5.29 (2H, s), 5.24 (2H, s), 4.88 (2H, s), 4.62 (2H, s). MS: [M+H]$^+$ 504.

20C. (1,3-Dihydro-isoindol-2-yl)-(2,4-dihydroxy-5-trifluoromethyl-phenyl)-methanone

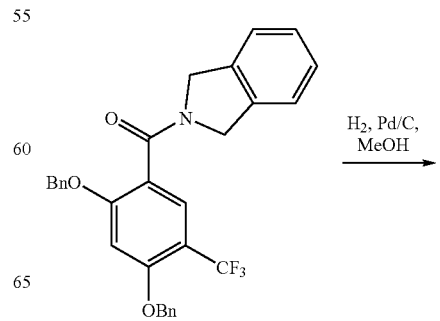

153

-continued

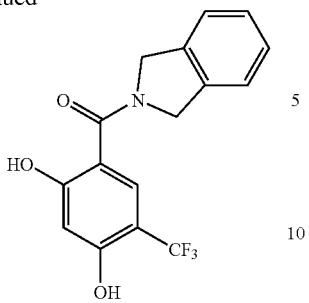

A solution of (2,4-bis-benzyloxy-5-trifluoromethyl-phenyl)-(1,3-dihydro-isoindol-2-yl)-methanone (140 mg, 0.28 mmol) in methanol (5 mL) was hydrogenated at atmospheric pressure over 10% palladium on charcoal (34 mg) for 4 hours. A further portion of catalyst was added (31 mg) and hydrogenation continued for a further 1.5 hours. The mixture was filtered through Celite, eluting with methanol, then the filtrate was concentrated in vacuo to afford the title compound as a white solid (91 mg, quant.). $^1$H NMR (DMSO-$d_6$) 10.79 (1H, s), 10.70 (1H, s), 7.40-7.35 (2H, m), 7.31-7.35 (3H, m), 6.61 (1H, s), 4.79 (2H, br.s), 4.68 (2H, br.s). MS: [M+H]$^+$ 324.

Example 21

(2,4-Dihydroxy-5-isopropyl-phenyl)-{4-[2-(2-methoxy-ethoxy)-ethoxy]-1,3-dihydro-isoindol-2-yl}methanone

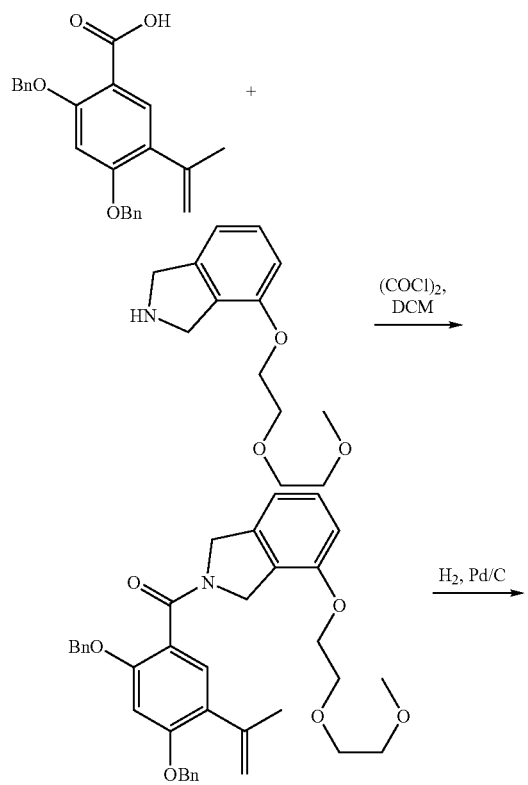

154

-continued

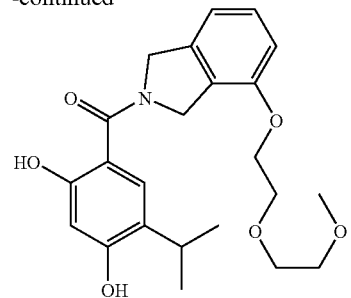

A solution of 2,4-bis-benzyloxy-5-isopropenyl-benzoic acid (96 mg, 0.26 mmol) and DMF (1 drop, cat.) in DCM (3 mL) was cooled in ice then treated with oxalyl chloride (112 □L, 1.28 mmol). After 2 hours the mixture was concentrated in vacuo then azeotroped with toluene. The resulting acid chloride was dissolved in DCM (4 mL) and added to a solution of 4-[2-(2-methoxy-ethoxy)-ethoxy]-2,3-dihydro-1H-isoindole (0.26 mmol, assuming a quantitative yield from the preceding step (debenzylation procedure C16)) and triethylamine (0.20 mL, 1.4 mmol) in DCM (1 mL). After 2 hours the mixture was diluted with ethyl acetate and washed with 1N hydrochloric acid, brine, sodium bicarbonate solution and brine. The organic phase was dried (MgSO$_4$) and concentrated to give a black residue. This was partially purified by flash chromatography on silica (ethyl acetate/petrol gradient, 20-33%) to afford an impure sample of the intermediate (2,4-bis-benzyloxy-5-isopropenyl-phenyl)-{4-[2-(2-methoxy-ethoxy)-ethoxy]-1,3-dihydro-isoindol-2-yl}-methanone.

A solution of (2,4-bis-benzyloxy-5-isopropenyl-phenyl)-{4-[2-(2-methoxy-ethoxy)-ethoxy]-1,3-dihydro-isoindol-2-yl}-methanone in methanol (5 mL) was hydrogenated at atmospheric pressure over 10% palladium on charcoal (12 mg) for 3 hours. A further portion of catalyst (12 mg) was added and hydrogenation continued for a further 7 hours. The mixture was filtered through Celite, eluting with methanol, then the filtrate was concentrated in vacuo to give a residue which was purified by preparative HPLC (basic method). This afforded the title compound as a white solid (17 mg, 16% over two steps). $^1$H NMR (methanol-$d_4$) 7.25 (1H, t), 7.17 (1H, s), 6.95-6.82 (2H, m), 6.37 (1H, s), 4.89 (2H, br.s), 4.83 (overlaps with H$_2$O, br.s), 4.16 (2H, br.s), 3.82 (2H, br.s), 3.66 (2H, br.s), 3.52 (2H, br.s), 3.39-3.28 (overlaps with MeOH, m), 3.20 (1H, sept), 1.21 (6H, d). MS: [M+H]$^+$ 416.

Example 22

(2,4-Dihydroxy-5-isopropyl-phenyl)-[4-(2-dimethylamino-ethoxy)-1,3-dihydro-isoindol-2-yl]-methanone

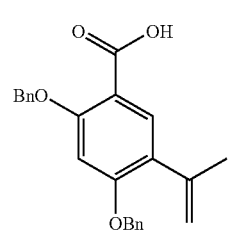

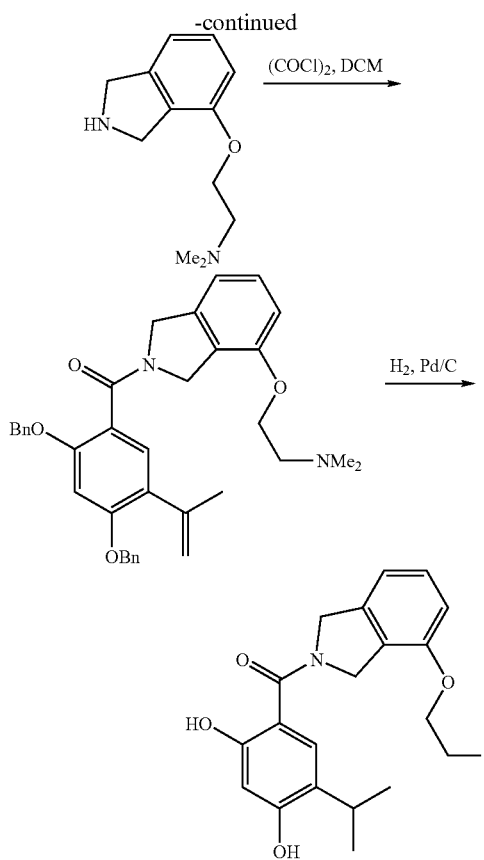

Example 23

(2,4-Dihydroxy-5-isopropyl-Phenyl)-[4-(3-morpholin-4-yl-propoxy)-1,3-dihydro-isoindol-2-yl]methanone

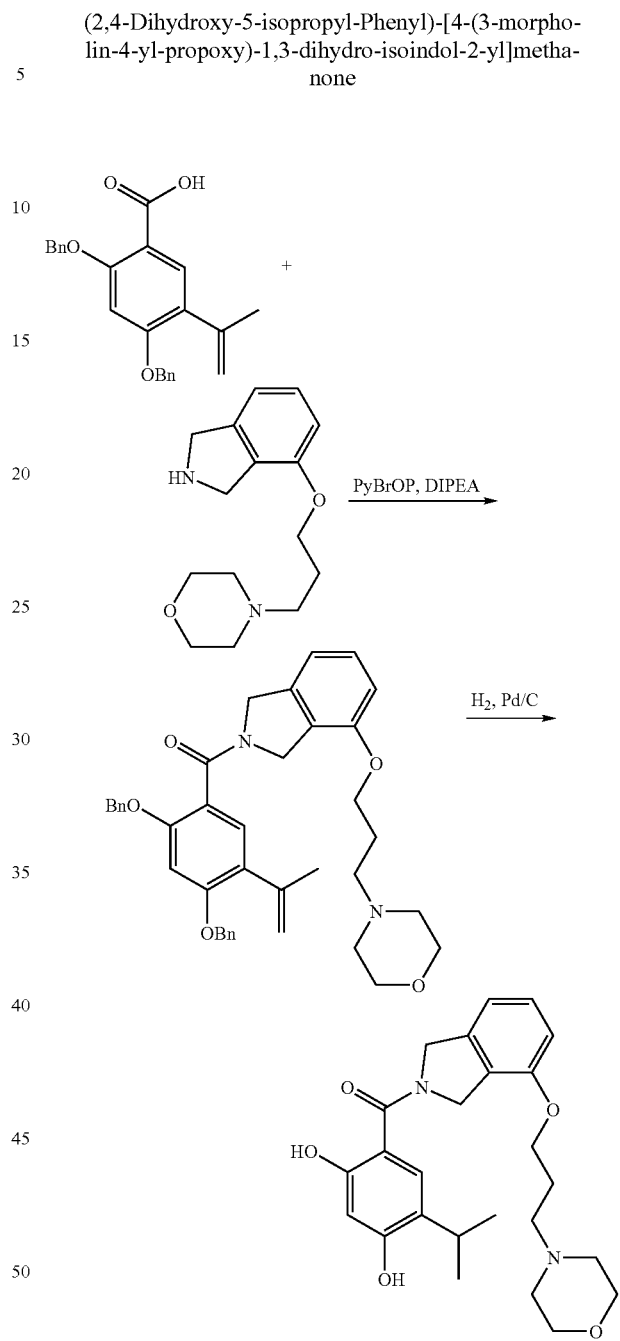

A solution of 2,4-bis-benzyloxy-5-isopropenyl-benzoic acid (189 mg, 0.50 mmol) and DMF (1 drop, cat.) in DCM (5 mL) was cooled in ice then treated with oxalyl chloride (1120 L, 1.28 mmol). After 2 hours the mixture was concentrated in vacuo then azeotroped with toluene. The resulting acid chloride was dissolved in DCM (5 mL) and added to a solution of [2-(2,3-dihydro-1H-isoindol-4-yloxy)-ethyl]-dimethyl-amine (0.48 mmol, assuming a quantitative yield from the preceding step (C17)) and triethylamine (0.50 mL, 3.6 mmol) in DCM (3 mL). After 16 hours the mixture was diluted with ethyl acetate and washed with saturated potassium carbonate solution and brine. The organic phase was dried (MgSO$_4$) and concentrated to give a residue which was partially purified by flash chromatography on silica (methanol/DCM gradient, 5-10% followed by 10% 2M methanolic ammonia/DCM) to afford an impure sample of the intermediate (2,4-bis-benzyloxy-5-isopropenyl-phenyl)-[4-(2-dimethylamino-ethoxy)-1,3-dihydro-isoindol-2-yl]-methanone.

A solution of (2,4-bis-benzyloxy-5-isopropenyl-phenyl)-[4-(2-dimethylamino-ethoxy)-1,3-dihydro-isoindol-2-yl]-methanone in methanol (5 mL) was hydrogenated at atmospheric pressure over 10% palladium on charcoal (40 mg) for 22 hours. The mixture was filtered through Celite, eluting with methanol, then the filtrate was concentrated in vacuo to give a residue which was purified by preparative HPLC (acidic method). This afforded the formate salt of the title compound as a white solid (9 mg, 5% over two steps). $^1$H NMR (methanol-d$_4$) 8.52 (0.7H, s), 7.29 (1H, t), 7.17 (1H, s), 6.98-6.86 (2H, m including 6.90 (1H, d)), 6.37 (1H, s), 4.89 (2H, br.s), 4.87 (2H, br.s), 4.28 (2H, br.s), 3.29-3.5 (3H, m including 3.20 (1H, sept)), 2.81-2.51 (6H, br.d), 1.21 (6H, d). MS: [M+H]$^+$ 385.

A solution of 2,4-bis-benzyloxy-5-isopropenyl-benzoic acid (210 mg, 0.56 mmol) and diisopropylethylamine (0.25 mL, 1.4 mmol) in DCM (5 mL) was treated with bromo-tris-pyrrolidino-phosphonium hexafluorophosphate (PyBrOP) (287 mg, 0.62 mmol). After 1 hour a solution of 4-(3-morpholin-4-yl-propoxy)-2,3-dihydro-1H-isoindole (0.56 mmol, assuming a quantitative yield from the preceding step(C18)) in DCM (5 mL) was added. After 4 hours the mixture was diluted with ethyl acetate and washed with water, 1N sodium hydroxide solution and brine. The organic phase was dried (MgSO$_4$) and concentrated to give a residue which was absorbed onto an SCX column. This was washed with 10% methanol/DCM then the product was eluted with 25% 2M methanolic ammonia/DCM) to afford an impure sample of the intermediate (2,4-bis-benzyloxy-5-isopropenyl-phenyl)-[4-(3-morpholin-4-yl-propoxy)-1,3-dihydro-isoindol-2-yl]-methanone.

A solution of (2,4-bis-benzyloxy-5-isopropenyl-phenyl)-[4-(3-morpholin-4-yl-propoxy)-1,3-dihydro-isoindol-2-yl]-methanone in methanol (5 mL) was hydrogenated at atmospheric pressure over 10% palladium on charcoal (45 mg) for 4 hours. The mixture was filtered through Celite, eluting with methanol, then the filtrate was concentrated in vacuo to give a residue which was purified by preparative HPLC (basic method). This afforded the title compound as a white solid (16 mg, 6% over two steps). $^1$H NMR (methanol-$d_4$) 7.24 (1H, t), 7.18 (1H, s), 6.89 (1H, d), 6.84 (1H, d), 6.37 (1H, s), 4.87 (2H, br.s), 4.78 (2H, br.s), 4.11-4.04 (2H, m), 3.72-3.66 (4H, m), 3.21 (1H, sept), 2.60-2.42 (6H, m), 2.05-1.92 (2H, m), 1.21 (6H, d). MS: [M+H]$^+$ 441.

Examples 24 to 47

By following the methods described above, the compounds of Examples 24 to 47 were prepared.

| Example Number | Compound | Chemical Name | Method | N.M.R. Data | M.S. |
|---|---|---|---|---|---|
| 24 | | (3-sec-Butyl-4-hydroxy-phenyl)-(1,3-dihydro-isoindol-2-yl)-methanone | A2 and A5. From (Z)-4-benzyloxy-3-(1-methyl-propenyl)-benzoic acid and isoindoline | $^1$H NMR (DMSO-$d_6$) 9.73 (1 H, br s), 7.37 (1 H, d), 7.32 (1 H, dd), 7.30 (4 H, br s), 6.86 (1 H, d), 4.87 (2 H, s), 4.82 (2 H, s), 3.03 (1 H, m), 1.63 (1 H, m), 1.57 (1 H, m), 1.19 (3 H, d), 0.82 (3 H, t) | MS: [M + H]$^+$ 296 |
| 25 | | (5-tert-Butyl-2,4-dihydroxy-phenyl)-(1,3-dihydro-isoindol-2-yl)-methanone | A2 and A5. From 2,4-bis-benzyloxy-5-tert-butyl-benzoic acid and isoindoline | $^1$H NMR (DMSO-$d_6$) 7.34 (2 H, m), 7.29 (2 H, m), 7.10 (1 H, s), 6.33 (1 H, s), 4.83 (4 H, s), 1.35 (9 H, s) | MS: [M + H]$^+$ 312 |
| 26 | | (5-Chloro-2,4-dihydroxy-phenyl)-(1,3-dihydro-isoindol-2-yl)-methanone | A2 and A3. From 2,4-bis-benzyloxy-5-chloro-benzoic acid and isoindoline | $^1$H NMR (DMSO-$d_6$) 10.42 (1 H, s), 10.33 (1 H, s), 7.38 (2 H, m), 7.30 (2 H, m), 7.24 (1 H, s), 6.60 (1 H, s), 4.78 (2 H, br s), 4.72 (2 H, br s) | MS: [M + H]$^+$ 290 |
| 27 | | (1,3-Dihydro-isoindol-2-yl)-(2-hydroxy-5-isopropyl-4-methoxy-phenyl)-methanone | A2, A5 & A7. From 2,4-bis-benzyloxy-5-isopropenyl-benzoic acid and isoindoline | H NMR (DMSO-$d_6$) 10.21 (1 H, br s), 7.33 (2 H, br s), 7.28 (2 H, br s), 7.13 (1 H, s), 6.50 (1 H, s), 4.80 (4 H, br s), 3.79 (3 H, s), 3.15 (1 H, m), 1.14 (6 H, d) | MS: [M + H]$^+$ 312 |

| Example Number | Compound | Chemical Name | Method | N.M.R. Data | M.S. |
|---|---|---|---|---|---|
| 28 | | (4,7-difluoro-1,3-dihydro-isoindol-2-yl)-(2,4-dihydroxy-5-isopropyl-phenyl)-methanone | A2 and A5. From 2,4-bis-benzyloxy-5-isopropenyl-benzoic acid and 4,7-difluoro-isoindoline | H NMR (DMSO-$d_6$) 9.97 (1 H, br s), 9.66 (1 H, br s), 7.22 (2 H, dd), 7.03 (1 H, s), 6.42 (1 H, s), 4.84 (4 H, br s), 3.10 (1 H, m), 1.13 (6 H, d) | MS: [M + H]$^+$ 334 |
| 29 | | (2,4-dihydroxy-5-isopropyl-phenyl)-(5-fluoro-1,3-dihydro-isoindol-2-yl)-methanone | A2 and A5. From 2,4-bis-benzyloxy-5-isopropenyl-benzoic acid and 5-fluoro-isoindoline [Ref. U.S. Pat. No. 5,026,856] | H NMR (DMSO-$d_6$) 10.02 (1 H, br s), 9.58 (1 H, s), 7.37 (1 H, br m), 7.20 (1 H, br m), 7.12 (1 H, td), 7.04 (1 H, s), 6.41 (1 H, s), 4.78 (2 H, br s), 4.75 (2 H, br s), 3.11 (1 H, m), 1.16 (6 H, d) | MS: [M + H]$^+$ 316 |
| 30 | | (1,3-dihydro-isoindol-2-yl)-(3-fluoro-2,4-dihydroxy-5-isopropyl-phenyl)-methanone | A8. From (1,3-dihydro-isoindol-2-yl)-(2,4-dihydroxy-5-isopropyl-phenyl)-methanone | H NMR (DMSO-$d_6$) 12.23 (1 H, br s), 7.39 (1 H, m), 7.35-7.25 (3 H, m), 6.84 (1 H, d), 5.53 (1 H, s), 4.74 (1 H, s), 4.59 (2 H, s), 2.52 (2 H, s), 1.11 (1 H, m), 0.84 (3 H, d); $^{19}$F NMR (DMSO-d6) 19.3 (3 H, d) | MS: [M + H]$^+$ 316 |
| 31 | | (1,3-dihydro-isoindol-2-yl)-(2-fluoro-4,6-dihydroxy-3-isopropyl-phenyl)-methanone | A8. From (1,3-dihydro-isoindol-2-yl)-(2,4-dihydroxy-5-isopropyl-phenyl)-methanone | H NMR (DMSO-$d_6$) 12.03 (1 H, br s), 7.40-7.35 (2 H, m), 7.33-7.28 (2 H, m), 6.53 (1 H, br d), 5.53 (1 H, s), 5.07 (1 H, brd), 4.98 (1 H, br d), 4.79 (2 H, s), 2.90 (1 H m), 1.03 (6 H, m); $^{19}$F NMR (DMSO-$d_6$) 24.9 | MS: [M + H]$^+$ 316 |

-continued

| Example Number | Compound | Chemical Name | Method | N.M.R. Data | M.S. |
|---|---|---|---|---|---|
| 32 | | (2,4-dihydroxy-5-isopropyl-phenyl)-(4-fluoro-1,3-dihydro-isoindol-2-yl)-methanone hydrochloride | From 2,4-bis-benzyloxy-5-isopropyl-benzoic acid (B10) and 4-fluoro-2,3-dihydro-1H-isoindole | H NMR (DMSO-$d_6$) 7.35 (2 H, m), 7.20 (1 H, m), 7.1 (1 H, t), 7.0 (1 H, s), 6.4 (1 H, s), 4.80 (4 H, br s), 1.20 (6 H, s) | MS: [M + H]$^+$ 316 |
| 33 | | (5-chloro-6-methoxy-1,3-dihydro-iso-indol-2-yl)-(2,4-dihydroxy-5-isopropyl-phenyl)-methanone | A2 and A5. From 2,4-bis-benzyloxy-5-isopropyl-benzoic acid (B10) and 5-chloro-6-methoxy-2,3-dihydro-1H-isoindole | $^1$H NMR (Me-$d_3$-OD) 7.32 (1 H, s), 7.17 (1 H, s), 7.05 (1 H, s), 6.37 (1 H, s), 4.89 (2 H, s), 3.89 (3 H, s), 3.36 (3 H, m), 1.23 (6 H, d) | MS: [M + H]$^+$ 362 |
| 34 | | (2,4-dihydroxy-5-isopropyl-phenyl)-[5-(2-methoxy-ethoxy)-1,3-dihydro-isoindol-2-yl]-methanone | A5. From (2,4-bis-benzyloxy-5-isopropyl-phenyl)-[5-(2-methoxy-ethoxy)-1,3-dihydro-isoindol-2-yl]-methanone | H NMR (DMSO-$d_6$) 10.02 (1 H, s), 9.60 (1 H, s), 7.22 (1 H, brs), 7.03 (1 H, s), 6.90 (1 H, br s), 6.85 (1 H, d), 6.4 (1 H, s), 4.74 (4 H, br d), 4.08 (2 H, br s), 3.65 (2 H, t), 3.18-3.03 (1 H, m), 1.15 (6 H, s), 3.30 (3 H, s) | MS: [M + H]$^+$ 372 |
| 35 | | (2,4-dihydroxy-5-isopropyl-phenyl)-[5-(3-morpholin-4-yl-propoxy)-1,3-dihydro-isoindol-2-yl]-methanone | A5. From (2,4-bis-benzyloxy-5-isopropyl-phenyl)-[5-(3-morpholin-4-yl-propoxy)-1,3-dihydro-isoindol-2-yl]-methanone | H NMR (DMSO-$d_6$) 10.02 (1 H, s), 9.60 (1 H, s), 7.22 (1 H, br s), 7.03 (1 H, s), 6.90 (1 H, br s), 6.85 (1 H, d), 6.4 (1 H, s), 4.74 (4 H, br d), 4.08 (2 H, br s), 3.55 (4 H, brs), 3.18-3.03 (1 H, m), 2.40 (2 H, s), 2.38 (4 H, br s), 1.85 (2 H, t), 1.15 (6 H, s) | MS: [M + H]$^+$ 441 |

-continued

| Example Number | Compound | Chemical Name | Method | N.M.R. Data | M.S. |
|---|---|---|---|---|---|
| 36 | | (2,4-dihydroxy-5-isopropyl-phenyl)-[5-(2-dimethylamino-ethoxy)-1,3-dihydro-isoindol-2-yl]-methanone | A5. From (2,4-bis-benzyloxy-5-isopropyl-phenyl)-[5-(2-dimethylamino-ethoxy)-1,3-dihydro-isoindol-2-yl]-methanone | H NMR (DMSO-$d_6$) 10.02 (1 H, s), 9.60 (1 H, s), 7.22 (1 H, br s), 7.03 (1 H, s), 6.90 (1 H, br s), 6.85 (1 H, d), 6.40 (1 H, s), 4.74 (4 H, br d), 4.08 (2 H, br s), 3.18-3.03 (1 H, m), 2.71 (2 H, br s), 2.30 (6 H, s), 1.15 (6 H, s) | MS: [M + H]$^+$ 385 |
| 37 | | (2,4-dihydroxy-5-isopropyl-phenyl)-(2-oxa-5-aza-bicyclo[2.2.1]hept-5-yl)-methanone | A2 and A5. From (2,4-bis-benzyloxy-5-isopropenyl-benzoic acid (Preparation B5) and 2-oxa-5-aza-bicyclo[2.2.1]-heptane | H NMR (DMSO-$d_6$) 9.64 (1 H, s), 7.02 (1 H, s), 6.31 (1 H, s), 4.65 (2 H, s), 3.78 (2 H, dd), 3.31 (2 H, s), 3.07 (1 H, m), 1.77 (2 H, m), 1.10 (6 H, m) | MS: [M + H]$^+$ 278 |
| 38 | | (3,4-dihydro-1H-isoquinolin-2-yl)-(2,4-dihydroxy-5-isopropyl-phenyl)-methanone | A2 and A5. From (2,4-bis-benzyloxy-5-isopropenyl-benzoic acid (Preparation B5) and 1,2,3,4-tetrahydro-isoquinoline | $^1$H NMR (Me-$d_3$-OD) 7.19 (1 H, s), 7.14-7.09 (1 H, br s), 7.02 (1 H, s), 6.37 (1 H, s), 4.75 (2 H, s), 3.80 (2 H, t), 3.24-3.15 (1 H, m), 2.95 (2 H, t), 1.19 (6 H, d) | MS: [M + H]$^+$ 312 |
| 39 | | (5-amino-1,3-dihydro-isoindol-2-yl)-(2,4-dihydroxy-5-isopropyl-phenyl)-methanone | A2 & A5. From 2,4-bis-benzyloxy-5-isopropenyl-benzoic acid (Preparation B5) and 5-nitro-isoindoline. TFA (C5 but omitting hydrogenation step) | H NMR (DMSO-$d_6$) 7.05 (1 H, s), 6.95-6.85 (1 H, m), 6.60-6.50 (2 H, m), 6.25 (1 H, s), 4.6-4.5 (4 H, m), 3.10 (1 H, h), 1.10 (6 H, d) | MS: [M + H] + 313 |

-continued

| Example Number | Compound | Chemical Name | Method | N.M.R. Data | M.S. |
|---|---|---|---|---|---|
| 40 | 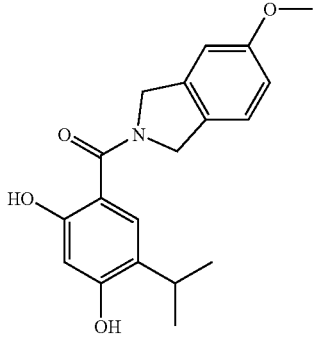 [SMILES: COc1ccc2c(c1)CN(C(=O)c1cc(C(C)C)c(O)cc1O)C2] | (2,4-dihydroxy-5-isopropyl-phenyl)-(5-methoxy-1,3-dihydro-isoindol-2-yl)-methanone | A2 and A5. From 2,4-bis-benzyloxy-5-isopropenyl-benzoic acid (Preparation B5) and 5-methoxy-isoindoline. | H NMR (DMSO-$d_6$) 10.05 (1 H, s), 9.60 (1 H, s), 7.30-7.15 (1 H, m), 7.05 (1 H, s), 7.00-6.85 (1 H, m), 6.82 (1 H, d), 6.40 (1 H, s), 4.75 (2 H, s) 4.70 (2 H, s), 3.75 (3 H, s), 3.10 (1 H, m), 1.13 (6 H, d) | MS: [M + H]+ 328 |
| 41 | 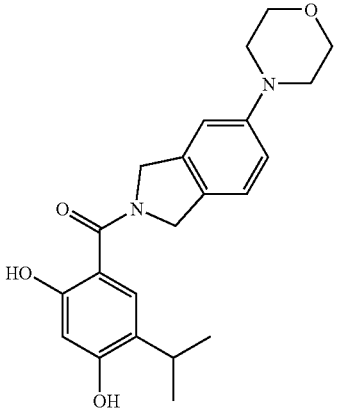 [SMILES: CC(C)c1cc(C(=O)N2Cc3ccc(N4CCOCC4)cc3C2)c(O)cc1O] | (2,4-dihydroxy-5-isopropyl-phenyl)-(5-morpholin-4-yl-1,3-dihydro-isoindol-2-yl)-methanone | A5 from (2,4-bis-benzyloxy-5-isopropyl-phenyl)-(5-morpholin-4-yl-1,3-dihydro-isoindol-2-yl)-methanone (D5). | H NMR (DMSO-$d_6$) 9.60 (1 H, br s), 7.30-7.15 (1 H, m), 7.05 (1 H, s), 7.00-6.90 (2 H, m), 6.40 (1 H, s), 4.75 (2 H, s) 4.70 (2 H, s), 3.75 (4 H, m), 3.15-3.05 (5 H, m), 1.15 (6 H, d) | MS: [M + H]+ 383 |
| 42 | 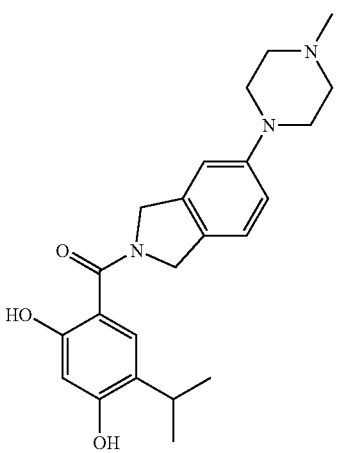 [SMILES: CC(C)c1cc(C(=O)N2Cc3ccc(N4CCN(C)CC4)cc3C2)c(O)cc1O] | (2,4-dihydroxy-5-isopropyl-phenyl)-[5-(4-methyl-piperazin-1-yl)-1,3-dihydro-isoindol-2-yl]-methanone | As for Example 41 but using bis(2-chloroethyl)-methylamine hydrochloride in step 2. | H NMR (DMSO-$d_6$) 7.30-7.15 (1 H, m), 7.05 (1 H, s), 6.95-6.85 (2 H, m), 6.40 (1 H, s), 4.70 (2 H, br s) 4.65 (2 H, brs), 3.15-3.05 (5 H, m), 2.45 (4 H, m), 2.20 (4 H, s), 1.85 (3 H, s), 1.15 (6 H, d) | MS: [M + H]+ 396 |

-continued

| Example Number | Compound | Chemical Name | Method | N.M.R. Data | M.S. |
|---|---|---|---|---|---|
| 43 | | 2-(2,4-dihydroxy-5-isopropyl-benzoyl)-2,3-dihydro-1H-isoindole-5-carboxylic acid methyl ester | A2 and A5. From 2,4-bis-benzyloxy-5-isopropenyl-benzoic acid (Preparation B5) and 2,3-dihydro-1H-isoindole-5-carboxylic acid methyl ester, TFA (Preparation C21) | H NMR (DMSO-$d_6$) 10.05 (1 H, br s), 9.60 (1 H, s), 8.00-7.92 (1 H, m), 7.90 (1 H, s), 7.55-7.42 (1 H, m), 7.05 (1 H, d), 6.40 (1 H, s), 4.85 (4 H, br s) 3.85 (3 H, s), 3.10 (1 H, m), 1.13 (6 H, d) | MS: [M + H]$^+$ 356 |
| 44 | | 2-(2,4-dihydroxy-5-isopropyl-benzoyl)-2,3-dihydro-1H-isoindole-5-carboxylic acid | A5, from 2-(2,4-bis-benzyloxy-5-isopropyl-benzoyl)-2,3-dihydro-1H-isoindole-5-carboxylic acid. | H NMR (DMSO-$d_6$) 12.90 (1 H, br s), 10.05 (1 H, br s), 9.60 (1 H, s), 8.00-7.92 (1 H, m), 7.90 (1 H, d), 7.55-7.40 (1 H, m), 7.05 (1 H, d), 6.45 (1 H, s), 4.85 (4 H, br s) 3.10 (1 H, m), 1.15 (6 H, d) | MS: [M + H]$^+$ 342 |
| 45 | | (2,4-dihydroxy-5-isopropyl-phenyl)-(5-morpholin-4-ylmethyl-1,3-dihydro-isoindol-2-yl)-methanone hydrochloride | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). | H NMR (DMSO-$d_6$) 11.03 (1 H, br s), 10.05 (1 H, br s), 9.78 (1 H, br s), 7.60-7.38 (3 H, m), 7.05 (1 H, s), 6.45 (1 H, s), 4.80 (4 H, m), 4.33 (2 H, d), 3.95-3.85 (2 H, m), 3.32-3.22 (2 H, m), 3.28-3.00 (5 H, m), 1.15 (6 H, d) | MS: [M + H]$^+$ 397 |
| 46 | | {3-[2-(2,4-dihydroxy-5-isopropyl-benzoyl)-2,3-dihydro-1H-isoindol-5-yloxy]-propyl}-carbamic acid tert-butyl ester | As for Example 34, A2 (from benzyloxy-5-isopropyl-benzoic acid (Preparation B5) and 5-hydroxy-isoindoline), alkylation using 3-(BOC-amino)propyl bromide, then A5. | H NMR (DMSO-$d_6$) 10.05 (1 H, br s), 9.60 (1 H, s), 7.30-7.15 (1 H, m), 7.05(1 H, s), 6.98-6.80 (3 H, m), 6.40 (1 H, s), 4.75 (2 H, br s) 4.70 (2 H, br s), 3.95 (2 H, s), 3.15-3.05 (3 H, m), 1.80 (2 H, tt), 1.37 (9 H, s), 1.15 (6 H, d) | MS: [M + H]$^+$ 471 |

| Example Number | Compound | Chemical Name | Method | N.M.R. Data | M.S. |
|---|---|---|---|---|---|
| 47 | ![structure] | (2,4-dihydroxy-5-isopropyl-phenyl)-(5-methyl-1,3-dihydro-isoindol-2-yl)-methanone | A2 and A5. From 2,4-bis-benzyloxy-5-isopropenyl-benzoic acid (Preparation B5) and 5-morpholin-4-ylmethyl-2,3-dihydro-1H-isoindole ditrifluoro-acetate (C6). Biproduct from Example 45. | H NMR (DMSO-d$_6$) 10.05 (1 H, s), 9.60 (1 H, s), 7.25-7.08 (3 H, m), 7.05 (1 H, s), 6.40 (1 H, s), 4.75 (4 H, m), 3.10 (1 H, m), 2.30 (1 H, s), 1.15 (6 H, d) | MS: [M + H]$^+$ 312 |

Example 48

Synthesis of (2,4-dihydroxy-5-isopropyl-Phenyl-[5-(2-isopropylamino-ethoxy)-1,3-dihydro-isoindol-2-yl]-methanone

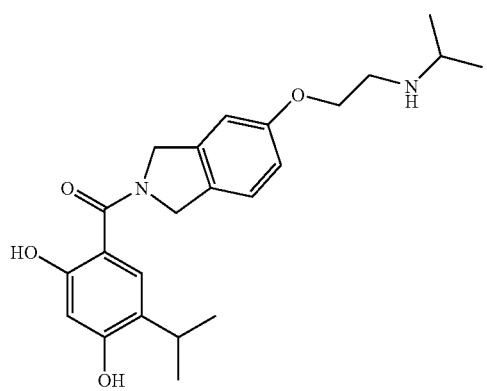 [SMILES: CC(C)NCCOc1ccc2c(c1)CN(C(=O)c1cc(C(C)C)c(O)cc1O)C2]

To a suspension of [5-(3-amino-ethoxy)-1,3-dihydro-isoindol-2-yl]-(2,4-dihydroxy-5-isopropyl-phenyl)-methanone hydrochloride (Example 57) (250 mg, 0.702 mmoles) in 1,2-dichloroethane (10 ml) was added acetone (62 µl, 0.842 mmoles), sodium triacetoxyborohydride (178 mg, 0.842 mmoles) and acetic acid (48 µl, 0.842 mmoles) and then heated at 60° C. for 24 hours. To the reaction mixture was added further acetone (52 µl, 0.702 mmoles), sodium triacetoxyborohydride (149 mg, 0.702 mmoles) and acetic acid (40 µl, 0.702 mmoles) and heated at 60° C. for a further 2 hours. The reaction mixture was then filtered and the mother liquor purified by flash chromatography [Biotage SP4: 25M, flow rate 25 ml/min, gradient 20% to 100% DMAW 90 in DCM) to give (2,4-dihydroxy-5-isopropyl-phenyl)-[5-(2-isopropylamino-ethoxy)-1,3-dihydro-isoindol-2-yl]-methanone as a light brown viscous oil (140 mg, 50%). $^1$H NMR (DMSO-d6) 10.05 (1H, br s); 9.60 (1H, br s); 7.23 (1H, br s); 7.05 (1H, s); 6.93 (1H, br s); 6.85 (1H, br d); 6.40 (1H, s); 4.70 (4H, br m); 4.00 (2H, t); 3.10 (1H, m); 2.90 (2H, t); 2.80 (1H, m); 1.15 (6H, d); 1.00 (6H, d). MS: [M+H]$^+$ 399.

Example 49

Synthesis of N-{2-[2,4-dihydroxy-5-isopropyl-benzoyl)-2,3-dihydro-1H-isoindol-5-yloxy]-ethyl}-2-morpholin-4-yl-acetamide

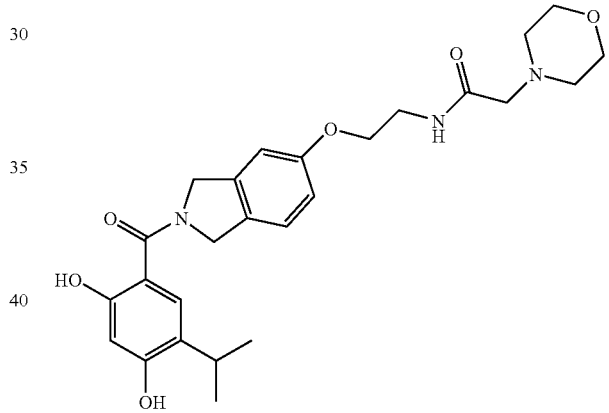

To a solution of [5-(3-amino-ethoxy)-1,3-dihydro-isoindol-2-yl]-(2,4-dihydroxy-5-isopropyl-phenyl)-methanone hydrochloride (100 mg, 0.255 mmoles) in DMF (10 ml) was added EDC (59 mg, 0.306 mmoles), HOBt (41 mg, 0.306 mmoles), morpholin-4-yl-acetic acid (37 mg, 0.255 mmoles) and triethylamine (43p1, 0.306 mmoles) and stirred at ambient temperature for one hour. To the reaction mixture was added further EDC (20 mg, 0.104 mmoles), HOBt (14 mg, 0.104 mmoles), morpholin-4-yl-acetic acid (12 mg, 0.083 mmoles) and triethylamine (14 µl, 0.100 mmoles) and stirred at ambient temperature for a further 2 hours. Solvent removed in vacuo. The residue was purified by flash chromatography [Biotage SP4: 25S, flow rate 25 ml/min, gradient 20% DMAW 90 in DCM to 100% DMAW 90] and then by preparative HPLC to give N-[2-[2,4-dihydroxy-5-isopropyl-benzoyl)-2,3-dihydro-1H-isoindol-5-yloxy]-ethyl]-2-morpholin-4-yl-acetamide as a colourless viscous oil (40 mg, 33%). $^1$H NMR (Me-d3-OD) 7.20 (1H, br s); 7.18 (1H, s); 6.90 (1H, br m); 6.40 (1H, s); 4.10 (2H, t); 3.73 (4H, m); 3.63 (2H, t); 3.20 (1H, m); 3.18 (2H, s); 2.60 (4H, m); 1.25 (6H, d). MS: [M+H]$^+$ 484.

Example 50

Synthesis of (2,4-dihydroxy-5-isopropylphenyl)-[5-(4-hydroxy-1-methyl-piperidin-4-yl)-1,3-dihydro-isoindol-2-yl]-methanone

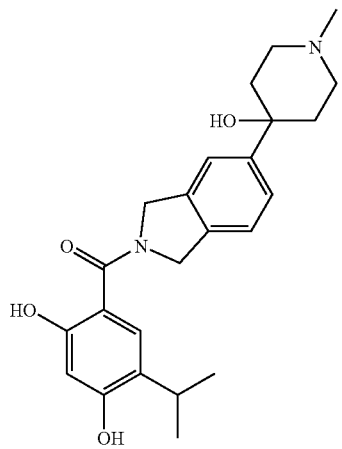 [SMILES: CC(C)c1cc(C(=O)N2Cc3ccc(C4(O)CCN(C)CC4)cc3C2)c(O)cc1O]

50A: Synthesis of 5-bromo-1,3-dihydro-isoindole-2-carboxylic acid tert-butyl ester A mixture of 5-bromo-2,3-dihydro-1H-isoindole (1.26 g; 6.4 mmol), di-tert-butyl dicarbonate (1.53 g; 1.1 equiv.) and 4-dimethylaminopyridine (catalytic amount) in DMF (20 ml) was stirred at room temperature overnight then evaporated. The residue was partitioned between EtOAc and brine, the EtOAc layer was separated, dried (MgSO$_4$) and evaporated. Purification by flash column chromatography using a Biotage SP4 (40S, 40 ml/m in) eluting with 0% to 5% MeOH/DCM gave 695 mg of 5-bromo-1,3-dihydro-isoindole-2-carboxylic acid tert-butyl ester as a brown gum. $^1$HNMR (DMSO-d6) 7.55 (1H, d), 7.48 (1H, d), 7.30 (1H, dd), 4.63-4.51 (4H, m), 1.46 (9H, s).

50B. Synthesis of 5-(4-hydroxy-1-methyl-piperidin-4-yl)-1,3-dihydro-isoindole-2-carboxylic acid tert-butyl ester 0.69 ml of n-Butyl lithium (2.5M solution in hexane) was added dropwise to a stirred solution of 5-bromo-1,3-dihydro-isoindole-2-carboxylic acid tert-butyl ester (429 mg; 1.44 mmol) in anhydrous THF (10 ml) at −78° C. under an atmosphere of nitrogen. The reaction was stirred for 50 minutes then 1-methyl-4-piperidone (212 µl; 1.2 equiv.) was added and stirred at −78° C. for a further 60 minutes then warmed to room temperature. The reaction was quenched with saturated ammonium chloride solution then extracted with EtOAc. The EtOAc layer was washed with saturated NaHCO$_3$, brine, dried (MgSO$_4$) and evaporated. Purification by flash column chromatography on SiO$_2$, gradient elution from 0% to 10% 2M methanolic ammonia/DCM gave 11 mg of 5-(4-hydroxy-1-methyl-piperidin-4-yl)-1,3-dihydro-isoindole-2-carboxylic acid tert-butyl ester as a colourless oil.

50C. Synthesis of 4-(2,3-dihydro-1H-isoindol-5-yl)-1-methyl-piperidin-4-ol

A solution of 5-(4-hydroxy-1-methyl-piperidin-4-yl)-1,3-dihydroisoindole-2-carboxylic acid tert-butyl ester (107 mg; 0.32 mmol) in THF (4 ml) was treated with concentrated hydrochloric acid (1.5 ml) then heated at reflux for 4 hours, then evaporated and re-evaporated with toluene to give 4-(2,3-dihydro-1H-isoindol-5-yl)-1-methyl-piperidin-4-ol dihydrochloride as a brown gum.

50D. Synthesis of (2,4-bis-benzyloxy-5-isopropenyl-phenyl)-[5-(4-hydroxy-1-methyl-piperidin-4-yl)-1,3-dihydro-isoindol-2-yl]-methanone A solution of 2,4-bis-benzyloxy-5-isopropenyl-benzoic acid (145 mg; 1.2 equiv.) in DCM (5 ml) was treated with EDC (80 mg; 1.3 equiv.) and HOAt (66 mg; 1.5 equiv.) then stirred at room temperature for 30 minutes. This solution was then added to a mixture of 4-(2,3-dihydro-1H-isoindol-5-yl)-1-methyl-piperidin-4-ol dihydrochloride (112 mg; 0.32 mmol) and triethylamine (90 µl; 2 equiv.) in THF (5 ml) and DMF (2 ml), the reaction was then stirred at room temperature overnight. The reaction mixture was diluted with EtOAc, washed with water, 1N NaOH and brine, the EtOAc layer was separated, dried (MgSO$_4$) and evaporated. Purification by flash column chromatography on SiO$_2$, gradient elution from 0% to 5% 2M methanolic ammonia/DCM gave 104 mg of (2,4-bis-benzyloxy-5-isopropenyl-phenyl)-[5-(4-hydroxy-1-methyl-piperidin-4-yl)-1,3-dihydro-isoindol-2-yl]-methanone as a yellow glass.

50E. Synthesis of (2,4-dihydroxy-5-isopropyl-phenyl)-[5-(4-hydroxy-1-methyl-piperidin-4-yl)-1,3-dihydro-isoindol-2-yl]-methanone Hydrogenation of (2,4-bis-benzyloxy-5-isopropenyl-phenyl)-[5-(4-hydroxy-1-methyl-piperidin-4-yl)-1,3-dihydro-isoindol-2-yl]-methanone (as described in method A5) afforded 72 mg of the title compound as a cream solid. $^1$H NMR (Me-d3-OD) 7.35 (2H, m), 7.18 (1H, br m) 7.08 (1H, s), 6.25 (1H, s), 4.78 (4H, m), 3.10 (1H, m), 2.65 (2H, m), 2.45 (2H, m), 2.25 (3H, s), 2.00 (2H, m), 1.65 (2H, m), 1.10 (6H, d). MS: [M+H]$^+$ 411.

Example 51

Synthesis of (2,4-dihydroxy-5-isopropyl-phenyl)-{5-[4-(4-methyl-piperazin-1-yl)-piperidin-1-yl]-1,3-dihydro-isoindol-2-yl}methanone

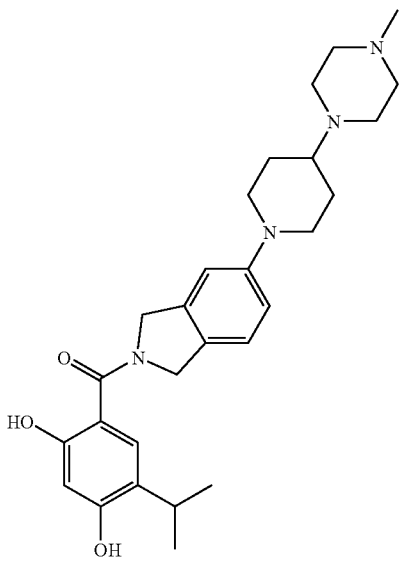 [SMILES: CC(C)c1cc(C(=O)N2Cc3ccc(N4CCC(N5CCN(C)CC5)CC4)cc3C2)c(O)cc1O]

51A. Synthesis of (2,4-bis-benzyloxy-5-isopropenyl-phenyl)-(5-bromo-1,3-dihydro-isoindol-2-yl)-methanone A solution of benzyloxy-5-isopropenyl-benzoic acid (2.85 g; 7.6 mmol), 5-bromo-2,3-dihydro-1H-isoindole (1.5 g; 1 equiv.), EDC (1.75 g; 1.2 equiv.) and HOBt (1.25 g; 1.2 equiv.) in DMF (25 ml) was stirred at room temperature overnight then evaporated. The residue was dissolved in EtOAc, washed with 2M HCl then saturated NaHCO$_3$, dried (MgSO$_4$) and evaporated. Purification using a Biotage SP4 (40S, 40 ml/min) eluting with 1:4-1:3-1:2 EtOAc/P.E. gave 2.45 g of (2,4-bis-benzyloxy-5-isopropenyl-phenyl)-(5-bromo-1,3-dihydro-isoindol-2-yl)-methanone as a light brown solid.

51B. (2,4-bis-benzyloxy-5-isopropenyl-phenyl)-{5-[4-(4-methyl-piperazin-1-yl)-piperidin-1-yl]-1,3-dihydro-isoindol-2-yl}-methanone A solution of (2,4-bis-benzyloxy-5-isopropenyl-phenyl)-(5-bromo-1,3-dihydro-isoindol-2-yl)-methanone (200 mg; 0.36 mmol) and 1-methyl-4-(piperidin-4-yl)piperazine (80 mg; 1.2 equiv.) in toluene (5 ml) was treated with (2-biphenyl)-di-tert-butylphosphine (6 mg; 5 mol %), tris(dibenzylidene)palladium(0) (10 mg; 2.5 mol %) and sodium tert-butoxide (50 mg; 1.4 equiv.) then heated at 120° C. for 30 minutes in a CEM explorer microwave synthesiser. The reaction mixture was diluted with DCM, washed with brine, dried (MgSO$_4$) and evaporated. Purification by flash column chromatography (Biotage SP4-25S, 25 ml/min) eluting with DMAW 240-120-90 followed by evaporation of product containing fractions gave 105 mg of (2,4-bis-benzyloxy-5-isopropenyl-phenyl)-{5-[4-(4-methyl-piperazin-1-yl)-piperidin-1-yl]-1,3-dihydro-isoindol-2-yl}-methanone as the acetic acid salt.

51C. (2,4-dihydroxy-5-isopropyl-phenyl)-{5-[4-(4-methyl-piperazin-1-yl)-piperidin-1-yl]-1, 3-dihydro-isoindol-2-yl}-methanone hydrochloride A solution of (2,4-bis-benzyloxy-5-isopropenyl-phenyl)-{5-[4-(4-methyl-piperazin-1-yl)-piperidin-1-yl]-1,3-dihydro-isoindol-2-yl}-methanone acetic acid salt in methanol (10 ml) was treated with 10% palladium on carbon (wet), hydrogenated at room temperature and pressure overnight then filtered and evaporated. The crude compound was purified by flash column chromatograph (Biotage SP4-25S, 25 ml/min) eluting with DMAW 240-120-90-60. Product containing fractions were evaporated, treated with saturated HCl/EtOAc then evaporated and re-evaporated with methanol and dried under high vacuum at 60° C. overnight. (2,4-dihydroxy-5-isopropyl-phenyl)-5-[4-(4-methyl-piperazin-1-yl)-piperidin-1-yl]-1,3-dihydro-isoindol-2-yl)-methanone hydrochloride was isolated as a cream solid (62 mg). $^1$H NMR (DMSO-d6) 12.40-12.00 (2H, br m), 9.75-9.55 (1H, br m), 7.45-7.05 (3H, m), 7.03 (1H, s), 6.45 (1H, s), 4.70-4.55 (4H, m), 3.85-3.65 (6H, m), 3.60-3.40 (5H, m), 3.15-3.05 (1H, m), 3.0-2.78 (5H, m), 2.30-2.20 (2H, m), 2.05-1.90 (2H, m), 1.15 (6H, d). MS: [M+H]$^+$ 479.

Example 52

Synthesis of (2,4-dihydroxy-5-isopropyl-phenyl)-[5-(4-piperazin-1-yl-phenyl)-1,3-dihydro-isoindol-2-yl]-methanone

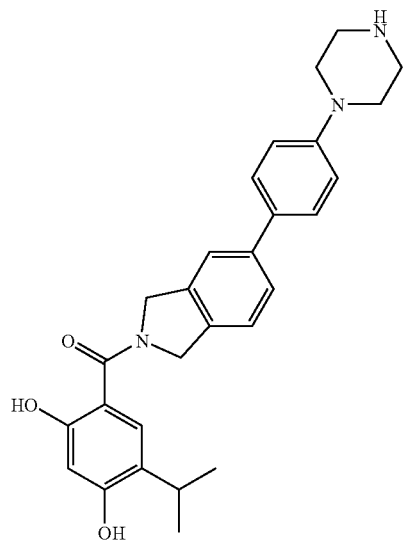 [SMILES: CC(C)c1cc(C(=O)N2Cc3ccc(-c4ccc(N5CCNCC5)cc4)cc3C2)c(O)cc1O]

52A. Synthesis of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester A mixture of (2,4-bis-benzyloxy-5-isopropenyl-phenyl)-(5-bromo-1,3-dihydro-isoindol-2-yl)-methanone (240 mg, 0.43 mmol), t-butyl-4-[4-(4,4,5,5-tetramethyl-1,3,2-dioxaborolan-2-yl)phenyl]piperazine carboxylate (210 mg, 1.25 equiv.), bis(tri-t-butylphosphine)palladium(0) (12.5 mg, 2.5 mol %) and potassium carbonate (350 mg, 6 equiv.) in toluene/water/ethanol (1 ml: 1 ml: 4 ml) was heated at 135° C. for 30 minutes in a CEM explorer microwave synthesiser. The reaction mixture was diluted with EtOAc, washed with saturated NaHCO$_3$, dried (MgSO$_4$) and evaporated. Purification by flash column chromatography (Biotage SP4-25S, 25 ml/min) eluting with 1:3 then 1:1 EtOAc/P.E. Evaporation of product containing fractions gave 85 mg of 4-{4-[2-(2,4-bis-benzyloxy-5-isopropenyl-benzoyl)-2,3-dihydro-1H-isoindol-5-yl]-phenyl}piperazine-1-carboxylic acid tert-butyl ester. MS: [M+H]$^+$ 736.

52B. Synthesis of (2,4-dihydroxy-5-isopropyl-phenyl)-[5-(4-piperazin-1-yl-phenyl)-1,3-dihydro-isoindol-2-yl]-methanone Hydrogenation of 4-(4-[2-(2,4-bis-benzyloxy-5-isopropenyl-benzoyl)-2,3-dihydro-1H-isoindol-5-yl]-phenyl)piperazine-1-carboxylic acid tert-butyl ester (as described in method A5), followed by BOC deprotection (as described in example 70) afforded 10 mg of the title compound as the hydrochloride salt after flash column chromatography (Biotage SP4, 25S) eluting with DMAW 240-120-90 and evaporation from saturated HCl/EtOAc. $^1$H NMR (Me-d3-OD) 7.63 (2H, d), 7.55 (2H, m) 7.45-7.30 (1H, m), 7.25 (1H, s), 7.20 (2H, d), 5.03 (4H, m), 3.55 (4H, m), 3.47 (4H, m), 3.23 (1H, m), 1.25 (6H, d). MS: [M+H]$^+$ 458.

Example 53

Synthesis of 2,4-dihydroxy-5-isopropyl-phenyl)-[5-(1-dimethylamino-2-hydroxy-ethyl)-1,3-dihydro-isoindol-2-yl]-methanone, and dihydroxy-5-isopropyl-phenyl)-[5-(2-dimethylamino-1-hydroxy-ethyl)-1,3-dihydro-isoindol-2-yl]-methanone

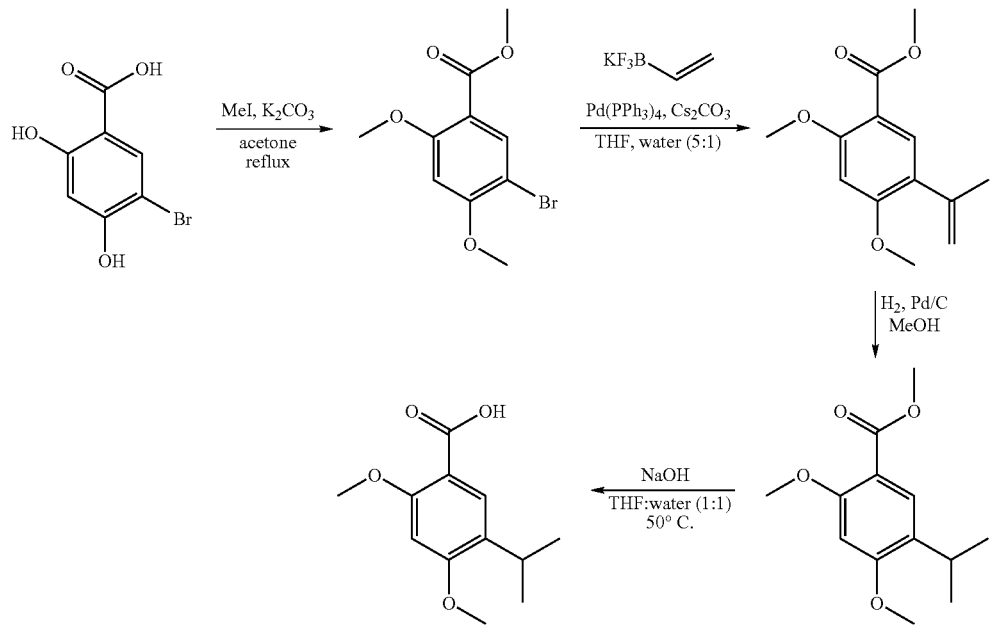

53A. Synthesis of 5-bromo-2,4-dimethoxybenzoic acid methyl ester

A solution of 5-bromo-2,4-dihydroxybenzoic acid (24.9 g, 107 mmol) in acetone (355 ml), was treated with methyl iodide (39.9 ml, 640 mmol) and $K_2CO_3$ (88 g, 640 mmol) then heated at reflux overnight. The salts were filtered off and washed with acetone. The filtrate was evaporated to dryness and the product was purified by flash column chromatography (100% DCM) to yield 5-bromo-2,4-dimethoxybenzoic acid methyl ester as a colourless solid (28 g). $^1$H NMR (Me-$d_3$-OD) 7.98 (1H, s), 6.74 (1H, s), 3.99 (3H, s), 3.94 (3H, s), 3.85 (3H, s). MS: [M+H]$^+$ 275/277.

53B. Synthesis of -isopropenyl-2,4-dimethoxy-benzoic acid methyl ester

To potassium isopropylidene trifluoroborate (4.87 g, 32.7 mmol) and 5-bromo-2,4-dimethoxybenzoic acid methyl ester (7.5 g, 27.3 mmol) in THF (195 ml) was added $Cs_2CO_3$ (26.6 g, 81.8 mmol) in water (39 ml). The reaction was degassed and Pd(PPh$_3$)$_4$ (1.58 g, 1.36 mmol) added. The reaction was heated at reflux for three days then quenched by adding water and extracted with EtOAc (x2). The combined organic layers were washed with brine, dried (MgSO$_4$), filtered and evaporated to leave an orange solid. The product was taken up in EtOAc again and the precipitate filtered. The filtrate was evaporated to dryness to yield 5-isopropenyl-2, 4-dimethoxy-benzoic acid methyl ester (6.2 g). $^1$H NMR (Me-$d_3$-OD) 7.68 (1H, s), 6.66 (1H, s), 5.10-5.08 (1H, m), 5.02-5.00 (1H, m), 3.93 (3H, s), 3.92 (3H, s), 3.84 (3H, s), 2.08-2.06 (3H, m). MS: [M+H]$^+$ 237.

53C. Synthesis of 5-isopropyl-2,4-dimethoxy-benzoic acid methyl ester

A solution of 5-isopropenyl-2,4-dimethoxy-benzoic acid methyl ester (6.0 g, 25.4 mmol) in MeOH (85 ml) was shaken with 10% Pd/C under an atmosphere of H$_2$ at room temperature for 3 hours. The catalyst was filtered through GF/A paper but a little fine powder passed through. The filtrate was passed through a small pad of silica and evaporated to dryness to yield a colourless solid. The product was purified by flash column chromatography (DCM:Petrol gradient elution) to yield 5-isopropyl-2,4-dimethoxy-benzoic acid methyl ester a colourless solid (5.5 g). $^1$H NMR (Me-$d_3$-OD) 7.68 (1H, s), 6.64 (1H, s), 3.94 (3H, s), 3.91 (3H, s), 3.84 (3H, s), 3.23 (1H, sept), 1.20 (6H, d). MS: [M+H]$^+$ 239.

53D. Synthesis of 5-isopropyl-2,4-dimethoxy-benzoic acid 5-isopropyl-2,4-dimethoxy-benzoic acid methyl ester (5.5 g, 23.1 mmol) and NaOH (1.38 g, 34.6 mmol) in THF (46 ml) and water (46 ml) was warmed to 50° C. overnight. The reaction was cooled and diluted with water and EtOAc. The aqueous layer was neutralized with HCl (1N, aq.). The product was extracted with EtOAc (x3) and the combined organic layers were washed with brine and dried over MgSO$_4$. The product was filtered and evaporated to dryness to yield 5-isopropyl-2,4-dimethoxy-benzoic acid as a pale peach solid (4.7 g). $^1$H NMR (DMSO-$d_6$) 12.1 (1H, br s), 7.62 (1H, s), 6.71 (1H, s), 3.95 (3H, s), 3.91 (3H, s), 3.19 (1H, sept), 1.18 (6H, d). MS: [M+H]+ 225.

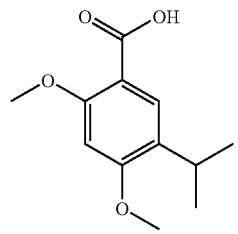 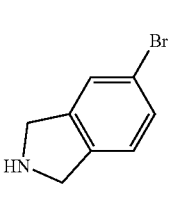 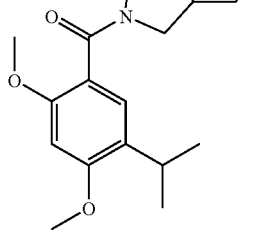 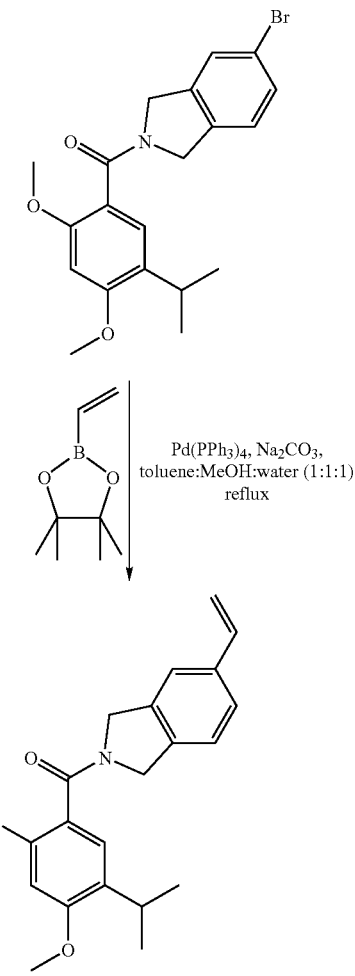

53E. Synthesis of (5-bromo-1,3-dihydro-isoindol-2-yl)-(5-isopropyl-2,4-dimethoxyphenyl)methanone To a mixture of 5-isopropyl-2,4-dimethoxybenzoic acid (2.45 g, 10.9 mmol), HOBt (1.61 g, 11.9 mmol) and EDC (1.85 g, 11.9 mmol) in anhydrous DMF (33 ml) under $N_2$ was added 5-bromo-2,3-dihydro-1H-isoindole (1.97 g, 9.95 mmol) and stirred at room temperature overnight. The reaction was quenched by diluting with NaOH (1M, aq.) and extracting the product with EtOAc (×2). The combined organic layers were washed with brine and dried over $MgSO_4$. The product was filtered and evaporated to dryness to leave a brown oil. The product was purified by flash column chromatography using gradient elution (ether/petrol) to yield (5-bromo-1,3-dihydro-isoindol-2-yl)-(5-isopropyl-2,4-dimethoxyphenyl)-methanone as a beige solid (3 g). 1H NMR (Me-d3-OD) 7.60-7.13 (3H, m), 7.14 (1H, s), 6.71 (1H, s), 4.89 (2H, d), 4.64 (2H, d), 3.93 (3H, s), 3.90 (3H, s), 3.27 (1H, sept), 1.20 (6H, d). MS: [M+H]+ 404/406.

53F. Synthesis of 5-isopropyl-2,4-dimethoxy-phenyl)-(5-vinyl-1,3-dihydro-isoindol-2-yl)-methanone To (5-bromo-1,3-dihydro-isoindol-2-yl)-(5-isopropyl-2,4-dimethoxyphenyl)methanone (2.2 g, 5.44 mmol), and 2-vinyl-4,4,5,5-tetramethyl-1,3,2-dioxaborolane (1.2 ml, 6.53 mmol) in MeOH (25 ml) and toluene (25 ml) was added $Na_2CO_3$ in water (25 ml). The reaction was degassed, $Pd(PPh_3)_4$ (0.38 g, 0.05 mmol) added then heated at 80° C. overnight. The reaction was worked up by adding water and extracting with EtOAc (×3). The combined organic layers were washed with brine and dried over $MgSO_4$. The product was filtered and evaporated to dryness then purified by flash column chromatography, gradient elution (ether:petrol) to yield 5-isopropyl-2,4-dimethoxy-phenyl)-(5-vinyl-1,3-dihydro-isoindol-2-yl)-methanone as a yellow oil (1.6 g). 1H NMR (Me-d3-OD) 7.47-7.15 (3H, m), 7.15 (1H, s), 6.82-6.72 (1H, m), 6.71 (1H, s), 5.79 (1H, dd), 5.24 (1H, dd), 4.90 (2H, d), 4.64 (2H, d), 3.93 (3H, s), 3.91 (3H, s), 3.27 (1H, sept), 1.23 (6H, d). MS: [M+H]+ 352.

53G. Synthesis of (5-isopropyl-2,4-dimethoxy-phenyl)-(5-oxiranyl-1,3-dihydro-isoindol-2-yl)-methanone To (5-isopropyl-2,4-dimethoxy-phenyl)-(5-vinyl-1,3-dihydro-isoindol-2-yl)-methanone (0.80 g, 2.28 mmol) in DCM (22 ml) was added mCPBA (0.61 g, 2.73 mmol) at 0° C. The reaction was stirred at room temperature for an hour. The reaction was diluted with NaOH (1M, aq.) and extracted the product with EtOAc. The EtOAc layer was washed with NaOH again. The organic layer was washed with brine and dried over MgSO₄. The product was filtered and evaporated to dryness to yield crude (5-isopropyl-2,4-dimethoxy-phenyl)-(5-oxiranyl-1,3-dihydro-isoindol-2-yl)-methanone as a very pale yellow oil. MS: [M+H]⁺ 368.

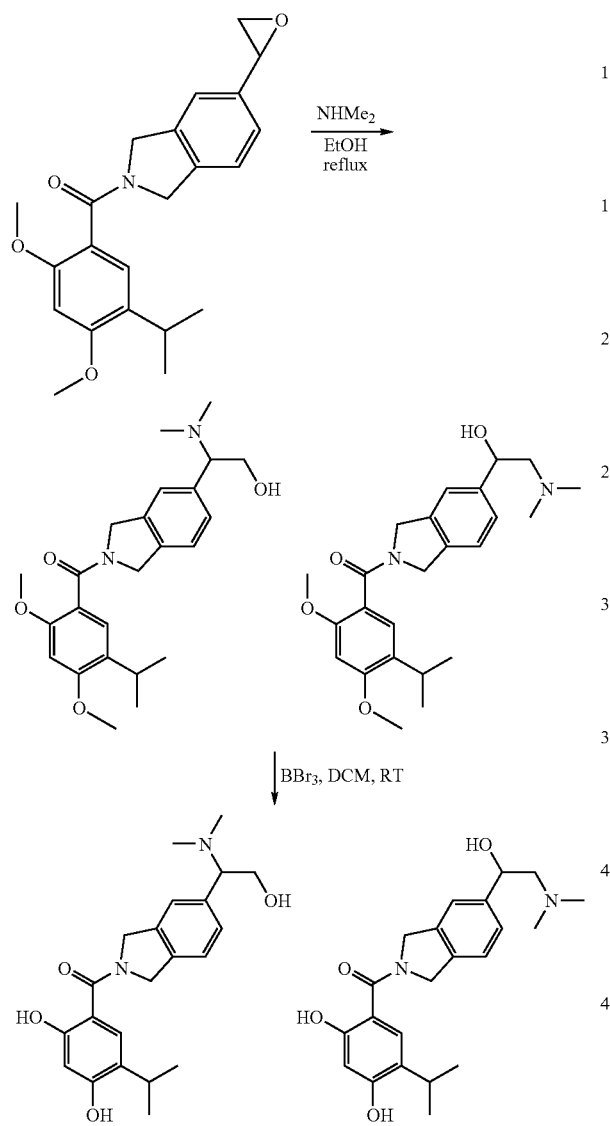

53H. Synthesis of (2,4-dihydroxy-5-isopropyl-phenyl)-[5-(1-dimethylamino-2-hydroxy-ethyl)-1,3-dihydro-isoindol-2-yl]-methanone (Compound 121H-i) and (2,4-dihydroxy-5-isopropyl-phenyl)-[5-(2-dimethylamino-1-hydroxy-ethyl)-1,3-dihydro-isoindol-2-yl]-methanone (Compound 121H-ii)

(5-isopropyl-2,4-dimethoxy-phenyl)-(5-oxiranyl-1,3-dihydro-isoindol-2-yl)-methanone (~120 mg, crude) was dissolved in dimethylamine in EtOH (20 ml, ~33%, 5.6 M) and heated at 60° C. overnight. The reaction was evaporated to dryness and the product crudely purified by flash column chromatography MeOH:DCM (1:5) to yield impure material which was used without further purification. To a mixture of [(5-(1-dimethylamino-2-hydroxy-ethyl)-1,3-dihydro-isoindol-2-yl]-(5-isopropyl-2,4-dimethoxy-phenyl)-methanone and [5-(2-dimethylamino-1-hydroxy-ethyl)-1,3-dihydro-isoindol-2-yl]-(5-isopropyl-2,4-dimethoxy-phenyl)-methanone (~100 mg) was added DCM (5 ml) and then boron tribromide (3 eq.) under N₂. The reaction was left to stir at room temperature until completion. The reaction was quenched with ice and diluted with water and EtOAc. The aqueous layer was extracted with EtOAc (×2). The combined organic layers were washed with brine, dried over MgSO₄ then filtered and evaporated to dryness, to leave a yellow residue which was purified by preparative HPLC to yield the two resorcinol isomers.

(2,4-Dihydroxy-5-isopropyl-phenyl)-[5-(1-dimethylamino-2-hydroxy-ethyl)-1,3-dihydro-isoindol-2-yl]-methanone, (Compound 121H-i) ¹H NMR (Me-d₃-OD) 7.42-7.30 (3H, m), 7.19 (1H, s), 6.39 (1H, s), 4.98-4.87 (4H, m), 4.03-3.97 (1H, m), 3.94-3.86 (1H, m), 3.68 (1H, br s), 3.22 (1H, sept), 2.40 (6H, s), 1.23 (6H, d). MS: [M+H]⁺ 384.

(2,4-Dihydroxy-5-isopropyl-phenyl)-[5-(2-dimethylamino-1-hydroxy-ethyl)-1,3-dihydro-isoindol-2-yl]-methanone, (Compound 121H-ii) ¹H NMR (Me-d₃-OD) 7.39-7.25 (3H, m), 7.18 (1H, s), 6.38 (1H, s), 6.94-6.88 (5H, m), 3.22 (1H, sept), 2.77-2.68 (1H, m), 2.61-2.51 (1H, m), 2.42 (6H, s), 1.23 (6H, d). MS: [M+H]⁺ 384.

Example 54

Synthesis of (2,4-dihydroxy-5-isopropyl-phenyl)-[5-(piperazine-1-carbonyl)-1,3-dihydro-isoindol-2-yl]-methanone hydrochloride

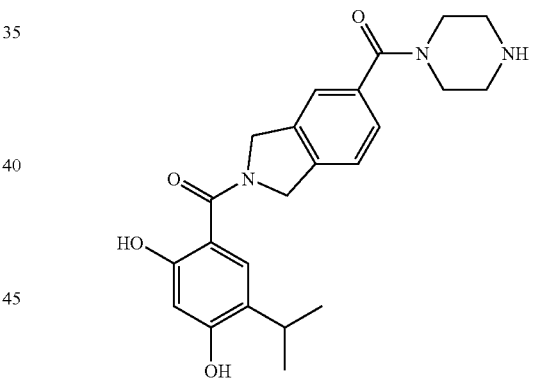

54A. Synthesis of 4-[2-(2,4-dihydroxy-5-isopropyl-benzoyl)-2,3-dihydro-1H-isoindole-5-carbonyl]-piperazine-1-carboxylic acid tert-butyl ester A solution of 2-(2,4-bis-benzyloxy-5-isopropyl-benzoyl)-2,3-dihydro-1H-isoindole-5-carboxylic acid (Preparation D6) (0.5 g, 0.96 mmol), EDC (0.22 g, 1.15 mmol), HOBT (0.196 g, 1.15 mmol) and BOC piperazine (0.117 ml, 1.06 mmol) in DMF (10 ml) was stirred at room temperature for 48 hours, then evaporated under vacuum. The crude material was dissolved in ethyl acetate and extracted twice with saturated NaHCO₃, organics washed with brine, dried (MgSO₄), filtered then evaporated under vacuum and purified by flash column chromatography (80% EtOAc-P.E. as eluant) to give 0.5 g of 4-[2-(2,4-dihydroxy-5-isopropyl-benzoyl)-2,3-dihydro-1H-isoindole-5-carbonyl]-piperazine-1-carboxylic acid tert-butyl ester. MS: [M+H]⁺ 688.

54B. Synthesis of (2,4-dihydroxy-5-isopropyl-phenyl)-[5-(piperazine-1-carbonyl)-1,3-dihydro-isoindol-2-yl]-methanone hydrochloride Hydrogenation as Method A5 to give (0.2 g, 0.30 mmol) 4-[2-(2,4-dihydroxy-5-isopropyl-benzoyl)-2,3-dihydro-1H-isoindole-5-carbonyl]-piperazine-1-carboxylic acid tert-butyl ester [used crude] dissolved in EtOAc then treated with saturated EtOAc/HCl, stirred at ambient for 3 hours, reaction diluted with ether, solid filtered to give 0.19 g of (2,4-dihydroxy-5-isopropyl-phenyl)-[5-(piperazine-1-carbonyl)-1,3-dihydro-isoindol-2-yl]-methanone hydrochloride. $^1$H NMR (Me-$d_3$-OD) 7.50-7.42 (3H, m), 7.18 (1H, s), 6.39 (1H, s), 5.00-4.95 (4H, br s), 3.92-3.79 (4H, br s), 3.35-3.28 (4H, br s), 3.26-3.15 (1H, m), 1.23 (6H, d). MS: [M+H]$^+$ 410.

Example 55

Synthesis of (2,4-dihydroxy-5-isopropyl-phenyl)-[5-(4-methyl-piperazin-1-ylmethyl)-1,3-dihydro-isoindol-2-yl]-methanone

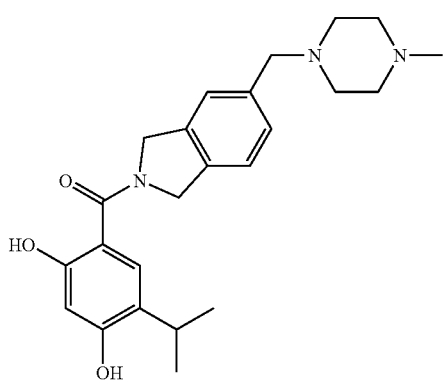 [SMILES: CC(C)c1cc(C(=O)N2Cc3ccc(CN4CCN(C)CC4)cc3C2)c(O)cc1O]

55A. Synthesis of 2-(2,4-bis-benzyloxy-5-isopropyl-benzoyl)-2,3-dihydro-1H-isoindole-5-carboxylic acid methoxy-methyl-amide A solution of 2-(2,4-bis-benzyloxy-5-isopropyl-benzoyl)-2,3-dihydro-1H-isoindole-5-carboxylic acid (Preparation D6) (1.76 g, 3.39 mmol), EDC (0.78 g, 4.06 mmol), HOBT (0.55 g, 4.06 mmol), Et$_3$N (1 ml, 6.78 mmol) and N,O-dimethylhydroxylamine hydrochloride (0.36 g, 3.72 mmol) in DMF (20 ml) was stirred at room temperature for 48 hours, then evaporated under vacuum. The crude material was dissolved in ethyl acetate and extracted twice with saturated NaHCO$_3$, organics washed with brine, dried (MgSO$_4$), filtered then evaporated to give 1.84 g of 2-(2,4-bis-benzyloxy-5-isopropyl-benzoyl)-2,3-dihydro-1H-isoindole-5-carboxylic acid methoxy-methyl-amide. MS: [M+H]$^+$ 563.

55. Synthesis of 2-(2,4-bis-benzyloxy-5-isopropyl-benzoyl)-2,3-dihydro-1H-isoindole-5-carbaldehyde A solution of 2-(2,4-bis-benzyloxy-5-isopropyl-benzoyl)-2,3-dihydro-1H-isoindole-5-carboxylic acid methoxy-methyl-amide (0.226 g, 0.4 mmol) in THF (5 ml) cooled to 0° C., treated with 1M LiAlH$_4$/THF (0.3 ml, 0.3 mmol), stirred 1 hour, further LiAlH$_4$ (0.05 ml) added then stirred for 30 minutes. The reaction was quenched with saturated KHSO$_4$ solution, extracted with EtOAc, dried (MgSO$_4$), filtered and evaporated to give 0.2 g of 2-(2,4-bis-benzyloxy-5-isopropyl-benzoyl)-2,3-dihydro-1H-isoindole 5-carbaldehyde. MS: [M+H]$^+$ 504.

55C. Synthesis of (2,4-bis-benzyloxy-5-isopropyl-phenyl)-[5-(4-methyl-piperazin-1-ylmethyl)-1,3-dihydro-isoindol-2-yl]-methanone To a solution of 2-(2,4-bis-benzyloxy-5-isopropyl-benzoyl)-2,3-dihydro-1H-isoindole-5-carbaldehyde (0.316 g, 0.63 mmol) and n-methyl piperazine (63 mg, 0.63 mmol) in CH$_2$Cl$_2$ (10 ml) was added AcOH (38 mgs 0.63 mmol) and NaBH(OAc)$_3$ (0.28 g, 1.33 mmol), then stirred at ambient for 5 hours. The reaction was quenched with water, layers separated and aqueous washed CH$_2$Cl$_2$. The organics were combined, washed with brine, dried (MgSO$_4$), filtered and evaporated to give 0.32 g of (2,4-bis-benzyloxy-5-isopropyl-phenyl)-[5-(4-methyl-piperazin-1-ylmethyl)-1,3-dihydro-isoindol-2-yl]-methanone. MS: [M+H]$^+$ 588.

55D. Synthesis of (2,4-dihydroxy-5-isopropyl-phenyl)-[5-(4-methyl-piperazin-1-ylmethyl)-1,3-dihydro-isoindol-2-yl]-methanone Hydrogenation was carried out using Method A5 but with the addition of K$_2$CO$_3$ (2 equiv.) in a MeOH/H$_2$O [9.1]. After evaporation of methanol the reaction was diluted with water, neutralised using 1M HCl and extracted with CH$_2$Cl$_2$ (×2). Organics dried (MgSO$_4$), filtered and evaporated under vacuum then purified by preparative HPLC to give 21 mg of (2,4-dihydroxy-5-isopropyl-phenyl)-[5-(4-methyl-piperazin-1-ylmethyl)-1,3-dihydro-isoindol-2-yl]-methanone. MS: [M+H]$^+$ 410. $^1$H NMR (Me-$d_3$-OD) 7.37-7.23 (3H, br s), 7.19 (1H, s), 6.39 (1H, s), 4.94-4.87 (4H, br s), 3.57 (2H, s), 3.27-3.16 (1H, m), 2.67-2.39 (8H, m), 2.31 (3H, s), 1.23 (6H, d).

Example 56

Synthesis of (2,4-dihydroxy-5-isopropyl-phenyl)-[4-(3-morpholin-4-yl-propoxy)-1,3-dihydro-isoindol-2-yl]methanone

56A. Synthesis of 4-hydroxyisoindoline hydrobromide

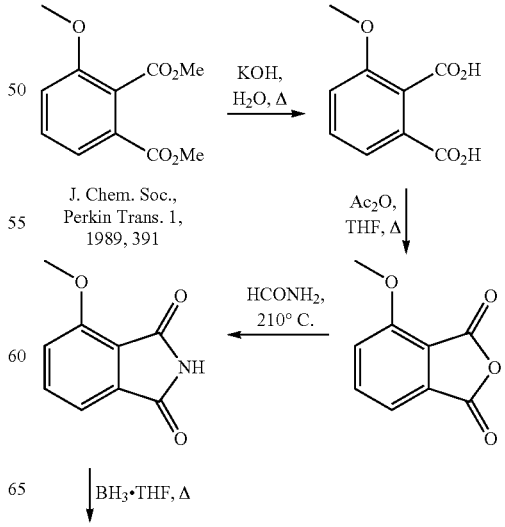

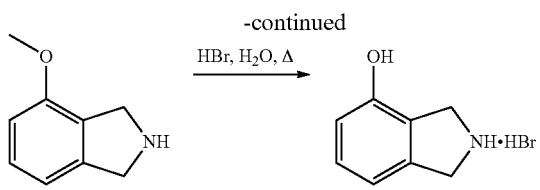

A suspension of dimethyl 3-methoxyphthalate (69.45 g, 0.31 mol) [prepared as per *J. Chem. Soc., Perkin Trans. 1*, 1989, 391] in water (300 ml) was treated with potassium hydroxide (43.7 g, 0.78 mol) and the mixture was stirred and held at reflux for 4 hours. Upon cooling to room temperature the methanol liberated during the course of the reaction was removed in vacuo, the mixture acidified to pH 2 or below by the addition of 5M hydrochloric acid and evaporated gently in vacuo to induce crystallization. The solid material was filtered off, washed with a little ice cooled water, sucked dry under reduced pressure and dried in a vacuum oven at 50° C. overnight to afford 3-methoxyphthalic acid (51.0 g, 84%) as a colourless solid. $^1$H NMR (DMSO-d$_6$) 13.05 (2H, br s), 7.48 (2H, m), 7.33 (1H, m), 3.82 (3H, s). MS: [M+H]$^+$ 197.

Acetic anhydride (70 ml) was added to a mixture of 3-methoxyphthalic acid (51.0 g, 0.26 mol) in anhydrous tetrahydrofuran (250 ml) and the mixture was stirred and held at reflux for 4 hours. Upon cooling to room temperature the solvent was removed in vacuo and the resulting solid material was dried in a vacuum oven at 50° C. overnight to afford 3-methoxyphthalic anhydride (45.9 g, 99%) as a colourless solid. $^1$H NMR (DMSO-d$_6$) 7.97 (1H, dd), 7.63 (1H, d), 7.60 (1H, d), 4.02 (3H, s). MS: [M+H]$^+$ 179.

A mixture of 3-methoxyphthalic anhydride (24.0 g, 134.8 mmol) and formamide (120 ml) was stirred and held at 210° C. for 5 hours and was then allowed to cool to room temperature overnight. Water (100 ml) was added and the solid material filtered off under reduced pressure. The crude product was washed sequentially with 50% aqueous acetone (50 ml) and diethyl ether (200 ml) and sucked dry under reduced pressure to afford 3-methoxyphthalimide (8.95 g, 37%) as an off-white solid. $^1$H NMR (DMSO-d$_6$) 11.08 (1H, br s), 7.78 (1H, dd), 7.45 (1H, d), 7.36 (1H, d), 3.93 (3H, s). MS: [M+H]$^+$ 178.

A stirred solution of 3-methoxyphthalimide (8.95 g, 50.56 mmol) in anhydrous tetrahydrofuran (200 ml) at 0° C. was treated dropwise with a solution of borane in tetrahydrofuran (1M, 150 ml, 0.15 mol) and the resulting mixture was stirred and held at reflux for 16 hours. The mixture was cooled to 0° C., methanol (60 ml) was added dropwise followed by 5M hydrochloric acid (60 ml) and the mixture was stirred and held at reflux for 4 hours. Upon cooling to room temperature the organic solvent was removed in vacuo and the mixture diluted with water (250 ml) and extracted with dichloromethane (3×250 ml). The aqueous layer was basified to pH 12 or above by the addition of 5M sodium hydroxide, extracted with dichloromethane (3×250 ml) and the combined extracts were evaporated to dryness in vacuo to afford 4-methoxyisoindoline (4.44 g, 59%) as a green oil which was used without further purification. $^1$H NMR (DMSO-d$_6$) 7.18 (1H, t), 6.83 (1H, d), 6.78 (1H, d), 4.07 (2H, s), 4.02 (2H, s), 3.78 (3H, s). MS: [M+H]$^+$ 150.

4-Methoxyisoindoline (4.4 g, 29.53 mmol) in 48% aqueous hydrobromic acid (50 ml) was stirred and held at reflux for 16 hours. Upon cooling to room temperature the solvent was removed in vacuo to afford 4-hydroxyisoindoline hydrobromide (5.0 g, 78%) as a pale orange solid. $^1$H NMR (DMSO-d$_6$) 9.95 (1H, br s), 9.37 (2H, br s), 7.19 (1H, t), 6.84 (1H, d), 6.80 (1H, d), 4.48 (2H, t), 4.40 (2H, t). MS: [M+H]$^+$ 136.

56B. Synthesis of (2,4-bis-benzyloxy-5-isopropenyl-phenyl)-(4-hydroxy-1,3-dihydro-isoindol-2-yl)-methanone

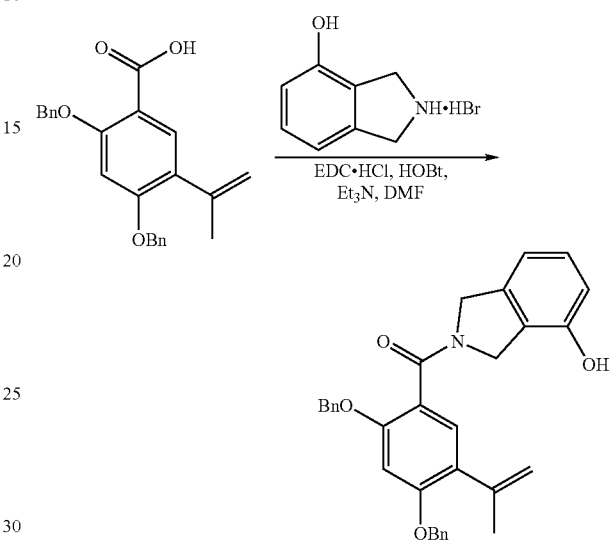

A mixture of 2,4-bis-benzyloxy-5-isopropenyl-benzoic acid (8.1 g, 21.65 mmol), 4-hydroxylsoindoline hydrobromide (4.91 g, 22.73 mmol), N-ethyl-N'-(3-dimethylaminopropyl)carbodiimide hydrochloride (5.0 g, 25.98 mmol), 1-hydroxybenzotriazole (3.5 g, 25.98 mmol) and triethylamine (6 ml, 43.3 mmol) in N,N-dimethylformamide (50 ml) was stirred at room temperature for 16 hours. The solvent was removed in vacuo and the residue was treated with a saturated aqueous solution of sodium hydrogen carbonate (200 ml). The mixture was filtered, the solid material was washed copiously with water, sucked dry under reduced pressure and dried in a vacuum oven at 50° C. overnight to afford (2,4-bis-benzyloxy-5-isopropenyl-phenyl)-(4-hydroxy-1,3-dihydro-isoindol-2-yl)-methanone (10.25 g, 96%) as a pale tan solid. $^1$H NMR (DMSO-d$_6$) (mixture of amide rotamers) 9.68 and 9.60 (1H, 2×br s), 7.45-7.25 (10H, m), 7.20-7.00 (3H, m), 6.82 and 6.72 (1H, 2×d), 6.68 (1H, m), 5.23 and 5.22 (2H, 2×s), 5.18 (2H, s), 5.11 (1H, s), 5.09 (1H, s), 4.77 and 6.67 (2H, 2×s), 4.53 and 4.44 (2H, 2×s), 2.04 (3H, s). MS: [M+H]$^+$ 492.

56C. Synthesis of (2,4-bis-benzyloxy-5-isopropenyl-phenyl)-[4-(3-morpholin-4-yl-propoxy)-1,3-dihydro-isoindol-2-yl]-methanone A mixture of (2,4-bis-benzyloxy-5-isopropenyl-phenyl)-(4-hydroxy-1,3-dihydro-isoindol-2-yl)-methanone (2 g; 4.07 mmol), 4-(3-chloropropyl)morpholine (1.66 g; 2.5 equiv.) and caesium carbonate (8.3 g; 6.25 equiv) in DMF was heated at 90° C. overnight then evaporated. The residue was dissolved in EtOAc, washed with brine, dried (MgSO$_4$) and evaporated. Purification of the crude material using a Biotage SP4 (40S, 40 ml/min), using gradient elution form 0% to 10% MeOH/EtOAc gave 1.8 g of (2,4-bis-benzyloxy- 5-isopropenyl-phenyl)-[4-(3-morpholin-4-yl-propoxy)-1,3-dihydro-isoindol-2-yl]-methanone as a pale yellow gum. MS: [M+H]⁺ 619.

56D. Synthesis of (2,4-dihydroxy-5-isopropyl-phenyl)-[4-(3-morpholin-4-yl-propoxy)-1,3-dihydro-isoindol-2-yl]methanone

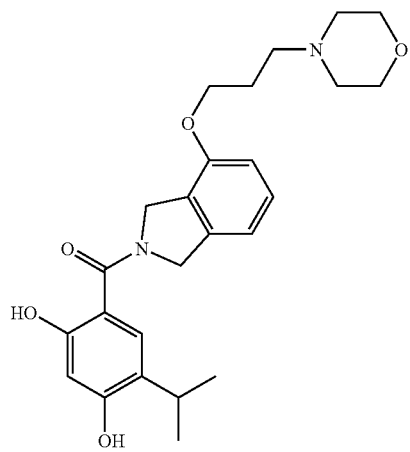 [SMILES: CC(C)c1cc(C(=O)N2Cc3cccc(OCCCN4CCOCC4)c3C2)c(O)cc1O]

Hydrogenation of (2,4-bis-benzyloxy-5-isopropenyl-phenyl)-[4-(3-morpholin-4-yl-propoxy)-1,3-dihydro-isoindol-2-yl]-methanone (as described in method A5) followed by treatment with saturated HCl/EtOAc and trituration with hot acetone afforded 890 mg of the title compound (hydrochloride salt) as a cream solid. $^1$H NMR (DMSO-$d_6$) 10.78 (1H, br s), 10.05 (1H, br s), 9.55 (1H, br s), 7.30 (1H, t), 7.08 (1H, s) 6.98-6.90 (2H, m), 6.45 (1H, s), 4.80 (2H, s), 4.75 (2H, s), 4.15 (2H, t), 3.95 (2H, br m), 2.80 (2H, br m), 3.50-3.35 (2H, br m), 3.25 (2H, br m,), 3.18-3.02 (3H, br m), 2.20 (2H, br m), 1.15 (6H, d). MS: [M+H]⁺ 441.

Examples 57 to 74

By following the methods described above, the following compounds were prepared.

| Example Number | Compound | Chemical Name | Method | N.M.R. Data | M.S. |
|---|---|---|---|---|---|
| 57 | | [5-(2-Amino-ethoxy)-1,3-dihydro-isoindol-2-yl]-(2,4-dihydroxy-5-isopropyl-phenyl)-methanone | As for Example 34, A2 (from 2,4-bis-benzyloxy-5-isopropenyl-benzoic acid (Preparation B5) and 5-hydroxy-isoindoline), alkylation using 3-(BOC-amino)ethyl tosylate, then A5. Final BOC deprotection using saturated HCl/EtOAC (Example 18). | $^1$H NMR (Me-$d_3$-OD) 8.55 (1 H, s), 7.30-7.20 (1 H, m), 7.15 (1 H, s), 7.05-6.95 (2 H, m), 6.40 (1 H, s), 4.95-4.80 (4 H, m) 4.25 (2 H, t), 3.35 (2 H, t), 3.25-3.15 (1 H, m), 1.25 (6 H, d) | MS: [M + H]⁺ 357 |
| 58 | | (2,4-Dihydroxy-5-isopropyl-phenyl)-(5-hydroxy-1,3-dihydro-isoindol-2-yl)-methanone | Isolated as a bi-product from synthesis of Example 57. | $^1$H NMR (Me-$d_3$-OD) 7.20 (1 H, s), 7.15-7.05 (1 H, m), 6.80-6.70 (2 H, m), 6.40 (1 H, s), 4.95-4.80 (4 H, m), 3.25-3.15 (1 H, m), 1.25 (6 H, d) | MS: [M + H]⁺ 314 |

| Example Number | Compound | Chemical Name | Method | N.M.R. Data | M.S. |
|---|---|---|---|---|---|
| 59 | | (2,4-Dihydroxy-5-isopropyl-phenyl)-{5-[4-(2-hydroxy-ethyl)-piperazin-1-yl]-1,3-dihydro-isoindol-2-yl}-methanone | As for Example 51, using N-(2-hydroxyethyl)-piperazine in the Buchwald reaction. | $^1$H NMR (DMSO-d$_6$) 10.40 (1 H, br s), 9.65 (1 H, br s), 7.40-7.15 (1 H, m), 7.05 (1 H, s), 7.05-6.90 (2 H, m), 6.45 (1 H, s), 4.80-4.60 (4 H, m), 3.85-3.70 (4 H, m), 3.65-3.55 (2 H, m), 3.25-3.05 (7 H, m), 1.15 (6 H, d) | MS: [M + H]$^+$ 426 |
| 60 | | (2,4-Dihydroxy-5-isopropyl-phenyl)-[5-(4-morpholin-4-yl-piperidin-1-yl)-1,3-dihydro-isoindol-2-yl]-methanone | As for Example 51, using 4-morpholino-piperidine in the Buchwald reaction. | $^1$H NMR (DMSO-d$_6$) 11.10 (1 H, br s), 9.65 (1 H, br s), 7.30-7.05 (3 H, m), 7.03 (1 H, s), 6.45 (1 H, s), 4.80-4.65 (4 H, m), 4.0-3.95 (2 H, m), 3.90-3.75 (4 H, m), 3.50-3.40 (2 H, m), 3.40-3.30 (1 H, m), 3.15-3.03 (3 H, m), 2.90-2.75 (2 H, m), 2.25-2.15 (2 H, m), 1.95-1.80 (2 H, m), 1.15 (6 H, d) | MS: [M + H]$^+$ 466 |
| 61 | | (2,4-Dihydroxy-5-isopropyl-phenyl)-[5-(1-methyl-piperidin-4-ylamino)-1,3-dihydro-isoindol-2-yl]-methanone | As for Example 51, using 4-amino-1-methyl-piperidine in the Buchwald reaction. | $^1$H NMR (DMSO-d$_6$) 10.60 (1 H, br s), 9.65 (1 H, br s), 7.20 (1 H, m), 7.03 (1 H, s), 6.95-6.80 (2 H, m), 6.45 (1 H, s), 4.80-4.65 (4 H, m), 3.45 (2 H, m), 3.25 (1 H, m), 3.10 (1 H, m), 3.00 (2 H, m), 2.70 (3 H, d), 2.15-2.05 (2 H, m), 1.90-1.75 (2 H, m), 1.15 (6 H, d) | MS: [M + H]$^+$ 410 |

| Example Number | Compound | Chemical Name | Method | N.M.R. Data | M.S. |
|---|---|---|---|---|---|
| 62 | | (2,4-Dihydroxy-5-isopropyl-phenyl)-[5-(4-isopropyl-piperazin-1-yl)-1,3-dihydro-isoindol-2-yl]-methanone | As for Example 51, using i-propyl-piperazine in the Buchwald reaction. | $^1$H NMR (DMSO-$d_6$) 10.70 (1 H, br s), 9.65 (1 H, br s), 7.25-7.10 (1 H, m), 7.05 (1 H, s), 7.00-6.90 (2 H, m), 6.45 (1 H, s), 4.80-4.60 (4 H, m), 3.80 (2 H, m), 3.55-3.40 (3 H, m), 3.23-3.05 (5 H, m), 1.33 (6 H, d), 1.15 (6 H d) | MS: [M + H]$^+$ 424 |
| 63 | | (2,4-Dihydroxy-5-isopropyl-phenyl)-(5-piperazin-1-yl-1,3-dihydro-isoindol-2-yl)-methanone | As for Example 51, using Boc-piperazine in the Buchward reaction. Boc deprotection using saturated HCl/dioxane (Example 18). | $^1$H NMR (DMSO-$d_6$) 9.70 (1 H, br s), 9.25 (2 H, br s), 7.23 (1 H, br m), 7.05 (1 H, s), 7.00-6.90 (2 H, m), 6.45 (1 H, s), 4.80-4.60 (4 H, m), 3.35 (4 H, m), 3.20 (4 H, m), 3.10 (1 H, m), 1.15 (6 H, d) | MS: [M + H]$^+$ 382 |
| 64 | | 4-[2-(2,4-Dihydroxy-5-isopropyl-benzoyl)-2,3-dihydro-1H-isoindol-5-ylamino]-piperidine-1-carboxylic acid tert-butyl ester | As for Example 51, using 1-Boc-4-amino-piperidine in the Buchwald reaction. | $^1$H NMR (Me-$d_3$-OD) 7.20 (1 H, s), 7.05 (1 H, m), 6.65-6.55 (2 H, m), 6.35 (1 H, s), 4.85-4.75 (4 H, m), 4.05 (2 H, m), 3.50 (1 H, m), 3.20 (1 H, m), 3.00 (2 H, m), 2.00 (2 H, m), 1.5 (9 H, s), 1.30 (2 H, m), 1.15 (6 H, d) | MS: [M + H]$^+$ 496 |

-continued

| Example Number | Compound | Chemical Name | Method | N.M.R. Data | M.S. |
|---|---|---|---|---|---|
| 65 | 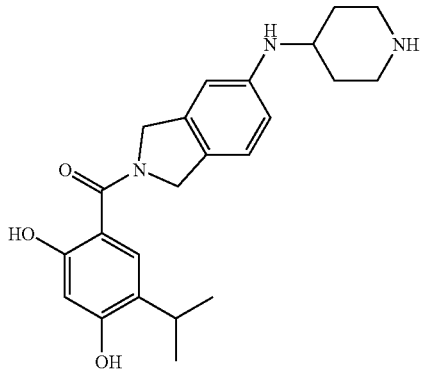 [SMILES: CC(C)c1cc(C(=O)N2Cc3ccc(NC4CCNCC4)cc3C2)c(O)cc1O] | (2,4-dihydroxy-5-isopropyl-phenyl)-[5-(piperidin-4-ylamino)-1,3-dihydro-isoindol-2-yl]-methanone | BOC deprotection using saturated HCl/EtOAC (Example 18). | $^1$H NMR (DMSO-d$_6$) 7.05 (1 H, s), 7.00 (1 H, m), 6.55-6.45 (2 H, m), 6.40 (1 H, s), 4.70-4.60 (4 H, m), 3.25 (1 H, m), 3.10 (1 H, m), 2.95 (2 H, m), 2.45 (2 H, m), 1.85 (2 H, m), 1.75 (3 H, s), 1.20 (2 H, m), 1.15 (6 H, d) | MS: [M + H]$^+$ 396 |
| 66 | 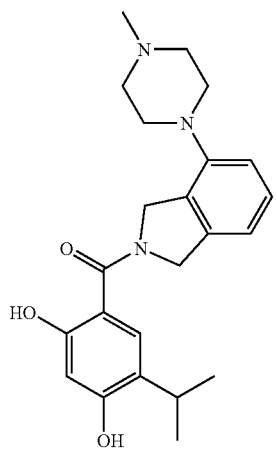 [SMILES: CC(C)c1cc(C(=O)N2Cc3cccc(N4CCN(C)CC4)c3C2)c(O)cc1O] | (2,4-dihydroxy-5-isopropyl-phenyl)-[4-(4-methyl-piperazin-1-yl)-1,3-dihydro-isoindol-2-yl]-methanone | As for Example 51, using (2,4-bis-benzyloxy-5-isopropenyl-phenyl)-(4-bromo-1,3-dihydro-isoindol-2-yl)-methanone (Prep: A2 between 2,4-bis-benzyloxy-5-isopropenyl-benzoic acid and 4-bromo-1,3-dihydro-1H-isoindoline) and N-methyl-piperazine in the Buchwald reaction. | $^1$H NMR (Me-d$_3$-OD) 7.35-7.18 (2 H, m), 7.10-6.95 (2 H, m), 6.95-6.85 (2 H, m), 6.40-4.85 (4 H, m), 3.25 (1 H, m), 3.20-3.05 (4 H, m), 3.05-2.80 (4 H, m), 2.60 (3 H, m), 2.00 (3 H, s), 1.25 (6 H, d) | MS: [M + H]$^+$ 396 |
| 67 | 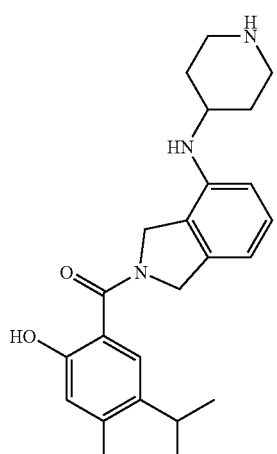 | (2,4-dihydroxy-5-isopropyl-phenyl)-[4-(piperidin-4-ylamino)-1,3-dihydro-isoindol-2-yl]-methanone | As for Example 65, using 1-Boc-4-amino-piperidine in the Buchwald reaction, followed by Boc deprotection using saturated HCl/EtOAc (Example 18). | $^1$H NMR (DMSO-d$_6$) 7.05 (1 H, s), 7.00 (1 H, m), 6.55-6.45 (2 H, m), 6.40 (1 H, s), 4.70-4.60 (4 H, m), 3.25 (1 H, m), 3.10 (1 H, m), 2.95 (2 H, m), 2.45 (2 H, m), 1.85 (2 H, m), 1.75 (3 H, s), 1.20 (2 H, m), 1.15 (6 H, d) | MS: [M + H]$^+$ 396 |

-continued

| Example Number | Compound | Chemical Name | Method | N.M.R. Data | M.S. |
|---|---|---|---|---|---|
| 68 | | (2,4-Dihydroxy-5-isopropyl-phenyl)-(5-dimethylamino-methyl-1,3dihydro-isoindol-2-yl)-methanone | A2 and A5. From 2,4-bis-benzyloxy-5-isopropenyl-benzoic acid (B5, and (2,3-dihydro-1H-isoindol-5-ylmethyl)-dimethyl-amine (Preparation A1) | $^1$H NMR (Me-$d_3$-OD) 7.26-7.12 (3 H, m), 7.07 (1 H, s), 6.27 (1 H, s), 4.85-4.77 (4 H, br s), 3.40 (2 H, s), 3.15-3.05 (1 H, m), 2.15 (6 H, s), 1.11 (6 H, d) | MS: [M + H]$^+$ 355 |
| 69 | | (2,4-Dihydroxy-5-isopropyl-phenyl)-[5-(4-methyl-piperazine-1-carbonyl)-1,3-dihydro-isoindol-2-yl]-methanone | A2 and A5. From 2-(2,4-bis-benzyloxy-5-isopropyl-benzoyl)-2,3-dihydro-1H-isoindole-5-carboxylic acid (D6) and N-methyl piperazine | $^1$H NMR (Me-$d_3$-OD) 7.60-7.38 (3 H, m), 7.19 (1 H, s), 6.39 (1 H, s), 4.96 (4 H, m), 3.85-3.71 (2 H, br s), 3.54-3.4 (2 H, br s), 3.26-3.15 (1 H, m), 2.59-2.39 (4 H, br d), 2.34 (3 H, s), 1.23 (6 H, d) | MS: [M + H]$^+$ 424 |
| 70 | | (2,4-Dihydroxy-5-isopropyl-phenyl)-{5-[2-(2,2-dimethyl-propylamino)-ethoxy]-1,3-dihydro-isoindol-2-yl}-methanone | As for the synthesis of (2,4-dihydroxy-5-isopropyl-phenyl)-[5-(2-isopropylamino-ethoxy)-1,3-dihydro-isoindol-2-yl]-methanone except using trimethyl acetaldehyde instead of acetone. Purified by preparative HPLC. | $^1$H NMR (Me-$d_3$-OD) 7.28 (1 H, br s); 7.20 (1 H, s); 7.00 (2 H, br m); 6.40 (1 H, s); 4.35 (2 H, t); 3.50 (2 H t); 3.20 (1 H, m); 3.00 (2 H, s); 1.23 (6 H, d); 1.10 (9 H, s) | MS: [M + H]$^+$ 427 |
| 71 | | [5-(2-Cyclopentyl-amino-ethoxy)-1,3-dihydro-isoindol-2-yl]-(2,4-dihydroxy-5-isopropyl-phenyl)-methanone | As for the synthesis of (2,4-dihydroxy-5-isopropyl-phenyl)-[5-(2-isopropylamino-ethoxy)-1,3-dihydro-isoindol-2-yl]-methanone except using cyclopentanone instead of acetone. Purified by preparative HPLC. | $^1$H NMR (DMSO-$d_6$) 10.05 (1 H, br s); 9.60 (1 H, br s); 7.23 (1 H, br s); 7.05 (1 H, s); 6.95 (1 H, br s); 6.88 (1 H, br d); 6.40 (1 H, s); 4.72 (4 H, br m); 4.02 (2 H, t); 3.10 (2 H, m); 2.93 (2 H, t); 1.78 (2 H, m); 1.63 (2 H, m); 1.48 (2 H, m); 1.35 (2 H, m); 1.15 (6 H, d) | MS: [M + H]$^+$ 425 |

| Example Number | Compound | Chemical Name | Method | N.M.R. Data | M.S. |
|---|---|---|---|---|---|
| 72 | (structure) | (2,4-Dihydroxy-5-isopropyl-phenyl)-(5-piperidin-1-ylmethyl-1,3-dihydro-isoindol-2-yl)-methanone | As for the synthesis of (2,4-dihydroxy-5-isopropyl-phenyl)-[5-(4-methyl-piperazin-1-ylmethyl)-1,3-dihydro-isoindol-2-yl]-methanone (Example 56) except using piperidine instead of N-methyl-piperazine. | $^1$H NMR (Me-d$_3$-OD) 7.35-7.24 (3 H, m), 7.19 (1 H, s), 6.39 (1 H, s), 4.94-4.49 (4 H, br s), 3.54 (2 H, s), 3.27-3.18 (1 H, m), 2.51-2.41 (4 H, br s), 1.66-1.58 (4 h br m), 1.53-1.42 (2 H, br s), 1.23 (6 H, d). | MS: [M + H]$^+$ 395. |
| 73 | (structure) | (2,4-Dihydroxy-5-isopropyl-phenyl)-[5-(4-hydroxypiperidin-4-yl)-1,3-dihydro-isoindol-2-yl]-methanone | As for the synthesis of (2,4-dihydroxy-5-isopropyl-phenyl)-[5-(4-hydroxy-1-methyl-piperidin-4-yl)-1,3-dihydro-isoindol-2-yl]-methanone (Example 50) except using N-benzyloxy-carbonyl-piperidin-4-one in step 2. | $^1$H NMR (Me-d$_3$-OD) 7.47 (2 H, m), 7.30 (1 H, br m) 7.20 (1 H, s), 6.40 (1 H, s), 4.90 (4 H, d), 3.22 (1 H, m), 3.15 (2 H, m), 2.95 (2 H, m), 2.05 (2 H, m), 1.75 (2 H, m), 1.25 (6 H, d) | MS: [M + H]$^+$ 397 |
| 74 | (structure) | (5-chloro-6-hydroxy-1,3-dihydro-isoindol-2-yl)-(2,4-dihydroxy-5-isopropyl-phenyl)-methanone | Isolated as a bi-product during the preparation of Example 33. | $^1$H NMR (DMSO-d$_6$) 10.00 (1 H, s), 9.58 (1 H, s), 7.48-7.38 (1 H, m), 7.02 (1 H, s), 7.97-6.85 (1 H, m), 6.40 (1 H, s), 4.68 (4 H, brs), 3.10 (1 H, m), 1.15 (6 H, d) | MS: [M + H]$^+$ 348 |

Example 75

(5-Chloro-2,4-dihydroxy-phenyl)-[5-(4-methyl-piperazin-1-yl)-1, 3-dihydro-isoindol-2-yl]-methanone

75A. 5-(4-Methyl-piperazin-1-yl)-1,3-dihydro-isoindole-2-carboxylic acid tert-butyl ester

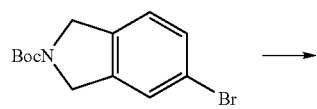

→

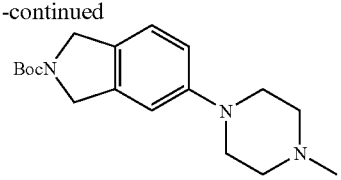

5-Bromo-1,3-dihydro-isoindole-2-carboxylic acid tert-butyl ester (2.97 g, 10 mmol) was azeotropically dried by evaporation from toluene. Tris(dibenzylideneacetone)dipalladium (0) (228 mg, 0.25 mmol), 2-(di-tert-butylphosphino)biphenyl (149 mg, 0.50 mmol) and sodium tert-butoxide (1.34 g, 13.9 mmol) were added and the flask was purged with nitrogen. Toluene (25 mL) then N-methylpiperazine (1.33 mL, 12 mmol) were added and the mixture was heated to 80° C. for 2 hours. After allowing to cool to r.t. the mixture was diluted with ether, filtered through Celite and concentrated to give a residue that was purified by flash chromatography on silica (2M methanolic ammonia/dichloromethane, 1% to 3% gradient). This afforded the title compound as a brown solid (1.45 g, 46%). $^1$H NMR (MeOH-d$_4$) 7.15 (1H, m), 6.94-6.88 (2H, m), 4.60-4.54 (4H, m), 3.20-3.17 (4H, m), 2.63-2.60 (4H, m), 2.34 (3H, s), 1.52 (9H, s). MS: [M+H]$^+$ 318.

75B. 5-(4-Methyl-piperazin-1-yl)-2,3-dihydro-1H-isoindole dihydrochloride

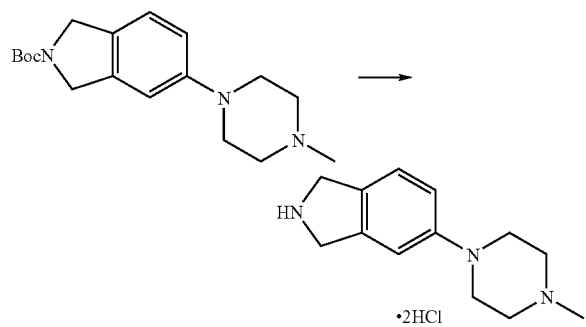

5-(4-Methyl-piperazin-1-yl)-1,3-dihydro-isoindole-2-carboxylic acid tert-butyl ester (247 mg, 0.78 mmol) was treated with 4M HCl in dioxane (4 mL, 4 mmol) for 24 hours. Concentration in vacuo afforded the title compound quantitatively, which was used directly in the coupling reaction. $^1$H NMR (DMSO-d$_6$) 11.13 (1H, br.s), 9.99 (2H, br.s), 7.27 (1H, d), 7.02-7.00 (2H, m), 4.43-4.37 (4H, m), 3.82-3.75 (2H, m), 3.49-3.43 (2H, m), 3.15-3.10 (4H, m), 2.79-2.78 (3H, s), 1.52 (9H, s). MS: [M+H]$^+$ 218.

75C. (5-Chloro-2,4-dihydroxy-phenyl)-[5-(4-methyl-piperazin-1-yl)-1,3-dihydro-isoindol-2-yl]-methanone

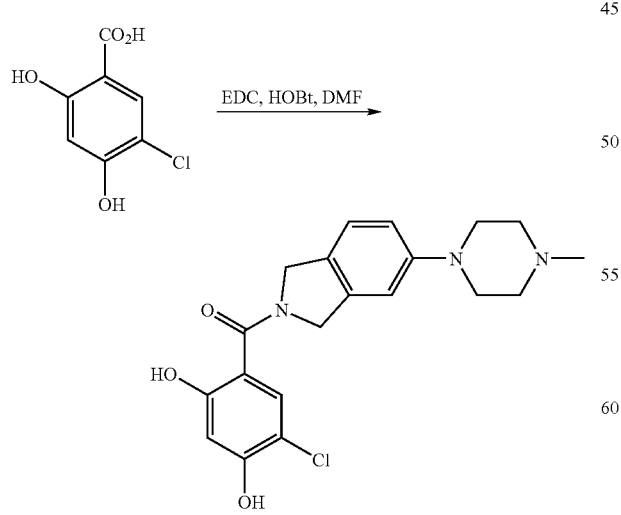

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 min, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried (MgSO$_4$), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). $^1$H NMR (DMSO-d$_6$) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]$^+$ 386/388.

Example 76

(2,4-dihydroxy-5-isopropyl-phenyl)-[5-(4-methyl-piperazin-1-yl)-1,3-di-hydro-isoindol-2-yl]-methanone 76A. Synthesis of (2,4-bis-benzyloxy-5-isopropenyl-phenyl)-(5-bromo-1,3-dihydro-isoindol-2-yl)-methanone

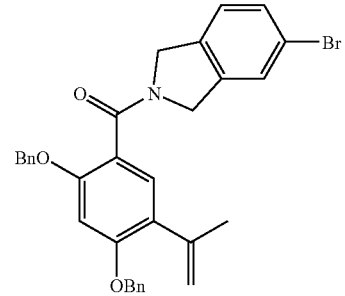 [SMILES: C=C(C)c1cc(C(=O)N2Cc3ccc(Br)cc3C2)c(OCc2ccccc2)cc1OCc1ccccc1]

Coupling of 2,4-bis-benzyloxy-5-isopropenyl-benzoic acid (5.0 g, 13.4 mmol) (Preparation B9) and 5-bromo-2,3-dihydro-1H-isoindole (Preparation C20) was completed according to method A4, using CH$_2$Cl$_2$ as the reaction solvent to give the title compound (8.34 g) as a beige solid.

76B. Synthesis of (2,4-bis-benzyloxy-5-isopropenyl-phenyl)-[5-(4-methyl-piperazin-1-yl)-1,3-dihydro-isoindol-2-yl]-methanone

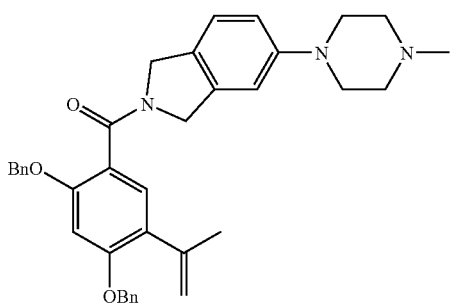 [SMILES: C=C(C)c1cc(C(=O)N2Cc3ccc(N4CCN(C)CC4)cc3C2)c(OCc2ccccc2)cc1OCc1ccccc1]

To a mixture of (2,4-bis-benzyloxy-5-isopropenyl-phenyl)-(5-bromo-1,3-dihydro-isoindol-2-yl)-methanone (8.30 g, 15.0 mmol), 2-(di-t-butylphosphino)biphenyl (223 mg, 0.75 mmol), tris(dibenzylideneacetone)dipalladium (344 mg, 0.38 mmol), sodium tert-butoxide (2.17 g, 22.5 mmol) and 1-methyl-piperazine (2.16 mL, 19.5 mmol) under a $N_2$ atmosphere was added anhydrous toluene (100 mL). The mixture was taken to 80° C. and heated at this temperature for 16 h. The mixture was allowed to cool to ambient temperature, diluted with ether (150 mL) and filtered through a plug of Celite, washing with ether. The filtrate was reduced in vacuo and the residue purified by column chromatography using an eluant of $CH_2Cl_2$-DMAW120 (1:0-0:1) to give the title compound (9.39 g) as a red gum.

76C. (2,4-dihydroxy-5-isopropyl-phenyl)-[5-(4-methyl-piperazin-1-yl)-1,3-di-hydro-isoindol-2-yl]-methanone

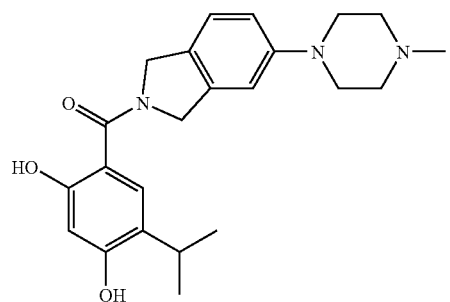 [SMILES: CC(C)c1cc(C(=O)N2Cc3ccc(N4CCN(C)CC4)cc3C2)c(O)cc1O]

A mixture of (2,4-bis-benzyloxy-5-isopropenyl-phenyl)-[5-(4-methyl-piperazin-1-yl)-1,3-dihydro-isoindol-2-yl]-methanone (8.61 g, 15.0 mmol) and 10% Pd/C (1.0 g) in methanol (200 mL) was stirred vigorously under a hydrogen atmosphere (~1 atm) for 18 h at ambient temperature. The mixture was filtered through a plug of Celite and reduced in vacuo to give a purple oil. This residue was purified by column chromatography using an eluant of DMAW120 to give the title compound as its acetate salt. This salt was taken up in MeOH (30 mL) and to the solution was added saturated HCl in EtOAc (20 mL). This mixture was stirred at ambient for 2 h and the solid formed collected by filtration and dried in vacuo to give the title compound as its hydrochloride salt (2.64 g) as a white solid.

Example 77

(5-Chloro-2,4-dihydroxy-phenyl)-[5-(4-methyl-piperazin-1-yl)-1,3-dihydro-isoindol-2-yl]-methanone

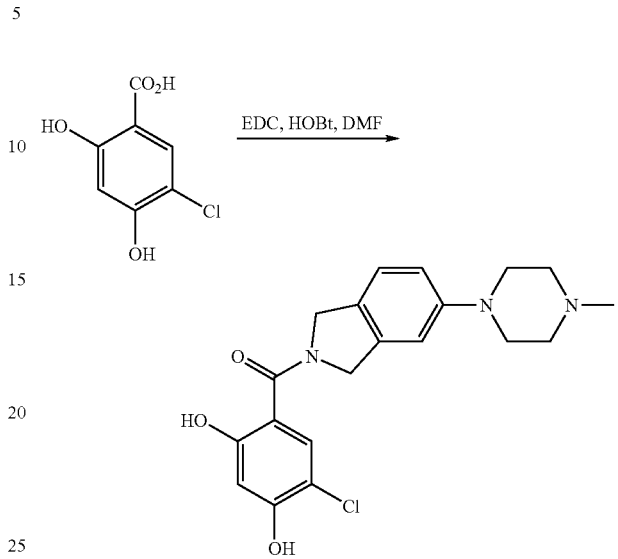

A solution of 5-chloro-2,4-dihydroxy-benzoic acid (176 mg, 0.93 mmol) in DMF (5 mL) was treated with 1-(3-dimethylaminopropyl)-3-ethylcarbodiimide hydrochloride (179 mg, 0.93 mmol) then HOBt (126 mg, 0.93 mmol). After 45 minutes, the solution of the activated acid was added to a mixture 5-(4-methyl-piperazin-1-yl)-2,3-dihydro-1H-isoindole dihydrochloride (290 mg, 0.78 mmol) and triethylamine (0.28 mL, 2 mmol) then the mixture was stirred at r.t. for 3 h. The solvent was removed in vacuo then the residue was partitioned between ethyl acetate and water (×3). Each extract was washed with saturated sodium bicarbonate solution and brine then dried ($MgSO_4$), combined and concentrated. Some insoluble material remained and this was dissolved in 1N hydrochloric acid and methanol then combined with the organic extracts. The pH was adjusted to 14 with solid sodium hydroxide and the mixture allowed to stand overnight. The pH was adjusted to 7 with 1N hydrochloric acid and the resulting precipitate was filtered off then subjected to purification by preparative HPLC to afford the title compound as a red solid. This was converted to its hydrochloride salt by treatment with 4M HCl in dioxane, concentration in vacuo and trituration with ether which gave a brown solid (91 mg, 27%). $^1$H NMR (DMSO-$d_6$) 11.10 (1H, br.s), 10.50 (1H, br.s), 7.26-7.15 (2H, m), 7.02-6.93 (2H, m), 6.69 (1H, s), 4.72-4.61 (4H, m), 3.78-3.72 (2H, m), 3.45 (2H, br.s), 3.12 (4H, br.s), 2.78 (3H, s). MS: [M+H]$^+$ 386/388.

Example 78

Alternative Synthesis of (2,4-Dihydroxy-5-isopropyl-phenyl)-[5-(4-hydroxy-1-methyl-piperidin-4-yl)-1,3-dihydro-isoindol-2-yl]-methanone 78A. 5-bromo-2-trityl-2,3-dihydro-1H-isoindole

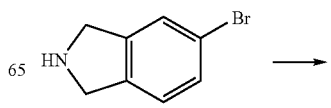

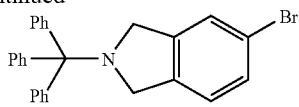

Trityl chloride (2.30 g, 8.23 mmol) was added to a solution of 5-bromo-2,3-dihydro-1H-isoindole (1.64 g, 8.23 mmol) and triethylamine (1.4 mL, 9.9 mmol) in dichloromethane (20 mL). After 18 hours the solvent was removed in vacuo, the residue taken up in ethyl acetate and washed with water (×2) and brine, dried (MgSO$_4$) and concentrated. The crude material was purified by flash chromatography on silica eluting with 1% triethylamine/10% ethyl acetate/petrol to give 5-bromo-2-trityl-2,3-dihydro-1H-isoindole as a reddish-brown solid (3.10 g, 85%). $^1$H NMR (CDCl$_3$) 7.91-7.84 (1H, m), 7.57 (6H, d), 7.45-7.41 (1H, m), 7.33-7.14 (9H, m), 6.95 (1H, d), 3.90 (2H, s), 3.86 (2H, s). MS: Ph$_3$C$^+$ 243.

78B. 1-methyl-4-(2-trityl-2,3-dihydro-1H-isoindol-5-yl)-piperidin-4-ol

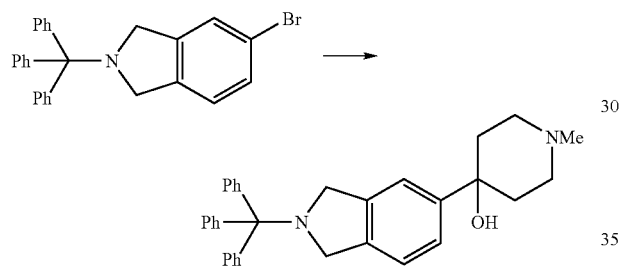

Under nitrogen, a solution of 5-bromo-2-trityl-2,3-dihydro-1H-isoindole (2.03 g, 4.6 mmol) in THF (20 mL) was cooled to −78° C. n-Butyllithium solution (2.5M in hexanes, 2.0 mL, 5 mmol) was added over 5 minutes, then after 10 minutes, 1-methyl-4-piperidone was added dropwise. After a further hour, the cooling bath was removed and the reaction quenched with sodium bicarbonate solution. The mixture was extracted with ethyl acetate then the organic phase was washed with brine, dried (MgSO$_4$) and concentrated. The residue was purified by flash chromatography on silica (gradient elution with 2M methanolic ammonia/dichloromethane, 0% to 5%) to afford 1-methyl-4-(2-trityl-2,3-dihydro-1H-isoindol-5-yl)-piperidin-4-ol as a pink foam (1.25 g, 57%). $^1$H NMR (MeOH-d$_4$) 7.56 (6H, dd), 7.28 (6H, t), 7.25-7.21 (2H, m), 7.15 (3H, t), 7.03 (1H, d), 3.92 (2H, s), 3.91 (2H, s), 2.70 (2H, d), 2.53 (2H, td), 2.33 (3H, s), 2.06 (2H, td), 1.70 (2H, d). MS: [M+H]$^+$ 475.

78C. 4-(2,3-Dihydro-1H-isoindol-5-yl)-1-methyl-piperidin-4-ol dihydrochloride

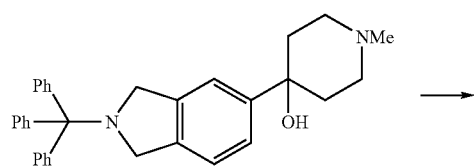

A mixture of 1-methyl-4-(2-trityl-2,3-dihydro-1H-isoindol-5-yl)-piperidin-4-ol (1.42 g, 3.0 mmol), 5N hydrochloric acid (5 mL) and methanol (10 mL) was placed under nitrogen then heated to reflux for 80 minutes. After cooling, the mixture was concentrated in vacuo to remove methanol, diluted with water and washed with ethyl acetate (×2). The aqueous phase was concentrated to dryness to afford the title compound in quantitative yield as a black solid. $^1$H NMR (MeOH-d$_4$) 7.62 (1H, s), 7.57 (1H, d), 7.45 (1H, d), 4.64 (2H, s), 4.63 (2H, s), 3.49-3.46 (4H, m), 2.95 (3H, s), 2.40-2.32 (2H, m), 1.97 (2H, dd).

78D. (2,4-Bis-benzyloxy-5-isopropenyl-phenyl)-[5-(4-hydroxy-1-methyl-piperidin-4-yl)-1,3-dihydro-isoindol-2-yl]-methanone

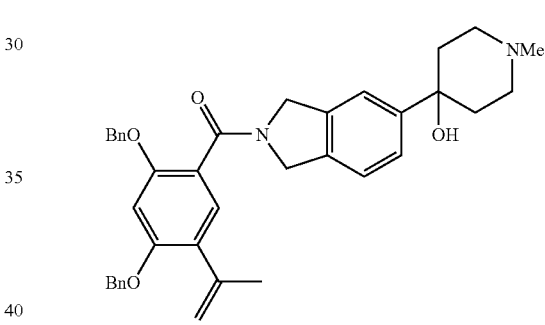

2,4-Bis-benzyloxy-5-isopropenyl-benzoic acid (1.65 g, 4.4 mmol), 1-[3-(dimethylamino)propyl]-3-ethylcarbodimide hydrochloride (843 mg, 4.4 mmol) and 1-hydroxybenzotriazole (595 mg, 4.4 mmol) were dissolved in DMF (20 mL). After 35 minutes, the solution was added to a suspension of 4-(2,3-dihydro-1H-isoindol-5-yl)-1-methyl-piperidin-4-ol dihydrochloride (1.22 g, 4.0 mmol) in DMF (5 mL) and triethylamine (1.4 mL, 10 mmol). The mixture was stirred for 3 hours then concentrated in vacuo. The residue was taken up in ethyl acetate and washed with a mixture of water (adjusted to pH 14 with 2N sodium hydroxide solution) and brine. The aqueous phase was extracted twice further with ethyl acetate then the combined organic extracts were washed with sodium bicarbonate solution and brine, dried (MgSO$_4$) and concentrated. The crude product was purified by flash chromatography (gradient elution with 2M methanolic ammonia/dichloromethane, 2% to 10%) to afford the title compound as a brown foam (1.62 g, 69%). $^1$H NMR (methanol-d$_4$) 7.51-7.14 (14H, m), 6.85 (0.5H, s), 6.84 (0.5H, s), 5.16 (2H, s), 5.15 (2H, s), 5.10-5.08 (1H, m), 5.07-5.05 (1H, m), 4.87 (1H, s), 4.86 (1H, s), 4.61 (2H, br.s), 2.78-2.70 (2H, m), 2.57 (1H, td), 2.54 (1H, td), 2.36 (1.5H, s), 2.34 (1.5H, s), 2.16-2.05 (5H, m including 2.09 (3H, s)), 1.78-1.70 (2H, m). MS: [M+H]$^+$ 589.

78E. (2,4-Dihydroxy-5-isopropyl-phenyl)-[5-(4-hydroxy-1-methyl-piperidin-4-yl)-1,3-dihydro-isoindol-2-yl]-methanone

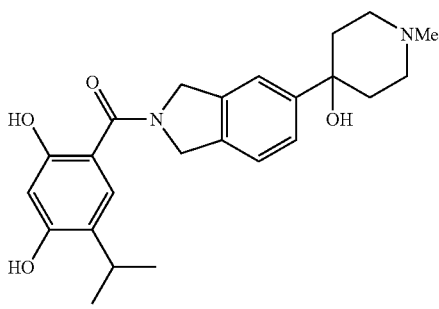 [SMILES: CC(C)c1cc(C(=O)N2Cc3ccc(C4(O)CCN(C)CC4)cc3C2)c(O)cc1O]

(2,4-Bis-benzyloxy-5-isopropenyl-phenyl)-[5-(4-hydroxy-1-methyl-piperidin-4-yl)-1,3-dihydro-isoindol-2-yl]-methanone (Example 50F) (1.62 g, 2.75 mmol) was dissolved in methanol (50 mL) and hydrogenated at 50° C. over 10% palladium on charcoal using an H-cube hydrogenation apparatus, under free hydrogen conditions. Concentration afforded the title compound (1.14 g, 100%) as a yellow solid, the NMR and mass spectrometric data of which were as set out in Example 50E.

Example 79

(2,4-Dihydroxy-5-isopropyl-phenyl)-[5-(2-dimethylamino-ethoxy)-7-methyl-1,3-dihydro-isoindol-2-yl]-methanone

79A. 7-Methyl-2,3-dihydro-1H-isoindol-5-ol hydrobromide

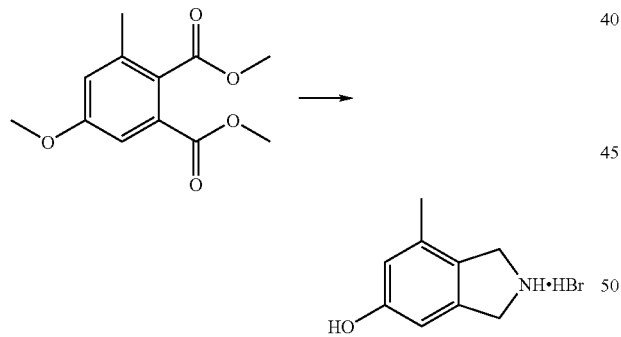

Using the method of preparation C2, 5-methoxy-3-methyl-phthalic acid dimethyl ester (prepared according to Tam and Coles, *Synthesis* 1988, 383) was hydrolysed to 5-methoxy-3-methyl-phthalic acid. $^1$H NMR (DMSO-$d_6$) 12.95 (2H, br.s), 7.15 (1H, d), 7.04 (1H, d), 3.80 (3H, s), 2.29 (3H, s). MS: [M−H]$^+$ 209.

5-Methoxy-3-methyl-phthalic acid was converted to 5-methoxy-3-methyl-phthalic anhydride. $^1$H NMR (DMSO-$d_6$) 7.40 (1H, d), 7.34-7.33 (1H, m), 3.94 (3H, s), 2.58 (3H, s).

5-Methoxy-3-methyl-phthalic anhydride was used to prepare 6-methoxy-4-methyl-isoindole-1,3-dione. $^1$H NMR (DMSO-$d_6$) 11.05 (1H, br.s), 7.13 (1H, d), 7.10 (1H, d), 3.88 (3H, s), 2.55 (3H, s).

Reduction of 6-methoxy-4-methyl-isoindole-1,3-dione according to the method of preparation C2 afforded 6-methoxy-4-methyl-isoindole. $^1$H NMR (DMSO-$d_6$) 6.64 (1H, s), 6.57 (1H, s), 4.05 (2H, s), 3.96 (2H, s), 3.70 (3H, s), 2.16 (3H, s). MS: [M+H]$^+$ 164.

6-Methoxy-4-methyl-isoindole was demethylated to give the title compound as its hydrobromide salt. $^1$H NMR (DMSO-$d_6$) 9.52 (1H, br.s), 9.29 (2H, br.s), 6.59 (1H, s), 6.56 (1H, s), 4.41 (2H, t), 4.34 (2H, t), 2.17 (3H, s).

79B. (2,4-Bis-benzyloxy-5-isopropenyl-phenyl)-(5-hydroxy-7-methyl-1,3-dihydro-isoindol-2-yl)-methanone

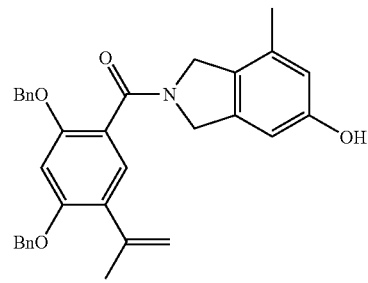 [SMILES: C=C(C)c1cc(C(=O)N2Cc3cc(O)cc(C)c3C2)c(OCc2ccccc2)cc1OCc1ccccc1]

2,4-Bis-benzyloxy-5-isopropenyl-benzoic acid (248 mg, 0.66 mmol), 1-[3-(dimethylamino)propyl)]-3-ethylcarbodiimide hydrochloride (127 mg, 0.66 mmol) and 1-hydroxybenzotriazole (89 mg, 0.661 mmol) were dissolved in DMF (5 mL). After 20 minutes, 7-methyl-2,3-dihydro-1H-isoindol-5-ol hydrobromide (152 mg, 0.66 mmol) and triethylamine (0.14 mL, 0.99 mmol) were added. After a further 3.5 hours the mixture was concentrated in vacuo and the residue was treated with 1N hydrochloric acid and ethyl acetate. The aqueous phase was removed, brine was added and the title compound was collected by filtration as a grey solid (168 mg, 57%). $^1$H NMR (DMSO-$d_6$) 9.30 (0.47H, s), 9.24 (0.53H, s), 7.48-7.25 (10H, m), 7.09 (0.47H, s), 7.08 (0.53H, s), 6.99 (0.47H, s), 6.98 (0.53H, s), 6.56 (0.47H, s), 6.50 (0.53H, s), 6.48 (0.47H, s), 6.44 (0.53H, s), 5.24 (0.47H, s), 5.22 (0.53, s), 5.18 (2H, s), 5.10-5.07 (2H, m), 4.70 (0.47H, s), 4.61 (0.53H, s), 4.46 (0.47H, s), 4.36 (0.53H, s), 2.17 (1.41H, s), 2.04 (3H, s), 1.99 (1.59H, s). MS: [M+H]$^+$ 506.

79B. (2,4-Bis-benzyloxy-5-isopropenyl-Phenyl)-[5-(2-dimethylamino-ethoxy)-7-methyl-1,3-dihydro-isoindol-2-yl]-methanone

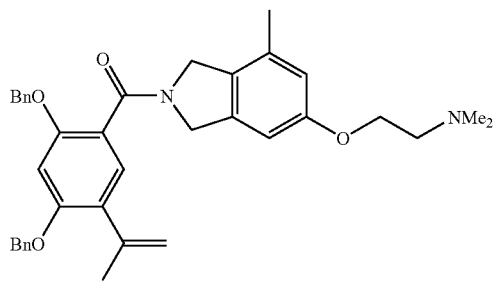 [SMILES: C=C(C)c1cc(C(=O)N2Cc3cc(OCCN(C)C)cc(C)c3C2)c(OCc2ccccc2)cc1OCc1ccccc1]

A mixture of (2,4-bis-benzyloxy-5-isopropenyl-phenyl)-(5-hydroxy-7-methyl-1,3-dihydro-isoindol-2-yl)-methanone (164 mg, 0.32 mmol), potassium carbonate (112 mg, 0.81 mmol) and 2-(dimethylamino)ethyl chloride hydrochloride (93 mg, 0.64 mmol) in DMF (5 mL) was heated at 60° C. for 17 hours then 90° C. for 6 hours. Further portions of potassium carbonate (112 mg, 0.81 mmol) and 2-(dimethylamino)ethyl chloride hydrochloride (93 mg, 0.64 mmol) were added and the mixture maintained at 60° C. for 72 hours and finally, a further 24 hours at 90° C. The mixture was concentrated in vacuo then the residue was partitioned between ethyl acetate and 0.5N aqueous sodium hydroxide. The organic phase was washed with brine (×2), dried (MgSO$_4$) and concentrated to give a residue which was purified by preparative HPLC (acidic method) to afford the title compound as a formate salt (37 mg, 20%). $^1$H NMR (MeOH-d$_4$) 8.51 (1H, br.s), 7.43-7.27 (7H, m), 7.24-7.20 (3H, m), 7.17 (0.5H, s), 7.16 (0.5H, s), 6.85 (0.5H, s), 6.84 (0.5H, s), 6.81 (0.5H, s), 6.77 (0.5H, s), 6.74 (0.5H, s), 6.62 (0.5H, s), 5.16 (1H, s), 5.14 (3H, s), 5.09 (1H, m), 5.06 (1H, m), 4.83 (1H, s), 4.74 (1H, s), 4.60 (1H, s), 4.48 (1H, s), 4.28 (1H, t), 4.23 (1H, t), 3.41 (1H, t), 3.37 (1H t), 2.84 (3H, s), 2.81 (3H, s), 2.27 (1.5H, s), 2.09 (3H, s), 2.07 (1.5H, s). MS: [M+H]$^+$ 577.

79C. (2,4-Dihydroxy-5-isopropyl-phenyl)-[5-(2-dimethylamino-ethoxy)-7-methyl-1,3-dihydro-isoindol-2-yl]-methanone

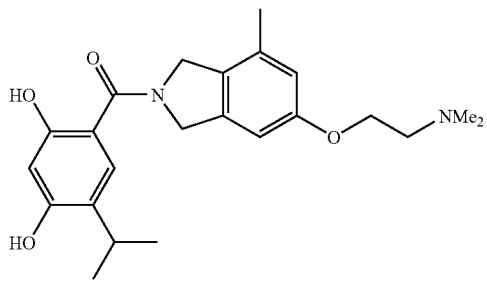 [SMILES: Cc1cc(OCCN(C)C)cc2c1CN(C(=O)c1cc(C(C)C)c(O)cc1O)C2]

(2,4-Bis-benzyloxy-5-isopropenyl-phenyl)-[5-(2-dimethylamino-ethoxy)-1,3-dihydro-isoindol-2-yl]-methanone (37 mg, 0.06 mmol) was hydrogenated in methanol at 50° C. over 10% palladium on charcoal using an H-cube hydrogenation apparatus, under free hydrogen conditions. The product was purified by preparative HPLC (basic method) to give the title compound as an off-white solid (9 mg, 35%). $^1$H NMR (MeOH-d$_4$) 7.18 (1H, s), 6.77-6.65 (2H, br.m), 6.37 (1H, s), 4.85 (water obscuring CH$_2$), 4.77 (2H, s), 4.08 (2H, t), 3.20 (1H, sept), 2.81 (2H, t), 2.39 (6H, s), 2.22 (3H, br.s), 1.21 (6H, d). MS: [M+H]$^+$ 399.

Example 80

(2,4-Dihydroxy-5-isopropyl-phenyl)-[5-(4-methyl-piperazin-1-ylmethyl)-1,3-dihydro-isoindol-2-yl]-methanone Step 1

4-Acetoxy-2-hydroxy-benzoic acid methyl ester

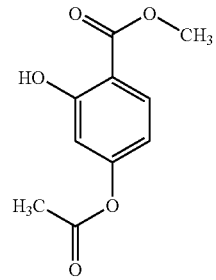

Resorcinol methyl ester (50 g, 0.298 mol) and N,N-dimethyl-4-aminopyridine (0.27 g, 0.0022 mol, 0.74 mol %) were added to toluene 0.2 L followed by acetic anhydride (30 mL, 0.318 mol). The solution was heated to 50° C. for 2 h. The solvent was removed by evaporation at 50° C. to a small volume and the residue was azeotroped once with toluene. To the residual oil was immediately added toluene (100 mL) whilst still warm and the solution used for Step 2 without further purification.

Step 2

5-Acetyl-2,4-dihydroxy-benzoic acid methyl ester

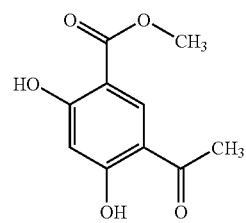

The toluene solution from Step 1 was cooled in an ice bath under N$_2$ and triflic acid (26 mL) added slowly over 30 min. On stirring a fine white solid was formed which dissolved on stirring for 16 h at RT to give a yellow solution. To the solution was added acetyl chloride (2 mL) and the solution stirred at RT for a further 1 h. This solution was cannulated into a stirred cooled (0° C.) solution of EtOAc (600 mL) and NaOAc.3H$_2$O (40 g) dissolved in water (400 mL). The organic phase was washed with water (twice, 200 mL), saturated brine and was evaporated to a small volume without drying. The residue was azeotroped with heptane (twice, 100 mL) and heptane (100 mL) was added and the crystalline solid removed by filtration, washed well on sinter with heptane and dried to give 49.5 g (79%).

Final Purification of Combined Batches

The combined batches of solid (96.3 g) was heated to boiling with 10% IPA/heptane (250 mL) then cooled to RT and finally to 0° C., filtered and the residue dried 72 h (oil pump) to give (88.04 g, 91.5%), pure by hplc, tlc and NMR.
$^1$H NMR (DMSO-$d_6$) 12.58 (1H, s), 11.22 (1H, s), 8.33 (1H, s), 6.45 (1H, s), 3.90 (3H, s), 2.62 (3H, s).

Step 3

5-Acetyl-2,4-dihydroxy-benzoic acid methyl ester

Alternative Procedure

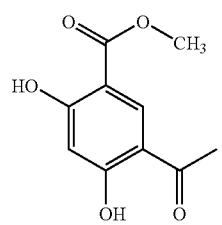

Resorcinol methyl ester (50 g, 0.298 mol) and Amberlyst 15 resin (40 g) were suspended in toluene 150 mL (under a nitrogen atmosphere) and the solution was heated in an oil bath at 70° C. (internal temp 56° C.). Acetyl chloride (22 mL, 308 mmol) was added in 5 mL portions over 30 mins giving evolution of gaseous HCl (which was scrubbed by passing the nitrogen stream through aqueous NaOH). The solution was stirred at 70° C. for 4.5 h then heated in an oil bath temp (internal temperature 96° C.) for 3.5 h. The solution was cooled to 50° C. and EtOAc (100 mL) was added and the solution filtered whilst at this temperature. The residual resin was washed with EtOAc (50 mL) and the combined filtrates were concentrated to slurry of crystalline solid (total weight of 128 g for solid plus solvent). To the slurry was added heptane (100 mL) and after 10 mins at RT the solid was removed by filtration. The residue was washed with heptane:toluene (2:1, 60 mL) then with petroleum ether bp 40-60° C. and dried in vacuo to give crop 1 29 g (46.4%) (NMR showed 3% of material resulting from saponification of the methyl ester).

The filtrate was evaporated to a small volume and 20% EtOAc in heptane (100 mL) was added. After standing at RT 16 h a second crop of 4.75 g (7.6%) was obtained (NMR identical to crop 1).

Step 4

5-Acetyl-2,4-bis-benzyloxy-benzoic acid methyl ester

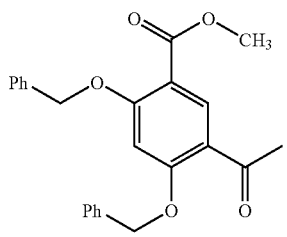 [SMILES: COC(=O)c1cc(C(C)=O)c(OCc2ccccc2)cc1OCc1ccccc1]

Benzyl bromide (70 ml, 0.59 mol) was added to a stirred mixture of methyl 5-acetyl-2,4-dihydroxybenzoate (60.7 g, 0.29 mol) and anhydrous potassium carbonate (87.8 g, 0.64 mol) in acetonitrile (800 ml) and the mixture was stirred and held at reflux for 16 hours. Upon cooling to room temperature the mixture was poured onto water (3 L) and stirred vigorously for 2 hours. The solids were collected by filtration, rinsed with water (2 L), sucked dry under reduced pressure and dried to constant mass in a vacuum oven at 60° C. overnight to afford methyl 5-acetyl-2,4-bis-benzyloxy-benzoate (112.1 g, 99%) as a cream solid. $^1$H NMR (DMSO-$d_6$) 8.21 (1H, s), 7.55 (4H, m), 7.43 (4H, m), 7.37 (2H, m), 7.04 (1H, s), 5.38 (4H, s), 3.79 (3H, s), 2.48 (3H, s). MS: [M+H]$^+$ 391.

Step 5

2,4-Bis-benzyloxy-5-isopropenyl-benzoic acid methyl ester

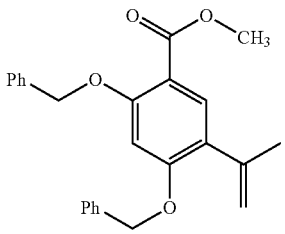 [SMILES: C=C(C)c1cc(C(=O)OC)c(OCc2ccccc2)cc1OCc1ccccc1]

Potassium tert-butoxide (29.1 g, 0.26 mol) was added to a stirred suspension of methyltriphenylphosphonium bromide (92.8 g, 0.26 mol) in anhydrous tetrahydrofuran (1 L) and the mixture was stirred at room temperature for 10 minutes whereupon methyl 5-acetyl-2,4-bis-benzyloxybenzoate (78.0 g, 0.2 mol) was added and the mixture stirred at room temperature for a further 30 minutes. Methanol (100 ml) was added to quench excess phosphorus ylide and the solvent was removed in vacuo to afford an orange oil that crystallized on standing. The residue was recrystallized from methanol (330 ml). The solids were collected by suction filtration, washed with methanol (50 ml) and sucked dry under reduced pressure to afford methyl 2,4-bis-benzyloxy-5-isopropenyl-benzoate as pale yellow needles. The mother liquor deposited a second crop of material upon standing overnight (combined yield: 56.55 g, 73%) $^1$H NMR (DMSO-$d_6$) 7.59 (1H, s), 7.52 (2H, d), 7.64-7.32 (8H, m), 6.97 (1H, s), 5.28 (2H, s), 5.22 (2H, s), 5.09 (1H, s), 5.04 (1H, s), 3.76 (3H, s), 2.02 (3H, s). MS: [M+H]$^+$ 389.

A further crop of the ester could be obtained as follows. The crystallization residues were evaporated to dryness in vacuo and the oily solid was treated with 5% ethyl acetate in heptane (250 ml). Ethyl acetate was added in small portions to the vigorously stirred mixture until the residue deposited a large quantity of solid triphenylphosphine oxide. The solids were removed by filtration and the filtrate evaporated to dryness in vacuo to afford an orange oil. Recrystallization from methanol (as described above) afforded further methyl 2,4-bis-benzyloxy-5-isopropenyl-benzoate as a pale yellow crystalline solid (total yield 85-90%).

Step 6

2,4-Bis-benzyloxy-5-isopropenyl-benzoic acid

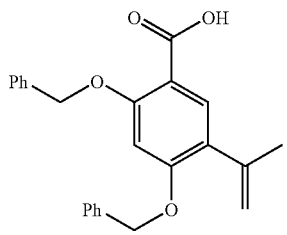 [SMILES: C=C(C)c1cc(C(=O)O)c(OCc2ccccc2)cc1OCc1ccccc1]

Potassium hydroxide (10.96 g, 0.19 mmol) was added to a stirred suspension of methyl 2,4-bis-benzyloxy-5-isopropenyl-benzoate (61.0 g, 0.16 mol) in methanol (750 ml) and water (250 ml) and the mixture was stirred and held at reflux for 16 hours. Upon cooling the organic solvent was removed in vacuo and the mixture acidified to pH 2 or below by the addition of 2M hydrochloric acid (200 ml). The mixture was diluted with water (2 L) and extracted with ethyl acetate (2 L), the organic layer was separated and the solvent removed in vacuo to afford 2,4-bis-benzyloxy-5-isopropenyl-benzoic acid (58.8 g, 100%) as a colourless solid. $^1$H NMR (DMSO-$d_6$) 7.52 (2H, d), 7.47-7.29 (9H, m), 6.82 (1H, s), 5.20 (2H, s), 5.17 (2H, s), 5.06 (1H, s), 5.04 (1H, s), 2.03 (3H, s). MS: [M+H]$^+$ 375.

Step 7

Di-prop-2-ynyl-carbamic acid benzyl ester

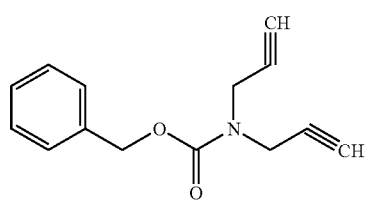 [SMILES: C#CCN(CC#C)C(=O)OCc1ccccc1]

To a cooled (0° C.) solution of dipropargylamine (46.7 g, 502 mmol) in EtOAc (200 mL) and 10% aqueous K$_2$CO$_3$ (700 mL, 507 mmol) was slowly added a solution of N-(benzyloxycarbonyloxy)succinimide (125 g, 502 mmol) in EtOAc (500 mL) over 20 mins. The solution was stirred at 0° C. for 2 h then at RT 16 h. The phases were separated and the organic phase was washed with 10% aqueous K$_2$CO$_3$ (700 mL, 507 mmol) and then with saturated brine (500 mL) and was diluted to 1000 mL with EtOAc to give a 0.5M solution.

Step 8

5-Hydroxymethyl-1,3-dihydro-isoindole-2-carboxylic acid benzyl ester

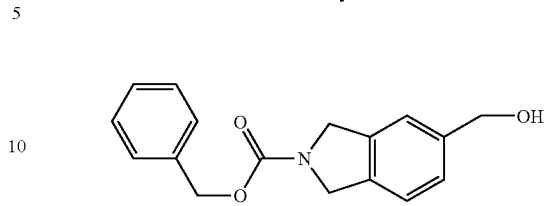

A solution of propargyl alcohol (26.4 mL, 424 mmol) in toluene (120 mL) was degassed. The 0.5M-diyne solution above (440 mL, 220 mmol) was evaporated and the residue dissolved in toluene (80 mL). This protected diyne solution and Wilkinson's catalyst (2.26 g, 2.44 mmol, 1.11% were added in 14 equal portions over a 2 h period with constant monitoring of the internal temperature such that the temperature remained 50-100° C. The solution was allowed to cool to 50° C. over 30 min when the solution was evaporated (to remove excess propargyl alcohol). The residue was heated with toluene (500 mL) and charcoal (Darco 4-12 mesh, 20 g) at 100° C. for 30 min and then filtered hot through a bed of Celite and the brown solution was evaporated. The residue was dissolve in EtOAc (400 mL) at 80° C. when silica gel (chromatography grade 65 g) was added and heating continued for 20 mins. The solution was filtered whilst hot and then evaporated (with seeding) to give a pale brown solid. 10% EtOAc/heptane (v/v, 100 mL) was added and the solid removed by filtration. The solid was washed on the sinter with heptane (100 mL) and the dried (50° C., oil pump, 16 h) to give the title compound 59.0 g (95%). $^1$H NMR (400 MHz, Me-d3-OD): 7.51-7.16 (m, 8H), 5.21 (s, 2H), 4.74 (s, 2H), 4.70 (s, 2H), 4.61 (s, 2H).

Step 9

5-Methanesulfonyloxymethyl-1,3-dihydro-isoindole-2-carboxylic acid benzyl ester

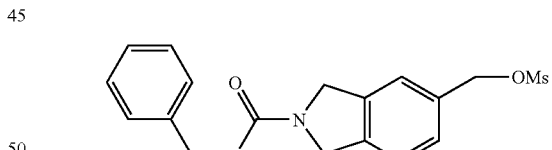

To a solution of 5-hydroxymethyl-1,3-dihydro-isoindole-2-carboxylic acid benzyl ester (65.75 g, 0.232 mol) in THF (470 mL) and EtOAc (770 mL) was added Et$_3$N (39 mL, 0.28 mol). The solution was cooled in an ice-bath and a solution of methanesulphonyl chloride (19 mL, 0.245 mol) dissolved in EtOAc (50 mL) was added (so that the internal temp <12° C.). After stirring for 2 h in the ice-bath further additions of methanesulphonyl chloride (1.9 mL and 0.95 mL) and Et$_3$N (3.9 mL) were made (so that by tlc there was no remaining starting material after a further 1 h of stirring). NaHCO$_3$ (550 mL) was added and the solution stirred for 20 mins then saturated brine (200 mL) was added and the phases were separated. The organic phase was dried (MgSO$_4$) and evaporated with seeding to give a damp solid which was used in the next step without thorough drying.

Step 10

5-(4-Methyl-piperazin-1-ylmethyl)-1,3-dihydro-isoindole-2-carboxylic acid benzyl ester dihydrochloride salt

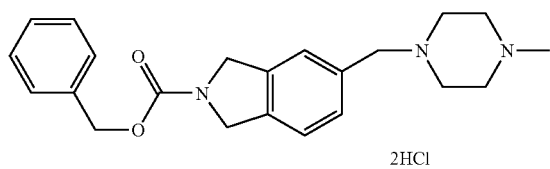 [SMILES: CN1CCN(Cc2ccc3c(c2)CN(C(=O)OCc2ccccc2)C3)CC1 ; "2HCl"]

2HCl

The solid from Step 9 (assume 0.232 mol) was dissolved in acetone (700 mL) and this solution was added over 45 mins to a cooled (internal temp 15-17° C.) suspension of $K_2CO_3$ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine. (150 mL) and finally washed with saturated brine (300 mL). The solution was dried ($MgSO_4$) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. $^1$H NMR (400 MHz, Me-d3-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Alternative Step 10A

5-(4-Methyl-piperazin-1-ylmethyl)-1,3-dihydro-isoindole-2-carboxylic acid benzyl ester dihydrochloride

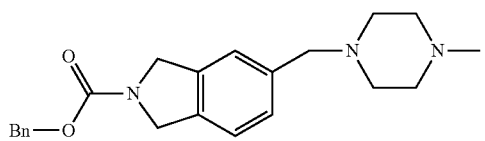 [SMILES: CN1CCN(Cc2ccc3c(c2)CN(C(=O)OCc2ccccc2)C3)CC1]

Step 10A can be used as an alternative route to replace steps 9 and 10 above.

To a suspension of manganese dioxide (15.5 g, 178 mmol) in DCM (100 mL) was added 5-hydroxymethyl-1,3-dihydro-isoindole-2-carboxylic acid benzyl ester (3.35 g, 11.8 mmol) and after 6 h stirring at RT a further addition of manganese dioxide (5 g, 57 mmol) was made. After a further 1 h stirring at RT Celite (7 g) was added and the solution was filtered through a bed of Celite™ giving a clear pale yellow solution. The Celite™ was washed with DCM and the volume of the combined organic solution adjusted to 100 mL by evaporation. N-Methylpiperazine (1.31 mL, 11.8 mmol) and acetic acid (0.68 mL) were added followed by sodium triacetoxyborohydride (4.98 g, 23.5 mmol). The yellow solution was stirred 16 h giving a colourless solution. To the solution was added 2M-HCl (10 mL, 20 mmol) giving an effervescence. After 30 min water (10 mL) and $K_2CO_3$ (5.5 g, 39.8 mmol) were added and the organic phase was dried ($Na_2SO_4$). After filtration 4M-HCl in dioxan (6 mL) was added with stirring and the suspension was evaporated to dryness. The residue was dissolved in MeOH with warming and after evaporation the solid was washed on a sinter with EtOAc then petrol (bp 40-60° C.) followed by drying in vacuo at 50° C. to give the title compound 3.61 g (70%). $^1$H NMR (400 MHz, Me-d3-OD): 7.65-7.51 (2H, m), 7.51-7.27 (6H, m), 5.23 (2H, s), 4.83-4.69 (4H, m), 4.49 (2H, s), 3.66 (8H, d), 3.03 (3H, s)

Step 11

5-(4-Methyl-piperazin-1-ylmethyl)-2,3-dihydro-1H-isoindole

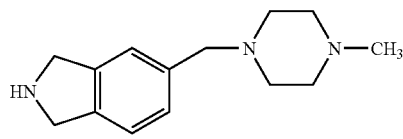 [SMILES: CN1CCN(Cc2ccc3c(c2)CNC3)CC1]

To 5-(4-Methyl-piperazin-1-ylmethyl)-1,3-dihydro-isoindole-2-carboxylic acid benzyl ester dihydrochloride salt (Step 10, 59.8 g, 136.7 mmol) was added EtOAc (400 mL) and 10% aqueous $K_2CO_3$ (400 mL). The organic phase was washed with saturated brine (200 mL) and then dried ($MgSO_4$). The solution was filtered and was evaporated to an oil (which crystallised on standing with petroleum ether (bp 40-60° C.)). The solid was dried in vacuo to give a colourless solid: 48.8 g (133.5 mmol).

A portion of the solid (24.4 g, 66.8 mmol) was dissolved in MeOH (170 mL) and after degassing the solution and purging with nitrogen 10% Pd/C (1.22 g) was added and the mixture hydrogenated at 1 atmosphere for 2.5 h. The solution was filtered and the solution evaporated and the residue was azeotroped twice with toluene at 30-40° C. The residue was dissolved in DMF (92 mL) and the solution was immediately degassed and purged with $N_2$.

(NB The product at this stage is sensitive to air and darkens on contact with oxygen. The DMF solution was used immediately but can be stored by degassing and storing under an atmosphere of $N_2$)

Step 12

(2,4-Bis-benzyloxy-5-isopropenyl-phenyl)-[5-(4-methyl-piperazin-1-ylmethyl)-1,3-dihydro-isoindol-2-yl]-methanone

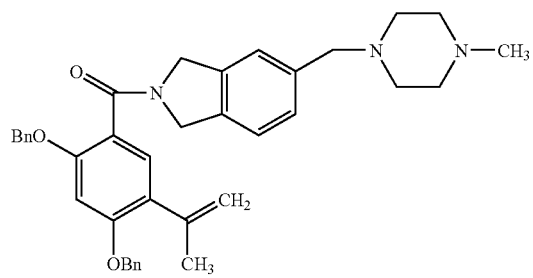 [SMILES: C=C(C)c1cc(C(=O)N2Cc3ccc(CN4CCN(C)CC4)cc3C2)c(OCc2ccccc2)cc1OCc1ccccc1]

A solution of the resorcinol acid (Step 6, 23.7 g, 63.4 mmol) and 1-hydroxybenzotriazole (10.21 g, 66.7 mmol) were dissolved in DMF (92 mL) and to this solution was added N-ethyl-N'-(3-dimethylaminopropyl)carbodiimide hydrochloride (12.8 g, 66.8 mmol). The solution was stirred at RT for 40 mins and this solution was added to the solution of the amine from Step 11 (66.8 mmol) together with DMF (5 mL) washings. The solution was degassed and the solution stirred at RT for 16 h. To the solution was added 10% $K_2CO_3$ (500 mL) and EtOAc (500 mL) and the organic phase was washed sequentially with 10% $K_2CO_3$ (500 mL), water (4×100 mL) and saturated brine (200 mL). The solution was evaporated to a small volume and 20% EtOAc in heptane (250 mL) was added and stored at 0° C. The solid which had formed was removed by filtration, washed with heptane twice and was dried in vacuo to give the title compound 35.05 g (94.4%). $^1$H NMR (400 MHz, Me-d3-OD): 7.49-7.10 (m, 14H), 6.86 (d, J=2.5 Hz, 1H), 5.17 (d, J=2.5 Hz, 4H), 5.09 (d, J=11.3 Hz, 2H), 4.88 (s, 2H), 4.63 (s, 2H), 3.54 (d, J=16.0 Hz, 2H), 2.50 (s, 7H), 2.28 (d, J=7.6 Hz, 3H), 2.11 (s, 3H).

Step 13

(2,4-Dihydroxy-5-isopropyl-phenyl)-[5-(4-methyl-piperazin-1-ylmethyl)-1,3-dihydro-isoindol-2-yl]-methanone

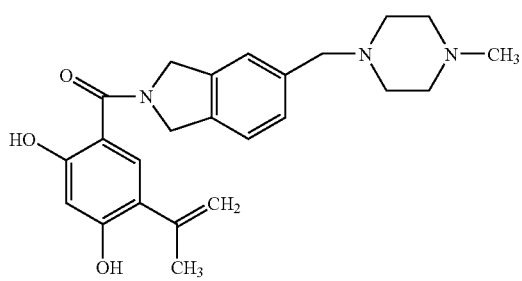 [SMILES: C=C(C)c1cc(C(=O)N2Cc3ccc(CN4CCN(C)CC4)cc3C2)c(O)cc1O]

The product from Step 12 (4.7 g) was dissolved in 1:1 MeOH/water (98 mL) and after purging with $N_2$ 10% Pd/C and $K_2CO_3$ (2.38 g, 17.2 mmol) were added and the suspension was hydrogenated for 16 h under an atmosphere of $H_2$. The solution was filtered and the solvent evaporated. To the residue was added aqueous 2M-HCl (40 mL) and the solution was washed with 1:1 EtOAc/petrol (40 mL×2) and then the pH adjusted to pH 8.5 by addition of NaOH and EtOAc (50 mL) added. The solution was heated to 60° C. and the aqueous phase removed. The hot organic phase was washed with water (30 mL) and then evaporated to a small volume (ca. 5 mL) and allowed to stand at RT 16 h with seeding. To the crystalline material was added 1:1 EtOAc/petrol (10 mL) and the mixture was filtered and dried to give the title compound as the free base 1.76 g. $^1$H NMR (400 MHz, Me-d3-OD): 7.29 (s, 3H), 7.19 (s, 1H), 6.39 (s, 1H), 4.91 (s, 4H), 3.56 (s, 2H), 3.28-3.15 (m, 1H), 2.53 (s, 8H), 2.31 (s, 3H), 1.23 (d, J=6.9 Hz, 7H).

Optional Step 14

Purification of (2,4-Dihydroxy-5-isopropyl-phenyl)-[5-(4-methyl-piperazin-1-ylmethyl)-1,3-dihydro-isoindol-2-yl]-methanone In some batches of product, the title compound (X═H in the formula) can contain small amounts of the impurity 2,4-Dihydroxy-5-(2-hydroxypropy-2-yl)-phenyl)-[5-(4-methyl-piperazin-1-ylmethyl)-1,3-dihydro-isoindol-2-yl]-methanone (X═OH in the formula). The impurities can be removed by the following method.

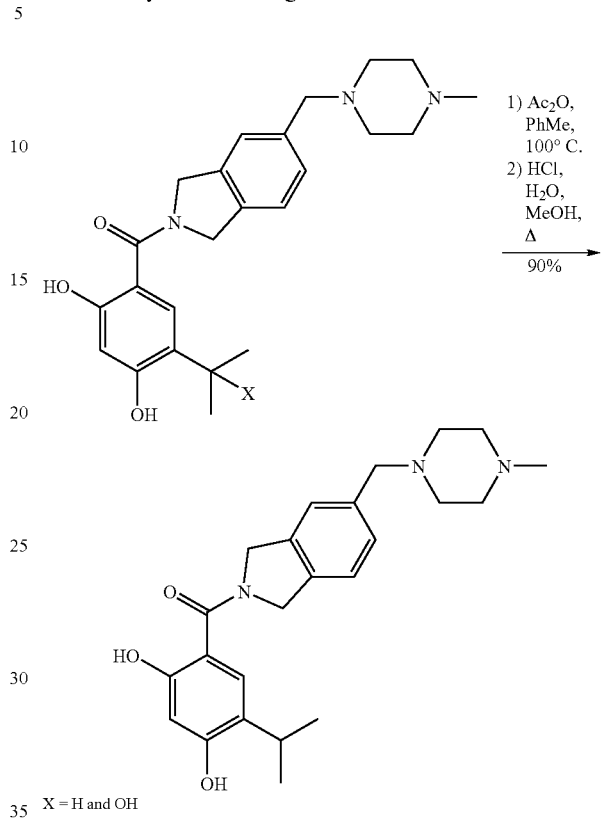

Acetic anhydride (1.04 ml, 11.0 mmol) was added to a stirred suspension of impure 2-(2,4-dihydroxy-5-isopropyl-benzoyl)-5-(4-methylpiperazin-1-ylmethyl)-1,3-dihydroisoindole (2.05 g, 5.0 mmol) in toluene (20 ml) and the resulting mixture was stirred and held at 100° C. for 16 hours. Upon cooling to room temperature the solvent was removed in vacuo to afford a brown oil which was dissolved in methanol (20 ml). Concentrated hydrochloric acid (1 ml) was added and the mixture was stirred and held at reflux for 5 hours. Upon cooling to room temperature, the organic solvent and volatile material were removed in vacuo and the aqueous residue was diluted with water (25 ml) and basified to pH 8 with vigorous stirring by the careful addition of 10% aqueous potassium carbonate solution. 50% Ethyl acetate in heptane (50 ml) was added and the mixture was stirred vigorously at room temperature for 16 hours. The solid material was collected by suction filtration, rinsed with 50% ethyl acetate in heptane (50 ml), sucked dry under reduced pressure and dried overnight in a vacuum oven at 50° C. to afford 2-(2,4-dihydroxy-5-isopropylbenzoyl)-5-(4-methyl-piperazin-1-ylmethyl)-1,3-dihydroisoindole (1.85 g, 90%) as an off-white solid. $^1$H NMR (DMSO-$d_6$) 10.07 (1H, br s), 9.60 (1H, br s), 7.24 (3H, m), 7.06 (1H, s), 6.40 (1H, s), 4.76 (4H, br s), 3.44 (2H, s), 3.10 (1H, m), 2.32 (8H, m), 2.14 (3H, s), 1.15 (6H, d). MS: $[M+H]^+$ 410.

Example 81

(2,4-Dihydroxy-5-isopropyl-phenyl)-[5-(4-methyl-piperazin-1-ylmethyl)-1,3-dihydro-isoindol-2-yl]-methanone L-lactate salt (form FL1)

The product of Example 1 (1.24 g, 3.303 mmol) was suspended in ethanol (3 mL) and EtOAc (5 mL) and a solution of L-lactic acid (0.285 g, 3.13 mmol) dissolved in ethanol (3 mL) was added. The solution was heated until clear and then was filtered. EtOAc (5 mL) was used to wash the filter and the combined filtrates were stirred at RT for 2 h with seeding. The crystalline mass which formed was removed by filtration, was washed with EtOAc and then dried in vacuum at 50° C. to give the title compound 1.29 g. $^1$H NMR (400 MHz, Me-d3-OD): 7.30 (s, 3H), 7.18 (s, 1H), 6.39 (s, 1H), 4.91 (s, 4H), 4.08 (q, J=6.8 Hz, 1H), 3.70-3.63 (m, 2H), 3.28-3.15 (m, 1H), 3.01 (s, 4H), 2.68 (m, 7H), 1.36 (d, J=6.8 Hz, 3H), 1.23 (d, J=6.9 Hz, 6H).

Example 82

(2,4-Dihydroxy-5-isopropyl-phenyl)-[5-(4-methyl-piperazin-1-ylmethyl)-1,3-dihydro-isoindol-2-yl]-methanone L-lactate salt Example 82 describes a synthetic route containing essentially the same process steps as the route described in Examples 80 and 81 but wherein the process conditions are more suited to larger scale reactions.

Step 1

4-Acetoxy-2-hydroxy-benzoic acid methyl ester

To a heated solution (50° C.) of resorcinol methyl ester (16.5 Kg, 98.1 mol) and N,N-dimethyl-4-aminopyridine (89.1 g, 0.73 mol, 7.4 mol %) in toluene (66 L) was slowly added (over 2 h) acetic anhydride (9.9 L, 104.9 mol). The solution was heated to 50° C. for a further 1.5 h and then the solvent was removed by evaporation at 50° C. to a small volume and the residue was azeotroped once with toluene. To the residual oil was immediately added toluene (33 L) whilst still warm and the solution used for Step 2 without further purification.

Step 2

5-Acetyl-2,4-dihydroxy-benzoic acid methyl ester

The toluene solution from Step 1 was cooled in an ice bath under $N_2$ and triflic acid (9.44 L) added slowly over 3 h. On stirring a fine white solid was formed which dissolved on warming to RT over 20 h and then stirring at RT for 37 h to give a yellow solution. To the solution was added acetyl chloride (726 mL) and the solution stirred at RT for a further 1 h. This solution was cannulated into a stirred cooled (0° C.) solution of EtOAc (217.8 L) and NaOAc.3H$_2$O (14.52 Kg) dissolved in water (145 L). The organic phase was washed with saturated brine (twice, 72.6 L), and was evaporated to 5.5 Kg. Toluene:Isopropanol (2:3) was added and the crystalline solid removed by filtration and dried to give 12.6 Kg (61% over 2 steps), mp 124-126° C.

Step 3

5-Acetyl-2,4-bis-benzyloxy-benzoic acid methyl ester

To a stirred solution of benzyl bromide (16.14 L, 136 mol) and anhydrous potassium carbonate (20.25 Kg, 147.6 mol) in acetonitrile (184.5 L) was added methyl 5-acetyl-2,4-dihydroxybenzoate (14 Kg, 66.6 mol, step 2) in 6 portions over 5 h. The mixture was stirred and held at reflux for 20 hours, cooled to room temperature the mixture was poured onto water (682 L) and stirred vigorously for 2 hours. The solids were collected by centrifugation and dried under reduced pressure to constant mass in a vacuum oven at 60° C. overnight to afford methyl 5-acetyl-2,4-bis-benzyloxy-benzoate (23.5 Kg, 97.3%) as a cream solid mp 114-115° C.

Step 4

2,4-Bis-benzyloxy-5-isopropenyl-benzoic acid methyl ester

A solution of potassium tert-butoxide (6.72 Kg, 60.1 mol) in anhydrous THF (60 L) was added over 3 h to a stirred suspension of methyltriphenylphosphonium bromide (21.43 Kg, 60.1 mol) and methyl 5-acetyl-2,4-bis-benzyloxybenzoate (21.3 Kg, 54.6 mol, step 3) in anhydrous tetrahydrofuran (213 L) at 15° C. The mixture was stirred at 15° C. for 70 mins and the warmed to 20° C. over 60 mins. Methanol (27.3 L) was added to quench excess phosphorus ylide and the solvent was concentrated in vacuo followed by addition of EtOAc and water. The organic phase was treated with activated charcoal, filtered and evaporated to a small volume. The residue was crystallised from boiling MeOH and the solids were collected by suction filtration, washed with methanol and dried under reduced pressure to afford methyl 2,4-bis-benzyloxy-5-isopropenyl-benzoate 18.1 Kg (85%) as pale yellow needles mp 92-94° C. (99.6% pure by hplc).

Step 5

2,4-Bis-benzyloxy-5-isopropenyl-benzoic acid

Potassium hydroxide (0.527 Kg, 9.4 mol) was added to a stirred suspension of methyl 2,4-bis-benzyloxy-5-isopropenyl-benzoate (3.1 Kg, 8 mol, step 4) in methanol (18.6 L) and water (12.4 L) and the mixture was stirred and held at reflux for 3 hours. The methanol was removed under partial vacuum from the vessel, and to the remaining solution was added toluene (62 L). The solution was heated to 40° C. and to the mixture was added conc HCl (1.36 L). The biphasic mixture is heated to 50° C. and the phases separated. The organic phase was washed with water (31 L) at 50° C. and the organic phase was evaporated under reduced pressure to give 2,4-bis-benzyloxy-5-isopropenyl-benzoic acid 2.851 Kg (95% yield) as a colourless solid.

Step 6

Di-prop-2-ynyl-carbamic acid benzyl ester

To a cooled (5° C.) solution of $K_2CO_3$ (4 Kg, 29.0 mol) in water (17.5 L) and toluene (12.5 L) was added dipropargylamine (2.50 Kg, 26.88 mol). Benzyloxychloroformate (4.8 Kg, 28.14 mol) was added at a rate such that T<10° C. The solution was stirred at 5° C. for 10 mins and then allowed to warm to RT. The aqueous phase was separated and the organic phase was washed with 0.2M HCl (12.5 L), sat NaHCO₃ (13.5 L) and brine (17 L) and the resultant solution used in step 7 (assayed to contain 6.23 Kg, 102% based on an evaporated portion).

Step 7

5-Hydroxymethyl-1,3-dihydro-isoindole-2-carboxylic acid benzyl ester

A solution of propargyl alcohol (2.11 Kg, 37.7 mol) in toluene (32.48 L) was degassed and heated to 55° C. The solution of di-prop-2-ynyl-carbamic acid benzyl ester (4.06 Kg, 17.86 mol, step 6) in toluene and Wilkinsons catalyst (0.162 Kg) were added in 10 equal portions such that temperature <65° C. (the exotherm was allowed to subside before the next addition was made). The solution was then stirred at 55° C. for 1 h and then cooled to 20° C. DCM (8.12 L) was added and the mixture was concentrated to a small volume. Toluene (8 L) was added and the solution evaporated to constant weight giving the title compound 5.72 Kg (113%).

Step 8

5-Methanesulfonyloxymethyl-1,3-dihydro-isoindole-2-carboxylic acid benzyl ester

To a cooled solution (5° C.) of 5-hydroxymethyl-1,3-dihydro-isoindole-2-carboxylic acid benzyl ester (11 Kg, 38.8 mol, step 7) and Et₃N (7.04 L, 50.6 mol) in DCM (55 L) was added methanesulphonyl chloride (2.97 L, 38.4 mol) so that the internal temp <10° C. After stirring for 0.5 h at 5° C. the solution was used below in step 9.

Step 9

5-(4-Methyl-piperazin-1-ylmethyl)-1,3-dihydro-isoindole-2-carboxylic acid benzyl ester dihydrochloride salt

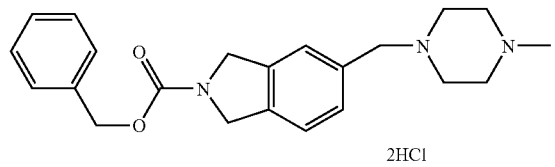

2HCl

The solid from Step 8 (assume 0.232 mol) was dissolved in acetone (700 mL) and this solution was added over 45 mins to a cooled (internal temp 15-17° C.) suspension of K₂CO₃ (48 g) and N-methylpiperazine (50 mL, 0.45 mol) in acetone (330 mL). The suspension was stirred at 15° C. for 3 h (complete removal of starting material by tlc) when the solution was evaporated to a small volume and the residue partition between EtOAc (1000 mL) and a mixture of water (500 mL) and saturated brine (50 mL). The organic phase was washed with a mixture of water (500 mL) and saturated brine (150 mL) and finally washed with saturated brine (300 mL). The solution was dried (MgSO₄) and filtered and to this solution was added 1M-HCl in MeOH (430 mL, 0.43 mol). The suspension was cooled (0° C. for 30 mins) and the solid removed by filtration which was washed with EtOAc and then heptane on the sinter and the solid dried (oil-pump, RT 72 h) to give crop 1 of the title compound 66.34 g (65%) as a colourless solid. ¹H NMR (400 MHz, Me-d3-OD): 7.64-7.51 (m, 2H), 7.51-7.29 (m, 6H), 5.23 (s, 2H), 4.79 (dd, J=16.2, 6.1 Hz, 4H), 4.49 (s, 2H), 3.66 (s, 8H), 3.03 (s, 3H).

Step 9

5-(4-Methyl-piperazin-1-ylmethyl)-1,3-dihydro-isoindole-2-carboxylic acid benzyl ester DCM (33 L) and N-methylpiperazine (21.45 L, 193.4 mol) were stirred at 25° C. and the solution from step 8 added over a minimum of 30 mins such that temperature 20-30° C. After stirring the solution for a further 30 mins water (55 L) was added and the organic phase was washed with water (2×55 L). The product was extracted into 0.8M HCl (66 L) and the layers separated. The aqueous phase was washed with DCM (55 L) and then basified with 2M NaOH to pH 10-11 and the product was extracted into EtOAc (2×55 L). The combined organic phase were filtered to remove solids and the evaporated followed by azeotroping with toluene and drying to constant weight to give the title compound, 6.63 kg (47% yield, 98% pure by hplc).

Step 10

5-(4-Methyl-piperazin-1-ylmethyl)-2,3-dihydro-1H-isoindole

To a degassed solution of 5-(4-Methyl-piperazin-1-ylmethyl)-1,3-dihydro-isoindole-2-carboxylic acid benzyl ester (Step 9, 1.3 Kg, 3.55 mol) dissolved in EtOH (13 L) was added 10% Pd/C (0.065 Kg). Hydrogen was passed through the mixture at 30° C. for 4 h or until complete by NMR. The solution was then stirred for 1 h under an atmosphere of N₂ and then filtered to remove the catalyst through a GF/F filter followed by filtration through a Cuno filter. The filtrate was evaporated to a small volume, azeotroped with toluene (3.9 L) and dried to constant weight yielding the title compound as a red/black oily solid (0.78 Kg) which was stored under nitrogen until required.

Step 11

(2,4-Bis-benzyloxy-5-isopropenyl-phenyl)-[5-(4-methyl-piperazin-1-ylmethyl)-1,3-dihydro-isoindol-2-yl]-methanone 1,1'-Carbonyldiimidazole (4.82 Kg, 29.8 mol) was added to a solution of 2,4-bis-benzyloxy-5-isopropenyl-benzoic acid (10.58 Kg, 28.3 mol, step 5) in DMF (21.2 L) at 25° C. After 20 mins at 25° C. a solution of 5-(4-Methyl-piperazin-1-ylmethyl)-2,3-dihydro-1H-isoindole (7.2 Kg, 31.1 mol, step 10) in DMF (7.2 L) maintaining a temperature below 35° C. and the solution stirred at 25° C. for a minimum of 12 h. The solid which had formed was removed by filtration, washed with isopropyl acetate (2×21.6 L) and dried at 35° C. to constant weight to give the title compound 8.7 Kg (77% yield, purity by hplc 97.5%).

Step 12

(2,4-Dihydroxy-5-isopropyl-phenyl)-[5-(4-methyl-piperazin-1-ylmethyl)-1,3-dihydro-isoindol-2-yl]-methanone The product from Step 11 (0.9 Kg, 1.53 mol) was dissolved in isopropanol (6.8 L) and water (1.04 L) and after purging with N₂ 10% Pd/C (90 g) and K₂CO₃ (0.212 Kg, 1.53 mol) were added and the suspension was hydrogenated for 60 to 70 mins under an 3 Barr pressure of H₂. The solution was diluted with water (0.5 L) and filtered. To the filtrate was added aqueous HCl (30% hydrochloric acid, 0.85 Kg diluted with water 5.42 Kg) and the solution was concentrated at 60° C. under vacuum (removing 10 L isopropanol). Water (0.45 L) was added to the solution and concentration continued (until a further 10 L isopropanol had been removed). The aqueous phase was washed with EtOAc (4.61 L), diluted with acetonitrile (4.06 L) and neutralized to pH 7.5-8.5 by addition of conc ammonia solution (0.35 Kg). The suspension was stirred for 2.5 h and then the solid was removed by filtration. The residue was washed with acetonitrile (2×0.8 L) and dried at 40° C. to constant weight to give the title compound 588 g (94% yield).

Step 13

(2,4-Dihydroxy-5-isopropyl-phenyl)-[5-(4-methyl-piperazin-1-ylmethyl)-1,3-dihydro-isoindol-2-yl]-methanone L-lactate salt (form FL1)

The product of Step 12 (646 g, 1.58 mol) was dissolved in ethanol (5.17 L) and the solution filtered. A solution of L-lactic acid (142 g, 1.58 mol) dissolved in ethanol (2.59 L) was filtered and added to the solution of the filtered solution (above) and then to the mixture was added EtOAc (7.75 L). The suspension was stirred at RT for 12 h and then cooled to 5° C. for a further 2 h. The solid which had formed was removed by filtration, washed with EtOAc (2×2.58 L) and heptane (2×1.94 L) and dried to constant weight at 35° C. giving the title compound (581 g, 74% yield).

Example 83

Alternative synthesis of 5-(4-Methyl-piperazin-1-ylmethyl)-2,3-dihydro-1H-isoindole 83A. Synthesis of 1-methyl-4-prop-2-ynyl-piperazine

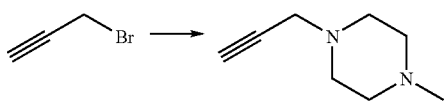

To 1-methylpiperazine (37.7 ml, 337 mmol) and K₂CO₃ (46.6 g, 337 mmol) in acetone (380 ml) was added propargyl bromide (25 ml, 225 mmol, 80% in toluene) in acetone (70 ml) dropwise at 0° C. under N₂. The internal temperature of the reaction was kept <10° C. The reaction was stirred at room temperature for 3 hours. The reaction was filtered, and the salts were washed with small portions of acetone (×2). The filtrates were combined evaporated to concentration (gently). To the residue was added water and the product was extracted with DCM (×3). The combined organic layers were washed with brine and dried over MgSO₄. The product was filtered and evaporated to dryness to yield 1-methyl-4-prop-2-ynyl-piperazine as a yellow oil.

83B. Synthesis of 5-(4-Methyl-piperazin-1-ylm-ethyl)-1,3-dihydro-isoindole-2-carboxylic acid tert-butyl ester

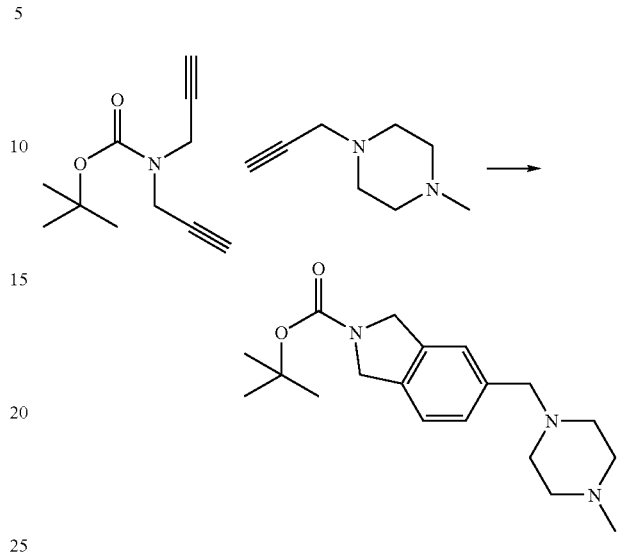

A solution of N-boc-dipropargylamine (36.3 ml, 226 mmol, 86% pure) in EtOAc (30 ml) was made up and degassed by bubbling through N₂, in a separating funnel. Tris(triphenylphosphine)rhodium(1) chloride (1.39 g, 1.50 mmol, 1 mol %) was added to pre-degassed EtOAc (15 ml) in a second separating funnel. (NB CpRu(COD)Cl) can also be used as an alternative catalyst).

In the main reactor flask, 1-propargyl-4-methylpiperazine (32.3 ml, 150 mmol, 90% pure) was diluted with EtOAc (75 ml) and was degassed by bubbling N₂ through the mixture The mixture was cooled in a ice-water bath and then the tris(triphenylphosphine)rhodium(1) chloride (1.39 g, 1 mol %) in EtOAc was added. Slow addition of N-boc-dipropargylamine/EtOAc was undertaken to yield a mild exotherm. The internal temperature rose to 25° C. and remained at this temperature. After addition was approximately one third complete (~45 minutes), the exotherm tailed off (despite the continual slow addition of N-boc-dipropargylamine/EtOAc). Another portion of tris(triphenylphosphine) rhodium(1) chloride catalyst (1.39 g, 1 mol %) in EtOAc (15 ml, pre-degassed) was made up and added very slowly to the reaction. After a couple of minutes a new exotherm started and grew to 30° C. The reaction temperature was cooled gently by the addition of a small amount of ice to the water bath. Once the exotherm began to subside, slow addition of N-boc-dipropargylamine/EtOAc was continued. The entire addition was carried out over a 2 hour period. The reaction mixture was then left at room temperature overnight before diluting with EtOAc and washing with NH₄Cl (×2) (aqueous, saturated) to remove excess 1-propargyl-4-methylpiperazine. The mixture was diluted with a small amount of water to dissolve the salts. The organic layer was washed with water, brine and dried over MgSO₄. The product was filtered and evaporated to dryness to leave a brown oil.

To the oil residue obtained was added n-heptane. The oil/heptane was left to stand (~10 minutes) until a red precipitate formed. The precipitate was filtered and washed with fresh n-heptane (×2). The filtrates were dried to yield the product as a red oil.

The desired product was further purified by forming the toluenesulphonic acid (TsOH) salt. Thus, the crude product was taken up in MeOH (20 ml) and the TsOH.H$_2$O (1 eq to estimated purity by NMR) was added. The solution was evaporated to dryness, and then dissolved in toluene (×1) and re-evaporated. The resulting product was taken up in ether. After a few minutes, a precipitate and solution formed. The precipitate was filtered and washed with more ether (×2) until the filtrate was colourless. The yellow solid was dried to yield the product as the TsOH salt. MS: [M+H]$^+$ 332.

83C. Synthesis of 5-(4-Methyl-piperazin-1-ylmethyl)-2,3-dihydro-1H-isoindole

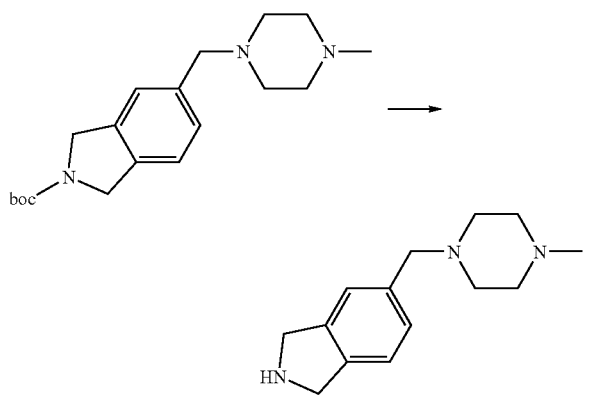

The isoindoline tosylate salt was taken up in DCM (0.3 M) and TFA (12 eq.) added slowly at 0° C. The reaction was stirred overnight at room temperature. The reaction was evaporated to dryness and then with toluene/MeOH(×3) to yield the product as a mixture of acid addition salts. MS: [M+H]$^+$ 232.

The compound of Example 83C can be used in the method of Example 80 Step 12.

Example 84

Alternative synthesis of 5-hydroxymethyl-1,3-dihydro-isoindole-2-carboxylic acid benzyl ester

84A. Methyl 2-benzyl-2,3-dihydro-1H-isoindole-5-carboxylate

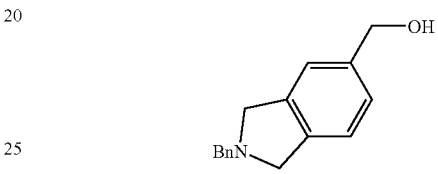

Benzylamine (3.21 g, 30.0 mmol) in anhydrous tetrahydrofuran (25 ml) was added to a stirred mixture of methyl 3,4-bis-(bromomethyl)benzoate (9.66 g, 30.0 mmol) (obtained from Fluorochem) and triethylamine (9 ml, 64.7 mmol) in anhydrous tetrahydrofuran (50 ml) and the resulting mixture was stirred at room temperature for 3 hours. The solvent was removed in vacuo at 40° C. and the residue partitioned between ethyl acetate (100 ml) and water (100 ml). The organic layer was washed with a further portion of water (100 ml), separated and the solvent removed in vacuo at 40° C. to afford methyl 2-benzyl-2,3-dihydro-1H-isoindole-5-carboxylate as a pale orange solid that was used immediately without further purification as described below. $^1$H NMR (DMSO-d$_6$) 7.82 (2H, m), 7.40-7.25 (6H, m), 3.90 (3H, s), 3.88 (2H, s), 3.84 (4H, s). MS: [M+H]$^+$ 268.

84B. (2-Benzyl-2,3-dihydro-1H-isoindol-5-yl)-methanol

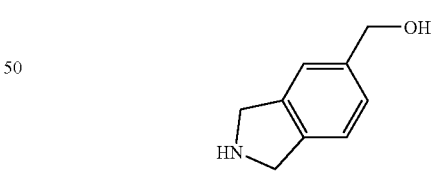

Methyl 2-benzyl-2,3-dihydro-1H-isoindole-5-carboxylate (from above) was dissolved in anhydrous tetrahydrofuran (75 ml) and added dropwise over 15 minutes to a rapidly stirred suspension of lithium aluminium hydride (1.71 g, 45.0 mmol) in anhydrous tetrahydrofuran (75 ml). The mixture was stirred at room temperature for 2 hours whereupon excess lithium aluminium hydride was destroyed by the slow dropwise addition of 1M sodium sulphate solution (12 ml). The solids were removed by filtration, rinsed with ethyl acetate (2×50 ml) and sucked dry. The solvent was removed in vacuo to afford (2-benzyl-2,3-dihydro-1H-isoindol-5-yl)-methanol (7.15 g, 99%) as a tan solid. $^1$H NMR (DMSO-d$_6$) 7.40-7.30 (4H, m), 7.28 (1H, m), 7.17-7.10 (3H, m), 5.10 (1H, t), 4.47 (2H, d), 3.85 (2H, s), 3.82 (2H, s), 3.80 (2H, s). MS: [M+H]$^+$ 240.

84C. (2,3-Dihydro-1H-isoindol-5-yl)-methanol

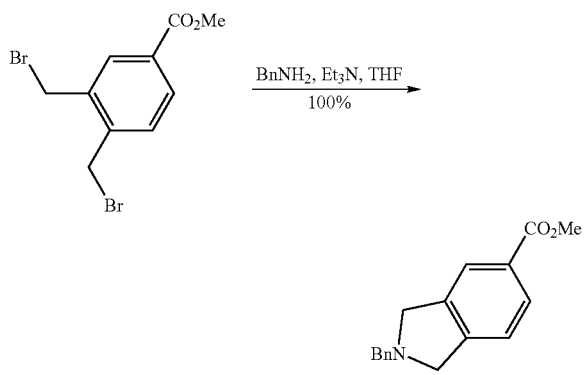

10% Palladium on activated carbon (200 mg) was added to a solution of (2-benzyl-2,3-dihydro-1H-isoindol-5-yl)-methanol (2.39 g, 10.0 mmol) in ethanol (60 ml) and the resulting mixture was placed in a Parr apparatus, heated to 50° C. and shaken under a hydrogen atmosphere at 60 psi for 30 hours. Upon cooling to room temperature the mixture was filtered under gravity, the solids were rinsed with ethanol (2×10 ml) and the solvent removed in vacuo to afford (2,3-dihydro-1H-isoindol-5-yl)-methanol (1.49 g, 100%) as an off-white solid. $^1$H NMR (DMSO-d$_6$) 7.20 (1H, s), 7.18 (1H, d), 7.12 (1H, d), 5.10 (1H, br s), 4.46 (2H, s), 4.05 (4H, s). MS: [M+H]$^+$ 150.

84D.
5-Hydroxymethyl-1,3-dihydro-isoindole-2-carboxylic acid benzyl ester

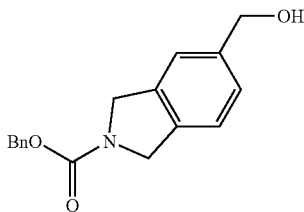 [SMILES: O=C(OCc1ccccc1)N1Cc2ccc(CO)cc2C1]

A mixture of (2,3-dihydro-1H-isoindol-5-yl)-methanol (1.34 g, 9.0 mmol) in anhydrous tetrahydrofuran (50 ml) was warmed gently to aid dissolution and allowed to cool to room temperature. Triethylamine (1.5 ml, 10.8 mmol) was added and the stirred mixture was treated dropwise with benzyl chloroformate (1.35 ml, 9.5 mmol) and stirred at room temperature for 3 hours. The solvent was removed in vacuo and the residue partitioned between ethyl acetate (30 ml) and 2M hydrochloric acid (30 ml). The organic layer was washed with water (30 ml), separated and the solvent removed in vacuo to afford a pink oil that solidified upon standing. The solids were triturated with 10% ethyl acetate in hexane (10 ml), filtered, rinsed with heptane (10 ml) and sucked dry to afford the title compound (2.5 g, 98%) as a pale pink solid. $^1$H NMR (DMSO-d$_6$) 7.45-7.21 (8H, m), 5.20 (1H, t), 5.17 (2H, s), 4.71 (2H, br s), 4.64 (2H, br s), 4.50 (2H, d). MS: [M+H]$^+$ 284.

The title compound can be used in Step 9 of Example 80.

Example 85

Crystal Structure Studies

The compound of formula (VIII), 2,4-Dihydroxy-5-isopropyl-phenyl)-[5-(4-methyl-piperazin-1-ylmethyl)-1,3-dihydro-isoindol-2-yl]-methanone, and its salts exist in a number of different crystalline forms. The L-lactate salts have been identified and characterised using the methods described below.

General Methods
Single Crystal Diffraction Methodology

Crystallographic data were collected at room temperature (20° C.) using synchrotron radiation ($\lambda$=0.775 Å) from ESRF ID23.1 beamline equipped with $\phi$ goniometer and an ADSC Quantum 315 CCD detector. Images were collected in two $\phi$ scans with $\phi$=0-180° and $\Delta\phi$=1°, one with high radiation dose and one with low dose. Detector to crystal distance was 110 mm. Data collection was controlled by ProDC software and images were processed and scaled by Dtrek.

The crystal structures were solved using direct methods implemented in SHELXS-97 and refined by SHELXL-97. Hydrogen atoms were generated on geometrical grounds while the location of heteroatom bound hydrogen atoms was confirmed by inspection of Fo-Fc difference maps. The positional and thermal parameters of hydrogen atoms were constricted to ride on corresponding non-hydrogen atoms. The thermal motion of non-hydrogen atoms was modelled by anisotropic thermal factors.

Powder Diffraction Methodology

Samples for X-ray powder diffraction (XRPD) data collection were gently ground by marble mortar and loaded into a crystallographic capillary (from Hampton Research, Quartz or Glass Type 10, 0.4 or 0.7 mm diameter). Diffraction patterns were collected at room temperature using CuK$\alpha$ radiation ($\lambda$=1.5418 Å) from a Rigaku rotating anode RU3HR, Osmic blue confocal optics, ¼ c goniometer and a Rigaku HTC image plate detector. 2D images were collected while spinning $\phi$ axis with a detector to crystal distance of 250 mm. Data collection was controlled by CrystalClear software and 2D images were converted to 1D plot (2$\theta$ vs. Intensity) by Datasqueeze (intensity averaged over the azimuthal angle $0 \leq \chi \leq 360°$ for 2$\theta$ range 3-30° in 0.02° steps). In house program AstexXRPD was used for manipulation and visualisation of 1D XRPD patterns.

Determination of Salt Stoichiometry by Titration Experiments

In the following examples, where they relate to salts and the stoichiometry of the salt is given, the stoichiometry was determined using the following titration method.

A solution (KCl/HCl solution) of 150 mM KCl and 20 mM HCl was freshly prepared for each batch of titration experiments. An aliquot of 1 ml of the solution was titrated and the potentiometric titration curve thus produced was used as the control curve. All titrations were performed at 25° C. and with 300 mM KOH in 2 µl steps using a Mettler Toledo MP220 pH meter. Electrode potential readings for 4 standard buffers were recorded before and after daily batch of measurement. Samples of Compound (VIII) salts of (1-3 mg) were dissolved in 1 ml of KCl/HCl solution and titrated with vigorous stirring using a small magnetic stirrer. The recorded electrode potentials were converted into pH values using a calibration curve from the 4 standard buffers. Sample and control titration data were processed to produce a Bjerrum plot in the pH range 2-12. The Bjerrum plot calculation and analysis method is described in the review "Physicochemical Profiling (Solubility, Permeability and Charge State)", A. Avdeef (Current Topics in Medicinal Chemistry 2001, p277-351).

The stoichiometry of the Compound (VIII) salts was deduced from the starting nH (number of protons at pH=2), (i.e. free base starts with −2 protons, mono-salt with −1 protons (Compound (VIII)$^+$ acid$^-$)), while double salts (Compound (VIII)$^{2+}$ acid$^{2-}$ or Compound (VIII)$^{2+}$ 2* acid$^-$) start at nH=0.

Compound (VIII) L-Lactate 1:1 Salt Crystal Forms
(85A) Compound (VIII) L-Lactate—Form FL1

The L-Lactate salt form FL1 was prepared as described in Example 81 above.

Form FL1 is stable in air and at 40° C. and 75% RH for at least one month. The XRPD pattern for form FL1 is shown in FIG. 1 and the main peaks are listed in Table EX85A.

TABLE EX85A

Main XRPD peaks for Compound (VIII) Lactate - Form FL1

| 2θ/° | d/Å | I/% |
|---|---|---|
| 6.18 | 14.30 | 15 |
| 6.53 | 13.52 | 50 |
| 8.39 | 10.54 | 19 |
| 11.08 | 7.98 | 7 |
| 13.10 | 6.75 | 85 |
| 14.13 | 6.26 | 33 |
| 14.40 | 6.15 | 23 |
| 15.21 | 5.82 | 4 |

TABLE EX85A-continued

Main XRPD peaks for Compound (VIII) Lactate - Form FL1

| 2θ/° | d/Å | I/% |
|---|---|---|
| 16.21 | 5.46 | 6 |
| 16.81 | 5.27 | 100 |
| 17.22 | 5.15 | 45 |
| 18.65 | 4.75 | 23 |
| 19.52 | 4.54 | 33 |
| 19.82 | 4.48 | 34 |
| 20.49 | 4.33 | 7 |
| 20.76 | 4.27 | 13 |
| 21.13 | 4.20 | 17 |
| 22.02 | 4.03 | 12 |
| 22.33 | 3.98 | 44 |
| 22.84 | 3.89 | 40 |
| 23.09 | 3.85 | 25 |
| 23.94 | 3.71 | 14 |
| 25.19 | 3.53 | 7 |
| 26.41 | 3.37 | 14 |
| 26.95 | 3.31 | 5 |
| 27.81 | 3.21 | 14 |

(85B) Compound (VIII) L-Lactate—Form FL2

Form FL2 was observed in precipitation experiments of methanol solutions of form FL1. Single crystal X-ray analysis showed that form FL2 is hydrated. It is nominally a tri-hydrate because there are 3 crystal water positions in the asymmetric unit, but they are not 100% occupied at room temperature and laboratory humidity. A saturated solution of form FL1 in methanol:water 9:1 was prepared at room temperature. Slow precipitation with approximately 4 volumes of acetone gave form FL2 which is stable in air. The XRPD pattern for form FL2 is shown in FIG. 2 and the main peaks are listed in Table 14 below. A crystal packing diagram is shown in FIG. 3 and the atom coordinates are listed in Table EX85B(i) below.

TABLE EX85B(i)

Main XRPD peaks for Compound (VIII) Lactate salt - form FL2

| 2θ/° | d/Å | I/% |
|---|---|---|
| 8.03 | 11.00 | 29 |
| 10.71 | 8.26 | 53 |
| 11.98 | 7.38 | 90 |
| 13.13 | 6.74 | 49 |
| 15.39 | 5.75 | 29 |
| 16.09 | 5.50 | 32 |
| 16.61 | 5.33 | 42 |
| 17.26 | 5.13 | 37 |
| 18.17 | 4.88 | 20 |
| 18.82 | 4.71 | 56 |
| 20.40 | 4.35 | 40 |
| 21.01 | 4.22 | 49 |
| 21.53 | 4.12 | 27 |
| 22.34 | 3.98 | 100 |
| 22.56 | 3.94 | 73 |
| 23.71 | 3.75 | 82 |
| 24.30 | 3.66 | 8 |
| 24.65 | 3.61 | 12 |
| 26.56 | 3.35 | 13 |
| 27.70 | 3.22 | 21 |
| 28.29 | 3.15 | 16 |

TABLE EX85B(II)

Unit cell parameters and coordinates in cif format for crystal structure of Compound (VIII) Lactate salt - form FL2 space group: P2$_1$
unit cell at 293K with a, b, c & β having 5% s.u.:

a = 5.8
b = 16.6
c = 14.9
beta = 98
alpha = gamma = 90
Coordinates in cif format:

```
loop_
_atom_site_label
_atom_site_type_symbol
_atom_site_fract_x
_atom_site_fract_y
_atom_site_fract_z
_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
C1    C   -0.643(2)    1.1037(6)   0.6763(7)   0.097(3)   Uani 1 1 d . . .
H1A   H   -0.6995      1.0577      0.6395      0.117      Uiso 1 1 calc . . .
H1B   H   -0.5231      1.1308      0.6484      0.117      Uiso 1 1 calc . . .
N2    N   -0.5563(16)  1.0791(5)   0.7694(6)   0.096(2)   Uani 1 1 d . . .
C3    C   -0.692(3)    1.1148(8)   0.8352(8)   0.124(4)   Uani 1 1 d . . .
H3A   H   -0.7713      1.0734      0.8651      0.148      Uiso 1 1 calc . . .
H3B   H   -0.5925      1.1454      0.8805      0.148      Uiso 1 1 calc . . .
C4    C   -0.8553(19)  1.1667(7)   0.7825(7)   0.094(3)   Uani 1 1 d . . .
C5    C   -0.8393(19)  1.1609(6)   0.6900(7)   0.092(3)   Uani 1 1 d . . .
C6    C   -1.036(3)    1.2141(8)   0.8083(8)   0.110(3)   Uani 1 1 d . . .
H6    H   -1.0636      1.2139      0.8682      0.132      Uiso 1 1 calc . . .
C7    C   -1.172(2)    1.2611(8)   0.7456(8)   0.105(3)   Uani 1 1 d . . .
C8    C   -1.145(2)    1.2560(8)   0.6564(9)   0.111(3)   Uani 1 1 d . . .
H8    H   -1.2387      1.2867      0.6138      0.133      Uiso 1 1 calc . . .
C9    C   -0.979(2)    1.2053(9)   0.6287(7)   0.109(3)   Uani 1 1 d . . .
```

TABLE EX85B(II)-continued

Unit cell parameters and coordinates in cif format for crystal structure of Compound (VIII) Lactate salt - form FL2

| | | | | | | |
|---|---|---|---|---|---|---|
| H9 | H | −0.9640 | 1.2017 | 0.5677 | 0.130 | Uiso 1 1 calc . . . |
| C10 | C | −1.3561(18) | 1.3173(8) | 0.7739(9) | 0.106(3) | Uani 1 1 d . . . |
| H10A | H | −1.4455 | 1.3402 | 0.7202 | 0.127 | Uiso 1 1 calc . . . |
| H10B | H | −1.4617 | 1.2864 | 0.8055 | 0.127 | Uiso 1 1 calc . . . |
| N11 | N | −1.2550(14) | 1.3836(6) | 0.8332(6) | 0.096(2) | Uani 1 1 d . . . |
| C12 | C | −1.1136(17) | 1.4353(6) | 0.7839(7) | 0.091(3) | Uani 1 1 d . . . |
| H12A | H | −1.2098 | 1.4591 | 0.7324 | 0.109 | Uiso 1 1 calc . . . |
| H12B | H | −0.9935 | 1.4035 | 0.7615 | 0.109 | Uiso 1 1 calc . . . |
| C13 | C | −1.0015(17) | 1.5021(7) | 0.8462(8) | 0.100(3) | Uani 1 1 d . . . |
| H13A | H | −0.8991 | 1.4783 | 0.8961 | 0.121 | Uiso 1 1 calc . . . |
| H13B | H | −0.9092 | 1.5368 | 0.8128 | 0.121 | Uiso 1 1 calc . . . |
| N14 | N | −1.1853(15) | 1.5509(5) | 0.8822(6) | 0.094(2) | Uani 1 1 d . . . |
| H14 | H | −1.2741 | 1.5755 | 0.8352 | 0.113 | Uiso 1 1 calc . . . |
| C15 | C | −1.3350(18) | 1.4966(7) | 0.9279(7) | 0.095(3) | Uani 1 1 d . . . |
| H15A | H | −1.4599 | 1.5276 | 0.9479 | 0.114 | Uiso 1 1 calc . . . |
| H15B | H | −1.2441 | 1.4730 | 0.9808 | 0.114 | Uiso 1 1 calc . . . |
| C16 | C | −1.4358(17) | 1.4308(7) | 0.8658(8) | 0.098(3) | Uani 1 1 d . . . |
| H16A | H | −1.5310 | 1.3959 | 0.8977 | 0.117 | Uiso 1 1 calc . . . |
| H16B | H | −1.5346 | 1.4542 | 0.8148 | 0.117 | Uiso 1 1 calc . . . |
| C17 | C | −1.068(2) | 1.6140(9) | 0.9439(9) | 0.119(4) | Uani 1 1 d . . . |
| H17A | H | −1.1835 | 1.6447 | 0.9694 | 0.178 | Uiso 1 1 calc . . . |
| H17B | H | −0.9807 | 1.6492 | 0.9103 | 0.178 | Uiso 1 1 calc . . . |
| H17C | H | −0.9658 | 1.5886 | 0.9916 | 0.178 | Uiso 1 1 calc . . . |
| C18 | C | −0.382(2) | 1.0287(9) | 0.7999(8) | 0.113(4) | Uani 1 1 d . . . |
| O19 | O | −0.345(2) | 1.0216(8) | 0.8837(6) | 0.156(4) | Uani 1 1 d . . . |
| C20 | C | −0.228(2) | 0.9847(6) | 0.7418(7) | 0.096(3) | Uani 1 1 d . . . |
| C21 | C | −0.069(3) | 0.9286(9) | 0.7863(9) | 0.119(4) | Uani 1 1 d . . . |
| C22 | C | 0.064(2) | 0.8867(9) | 0.7367(9) | 0.114(4) | Uani 1 1 d . . . |
| H22 | H | 0.1812 | 0.8547 | 0.7669 | 0.137 | Uiso 1 1 calc . . . |
| C23 | C | 0.038(2) | 0.8879(7) | 0.6447(8) | 0.097(3) | Uani 1 1 d . . . |
| C24 | C | −0.1201(18) | 0.9425(7) | 0.5972(8) | 0.096(3) | Uani 1 1 d . B . |
| C25 | C | −0.253(2) | 0.9882(7) | 0.6463(8) | 0.100(3) | Uani 1 1 d . . . |
| H25 | H | −0.3632 | 1.0228 | 0.6160 | 0.120 | Uiso 1 1 calc . . . |
| O26 | O | −0.036(2) | 0.9229(9) | 0.8775(6) | 0.169(5) | Uani 1 1 d . . . |
| H26 | H | −0.1427 | 0.9456 | 0.8980 | 0.253 | Uiso 1 1 calc R . . |
| O27 | O | 0.1658(15) | 0.8404(5) | 0.5948(6) | 0.118(3) | Uani 1 1 d . . . |
| H27 | H | 0.2091 | 0.7999 | 0.6238 | 0.176 | Uiso 1 1 calc R . . |
| C28 | C | −0.141(4) | 0.9478(11) | 0.4948(10) | 0.138(6) | Uani 1 1 d . . . |
| H28 | H | −0.0894 | 0.8953 | 0.4750 | 0.166 | Uiso 1 1 calc . A 1 |
| C29 | C | −0.029(11) | 1.004(4) | 0.449(3) | 0.24(3) | Uani 0.58(6) 1 d P B 1 |
| H29A | H | −0.0741 | 0.9976 | 0.3847 | 0.363 | Uiso 0.58 1 calc P B 1 |
| H29B | H | 0.1361 | 0.9972 | 0.4628 | 0.363 | Uiso 0.58 1 calc P B 1 |
| H29C | H | −0.0703 | 1.0575 | 0.4662 | 0.363 | Uiso 0.58 1 calc P B 1 |
| C30 | C | −0.417(7) | 0.950(3) | 0.4621(19) | 0.159(19) | Uani 0.58(6) 1 d P B 1 |
| H30A | H | −0.4911 | 0.9083 | 0.4918 | 0.239 | Uiso 0.58 1 calc P B 1 |
| H30B | H | −0.4462 | 0.9424 | 0.3978 | 0.239 | Uiso 0.58 1 calc P B 1 |
| H30C | H | −0.4773 | 1.0016 | 0.4772 | 0.239 | Uiso 0.58 1 calc P B 1 |
| C29 | C | −0.156(11) | 1.040(2) | 0.465(2) | 0.14(2) | Uani 0.42(6) 1 d P B 2 |
| H29D | H | −0.0071 | 1.0655 | 0.4814 | 0.215 | Uiso 0.42 1 calc P B 2 |
| H29E | H | −0.2703 | 1.0675 | 0.4943 | 0.215 | Uiso 0.42 1 calc P B 2 |
| H29F | H | −0.1983 | 1.0438 | 0.4003 | 0.215 | Uiso 0.42 1 calc P B 2 |
| C30 | C | −0.295(12) | 0.897(4) | 0.446(2) | 0.150(19) | Uani 0.42(6) 1 d P B 2 |
| H30D | H | −0.3403 | 0.9185 | 0.3870 | 0.224 | Uiso 0.42 1 calc P B 2 |
| H30E | H | −0.4300 | 0.8910 | 0.4766 | 0.224 | Uiso 0.42 1 calc P B 2 |
| H30F | H | −0.2234 | 0.8451 | 0.4418 | 0.224 | Uiso 0.42 1 calc P B 2 |
| O1L | O | −1.5549(12) | 1.6174(6) | 0.7786(6) | 0.124(3) | Uani 1 1 d . . . |
| O2L | O | −1.7419(12) | 1.7087(6) | 0.6890(7) | 0.125(3) | Uani 1 1 d . . . |
| C1L | C | −1.5569(17) | 1.6742(7) | 0.7238(8) | 0.098(3) | Uani 1 1 d . . . |
| C2L | C | −1.3365(17) | 1.6989(8) | 0.6926(9) | 0.108(4) | Uani 1 1 d . . . |
| H2L | H | −1.3065 | 1.7549 | 0.7117 | 0.129 | Uiso 1 1 calc . . . |
| C3L | C | −1.355(2) | 1.6971(12) | 0.5917(11) | 0.143(5) | Uani 1 1 d . . . |
| H3L1 | H | −1.2130 | 1.7162 | 0.5734 | 0.214 | Uiso 1 1 calc . . . |
| H3L2 | H | −1.4813 | 1.7312 | 0.5662 | 0.214 | Uiso 1 1 calc . . . |
| H3L3 | H | −1.3842 | 1.6429 | 0.5706 | 0.214 | Uiso 1 1 calc . . . |
| O3L | O | −1.1538(13) | 1.6538(7) | 0.7316(8) | 0.150(4) | Uani 1 1 d . . . |
| H3L | H | −1.0243 | 1.6711 | 0.7191 | 0.224 | Uiso 1 1 d . . . |
| O1W | O | −0.448(6) | 1.237(6) | 1.045(2) | 0.45(5) | Uani 0.78(6) 1 d P . . . |
| O2W | O | −0.021(15) | 0.8037(17) | 0.9990(19) | 0.74(7) | Uani 1 1 d . . . |
| O3W | O | −0.35(3) | 0.773(9) | 0.953(15) | 0.77(8) | Uani 0.22(6) 1 d P . . . |

(85C) Compound (VIII) L-Lactate—Form FL3

Form FL3 was observed in precipitation experiments of THF solutions of form FL1. Form FL3 transforms in air into form FL1. A saturated solution of form FL1 in THF was prepared at room temperature. Slow precipitation with approximately 4 volumes of heptane gave form FL3. The XRPD pattern of a fresh sample of form FL3 is shown in FIG. 4 and the main peaks are listed in Table EX85C(i) below. A sample of FL3 was dried in air for 2 days after which XRPD analysis showed that conversion to form FL1 had occurred.

TABLE EX85C

Main XRPD peaks for Compound (VIII) Lactate salt - form FL3

| 2θ/° | d/Å | I/% |
|---|---|---|
| 5.53 | 15.98 | 100 |
| 8.36 | 10.56 | 5 |
| 11.07 | 7.98 | 41 |
| 13.16 | 6.72 | 12 |
| 13.85 | 6.39 | 8 |
| 16.69 | 5.31 | 39 |
| 17.17 | 5.16 | 21 |
| 18.00 | 4.92 | 49 |
| 18.49 | 4.80 | 11 |
| 19.28 | 4.60 | 14 |
| 19.79 | 4.48 | 5 |
| 20.34 | 4.36 | 7 |
| 21.05 | 4.22 | 21 |
| 21.47 | 4.14 | 7 |
| 21.93 | 4.05 | 4 |
| 22.47 | 3.95 | 16 |
| 22.84 | 3.89 | 23 |
| 24.56 | 3.62 | 4 |
| 26.28 | 3.39 | 6 |
| 27.06 | 3.29 | 3 |
| 27.47 | 3.24 | 3 |
| 29.11 | 3.07 | 6 |

BIOLOGICAL ACTIVITY

Example 86

Isothermal Titration Calorimetry

The ability of the compounds of the invention to bind to human Hsp90 proteins was determined using isothermal titration calorimetry.

Isothermal titration calorimetry (ITC) experiments were performed with a VP-ITC titration calorimeter (Microcal Inc., Northampton, Mass., USA). Cloning, expression, and purification of the Human Hsp90a N-terminal domain were performed according to published methods (Jez, J. M. et al, Chem. Biol. 2003 April; 10(4):361-8.) Solutions of the human Hsp90α N-terminal domain and compound were prepared in a buffer comprising 25 mM Tris, 100 mM NaCl, 1 mM $MgCl_2$, 1 mM TCEP, 5% DMSO, pH 7.4. All solutions were filtered and degassed prior to a titration being carried out. The enthalpy change resulting from each injection of ligand was obtained through integration of the calorimetric signal. Data were analysed using Origin 7.0 (Microcal Software Inc., Northampton, Mass.). Heats of dilution were estimated using the final injections of each individual titration and subtracted before data fitting. Different ITC experimental formats were employed in order to obtain compound dissociation constants (Kd's) over a wide range of affinities. For weakly binding compounds a low c-value ITC method was used (Turnbull W. B. & Daranas A. H. J. Am. Chem. Soc. 2003 Dec. 3; 125(48):14859-66) in which the protein was present at 10-20 μM in the calorimetric cell and the compound concentration was 1-20 mM in the injection syringe. In this type of experiment the stoichiometry parameter (N) was locked at 1 for data fitting. For Kd's in the 20-0.004 μM range the experiment was configured such that the binding site concentration divided by the Kd (c-value) was between 5 and 1000. For the majority of these experiments the protein concentration in the calorimetric cell was in the range 4-100 μM and the ligand concentration in the injection syringe ranged from 50-1500 μM. In rare cases where compound solubility was limiting, the compound solution was placed in the calorimetric cell and titrated with protein from the injection syringe, maintaining a c-value between 5 and 1000. Competition ITC experiments were used to access Kd's <4 nM by performing the titration in the presence of a weaker binding competitor according to the method described in Sigurskjold B. W. Anal Biochem. 2000 Jan. 15; 277(2):260-6.

The compounds of examples 5, 10, 11, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 52, 53, 54, 55, 59, 60, 61, 62, 63, 65, 66, 67, 68, 69, 70, 71, 72, 73, 74 and 75 were tested and were found to have $K_d$ values of less than 1 micromolar.

The compounds of examples 5, 10, 12, 13, 14, 16, 17, 18, 19, 21, 22, 23, 25, 26, 27, 28, 29, 32, 33, 34, 35, 36, 37, 38, 39, 40, 41, 42, 43, 44, 45, 48, 49, 50, 51, 53, 54, 55, 59, 60, 61, 62, 63, 65, 66, 67, 68, 69, 70, 71, 72, 73, 74 and 75 have $K_d$ values of less than 0.1 micromolar and most of these compounds have $K_d$ values of less than 0.01 micromolar.

Example 87

Methods of Testing for Pain Reducing or Pain Preventing Activity (I) Inflammatory Hyperalgesia Test Mechanical hyperalgesia can be examined in a rat model of inflammatory pain. Paw withdrawal thresholds to an increasing pressure stimulus are measured by the Randal-Sellito technique using an analgesymeter (Ugo Basile, Milan), in naïve animals prior to an intraplantar injection of complete Freund's complete adjuvant (FCA) into the left hind paw. 24 h later paw withdrawal thresholds are measured again prior to (predose) and then from 10 min to 6 h following drug or vehicle administration. Reversal of hyperalgesia in the ipsilateral paw is calculated according to the formula:

$$\% \text{ reversal} = \frac{\text{postdose threshold} - \text{predose threshold}}{\text{naive threshold} - \text{predose threshold}} \times 100$$

(ii) Neuropathic Hyperalgesia Test

Mechanical hyperalgesia can be examined in a rat model of neuropathic pain induced by partial ligation of the left sciatic nerve. Approximately 14 days following surgery mechanical withdrawal thresholds of both the ligated (ipsilateral) and non-ligated (contralateral) paw are measured prior to (predose) and then from 10 min to 6 h following drug or vehicle administration. Reversal of hyperalgesia at each time point is calculated according to the formula:

$$\% \text{ reversal} = \frac{\text{ipsilateral threshold postdose} - \text{ipsilateral threshold predose}}{\text{contralateral threshold predose} - \text{ipsilateral threshold predose}} \times 100$$

All experiments are carried out using groups of 6 animals. Stock concentrations of drugs are dissolved in distilled water and subsequent dilutions were made in 0.9% saline for subcutaneous administration in a volume of 4 mlkg$^{-1}$. All drugs are made up in plastic vials and kept in the dark.

Statistical analysis are carried out on withdrawal threshold readings (g) using ANOVA with repeated measures followed by Tukey's HSD test. Efficacy refers to the maximal reversal of hyperalgesia observed at the doses used.
(iii) Testing the Effects of Compounds of Formula (0) a Rat Model of Bone Cancer Pain Adult female rats are given intra-tibial injections of MRMZ-1 rat mammary gland carcinoma cells (3 μl, 10$^7$ cells/ml). The animals typically gradually develop mechanical hyperalgesia, mechanical allodynia (skin sensitivity to non-noxious stimuli) and hind limb sparing, beginning on day 12-14 following cell injection. A compound of formula (0) (e.g. at a dose of 10 and 30 μg/kg s.c.) is administered 3 times a week from the day of cell injection, and the extent of inhibition of hind limb sparing and mechanical allodynia is determined in comparison to vehicle-treated controls.

Example 88

Determination of Antifungal Activity

The antifungal activity of the compounds of the formula (I) is determined using the following protocol.

The compounds are tested against a panel of fungi including *Candida parapsilosis, Candida tropicalis, Candida albicans*-ATCC 36082 and *Cryptococcus neoformans*. The test organisms are maintained on Sabourahd Dextrose Agar slants at 4° C. Singlet suspensions of each organism are prepared by growing the yeast overnight at 27° C. on a rotating drum in yeast-nitrogen base broth (YNB) with amino acids (Difco, Detroit, Mich.), pH 7.0 with 0.05 morpholine propanesulphonic acid (MOPS). The suspension is then centrifuged and washed twice with 0.85% NaCl before sonicating the washed cell suspension for 4 seconds (Branson Sonifier, model 360, Danbury, Conn.). The singlet blastospores are counted in a haemocytometer and adjusted to the desired concentration in 0.85% NaCl.

The activity of the test compounds is determined using a modification of a broth microdilution technique. Test compounds are diluted in DMSO to a 1.0 mg/ml ratio then diluted to 64 μg/ml in YNB broth, pH 7.0 with MOPS (Fluconazole is used as the control) to provide a working solution of each compound. Using a 96-well plate, wells 1 and 3 through 12 are prepared with YNB broth, ten fold dilutions of the compound solution are made in wells 2 to II (concentration ranges are 64 to 0.125 μg/ml). Well 1 serves as a sterility control and blank for the spectrophotometric assays. Well 12 serves as a growth control. The microtitre plates are inoculated with 10 μl in each of well 2 to 11 (final inoculum size is 10$^4$ organisms/ml). Inoculated plates are incubated for 48 hours at 35° C. The MIC values are determined spectrophotometrically by measuring the absorbance at 420 nm (Automatic Microplate Reader, DuPont Instruments, Wilmington, Del.) after agitation of the plates for 2 minutes with a vortex-mixer (Vorte-Genie 2 Mixer, Scientific industries, Inc., Bolemia, N.Y.). The MIC endpoint is defined as the lowest drug concentration exhibiting approximately 50% (or more) reduction of the growth compared with the control well. With the turbidity assay this is defined as the lowest drug concentration at which turbidity in the well is <50% of the control (IC$_{50}$). Minimal Cytolytic Concentrations (MCC) are determined by sub-culturing all wells from the 96-well plate onto a Sabourahd Dextrose Agar (SDA) plate, incubating for 1 to 2 days at 35° C. and then checking viability.

Pharmaceutical Formulations

Example 89

(i) Tablet Formulation

A tablet composition containing a compound of the invention is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the invention with 100 mg lactose and filling the resulting mixture into standard opaque hard gelatin capsules.

(iii) Injectable Formulation I

A parenteral composition for administration by injection can be prepared by dissolving a compound of the invention (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the invention (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of the invention (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of the invention (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the invention with pharmaceutical grade corn oil to give a concentration of 5 mg/ml. The composition is sterilised and filled into a suitable container.

(viii) Lyophilised Formulation

Aliquots of formulated compound of the invention (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitorr.

| (ix) 2% Topical Gel Formulation | |
|---|---|
| | % w/w |
| Compound | 2.00 |
| Hydroxypropyl Methyl cellulose (Methocel F4M) | 2.50 |
| Polyethyleneoxide (Polyox WSR -205) | 0.25 |
| Propylene glycol | 10.00 |
| Methylparaben | 0.15 |
| Propylparaben | 0.05 |
| Purified Water to | 100.00 |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the Invention. All such modifications and alterations are intended to be embraced by this application.

The invention claimed is:

1. A method for treating a pain in a subject in need thereof, which comprises administrating to said subject a therapeutically effective amount of (2,4-dihydroxy-5-isopropyl-phenyl)-[5-(4-methyl-piperazin-1-ylmethyl)-1,3-dihydro-isoindol-2-yl]methanone or a salt thereof wherein said pain is nociceptive pain.

2. The method according to claim 1, wherein the salt is a L-lactate salt of (2,4-dihydroxy-5-isopropyl-phenyl)-[5-(4-methyl-piperazin-1-ylmethyl)-1,3-dihydro-isoindol-2-yl]methanone.

* * * * *